United States Patent
Thompson et al.

(10) Patent No.: US 8,754,057 B2
(45) Date of Patent: *Jun. 17, 2014

(54) INHIBITION OF APOPTOSIS-SPECIFIC EIF-5A(EIF-5A1") WITH ANTISENSE OLIGONUCLEOTIDES AND SIRNA AS ANTI-INFLAMMATORY THERAPEUTICS

(75) Inventors: John E. Thompson, Waterloo (CA); Bruce C. Galton, Madison, NJ (US); Catherine Taylor, Waterloo (CA); Charles Dinarello, Boulder, CO (US); Leonid Reznikov, Aurora, CO (US); Adrienne Boone, Waterloo (CA); Marianne Hopkins, New Hamburg (CA)

(73) Assignee: Senesco Technologies, Inc., New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,171

(22) Filed: May 2, 2011

(65) Prior Publication Data

US 2012/0129910 A1    May 24, 2012

Related U.S. Application Data

(63) Continuation of application No. 11/134,445, filed on May 23, 2005, now abandoned, which is a continuation of application No. 10/861,980, filed on Jun. 7, 2004, now abandoned.

(60) Provisional application No. 60/476,194, filed on Jun. 6, 2003, provisional application No. 60/504,731, filed on Sep. 22, 2003, provisional application No. 60/528,249, filed on Dec. 10, 2003, provisional application No. 60/557,671, filed on Mar. 31, 2004, provisional application No. 60/575,814, filed on Jun. 2, 2004.

(51) Int. Cl.
*C12N 15/11* (2006.01)
*C12N 15/113* (2010.01)

(52) U.S. Cl.
CPC .................................... *C12N 15/113* (2013.01)
USPC ....................................................... 514/44 A

(58) Field of Classification Search
None
See application file for complete search history.

(56) References Cited

U.S. PATENT DOCUMENTS

2002/0086356 A1 * 7/2002 Tuschl et al. ................. 435/69.1
2003/0050272 A1 * 3/2003 Taylor et al. .................... 514/44

FOREIGN PATENT DOCUMENTS

WO    WO 03016572 A1 * 2/2003

OTHER PUBLICATIONS

Zhang et al, Small Interfering RNA Targeting Heme Oxygenase-1 Enhances Ischemia-Reperfusion-induced Lung Apoptosis, Mar. 12, 2004, J. Biol. Chemistry, vol. 279, No. 11: 10677-10684.*
Reynolds et al, Rational siRNA design for RNA interference, Mar. 2004, Nature Biotechnology, 22, 3:326-330.*
Elbashir et al, Duplexes of 21-nucleotide RNAs mediate RNA interference in cultured mammalian cells, May 2001, Nature, vol. 411, 494-498.*
Ruhl et al, Eukaryotic Initiation Factor 5A Is a Cellular Target of the Human Immunodeficiency Virus Type 1 Rev Activation Domain Mediating Trans-Activation, Dec. 1993, JCB, 123, 6, 1: 1309-1320.*

* cited by examiner

*Primary Examiner* — Tracy Vivlemore
*Assistant Examiner* — Kate Poliakova-Georgan
(74) *Attorney, Agent, or Firm* — Morgan Lewis & Bockius LLP

(57) ABSTRACT

The present invention relates to apoptosis specific eucaryotic initiation factor 5A (eIF-5A), referred to as apoptosis-specific eIF-5A or eIF5A1, nucleic acids and polypeptides and methods for inhibiting or suppressing apoptosis in cells using antisense nucleotides or siRNAs to inhibit expression of apoptosis-specific eIF-5A. The invention also relates to suppressing or inhibiting expression of pro-inflammatory cytokines or inhibiting activation of NFkB by inhibiting expression of apoptosis-specific eIF-5A.

12 Claims, 131 Drawing Sheets

```
TCGAAGACCGGTAAGCACGGCCATGCCAAGGTCCATCTGGTTGGTATTGATATTTTTACTGGGAAGAAATAT
  S   K   T   G   K   H   G   H   A   K   V   H   L   V   G   I   D   I   F   T   G   K   K   Y
GAAGATATCTGCCCGTCGACTCATAACATGGATGTCCCCAACATCAAAAGGAATGATTTCCAGCTGATTGGC
  E   D   I   C   P   S   T   H   N   M   D   V   P   N   I   K   R   N   D   F   Q   L   I   G
ATCCAGGATGGGTACCTATCCCTGCTCCAGGACAGTGGGGAGGTACGAGAGGACCTTCGTCTGCCTGAGGGA
  I   Q   D   G   Y   L   S   L   L   Q   D   S   G   E   V   R   E   D   L   R   L   P   E   G
GACCTTGGCAAGGAGATTGAGCAGAAGTATGACTGTGGAGAAGAGATCCTGATCACAGTGCTGTCCGCCATG
  D   L   G   K   E   I   E   Q   K   Y   D   C   G   E   E   I   L   I   T   V   L   S   A   M
ACAGAGGAGGCAGCTGTTGCAATCAAGGCCATGGCAAAATAACTGGCTTCCAGGGTGGCGGTGGTGGCAGCA
  T   E   E   A   A   V   A   I   K   A   M   A   K
GTGATCCATGAGCCTACAGAGGCCCCTCCCCCAGCTCTGGCTGGGCCCTTGGCTGGACTCCTATCCAATTTA
TTTGACGTTTTATTTTGGTTTTCCTCACCCCTTCAAACTGTCGGGGAGACCCTGCCCTTCACCTAGCTCCCT
TGGCCAGGCATGAGGGAGCCATGGCCTTGGTGAAGCTACCTGCCTCTTCTCTCGCAGCCCTGATGGGGGAAA
GGGAGTGGGTACTGCCTGTGGTTTAGGTTCCCCTCTCCCTTTTTCTTTTTAATTCAATTTGGAATCAGAAAG
CTGTGGATTCTGGCAAATGGTCTTGTGTCCTTTATCCCACTCAAACCCATCTGGTCCCCTGTTCTCCATAGT
CCTTCACCCCCAAGCACCACTGACAGACTGGGGACCAGCCCCCTTCCCTGCCTGTGTCTCTTCCCAAACCCC
TCTATAGGGGTGACAAGAAGAGGAGGGGGGGAGGGGACACGATCCCTCCTCAGGCATCTGGGAAGGCCTTGC
CCCCATGGGCTTTACCCTTTCCTGTGGGCTTTCTCCCTGACACATTTGTTAAAAATCAAACCTGAATAAAAC
TACAAGTTTAATATGAAAAAAAAAAAAAAAAAAAAAA
```
(972 NT, 109 aa) (SEQ ID NO: 11, 12)

FIG.1

```
CAGGTCTAGAGTTGGAATCGAAGCCTCTTAAAATGGCAGATGATTTGGACTTCGAGACAGGAGATGCAGGGG
                                 M  A  D  D  L  D  F  E  T  G  D  A  G
CCTCAGCCACCTTCCCAATGCAGTGCTCAGCATTACGTAAGAATGGTTTTGTGGTGCTCAAGGGCCGGCCAT
 A  S  A  T  F  P  M  Q  C  S  A  L  R  K  N  G  F  V  V  L  K  G  R  P
GTAAGATCGTCGAGATGTCTACTTCGAAGACTGGCAAGCATGGCCATGCCAAGGTCCATCTGGTTGGTATTG
 C  K  I  V  E  M  S  T  S  K  T  G  K  H  G  H  A  K  V  H  L  V  G  I
ATATTTTTACTGGGAAGAAATATGAAGATATCTGCCCGTCGACTCATAACATGGATGTCCCCAACATCAAAA
 D  I  F  T  G  K  K  Y  E  D  I  C  P  S  T  H  N  M  D  V  P  N  I  K
GGAATGATTTCCAGCTGATTGGCATCCAGGATGGGTACCTATCCCTGCTCCAGGACAGTGGGGAGGTACGAG
 R  N  D  F  Q  L  I  G  I  Q  D  G  Y  L  S  L  L  Q  D  S  G  E  V  R
AGGACCTTCGTCTGCCTGAGGGAGACCTTGGCAAGGAGATTGAGCAGAAGTATGACTGTGGAGAAGAGATCC
 E  D  L  R  L  P  E  G  D  L  G  K  E  I  E  Q  K  Y  D  C  G  E  E  I
TGATCACAGTGCTGTCCGCCATGACAGAGGAGGCAGCTGTTGCAATCAAGGCTCGAG
 L  I  T  V  L  S  A  M  T  E  E  A  A  V  A  I  K  A
```

(488 NT, 151 aa)   (SEQ ID NO: 15, 16)

FIG.2

```
CAGGTCTAGAGTTGGAATCGAAGCCTCTTAAAAATGGCAGATGATTTGGACTTCGAGACAGGAGATGCAGGGG
                                 M  A  D  D  L  D  F  E  T  G  D  A  G          13
CCTCAGCCACCTTCCCAATGCAGTGCTCAGCATTACGTAAGAATGGTTTTGTGGTGCTCAAGGGCCGGCCAT   144
 A  S  A  T  F  P  M  Q  C  S  A  L  R  K  N  G  F  V  V  L  K  G  R  P
GTAAGATCGTCGAGATGTCTACTTCGAAGACTGGCAAGCATGGCCATGCCAAGGTCCATCTGGTTGGTATTG
 C  K  I  V  E  M  S  T  S  K  T  G  K  H  G  H  A  K  V  H  L  V  G  I     61
ATATTTTTACTGGGAAGAAATATGAAGATATCTGCCCGTCGACTCATAACATGGATGTCCCCAACATCAAAA   288
 D  I  F  T  G  K  K  Y  E  D  I  C  P  S  T  H  N  M  D  V  P  N  I  K
GGAATGATTTCCAGCTGATTGGCATCCAGGATGGGTACCTATCCCTGCTCCAGGACAGTGGGGAGGTACGAG
 R  N  D  F  Q  L  I  G  I  Q  D  G  Y  L  S  L  L  Q  D  S  G  E  V  R    109
AGGACCTTCGTCTGCCTGAGGGAGACCTTGGCAAGGAGATTGAGCAGAAGTATGACTGTGGAGAAGAGATCC   432
 E  D  L  R  L  P  E  G  D  L  G  K  E  I  E  Q  K  Y  D  C  G  E  E  I
TGATCACAGTGCTGTCCGCCATGACAGAGGAGGCAGCTGTTGCAATCAAGGCCATGGCAAAATAACTGGCTT
 L  I  T  V  L  S  A  M  T  E  E  A  A  V  A  I  K  A  M  A  K  *           154
CCAGGGTGGCGGTGGTGGCAGCAGTGATCCATGAGCCTACAGAGGCCCCTCCCCCAGCTCTGGCTGGGCCCT   576
TGGCTGGACTCCTATCCAATTTATTTGACGTTTTATTTTGGTTTTCCTCACCCCTTCAAACTGTCGGGGAGA
CCCTGCCCTTCACCTAGCTCCCTTGGCCAGGCATGAGGGAGCCATGGCCTTGGTGAAGCTACCTGCCTCTTC   720
TCTCGCAGCCCTGATGGGGGAAAGGGAGTGGGTACTGCCTGTGGTTTAGGTTCCCCTCTCCCTTTTTCTTTT
TAATTCAATTTGGAATCAGAAAGCTGTGGATTCTGGCAAATGGTCTTGTGTCCTTTATCCCACTCAAACCCA   864
TCTGGTCCCCTGTTCTCCATAGTCCTTCACCCCCAAGCACCACTGACAGACTGGGGACCAGCCCCCTTCCCT
GCCTGTGTCTCTTCCCAAACCCCTCTATAGGGGTGACAAGAAGAGGAGGGGGGGAGGGGACACGATCCCTCC  1008
TCAGGCATCTGGGAAGGCCTTGCCCCCATGGGCTTTACCCTTTCCTGTGGGCTTTCTCCCTGACACATTTGT
TAAAAATCAAACCTGAATAAAACTACAAGTTTAATATGAAAAAAAAAAAAAAAAAAAAAA               1139
```

(1139 NT. 154 aa)    (SEQ ID NO: 1, 2)

FIG.3

```
GCTGTGTATTATTGGGCCCATAAGAACCACATACCTGTGCTGAGTCCTGCACTCACAGACGGCTCACTGGGT
  A  V  Y  Y  W  A  H  K  N  H  I  P  V  L  S  P  A  L  T  D  G  S  L  G
GACATGATCTTTTTCCATTCCTATAAAAACCCAGGCTTGGTCCTGGACATCGTTGAAGACCTGCGGCTCATC
  D  M  I  F  F  H  S  Y  K  N  P  G  L  V  L  D  I  V  E  D  L  R  L  I
AACATGCAGGCCATTTTCGCCAAGCGCACTGGGATGATCATCCTGGGTGGAGGCGTGGTCAAGCACCACATC
  N  M  Q  A  I  F  A  K  R  T  G  M  I  I  L  G  G  G  V  V  K  H  H  I
GCCAATGCTAACCTCATGCGGAATGGAGCTGACTACGCTGTTTATATCAACACAGCCCAGGAGTTTGATGGC
  A  N  A  N  L  M  R  N  G  A  D  Y  A  V  Y  I  N  T  A  Q  E  F  D  G
TCAGACTCAGGAGCCCGGCCAGATGAGGCTGTCTCCTGGGGCAAGATCCGGATGGATGCACAGCCAGTAAAG
  S  D  S  G  A  R  P  D  E  A  V  S  W  G  K  I  R  M  D  A  Q  P  V  K
GTCTATGCTGATGCATCTCTGGTTTTCCCCTTGCTGGTGGCTGAGACATTCGCCCAAAAGGCAGATGCCTTC
  V  Y  A  D  A  S  L  V  F  P  L  L  V  A  E  T  F  A  Q  K  A  D  A  F
AGAGCTGAGAAGAATGAGGACTGAGCAGATGGGTAAAGACGGAGGCTTCTGCCACACCTTTATTTATTATTT
  R  A  E  K  N  E  D
GCATACCAACCCCTCCTGGGCCCTCTCCTTGGTCAGCAGCATCTTGAGAATAAATGGCCTTTTTGTTGGTTT
CTGTAAAAAAGGACTTTAAAAAAAAAAAA
```

(606 NT, 151 aa)  (SEQ ID NO: 6, 7)

FIG.4 rat vs. human(BC000751 or NM_001970) 96.5% identity (coding)

```
              10        20        30        40        50        60
rat    ATGGCAGATGATTTGGACTTCGAGACAGGAGATGCAGGGGCCTCAGCCACCTTCCCAATG
       ::::::::::: :::::::::::::::::::::::::::::::::::::::::::::::
human  ATGGCAGATGACTTGGACTTCGAGACAGGAGATGCAGGGGCCTCAGCCACCTTCCCAATG
              10        20        30        40        50        60

70        80        90       100       110       120
rat    CAGTGCTCAGCATTACGTAAGAATGGTTTTGTGGTGCTCAAGGGCCGGCCATGTAAGATC
       :::::::::::::::::::::::::::::: ::::::::::::: :::::::::::::::
human  CAGTGCTCAGCATTACGTAAGAATGGCTTTGTGGTGCTCAAAGGCCGGCCATGTAAGATC
              70        80        90       100       110       120

130       140       150       160       170       180
rat    GTCGAGATGTCTACTTCGAAGACTGGCAAGCATGGCCATGCCAAGGTCCATCTGGTTGGT
       ::::::::::::::::::::::::::::::::: ::::: :::::::::::::::::::
human  GTCGAGATGTCTACTTCGAAGACTGGCAAGCACGGCCACGCCAAGGTCCATCTGGTTGGT
             130       140       150       160       170       180

190       200       210       220       230       240
rat    ATTGATATTTTTACTGGGAAGAAATATGAAGATATCTGCCCGTCGACTCATAACATGGAT
       ::::: :: :::::::::::::::::::::::::::::::::: :::::::: ::::::
human  ATTGACATCTTTACTGGGAAGAAATATGAAGATATCTGCCCGTCAACTCATAATATGGAT
             190       200       210       220       230       240

250       260       270       280       290       300
rat    GTCCCCAACATCAAAAGGAATGATTTCCAGCTGATTGGCATCCAGGATGGGTACCTATCC
       ::::::::::::::::::::::: ::::::::::::::::::::::::::::::::::
human  GTCCCCAACATCAAAAGGAATGACTTCCAGCTGATTGGCATCCAGGATGGGTACCTATCA
             250       260       270       280       290       300

310       320       330       340       350       360
rat    CTGCTCCAGGACAGTGGGGAGGTACGAGAGGACCTTCGTCTGCCTGAGGGAGACCTTGGC
       :::::::::::::: ::::::::::::::::::::::::::: :::::::::::::::::
human  CTGCTCCAGGACAGCGGGGAGGTACGAGAGGACCTTCGTCTCCCTGAGGGAGACCTTGGC
             310       320       330       340       350       360

370       380       390       400       410       420
rat    AAGGAGATTGAGCAGAAGTATGACTGTGGAGAAGAGATCCTGATCACAGTGCTGTCCGCC
       :::::::::::::::::::: :::::::::::::::::::::::::::: :::::: :::
human  AAGGAGATTGAGCAGAAGTACGACTGTGGAGAAGAGATCCTGATCACGGTGCTGTCTGCC
             370       380       390       400       410       420

430       440       450       460
rat    ATGACAGAGGAGGCAGCTGTTGCAATCAAGGCCATGGCAAAA (SEQ ID NO: 20)
       :::::::::::::::::::::::::::::::::::::::::
human  ATGACAGAGGAGGCAGCTGTTGCAATCAAGGCCATGGCAAAA (SEQ ID NO: 3)
             430       440       450       460
```

FIG.5 rat vs. human(NM_020390) 72.5% identity (coding)

```
              10        20        30        40        50        60
rat     ATGGCAGATGATTTGGACTTCGAGACAGGAGATGCAGGGGCCTCAGCCACCTTCCCAATG
        ::::::::  ::  :   ::  :::     ::  :::::: :::::  :::  ::: :::
human   ATGGCAGACGAAATTGATTTCACTACTGGAGATGCCGGGGCTTCCAGCACTTACCCTATG
              10        20        30        40        50        60

70        80        90       100       110       120
rat     CAGTGCTCAGCATTACGTAAGAATGGTTTTTGTGGTGCTCAAGGGCCGGCCATGTAAGATC
        ::::::::  ::  ::  ::  ::  ::  :: :::::::::::  :: ::::::  :: ::
human   CAGTGCTCGGCCTTGCGCAAAAACGGCTTCGTGGTGCTCAAAGGACGACCATGCAAAATA
              70        80        90       100       110       120

130       140       150       160       170       180
rat     GTCGAGATGTCTACTTCGAAGACTGGCAAGCATGGCCATGCCAAGGTCCATCTGGTTGGT
        ::  ::::::::  ::::: ::  :::::  :::::::::::::::::: ::  :::::
human   GTGGAGATGTCAACTTCCAAAACTGGAAAGCATGGTCATGCCAAGGTTCACCTTGTTGGA
              130       140       150       160       170       180

190       200       210       220       230       240
rat     ATTGATATTTTTACTGGGAAGAAATATGAAGATATCTGCCCGTCGACTCATAACATGGAT
        :::::::::::: :: :: :: :::::::::::::::: :: :: :: ::::: ::::::::
human   ATTGATATTTTTCACGGGCAAAAAATATGAAGATATTTGTCCTTCTACTCACAACATGGAT
              190       200       210       220       230       240

250       260       270       280       290       300
rat     GTCCCCAACATCAAAAGGAATGATTTCCAGCTGATTGGCATCCAGGATGGGTACCTATCC
        ::  :: ::  :: ::  ::  :::::::::  :::::  ::::  :: :::::  :::
human   GTTCCAAATATTAAGAGAAATGATTATCAACTGATATGCATTCAAGATGGTTACCTTTCC
              250       260       270       280       290       300

310       320       330       340       350       360
rat     CTGCTCCAGGACAGTGGGGAGGTACGAGAGGACCTTCGTCTGCCTGAGGGAGACCTTGGC
        :::::    ::  :  :::  ::  ::  :: :::::  :::      :::::  ::  :::
human   CTGCTGACAGAAACTGGTGAAGTTCGTGAGGATCTTAAACTGCCAGAAGGTGAACTAGGC
              310       320       330       340       350       360

370       380       390       400       410       420
rat     AAGGAGATTGAGCAGAAGTATGACTGTGGAGAAGAGATCCTGATCACAGTGCTGTCCGCC
        ::  ::  ::   :::   ::  ::  :     ::  :::::  :   :   :   ::  ::
human   AAAGAAATAGAGGGAAAATACAATGCAGGTGAAGATGTACAGGTGTCTGTCATGTGTGCA
              370       380       390       400       410       420

430       440       450       460
rat     ATGACAGAGGAGGCAGCTGTTGCAATCAAGGCCATGGCAAAA (SEQ ID NO: 20)
        ::::  ::  ::   :::::  ::  ::  ::   :::::
human   ATGAGTGAAGAATATGCTGTAGCCATAAAACCCT--GCAAAT (SEQ ID NO: 4)
              430       440       450       460
```

FIG. 6 rat vs. mouse (BC003889) 98.3% identity (coding)

```
            10         20         30         40         50         60
rat   ATGGCAGATGATTTGGACTTCGAGACAGGAGATGCAGGGGCCTCAGCCACCTTCCCAATG
      ::::::::::::::::::::::::::::::::::::::::::::::::::::::::::::
mouse ATGGCAGATGATTTGGACTTCGAGACAGGAGATGCAGGGGCCTCAGCCACCTTCCCAATG
            10         20         30         40         50         60

70         80         90        100        110        120
rat   CAGTGCTCAGCATTACGTAAGAATGGTTTTGTGGTGCTCAAGGGCCGGCCATGTAAGATC
      ::::::::::::::::::::::::::::::::::::::::: ::::::::::::::::::
mouse CAGTGCTCAGCATTACGTAAGAATGGTTTTGTGGTGCTCAAAGGCCGGCCATGTAAGATC
            70         80         90        100        110        120

130        140        150        160        170        180
rat   GTCGAGATGTCTACTTCGAAGACTGGCAAGCATGGCCATGCCAAGGTCCATCTGGTTGGT
      :::::::::::::::::::::::::::::::::::::::::::::::::::::::::::
mouse GTCGAGATGTCTACTTCGAAGACTGGCAAGCATGGCCATGCCAAGGTCCATCTGGTTGGC
           130        140        150        160        170        180

190        200        210        220        230        240
rat   ATTGATATTTTTACTGGGAAGAAATATGAAGATATCTGCCCGTCGACTCATAACATGGAT
      ::::: :::::::::::::::::::::::::::::::::::::::::::::::  ::::::
mouse ATTGACATTTTTACTGGGAAGAAATATGAAGATATCTGCCCGTCGACTCATAATATGGAT
           190        200        210        220        230        240

250        260        270        280        290        300
rat   GTCCCCAACATCAAAAGGAATGATTTCCAGCTGATTGGCATCCAGGATGGGTACCTATCC
      ::::::::::::::::: ::::::::: ::::::::::::::::::::::::::::::::
mouse GTCCCCAACATCAAACGGAATGACTTCCAGCTGATTGGCATCCAGGATGGGTACCTATCC
           250        260        270        280        290        300

310        320        330        340        350        360
rat   CTGCTCCAGGACAGTGGGGAGGTACGAGAGGACCTTCGTCTGCCTGAGGGAGACCTTGGC
      :::::::::::::::::::::::::::::::::::::::::::::::::: :::::::::
mouse CTGCTCCAGGACAGTGGGGAGGTACGAGAGGACCTTCGTCTGCCTGAAGGAGACCTTGGC
           310        320        330        340        350        360

370        380        390        400        410        420
rat   AAGGAGATTGAGCAGAAGTATGACTGTGGAGAAGAGATCCTGATCACAGTGCTGTCCGCC
      :::::::::::::::::::::::::::::::::::::::::::::::::::::::: :::
mouse AAGGAGATTGAGCAGAAGTATGACTGTGGAGAAGAGATCCTGATCACAGTGCTGTCTGCC
           370        380        390        400        410        420

430        440        450        460
rat   ATGACAGAGGAGGCAGCTGTTGCAATCAAGGCCATGGCAAAA (SEQ ID NO: 20)
      :::::::::::::::::::::::::::::::::::::::::
mouse ATGACAGAGGAGGCAGCTGTTGCAATCAAGGCCATGGCAAAA (SEQ ID NO: 5)
           430        440        450        460
```

FIG. 7 rat vs. human(BC000751 or NM_001970) 100.0% identity

```
              10        20        30        40        50        60
rat     MADDLDFETGDAGASATFPMQCSALRKNGFVVLKGRPCKIVEMSTSKTGKHGHAKVHLVG
        ::::::::::::::::::::::::::::::::::::::::::::::::::::::::::::
human   MADDLDFETGDAGASATFPMQCSALRKNGFVVLKGRPCKIVEMSTSKTGKHGHAKVHLVG
              10        20        30        40        50        60

70        80        90       100       110       120
rat     IDIFTGKKYEDICPSTHNMDVPNIKRNDFQLIGIQDGYLSLLQDSGEVREDLRLPEGDLG
        ::::::::::::::::::::::::::::::::::::::::::::::::::::::::::::
human   IDIFTGKKYEDICPSTHNMDVPNIKRNDFQLIGIQDGYLSLLQDSGEVREDLRLPEGDLG
              70        80        90       100       110       120

130       140       150
rat     KEIEQKYDCGEEILITVLSAMTEEAAVAIKAMAK  (SEQ ID NO: 2)
        :::::::::::::::::::::::::::::::::
human   KEIEQKYDCGEEILITVLSAMTEEAAVAIKAMAK  (SEQ ID NO: 21)
              130       140       150
```

FIG.8 rat vs. human(NM_020390) 82.5% identity

```
                  10        20        30        40        50        60
rat     MADDLDFETGDAGASATFPMQCSALRKNGFVVLKGRPCKIVEMSTSKTGKHGHAKVHLVG
        :::..::  :::::::::.:.::::::::::::::::::::::::::::::::::::::
human   MADEIDFTTGDAGASSTYPMQCSALRKNGFVVLKGRPCKIVEMSTSKTGKHGHAKVHLVG
                  10        20        30        40        50        60

70        80        90       100       110       120
rat     IDIFTGKKYEDICPSTHNMDVPNIKRNDFQLIGIQDGYLSLLQDSGEVREDLRLPEGDLG
        :::::::::::::::::::::::::::::: ::: :::::::: ..:::::::.:::.::
human   IDIFTGKKYEDICPSTHNMDVPNIKRNDYQLICIQDGYLSLLTETGEVREDLKLPEGELG
                  70        80        90       100       110       120

130       140       150
rat     KEIEQKYDCGEEILITVLSAMTEEAAVAIKAMAK    (SEQ ID NO: 2)
        ::::  ::. ::.. ...: .::.:: :::::   :
human   KEIEGKYNAGEDVQVSVMCAMSEEYAVAIKP-CK    (SEQ ID NO: 22)
                 130       140       150
```

FIG.9 rat vs. mouse (BC003889)100.0% identity

```
             10         20         30         40         50         60
rat    MADDLDFETGDAGASATFPMQCSALRKNGFVVLKGRPCKIVEMSTSKTGKHGHAKVHLVG
       ::::::::::::::::::::::::::::::::::::::::::::::::::::::::::::
mouse  MADDLDFETGDAGASATFPMQCSALRKNGFVVLKGRPCKIVEMSTSKTGKHGHAKVHLVG
             10         20         30         40         50         60

70         80         90        100        110        120
rat    IDIFTGKKYEDICPSTHNMDVPNIKRNDFQLIGIQDGYLSLLQDSGEVREDLRLPEGDLG
       ::::::::::::::::::::::::::::::::::::::::::::::::::::::::::::
mouse  IDIFTGKKYEDICPSTHNMDVPNIKRNDFQLIGIQDGYLSLLQDSGEVREDLRLPEGDLG
             70         80         90        100        110        120

130        140        150
rat    KEIEQKYDCGEEILITVLSAMTEEAAVAIKAMAK  (SEQ ID NO: 2)
       :::::::::::::::::::::::::::::::::
mouse  KEIEQKYDCGEEILITVLSAMTEEAAVAIKAMAK  (SEQ ID NO: 23)
             130        140        150
```

FIG.10 rat vs. human (BC000333) 87.4% identity (coding)

```
             10        20        30        40        50        60
rat     GCTGTGTATTATTGGGCCCATAAGAACCACATACCTGTGCTGAGTCCTGCACTCACAGAC
         : :::::::: :::::::: :::::::::::: :::::: : ::::: ::::: ::::::
human   TCCGTGTATTACTGGGCCCAGAAGAACCACATCCCTGTGTTTAGTCCCGCACTTACAGAC
             10        20        30        40        50        60

70        80        90       100       110       120
rat     GGCTCACTGGGTGACATGATCTTTTTCCATTCCTATAAAAACCCAGGCTTGGTCCTGGAC
        ::::: :::::   ::::::::::::: :::::::::: :: ::::: ::: ::::::::::::
human   GGCTCGCTGGGCGACATGATCTTCTTCCATTCCTACAAGAACCCGGGCCTGGTCCTGGAC
             70        80        90       100       110       120

130       140       150       160       170       180
rat     ATCGTTGAAGACCTGCGGCTCATCAACATGCAGGCCATTTTCGCCAAGCGCACTGGGATG
        :::::::::  ::::::  ::::::::::::::  :::::::: :: :::::: ::::::::::::
human   ATCGTTGAGGACCTGAGGCTCATCAACACACAGGCCATCTTTGCCAAGTGCACTGGGATG
            130       140       150       160       170       180

190       200       210       220       230       240
rat     ATCATCCTGGGTGGAGGCGTGGTCAAGCACCACATCGCCAATGCTAACCTCATGCGGAAT
        :::::  ::::: ::  ::::::::::::::::::::::: :::::::: :::::::::::::::
human   ATCATTCTGGGCGGGGGCGTGGTCAAGCACCACATTGCCAATGCCAACCTCATGCGGAAC
            190       200       210       220       230       240

250       260       270       280       290       300
rat     GGAGCTGACTACGCTGTTTATATCAACACAGCCCAGGAGTTTGATGGCTCAGACTCAGGA
        ::  :: :::::::::::::: ::::::::::::::::::::::::::::::::: ::::::::
human   GGGGCCGACTACGCTGTTTACATCAACACAGCCCAGGAGTTTGATGGCTCTGACTCAGGT
            250       260       270       280       290       300

310       320       330       340       350       360
rat     GCCCGGCCAGATGAGGCTGTCTCCTGGGGCAAGATCCGGATGGATGCACAGCCAGTAAAG
        :::::  ::::: ::::::::::::::::::::::::::::::: ::::::::::::::: :: :::
human   GCCCGACCAGACGAGGCTGTCTCCTGGGGCAAGATCCGGGTGGATGCACAGCCCGTCAAG
            310       320       330       340       350       360

370       380       390       400       410       420
rat     GTCTATGCTGATGCATCTCTGGTTTTCCCCTTGCTGGTGGCTGAGACATTCGCCCCAAAAG
        :::::::::::: :: ::::: :::::::: :::: :::::::::: :: :: ::::: :::
human   GTCTATGCTGACGCCTCCCTGGTCTTCCCCCTGCTTGTGGCTGAAACCTTTGCCCAGAAG
            370       380       390       400       410       420

430       440       450
rat     GCAGATGCCTTCAGAGCTGAGAAGAATGAGGAC    (Residues 1-453 of SEQ ID NO: 6)
        ::::::::::   ::::::::::  ::::::
human   ATGGATGCCTTCATGCATGAGAAGAACGAGGAC   (SEQ ID NO: 8)
            430       440       450
```

FIG.11

Hoescht Staining of Transformed
COS-7 Cells Deprived of Serum
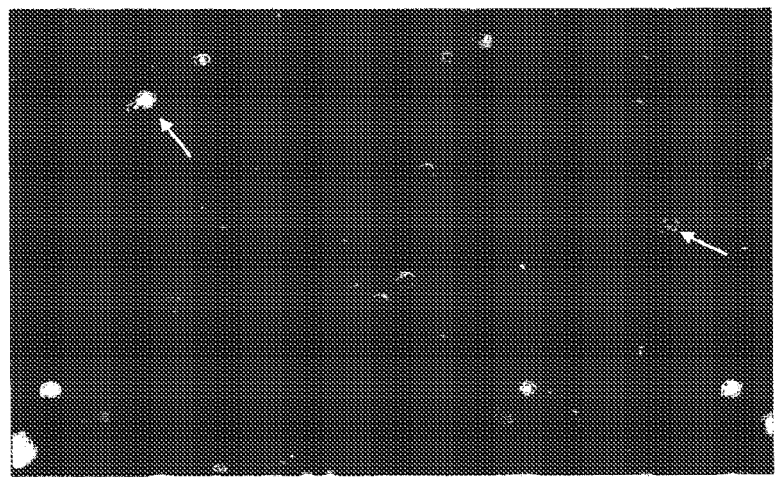
Mock Transformed
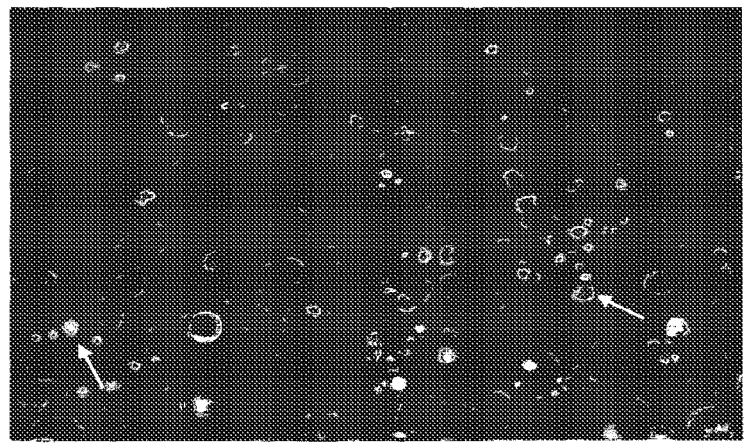
pHm6-Sense rat F5A
FIG.27

Sequence and Alignment of human eIF5A2 isolated from RKO cells with
sequence of human eIF5A2 in Genbank (ACCESSION XM_113401)

```
XM_113401    MADEIDFTTG DAGASSTYPM QCSALRKNGF VVLKGRPCKI VEMSTSKTGK
      PCR    MADEIDFTTG DAGASSTYPM QCSALRKNGF VVLKGRPCKI VEMSTSKTGK
Consensus    MADEIDFTTG DAGASSTYPM QCSALRKNGF VVLKGRPCKI VEMSTSKTGK 51                                                 100
XM_113401    HGHAKVHLVG IDIFTGKKYE DICPSTHNMD VPNIKRNDYQ LICIQDGYLS
      PCR    HGHAKVHLVG IDIFTGKKYE DICPSTHNMD VPNIKRNDYQ LICIQDGCLS
Consensus    HGHAKVHLVG IDIFTGKKYE DICPSTHNMD VPNIKRNDYQ LICIQDGcLS 101                                                150
XM_113401    LLTETGEVRE DLKLPEGELG KEIEGKYNAG EDVQVSVMCA MSEEYAVAIK
      PCR    LLTETGEVRE DLKLPEGELG KEIEGKYNAG EDVQVSVMCA MSEEYAVAIK
Consensus    LLTETGEVRE DLKLPEGELG KEIEGKYNAG EDVQVSVMCA MSEEYAVAIK 151
XM_113401    PCK  (SEQ ID NO: 22)
      PCR    PCK  (SEQ ID NO: 24)
Consensus    PCK  (SEQ ID NO: 28)
``` eIF5A2 = proliferating eIF-5A

FIG. 38

| PATIENT | Ds | IF5a1 pg/ng rRNA | IF5a2 pg/ng rRNA | 0.5 | 2.0 | IL-18 pg/ng rRNA | IL-1b pg/ng rRNA |
|---|---|---|---|---|---|---|---|
| 207 | CABG | 9.0 | 2.4 | 3.8 | 0.3 | 10.1 | 7.2 |
| 21 | CABG | 123.2 | 81.6 | 1.5 | 0.7 | 405.9 | 41.5 |
| 23 | CABG | 0.1 | 0.0 | 11.0 | 0.1 | 0.0 | 0.0 |
| 26 | CABG | | | | | | |
| 28 | CABG | 200.4 | 294.6 | 0.7 | 1.5 | 894.1 | 49.7 |
| 30 | CABG | 279.4 | 921.2 | 0.3 | 3.3 | 669.8 | 71.0 |
| 33 | CABG | 260.1 | 723.9 | 0.4 | 2.8 | 545.6 | 105.1 |
| 34 | CABG | 263.4 | 309.3 | 0.9 | 1.2 | 520.0 | 19.9 |
| 65 | CABG | 82.9 | 43.1 | 1.9 | 0.5 | 98.2 | 20.2 |
| 139 | CABG | 23.9 | 7.0 | 3.4 | 0.3 | 22.7 | 57.3 |
| 140 | CABG | 0.9 | 0.0 | #DIV/0! | 0.0 | 0.1 | 0.0 |
| 143 | CABG | 137.7 | 169.5 | 0.8 | 1.2 | 338.7 | 77.9 |

FIG.50A

| PATIENT | Ds | IF5a1 pg/ng rRNA | IF5a2 pg/ng rRNA | 0.5 | 2.0 | IL-18 pg/ng rRNA | IL-1b pg/ng rRNA |
|---|---|---|---|---|---|---|---|
| 206 | VALVE | 44.4 | 33.1 | 1.3 | 0.7 | 50.0 | 67.2 |
| 330 | VALVE | | | | | | |
| 331 | VALVE | 11.3 | 0.2 | 68.9 | 0.0 | 0.1 | 0.0 |
| 332 | VALVE | 224.5 | 194.0 | 1.2 | 0.9 | 510.5 | 37.2 |
| 289 | VALVE | 286.3 | 674.1 | 0.4 | 2.4 | 888.0 | 167.5 |
| 290 | VALVE | 303.9 | 540.4 | 0.6 | 1.8 | 545.8 | 20.6 |
| 291 | VALVE | 148.1 | 311.8 | 0.5 | 2.1 | 229.2 | 31.1 |
| 292 | VALVE | 221.1 | 367.2 | 0.6 | 1.7 | 280.8 | 55.0 |
| 312 | VALVE | 361.1 | 262.5 | 1.4 | 0.7 | 198.0 | 44.2 |
| 314 | VALVE | 6.5 | 1.6 | 4.0 | 0.2 | 74.7 | 18.6 |
| 318 | VALVE | 83.3 | 48.5 | 1.7 | 0.6 | 69.3 | 13.3 |
| 324 | VALVE | 485.9 | 414.1 | 1.2 | 0.9 | 584.9 | 98.6 |

FIG.50B

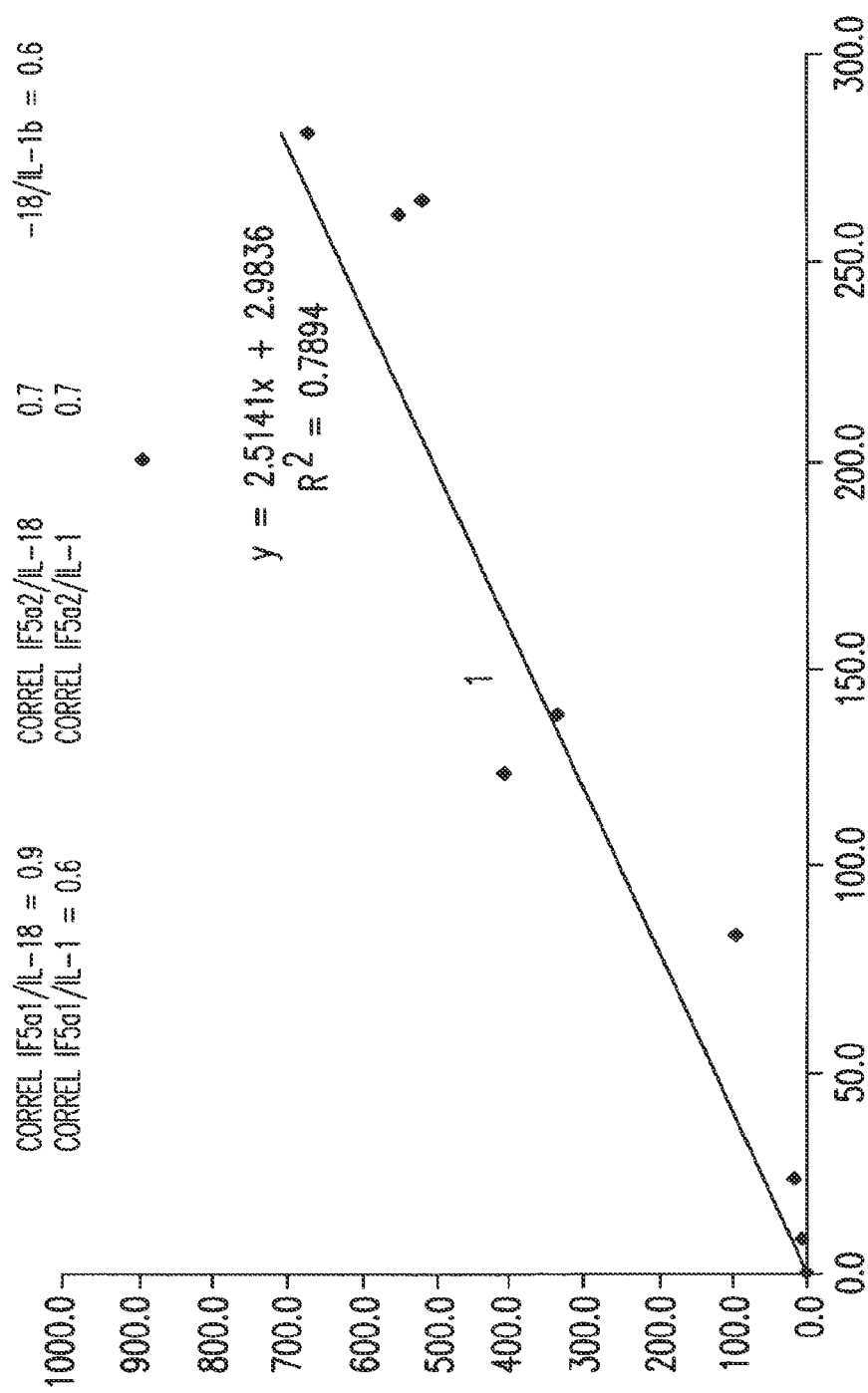

| Expt # | Age | Sex | DM | Unstable engine | Operation | Misc..... | date RNA |
|---|---|---|---|---|---|---|---|
| 19 | 61 | M | Y | N | CABG | Metoprolol, Lovastatin, NTG | |
| 20 | 72 | M | Y | N | CABG | Metoprolol, Lipitor | |
| 21 | 55 | M | N | N | CABG | CYA, Imuran, Prednisone, Lasix, INS, Metoprolol | 7/30/02 |
| 23 | 71 | M | N | N | CABG | Imipramine, Isordil, NTG, Metoprolol | 7/30/02 |
| 24 | 75 | M | Y | Y | CABG | Lisinopril, Glipizide, Metoprolol, NTG | |
| ? | 61 | M | N | N | CABG | Lisinopril, digoxin, Lasix, NTG, ASA | |
| 26 | 57 | M | N | N | CABG | Atenolol, Norvasc, HCTZ, NTG, ASA | 7/30/02 |
| 28 | 48 | F | N | N | CABG | Atenolol, INS, Lisinopril | 9-Aug |
| 29 | 64 | M | N | N | MVR | Losix, Lisinopril | |
| 30 | 76 | M | N | N | CABG | | 9-Aug |
| 31 | 65 | M | Y | N | CABG | | |
| 33 | 54 | M | N | N | CABG | Simvastatin, metoprolol | 9-Aug |
| 34 | 63 | M | N | N | CABG | Lisinopril, Felodipoine, NTG | 9-Aug |
| 35 | 74 | M | Y | N | CABG | Amiodipine, Glyburide, Prazosin | |
| 36 | 62 | M | Y | N | CABG | Simvastatin, INS, Felodipine, Spironolactone, Metoprotoiol, Lisinopril, | |
| 37 | 63 | M | N | N | CABG | Famotidine, Atenolol, Fosinopril, Procardia, Zocor, NTG | |
| 38 | 63 | M | N | N | CABG | A-fib, Dig, Atenolol, Zocor, Coumadin | |

CONT'D FROM FIG.51

| | | | | | |
|---|---|---|---|---|---|
| 39 | 77 | M | N | N | CABG | Coumadin, Cozar, Zocor, HCTZ, Cortioarone |
| 41 | 74 | F | N | Y | AVR/CABG | Dig, Zestril |
| 42 | 59 | M | Y | N | CABG | Statin, Atenolol, Glucotrol, Lisinopril |
| 44 | 64 | M | Y | N | CABG | Atenolol, NTG, Lisinopril, Simvastatin, Verapamil |
| 47 | 64 | M | N | N | CABG | NTG, Lisinopril, Synthroid, simvastatin |
| 48 | 56 | M | Y | Y | CABG | NTG, Metoprolol, Glipizide, Simvastatin |
| 52 | 70 | M | Y | N | CABG | Fosinopril, Glipizide, HCTZ, Felodipine, Metoprolol, |
| 53 | 55 | M | Y | N | CABG | Lasix, Lisinopril, Glyburide, Nifedipine |
| 54 | 48 | M | Y | Y | CABG | Lisinopril, Metoprolol, NTG, Lasix, ASA, Simvastatin, INS |
| 55 | 67 | M | N | N | CABG | ASA, prednisone, Atenolol |
| 56 | 71 | M | Y | N | CABG | ASA, Simvastatin, Atenolol, Lisinopril, NTG |
| 58 | 70 | M | Y | Y | CABG | Coumadin, Synthroid, NTG, Glyburide |
| 59 | 55 | M | Y | N | CABG | Lisinopril, NTG, Glyburide, metoprolol, Simvastatin |
| 60 | 55 | M | Y | N | CABG | Metformin, Glyburide, ASA, Atenolol, Lisinopril, Simvastatin |
| 61 | 68 | M | Y | N | CABG | Atenolol, Lasix, Fosinopril, Simvastatin, Glyburide |
| 61 | 68 | M | Y | N | CABG | Atenolol, Lasix, Fosinopril, Simvastatin, Glyburide |
| 62 | 76 | M | N | N | CABG | Gemfibrozil, ASA, Metoprolol, NTG |
| 64 | 61 | M | N | N | MVR | |

CONT'D FROM FIG.51A

| | | | | | | | |
|---|---|---|---|---|---|---|---|
| 64 | 61 | M | N | N | MVR | | |
| 65 | 72 | M | N | Y | CABG | ASA, NTG | 12-Sep |
| 67 | 69 | M | Y | N | CABG | | |
| 138 | 75 | M | Y | N | CABG | Lisinopril, Simvastatin, metoprolol, Metformin, glyburide | |
| 139 | 71 | M | N | Y | CABG | Metoprolol, Dyazide, Lipitor, Cardura, Lotrol | 12-Sep |
| 140 | 86 | M | N | Y | CABG | Metoprolol, Amlodipine, NTG, Heparin | 12-Sep |
| 141 | 65 | M | Y | N | CABG | ASA, Clopidogrel, Glipizide, Lisinopril, INS, | |
| 142 | 75 | F | Y | N | CABG | Glyburide, Atenolol, Lisinopril, Moxide, Methyldopa | |
| 141 | 44 | M | N | N | CABG | Atenolol, Lisinopril, Simvastatin, | 12-Sep |
| 144 | 57 | M | N | N | AVR | Allopurinol, Colchicine, Minoxidil, Atenol, Losix, Prednisone, Simvastatin | |
| 145 | 67 | M | N | N | CABG | Lipitor, Metoprolol, NTG, ASA | |
| 146 | 42 | M | N | N | CABG | Atenolol, Norvasc, NTG | |
| 147 | 71 | M | N | N | MVR | Dig, Verapamil, Coumadin | |
| 148 | 71 | F | N | N | CABG | | |
| 150 | 70 | M | Y | N | CABG | Felodipine, HCTZ, INS, Synthroid, Losartin, Simvastatin, Atenolol, | |
| 151 | 78 | F | Y | N | CABG | Dig, NTG, Lisinopril, Cavedolol, INS | |

CONT'D FROM FIG.51B

| | | | | | | CONT'D ON FIG.51D |
|---|---|---|---|---|---|---|
| 152 | 50 | M | N | N | CABG | Lisinopril, NTG, Lasix, Metoprolol |
| 153 | 48 | M | N | N | AVR | |
| 154 | 67 | M | N | N | CABG | Simvastatin, Lisinopril, Atenolol |
| 155 | 59 | M | N | N | CABG | Lisinopril, ASA, Metoprolol, Simvastatin |
| 156 | 62 | M | Y | N | CABG | NTG, Glyburide, Atorvastatin, Atenolol |
| 161 | 56 | M | Y | N | MVR | INS, Metoprolol, NTG, Simvastatin, Lisinopril |
| 162 | 23 | F | N | N | MVR | |
| 163 | 72 | M | N | N | AVR | Simvastatin, Felodipine, Cimetidine |
| 164 | 65 | F | N | N | MVR | Multi valve Dz. A-fib Metoprolol, DIG, Coumadin |
| 166 | 57 | F | N | N | MVR | Synthroid |
| 173 | 60 | M | N | N | AVR | |
| 177 | 66 | F | N | N | MVR | Severe MR, Lisinopril |
| 184 | 46 | M | N | N | MVR | Vasotec |
| 185 | 75 | M | N | Y | CABG,MVR | Tropolol, Capoten, Plavix, Synthroid |
| 201 | 50 | M | N | N | AVR | Lasix, Incubated in ICE prior to D/C |

FIG.51C

CONT'D FROM FIG.51C

| | | | | | | |
|---|---|---|---|---|---|---|
| 206 | 58 | M | N | | AVR | Vasotec | |
| 207 | 68 | M | N | | CABG | Simvastatin, Atenolol | |
| 211 | 51 | M | N | | AVR | EF<20% | |
| 289 | 45 | M | N | | AVR | | 9-Aug |
| 290 | 77 | M | N | | MVR | | 9-Aug |
| 291 | 55 | F | N | | AVR | | 9-Aug |
| 292 | 39 | M | N | | MVR | | 9-Aug |
| 310 | 67 | F | N | | AVR/MVR | | |
| 312 | 72 | F | N | | AVR | | 12-Sep |
| 314 | 75 | F | N | | AVR | | 12-Sep |
| 318 | 62 | M | N | | AVR | | 12-Sep |
| 329 | 70 | M | N | | AVR | | 12-Sep |
| 330 | 67 | M | N | | AVR | | 7/30/02 |
| 331 | 58 | M | N | | AVR | | 7/30/02 |
| 339 | 69 | M | N | | AVR | | 7/30/02 |

FIG.51D

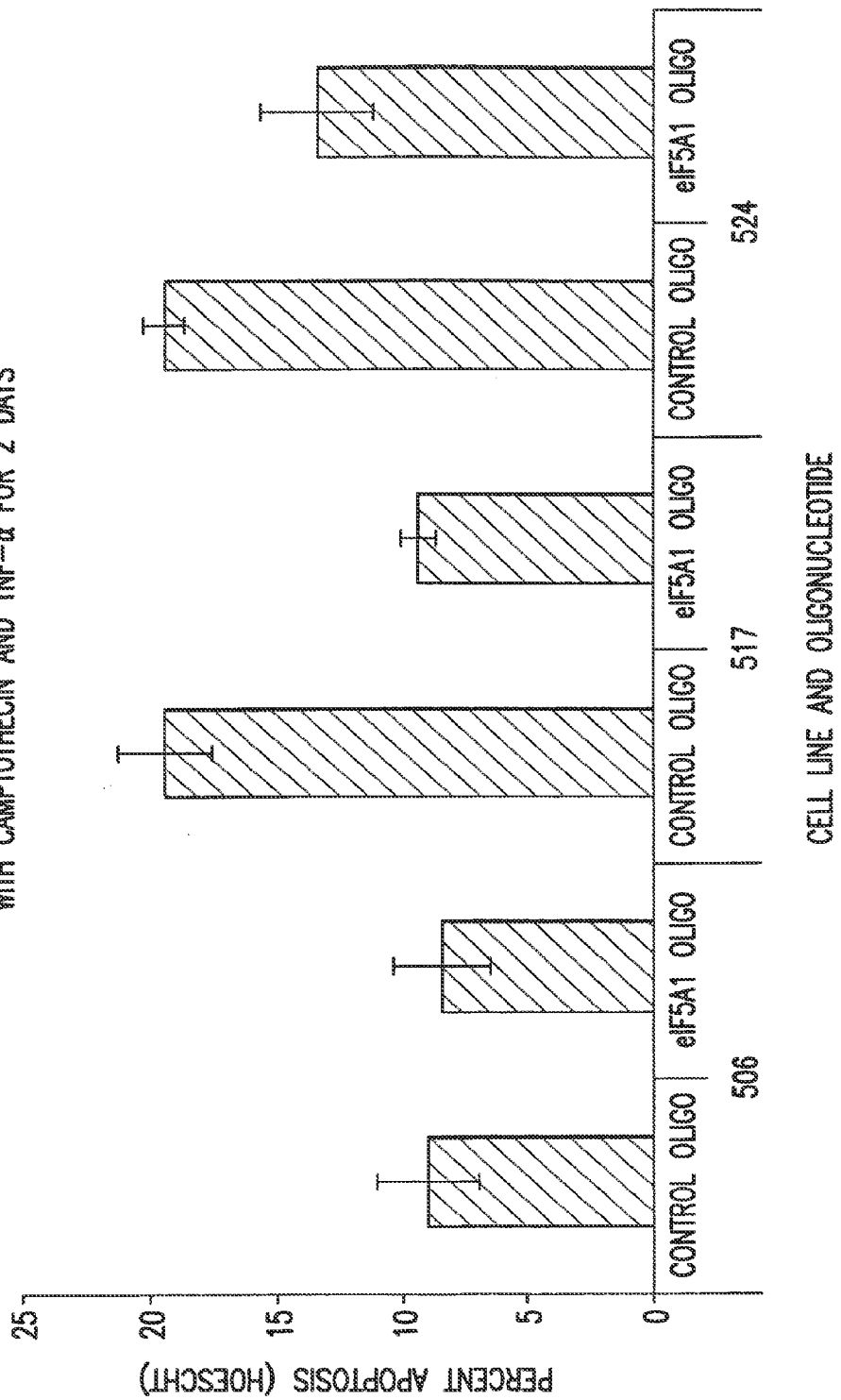

+ serum

− serum

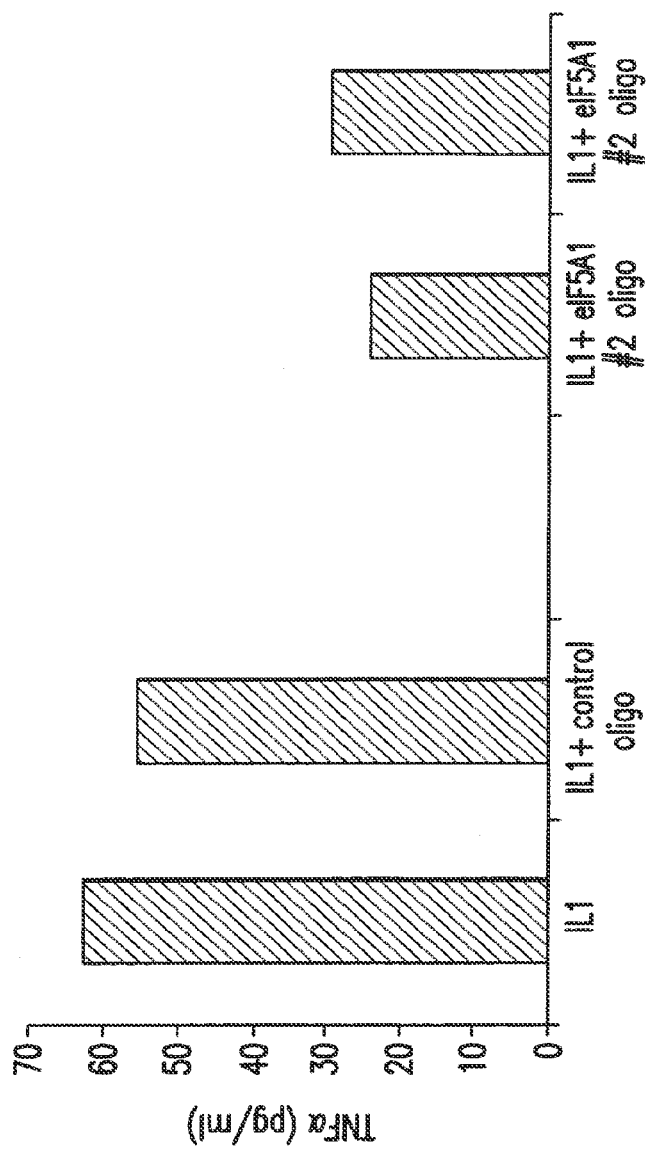

siRNA #1    target 5' AA(AGGAATGACTTCCAGCTGA)TT 3' SEQ ID NO:30
siRNA #2    target 5' AA(GATCGTCGAGATGTCTACT)TC 3' SEQ ID NO:31
siRNA #3    target 5' AA(GGTCCATCTGGTTGGTATT)GA 3' SEQ ID NO:32
siRNA #4    target 5' AA(GCTGGACTCCTCCTACACA)AT 3' SEQ ID NO:33
siRNA #5    REVERSE OF siRNA #1 5' AA(AGTCGACCTTCAGTAAGGA)TT 3' SEQ ID NO:34

```
   1 ggcacgaggg tagaggcggc ggcggcggcg gcagcgggct cggaggcagc ggttgggctc
  61 gcggcgagcg gacggggtcg agtcagtgcg ttcgcgcgag ttggaatcga agcctcttaa
 121 aatggcagat gacttggact tcagacagg agatgcaggg gcctcagcca ccttcccaat
 181 gcagtgctca gcattacgta agaatggctt tgtggtgctc aaaggccggc catgtaagat
 241 cgtcgagatc tctacttcga agactggcaa gcacgccac gccaaggtcc atctggttgg
 301 tattgacatc tttactggga agaaatatga agatatctgc ccgtcaactc ataatatgga
 361 tgtccccaac atcaaagga atgacttcca gctgaggc atccaggatg ggtacctatc
 421 actgctccag gacagcgggg aggtacgaga ggaccttcgt ctccctgagg gagaccttgg
 481 caaggagatt gagcagaagt acgactgtgg agaagagatc ctgatcacgg tgctgtctgc
 541 catgacagag gaggcagctg ttgcaatcaa ggccatggca aaataactgg ctcccaggat
 601 ggcggtggtg gcagcagtga tcctctgaac ctgcagaggc cccctccccg agcctggcct
 661 ggctctggcc cggtcctaac ctggactgct cctacacaat ttatttgacg tttatttg
 721 gttttcccca cccctcaat ctgtcgggga gcccctgccc ttcacctagc tcccttggcc
 781 aggagcgagc gaagctgtgg ccttggtgaa gctgccctcc tcttctcccc tcacactaca
 841 gcctgtgg gggagaaggg ggtgggtgct gcttgtggtt tagtcttttt ttttttttt
 901 tttttttttt aaattcaatc tggaatcaga aagcggtgga ttctggcaaa tggtccttgt
 961 gccctcccca ctcatccctg gtctggtccc ctgttgccca tagccctta ccctgagcac
1021 caccccaaca gactggggac cagccccctc gcctgcctgt gtctctcccc aaacccctt
1081 agatggggag ggaagaggag gagaggggag gggacctgcc cctcctcag gcatctggga
1141 gggccctgcc cccatgggct ttaccctcc ctgcgggctc tctccccgac acatttgtta
1201 aaatcaaacc tgaataaaac tacaagttta atatgaaaaa aaaaaaaaaa aaaaaaaaaa
1261 aaaaaaaaaa aaaaaaaaa aaaaaaaaaa aaaaaaaaaa aaaaaaaaaa   SEQ ID No:29
```

FIG. 70

| | | |
|---|---|---|
| ANTISENSE OLIGO #1 | 5'- CCT GTC TCG AAG TCC AAG TC-3' | (SEQ ID NO: 35) |
| TARGET | 5'- GACTTGGACTTCGAGACA GG-3' | (SEQ ID NO: 36) |
| ANTISENSE OLIGO #2 | 5'- GGA CCT TGG CGT GGC CGT GC-3' | (SEQ ID NO: 37) |
| TARGET | 5'- GCACGGCC ACGCCAAGGTCC-3' | (SEQ ID NO: 38) |
| ANTISENSE OLIGO #3 | 5'- CTC GTA CCT CCC CGC TCT CC 3' | (SEQ ID NO: 39) |
| TARGET | 5'- GGACAGCGG GGAGGTACGA-3' | (SEQ ID NO: 40) |

```
   1 ggcacgaggg tagaggcggc ggcggcggcg cagcgggct cggaggcagc ggttgggctc
  61 gcggcgagcg gacggggtcg agtcagtgcg ttcgcgcgag ttggaatcga agcctcttaa
 121 aatggcagat gacttggact tcgagacagg agatgcaggg gcctcagcca ccttcccaat
 181 gcagtgctca gcattacgta agaatggctt tgtggtgctc aaaggccggc catgtaagat
 241 cgtcgagatg tctacttcga agactggcaa gcacggccac gccaaggtcc atctggttgg
 301 tattgacatc tttactggga agaaatatga agatatctgc ccgtcaactc ataatatgga
 361 tgtccccaac atcaaaagga atgacttcca gctgattggc atccaggatg ggtacctatc
 421 actgctccag gacagcgggg gaggtacgga ggacttcgt ctccctgagg gagaccttgg
 481 caaggagatt gagcagaagt acgactgtgg agaagagatc ctgatcacgg tgctgtctgc
 541 catgacagag gaggcagctg ttgcaatcaa ggccatggca aaataactgg ctcccaggat
 601 ggcggtggtg gcagcagtga tcctctgaac ctgcagaggc cccctccccg agcctggcct
 661 ggctctggcc cggtcctaag ctggactcct cctacacaat ttatttgacg ttttatttg
 721 gttttcccca ccccctcaat ctgtcgggga gccctgcc ttcacctagc tcccttggcc
 781 aggagcgagc gaagctgtgg ccttggtgaa gctgccctcc tcttctcccc tcacactaca
 841 gccctggtgg gggagaaggg ggtgggtgct gcttgtggtt tagtcttttt ttttttttt
 901 tttttttt aaattcaatc tggaatcaga aagcggtgga ttctggcaaa tggtccttgt
 961 gccctcccca ctcatccctg gtctggtccc ctgttgccca tagcccttta ccctgagcac
1021 caccccaaca gactggggac cagcccctc gcctgcctgt gtctctcccc aaacccctt
1081 agatggggag ggaagaggag gagaggggag gggacctgcc cctcctcag gcatctggga
1141 gggccctgcc cccatgggct ttacccttcc ctgcggctc tctccccgac acatttgtta
1201 aaatcaaacc tgaataaaac tacaagttta atatgaaaaa aaaaaaaaa aaaaaaaaa
1261 aaaaaaaaaa aaaaaaaaaa aaaaaaaaaa aaaaaaaaaa aaaaaaaa   (SEQ ID NO: 29)
```

FIG.71

POSITION OF ANTISENSE OLIGONUCLEOTIDES WITHIN NUCLEOTIDE SEQUENCE OF HUMAN eIF5A1 (ACCESSION NM_001970; TRANSLATION START AND STOP IN BOLD)

*ANTISENSE eIF5A1 #1 (SEQ ID NO:25) - BINDS TO GACTTGGACTTCGAGACAGG*
*ANTISENSE eIF5A1 #2 (SEQ ID NO:26) - BINDS TO GTACCCAAGCCAAGTC*
*ANTISENSE eIF5A1 #3 (SEQ ID NO:27) - BINDS TO GGACAGCGGGAGGTACGAG*

GGCACGAGGGCGGGGCGGCGAGAGGGGCGGTAGAGGGGCTCGGAGGGGCCCGGGAGCGGACGGGCTGGGCTTGGGCTCGAGGAGGGGTCGAGTCAGTGGCGTTCG
CGGCGAGTTGGAATCGGAAGCCTCTTAAAATGGCAGAT*GACTTGGACTTCGAGACAGG*AGAGATGCAGGGGCCTCAGCCACTTCCAATGCAGTGCTCAGCATTACGTA
AGAATGGCTTGTGGTGTCAAGGCCGGCCATGGGCCATGTAAGATGTCGAGATGTCTACTTCGAAGATCTTCGAAGTGCAACATCTGGTTGGTA
TTGA
CATCTTTACTGGGAAGAAATATGAAGATATCTGCCCGTCAACTCATATATGGATGTCCCAACATCAAAAGGAAATGACTTCCAGCTGATTGGCATCCAGGA
TGGG
TACCTATCACTGCTCCAGGA*CAGCGGGGAGGTACGAG*AGGACCTTCGTCTCCCTGAGGGAGACCTTGGCAAGGAATAACTGGCTCAAAATAACTGGCTCCAGGATGGCGGTGGCAGCAGTGATCCT
GAGA
TCCTGATCAGGTGCTGTCTGCCATGACAGGAGGCAGTCGTGTTGCAATCAAGGCCATCAAGGCCAAATAACTGGCTCCAGGATGGCGGTGGCAGCAGTGATCCT
CTGAACCTGCAGAGGCCCCCTGGGGAGCCTGGCTCTGGCCCCTGGCCCAGGAGGAGCAGCAGTGTGGGCCTTGGTGAGCTGCCCTCCCTCTCCCTCCCTCACAC
CCCCCTCAATCTGTGGGGAGCAGCCCTGGGGTGGGTCTGCTTGTGGTTAGTCTTTTTTTTTTTTTTTTTAAATTCAATCTGAATCAGAAAGGCGGTGGAT
TACAGCCCTGGTGGGGAGAAGGGGTGGGTCTGCTTGTGGTTAGTCTTTTTTTTTTTTTTAAATTCAATCTGAATCAGAAAGGGGTGGAT
TCTGGCAAATGGTCTGTGCCTCCCCAAGTCTGTGCCTCGGTCCATAGCCCTGTTGCCCATAGCCCTTTACCCTGAGCACCACCCAACAGACTGGGACCAGCCC
CTCGCCTGCCTGTGTCTCCCCAAACCCTTAGATGGGAGGGGAAGGGAGAGGAGGGGAAGGGCACCTGCCCCCTCCTCAGGCATCTGGGAGGGCCCTGCCCCC
ATGGGCTTTACCCTTCCCTGCGGGCTCTCCCGACACATTTGTTAAAATCAAGATGTTGAAAATCAAACTGAATAAACTACAAGTTAATATGAAAAAAAAAAAAA
AAAAAAAAAAAAAAAAAAAAAAAA (SEQ ID NO: 19)

FIG.72

NUCLEOTIDE ALIGNMENT OF HUMAN eIF5A1 (ACC. NM_001970) AND HUMAN eIF5A2 (ACC. NM_020390)

```
eIF5a1    1    ATGgCAGATG  ACTTGGACTT  CGAGACAGGA  GATGCAGgGG  CCTCAGCCAC
eIF5a2    1    ATGGCAGACG  AAATTGATTT  CACTACTGGA  GATGCCGGGG  CTTCCAGCAC eIF5a1   51    CTTCCCAATG  CAGTGCTCAG  CATTACGtAA  GAATGGCTTT  GTtGTGCTCA
eIF5a2   51    TTACCCTATG  CAGTGCTCGG  GCTTGCGCAA  AAACGGCTTC  GTGGTGCTCA eIF5a1  101    AAGGCCGGCC  ATGtAAGATC  GTCGAGATGT  CTACTTCGAA  GACTGGCAAG
eIF5a2  101    AAGGAGGACC  ATGCAAAATA  GTGGAGATGT  CAACTTCCAA  AACTGGAAAG eIF5a1  151    CACGGCCACG  CCAAGGTCCA  TCTGGTTGGT  ATTGACATCT  TtACTGGGAA
eIF5a2  151    CAtGGTCATG  CCAAGGTTCA  CCTTGTTGGA  ATTGATATTT  TCACGGGCAA eIF5a1  201    GAAATATGAA  GATATCTGCC  CGTCAACTCA  GTCCCAACA   GTACCTATCA
eIF5a2  201    AAAATATGAA  GATATTTGTC  CTTCTACTCA  CAACATGGAT  GTTCCAAATA eIF5a1  251    TCAAAAGGAA  TGACTtccAG  CTGATTGGCA  TCCAGGATGG  GTACCTATCA
eIF5a2  251    TTAAGAGAAA  TGATTatCAA  CTGATATGCA  TTCAAGATGG  TtACCTTTCC eIF5a1  301    CTGCTccagG  ACAGCGGGGA  GGTACGAGAG  GACCTTCGTC  TcCCTGAGGG
eIF5a2  301    CTGCTgacaG  AAACTGGTGA  AGTTCGTGAG  GATCTTAAAC  TgCCAGAAGG eIF5a1  351    AGACCTTGGC  AAGGAGATTG  AGcagAAGTA  CGACTGTGGA  GAAGAGATCC
eIF5a2  351    TGAACTAGGC  AAAGAAATAG  AGggaAAATA  CAATGCAGGT  GAAGATGTAC eIF5a1  401    TGATCACGGT  GCTGTCTGCC  ATGACAGAGG  AGGCAGCTGT  TGCAATCAAG
eIF5a2  401    AGGTGTCTGT  CATGTGTGCA  ATGAGTGAAG  AATATGCTGT  AGCCATAAAA eIF5a1  451    GCCatgGCAA  AATAa-  (SEQ ID NO: 41)
eIF5a2  451    CCCt--GCAA  ATAA-   (SEQ ID NO: 42)
```

FIG. 73A

AMINO ACID ALIGNMENT OF HUMAN eIF5A1 (ACC. NM_001970) AND HUMAN eIF5A2 (ACC. NM_020390)

```
eIF5a1    1   MADDLDFETG  DAGASATFPM  QCSALRKNGF  VVLKGwPCKI  VEMSASKTGK
eIF5a2    1   MADEIDFTTG  DAGASSTYPM  QCSALRKNGF  VVLKGrPCKI  VEMSTSKTGK eIF5a1   51   HGHAKVHLVG  IDIFTGKKYE  DICPSTHNMD  VPNIKRNDFQ  LIGIQDGYLS
eIF5a2   51   HGHAKVHLVG  IDIFTGKKYE  DICPSTHNMD  VPNIKRNDYQ  LICIQDGYLS eIF5a1  101   LLQDSGEVPE  DLRLPEGDLG  KEIEQKYDCG  EEILITLLSA  MTEEAAVAIK
eIF5a2  101   LLTETGEVRE  DLKLPEGELG  KEIEGKYNAG  EDVQVSVMCA  MSEEYAVAIK eIF5a1  151   amak  (SEQ ID NO: 43)
eIF5a2  151   pck-  (SEQ ID NO: 22)
```

FIG. 73B

WESTERN BLOT OF HT-29 CELLS TREATED WITH
IFN GAMMA FOR 8 OR 24 HOURS

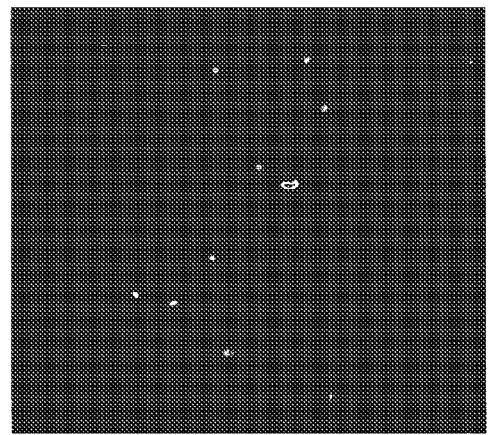
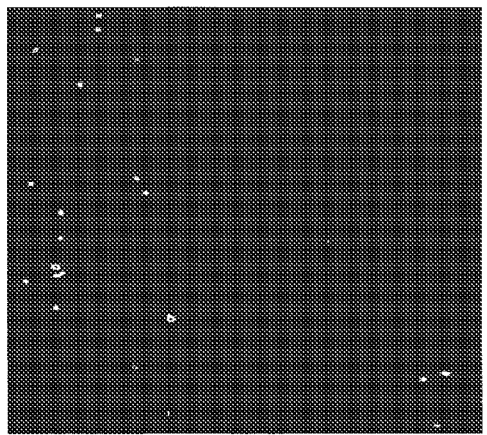
FIG.88B
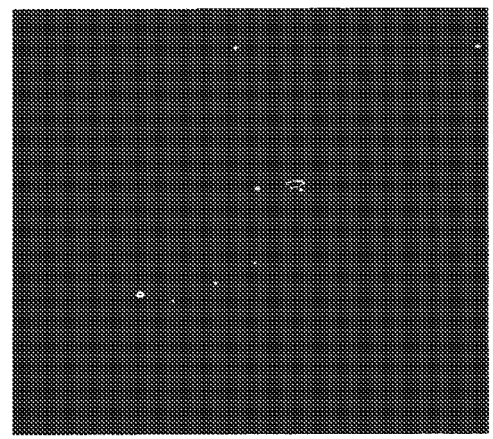
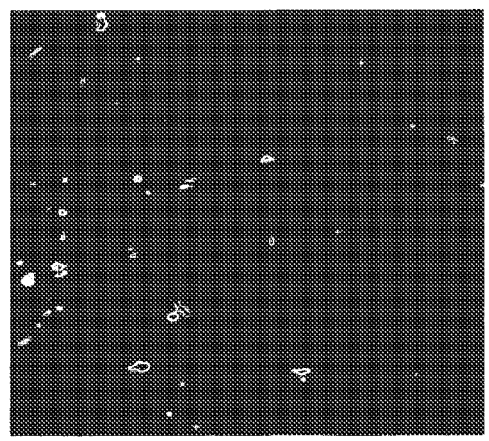
FIG.88A

DESIGN OF siRNAs AGAINST eIF5A1

POSITION OF siRNAs WITHIN eIF5AI mRNA
* TRANSLATION START AND STOP ARE BOLD AND UNDERLINED

```
   1 ggcacgaggg tagaggcggc ggcggcggcg gcagcgggct cggaggcagc ggttgggctc
  61 gcggcgagcg gacggggtcg agtcagtgcg ttcgcgcgag ttggaatcga agcctcttaa
 121 aatggcagat gactggact tcgagacagg atgcaggg gcctcagcca ccttcccaat
 181 gcagtgctca gcattacgta agaatggctt tgtggtgctc aaaggccggc catgtaagat
 241 cgtcgagatg tctacttcga agactggcaa gcacggccac gccaagatcc atctggttgg
 301 tattgacatc tttactggga agaaatgtga agatatctgc ccgtcaactc ataatatgga
 361 tgtccccaac atcaaaagga atgacttcca gctgattggc atccaggatg ggtacctatc
 421 actgctccag gacagcgggg aggtacgaga ggaccttcgt ctccctgagg gagaccttgg
 481 caaggagatt gagcagaagt acgactgtgg agaagagatc ctgatcacgg tgctgtctgc
 541 catgacagag gaggcagctg ttgcaatcaa ggccatggca aaataactgg ctcccaggat
 601 ggcggtggtg gcagcagtga tcctctgaac ctgcagaggc cccctccccg agcctggcct
 661 ggctctggcc cggtcctaag ctggactcct cctacacaat ttatttgacg ttttattttg
 721 gttttcccca cccctcaat ctgtcgggga gccctgcc ttcacctagc tcccttggcc
 781 aggagcgagc gaagctgtgg ccttggtgaa gctgccctcc tcttctcccc tcacactaca
 841 gccctggtgg gggagaaggg ggtgggtgct gcttgtggtt tagtcttttt ttttttttt
 901 ttttttttt aaattcaatc tggaatcaga aagcggtgga ttctggcaaa tggtccttgt
 961 gccctcccca ctcatccctg gtctggtccc ctgttgccca tagcccttta ccctgagcac
1021 caccccaaca gactggggac cagcccctc gcctgcctgt gtctctcccc aaaccccttt
1081 agatggggag ggaagaggag gagaggggag gggacctgcc ccctcctcag gcatctggga
1141 gggccctgcc cccatgggct ttaccctccc ctgcgggctc tctccccgac acatttgtta
1201 aaatcaaacc tgaataaaac tacaagttta atatgaaaaa aaaaaaaaaa aaaaaaaaaa
1261 aaaaaaaaaa aaaaaaaaaa aaaaaaaaaa aaaaaaaaaa aaaaaaaaa (SEQ ID NO: 29)
``` siRNA # 1 TARGET
siRNA # 2 TARGET
siRNA # 3 TARGET
siRNA # 4 TARGET

POSITION OF siRNA TARGETS AND SEQUENCES AND BLAST RESULTS
siRNA # 1 TARGET POSITION 375 TO 395 bp (POSITION 254 TO 274 bp RELATIVE TO START) % G/C = 39.1 BLAST = NONE BUT eIF5A

TARGET    5' AA(AGGAATGACTTCCAGCTGA) 3'   SEQ ID NO:44 siRNA    5'    AAAGGAAUGACUUCCAGCUGAdTdT 3'  SEQ ID NO:45
         3' dTdTUUUCCUUACUGAAGGUCGACU 5'    SEQ ID NO:46

FIG.89A siRNA # 2 TARGET POSITION 236 TO 256 (115 TO 135 bp RELATIVE TO START) % G/C = 43.4 BLAST = IDENTICAL TO HYPOTHETICAL PROTEIN IN RAT

TARGET    5' AA(GATCGTCGAGATGTCTACT) 3' SEQ ID NO:47 siRNA    5'    AAGAUCGUCGAGAUGUCUACUdTdT 3' SEQ ID NO:48
         3' dTdTUUCUAGCAGCUCUACAGAUGA 5' SEQ ID NO:49 siRNA # 3 TARGET POSITION 284 TO 304 (163 TO 183 bp RELATIVE TO START) % G/C = 43.4 BLAST = NONE BUT eIF5A

TARGET    5' AA(GGTCCATCTGGTTGGTATT) 3' SEQ ID NO:50 siRNA    5'    AAGGUCCAUCUGGUUGGUAUUdTdT 3' SEQ ID NO:51
         3' dTdTUUCCAGGUAGACCAACCAUAA 3' SEQ ID NO:52 siRNA # 4 TARGET POSITION 678 TO 698 (3'UTR;POSITION 557 TO 577 bp RELATIVE TO START) % G/C = 48 BLAST = NONE BUT eIF5A

TARGET    5' AA(GCTGGACTCCTCCTACACA) 3' SEQ ID NO:53 siRNA    5'    AAGCUGGACUCCUCCUACACAdTdT 3' SEQ ID NO:54
         3' dTdTUUCGACCUGAGGAGGAUGUGU 5' SEQ ID NO:55 siRNA # 5 CONTROL;REVERSE SEQUENCE OF siRNA # 1

% G/C = 39.1 BLAST = GOOD, NO MORE THAN 17/23 % IDENTITY

TARGET    5' AA(AGTCGACCTTCAGTAAGGA) 3' SEQ ID NO:56 siRNA    5'    AAAGUCGACCUUCAGUAAGGAdTdT 3' SEQ ID NO:57
         3' dTdTUUUCAGCUGGAAGUCAUUCCU 5' SEQ ID NO:58

FIG.89B

PBMCs TREATED WITH VARIOUS STIMULATING FACTORS
PEAK IN eIF5A EXPRESSION EARLY (WITHIN 24 HOURS)
WHERE EXPRESSION DECLINES THEREAFTER

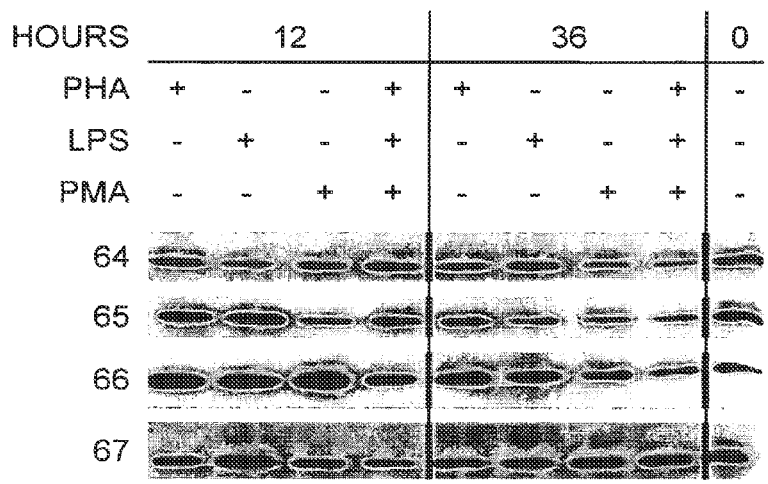

WESTERN BLOT OF CELL LYSATES FROM PBMCs THAT WERE
TREATED WITH VARIOUS STIMULATING FACTORS INCLUDING
PHA (100ng/ml), LPS (100ng/ml) AND PMA (100ng/ml). THE
NUMBERS ON THE LEFT CORRESPOND TO THE DONOR
INFORMATION QUESTIONNAIRE. THE CELL LYSATES WERE
HARVESTED, SEPARATED ON AN SDS-PAGE GEL,
TRANSFERRED TO A PVDF MEMBRANE, AND BLOTTED WITH
AN ANTIBODY AGAINST eIF5A (BD BIOSCIENCE
LABORATORIES). THE LEVEL OF TOTAL eIF5A EXPRESSION
WAS ELEVATED TO START WITH IN THE PURIFIED PBMCs,
BUT PEAKED WITHIN THE FIRST 24 HOURS AFTER
STIMULATION AND SUBSEQUENTLY DECLINED. THIS
EXPERIMENT DEMONSTRATED THAT THE PBMCs WOULD
RESPOND TO LPS WITHOUT PMA DIFFERENTIATION.

FIG.94

PBMCs TRANSFECTED WITH eIF5A1 siRNA DEMONSTRATE
SOME SUPPRESSION WHEN COMPARED TO CONTROL

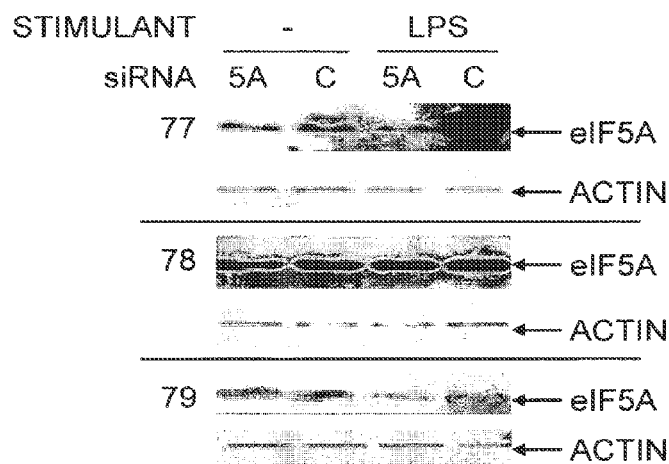

WESTERN BLOT OF CELL LYSATE FROM PBMCs THAT WERE
TRANSFECTED WITH EITHER CONTROL siRNA (C) OR HUMAN
eIF5A1 siRNA (5A). THE NUMBERS ON THE LEFT CORRESPOND TO
THE DONOR INFORMATION QUESTIONNAIRE. 72 HOURS AFTER
TRANSFECTION, THE PBMCs WERE TREATED WITH LPS FOR 24
HOURS. THE MEDIA AND CELL LYSATE WERE HARVESTED,
SEPARATED ON AN SDS-PAGE GEL, TRANSFERRED TO A PVDF
MEMBRANE, AND BLOTTED WITH AN ANTIBODY AGAINST eIF5A
(BD BIOSCIENCE LABORATORIES). THE BLOT WAS THEN
STRIPPED AND BLOTTED WITH AN ANTIBODY AGAINST β-ACTIN
(ONCOGENE). THE LEVEL OF SUPPRESSION IS DETERMINED BY
TRANSFECTION EFFICIENCY. ALSO THE ABOVE BLOTS INDICATE
TOTAL eIF5A EXPRESSION (i.e. BOTH eIF5A1 AND eIF5A2).

FIG.95

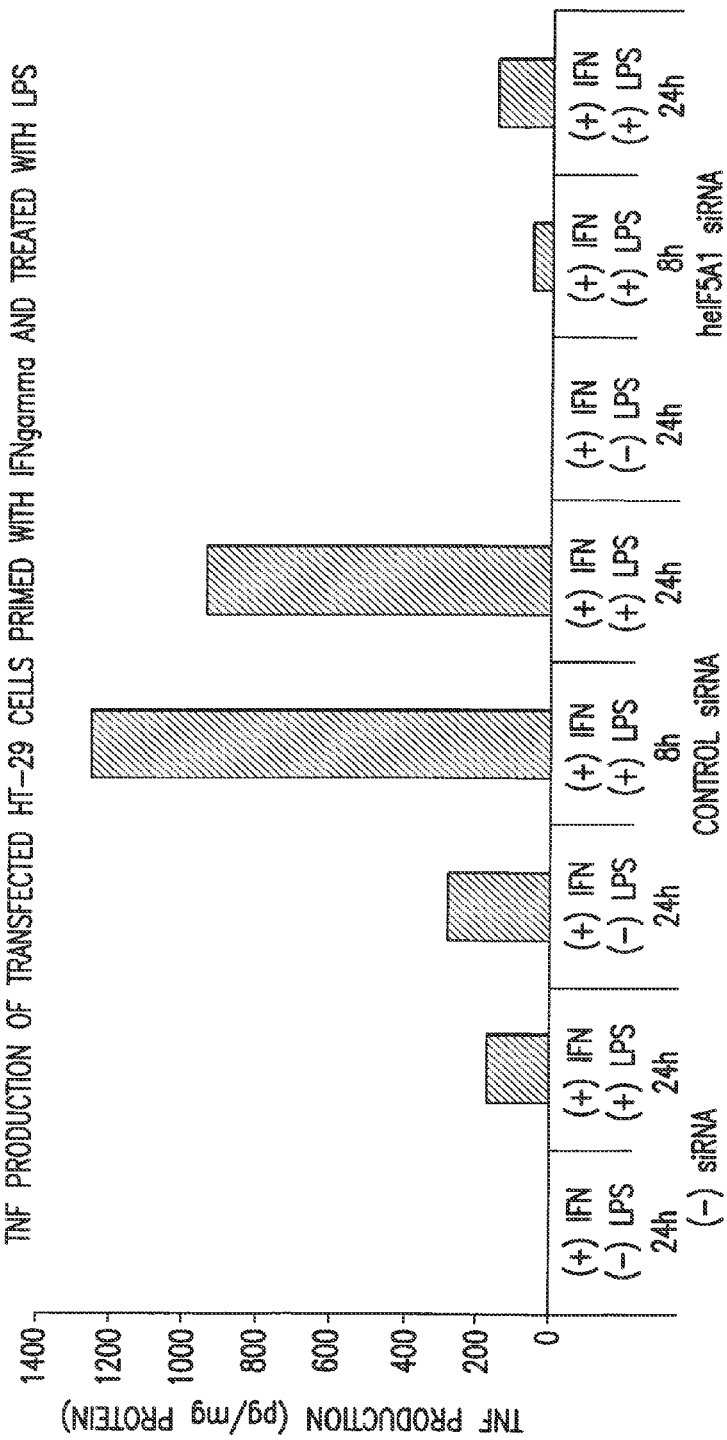

FIG. 99

TNF PRODUCTION OF HT-29 CELLS THAT WERE TRANSFECTED WITH EITHER CONTROL siRNA OR HUMAN (APOPTOSIS-SPECIFIC eIF5A "eIF5A1") siRNA. UNTRANSFECTED [(-) siRNA] OR TRANSFECTED HT-29 CELLS WERE PRIMED WITH INTERFERON GAMMA 48 HOURS AFTER TRANSFECTION. 16 HOURS AFTER INTERFERON GAMMA PRIMING, THE CELLS WERE TREATED WITH LPS FOR 8 OR 24 HOURS. CELLS WHICH WERE PRIMED BUT DID NOT RECEIVE LPS RECEIVED A MEDIA CHANGE. THE MEDIA WAS REMOVED FROM THE CELLS AND STORED AT −20° UNTIL THEY COULD BE ANALYZED BY TNFα ELISA (ASSAY DESIGNS). CELL LYSATE WAS HARVESTED. THE PROTEIN CONCENTRATION WAS DETERMINED USING THE BCA PROTEIN QUANTITATION KIT AND USED TO CORRECT FOR CELL NUMBER.

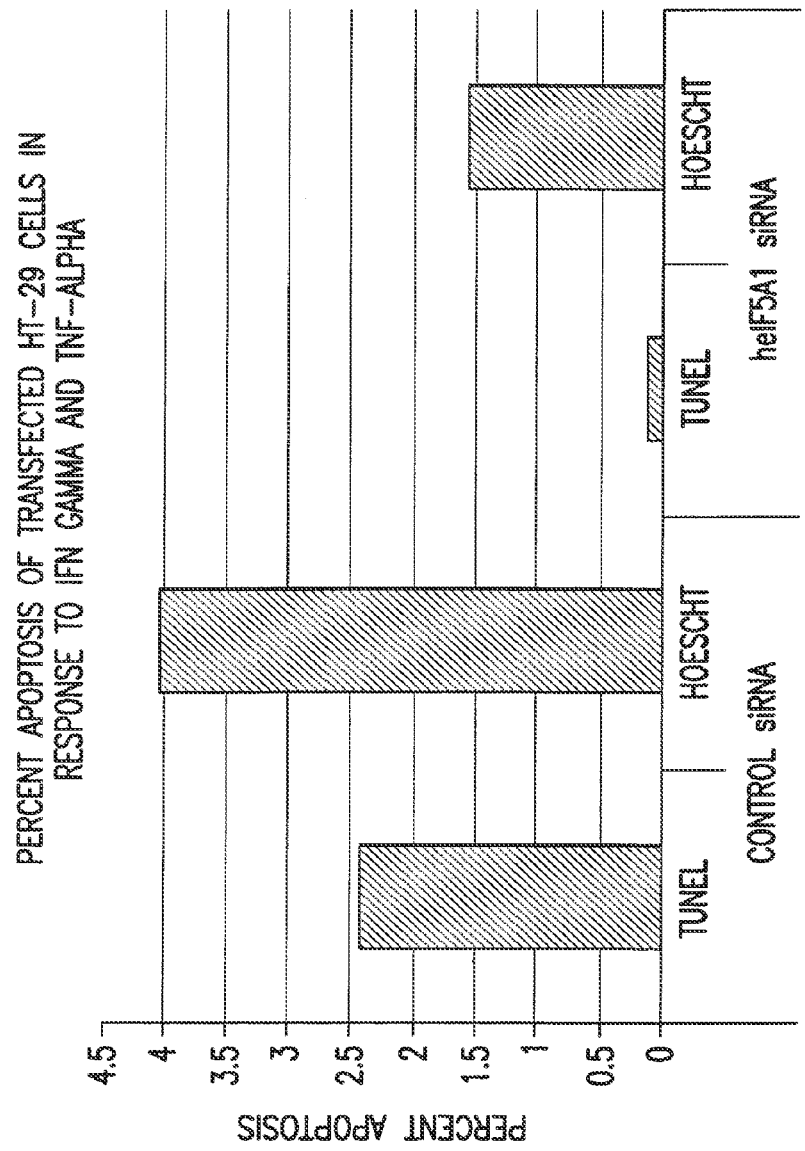

FIG. 100

PERCENT APOPTOSIS OF HT-29 CELLS THAT WERE TRANSFECTED WITH EITHER CONTROL siRNA OR HUMAN (APOPTOSIS-SPECIFIC "eIF5A1") siRNA. TRANSFECTED HT-29 CELLS WERE PRIMED WITH INTERFERON GAMMA 48 HOURS AFTER TRANSFECTION. 16 HOURS AFTER INTERFERON GAMMA PRIMING, THE CELLS WERE TREATED WITH TNFα FOR 24 HOURS. APOPTOSIS WAS DETECTED BY HOESCHT STAINING AND TUNEL LABELING OF FIXED CELLS.

HT-29 CELLS TRANSFECTED WITH eIF5A1 siRNA AND TREATED
WITH IFNγ FOR 8 OR 24 HOURS EXPRESS LESS TLR4 PROTEIN

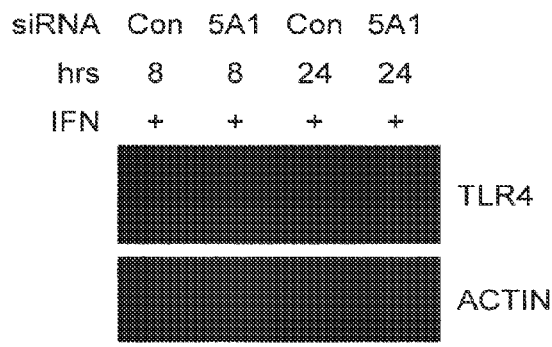

WESTERN BLOT OF CELL LYSATE FROM HT-29 CELLS THAT WERE
TRANSFECTED WITH EITHER CONTROL siRNA (con) OR HUMAN
eIF5A1 siRNA (5A1). 48 HOURS AFTER TRANSFECTION, THE HT-29
CELLS WERE TREATED WITH INTERFERON GAMMA FOR 8 OR 24
HOURS. THE CELL LYSATE WAS HARVESTED, SEPARATED ON AN
SDS-PAGE GEL, TRANSFERRED TO A PVDF MEMBRANE, AND
BLOTTED WITH AN ANTIBODY AGAINST TLR4 (SANTA CRUZ
BIOTECHNOLOGY). THE BLOT WAS THEN STRIPPED AND
BLOTTED WITH AN ANTIBODY AGAINST β-ACTIN (ONCOGENE).

FIG.101

*eIF5A1 siRNA INHIBITS iNOS EXPRESSION INDUCED BY IFNγ*

*HT-29 CELLS TRANSFECTED WITH eIF5A1 siRNA AND TREATED WITH IFNγ for 24 HOURS EXPRESS LESS iNOS PROTEIN*

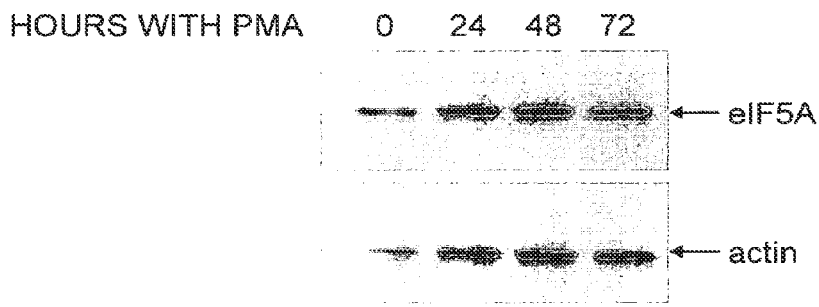

eIF5A PROTEIN IS UPREGULATED WITH PMA IN U937. U937 CELLS WERE ELECTROPORATED WITH CONTROL siRNA. 16h LATER, PMA (100ng/ml) WAS ADDED (AT TIME 0) AND CELLS WERE INCUBATED AT 37°C WITH SAMPLES COLLECTED AT 0h (BEFORE PMA ADDITION), 24h, 48h, AND 72h. SAMPLES (5ug) WERE SEPARATED BY SDS-PAGE, TRANSFERRED TO PVDF MEMBRANES AND ANALYZED BY WESTERN BLOTTING FOR eIF5A CONTENT AND FOR ACTIN (LOADING CONTROL). THE U937 CELLS DIFFERENTIATED FROM MONOCYTES IN SUSPENSION TO ADHERENT MACROPHAGES DURING THIS TIME COURSE. EARLY STAGES OF ADHERENCE WERE NOTICEABLE AFTER 6h WITH PMA.

FIG.106

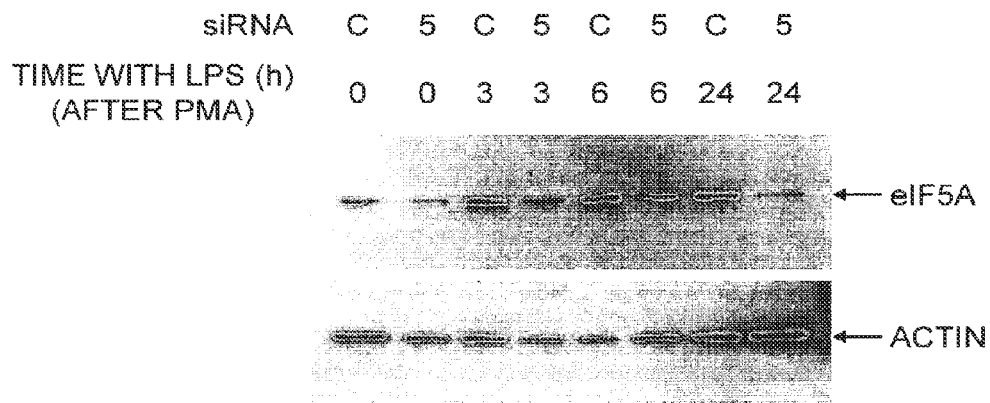

eIF5A PROTEIN EXPRESSION IS STILL REDUCED 112h FOLLOWING siRNA TREATMENT. U937 CELLS WERE ELECTROPORATED WITH eIF5A1 (5) OR CONTROL (C) siRNA. 16h LATER, PMA (100ng/ml) WAS ADDED AND THE CELLS DIFFERENTIATED INTO ADHERENT MACROPHAGES AND MADE QUIESCENT BEFORE LPS (100ng/ml) ADDITION AT 72h. CELLS WERE COLLECTED BEFORE LPS ADDITION (TIME 0) AND AT 3h, 6h, AND 24h AFTER ADDITION. REFER TO THE TIME COURSE SCHEME IN FIGURE 1 FOR CLARIFICATION. SAMPLES (5μg) WERE SEPARATED BY SDS-PAGE, TRANSFERRED TO PVDF MEMBRANES AND ANALYZED BY WESTERN BLOTTING FOR eIF5A CONTENT AND FOR ACTIN (LOADING CONTROL).

FIG.108

*eIF5A1 siRNA INHIBITS IFNγ-INDUCED UP-REGULATION OF TLR4*

*eIF5A1 siRNA INHIBITS IFNγ-INDUCED UP-REGULATION OF TNFR1*

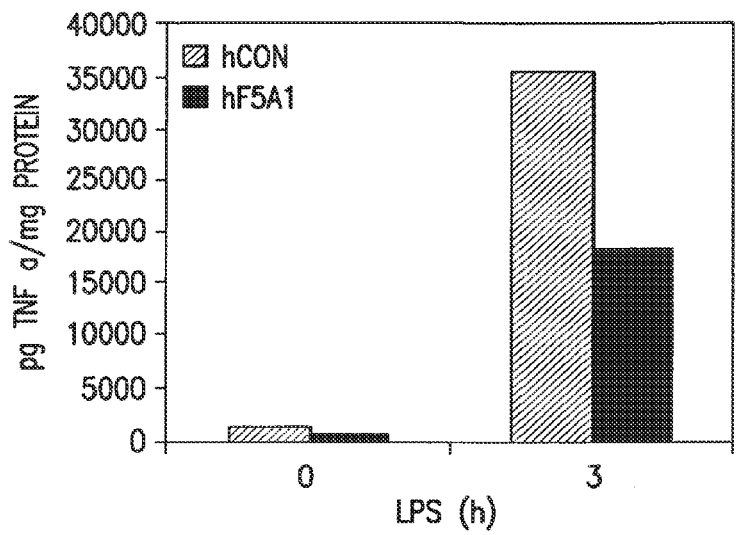

(siRNA-MEDIATED DOWNREGULATION OF APOPTOSIS-SPECIFIC eIF-5A "eIF5A1")
(siRNA-MEDIATED DOWNREGULATION OF APOPTOSIS-SPECIFIC "eIF-5A") COINCIDES WITH A REDUCTION IN LPS-INDUCED TNFα PRODUCTION IN U937. U937 CELLS WERE ELECTROPORATED WITH eIF5A1 OR CONTROL siRNA. 16h LATER, PMA (100 ng/ml) WAS ADDED AND THE CELLS DIFFERENTIATED INTO ADHERENT MACROPHAGES AND MADE QUIESCENT BEFORE LPS (100 ng/ml) ADDITION. SAMPLES WERE COLLECTED BEFORE AND 3 h AFTER LPS ADDITION. REFER TO THE TIME COURSE SCHEME IN FIGURE 105 FOR CLARIFICATION. SECRETED TNFα WAS QUANTIFIED BY ELISA AND CORRECTED FOR TOTAL CELLULAR PROTEIN. RESULTS ARE CHARACTERISTIC OF TWO INDEPENDENT EXPERIMENTS.

FIG.112

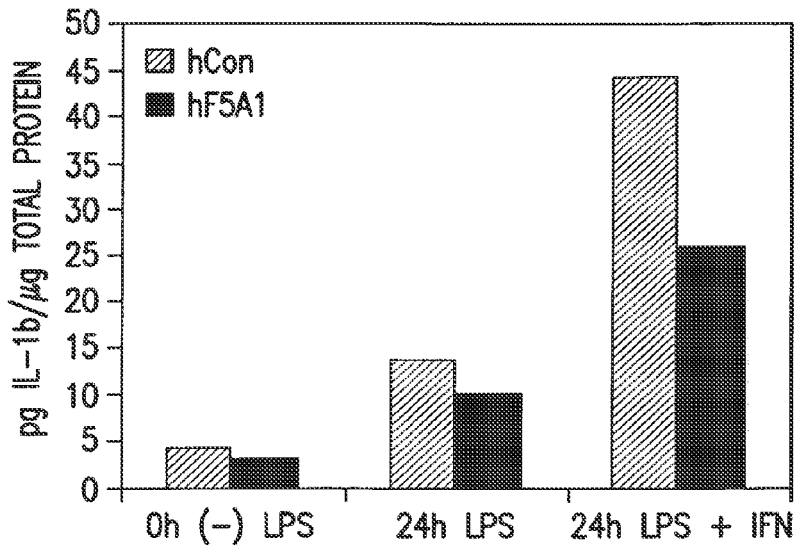

siRNA-MEDIATED DOWNREGULATION OF (APOPTOSIS-SPECIFIC eIF-5A "eIF5A1") COINCIDES WITH A REDUCTION IN IL-1β PRODUCTION IN U937. U937 CELLS WERE ELECTROPORATED WITH eIF5A1 OR CONTROL siRNA. 16h LATER, PMA (100 ng/ml) WAS ADDED AND THE CELLS DIFFERENTIATED INTO ADHERENT MACROPHAGES AND MADE QUIESCENT BEFORE LPS (100 ng/ml) +/- IFNγ (100 UNITS/ml) ADDITION. SAMPLES WERE COLLECTED BEFORE AND 24 h AFTER LPS OR LPS AND IFNγ ADDITION. REFER TO THE TIME COURSE SCHEME IN FIGURE 105 FOR CLARIFICATION. SECRETED IL-1β WAS QUANTIFIED BY LIQUID-PHASE ELECTROCHEMILUMINESCENCE (ECL) AND CORRECTED FOR TOTAL CELLULAR PROTEIN.

FIG.113

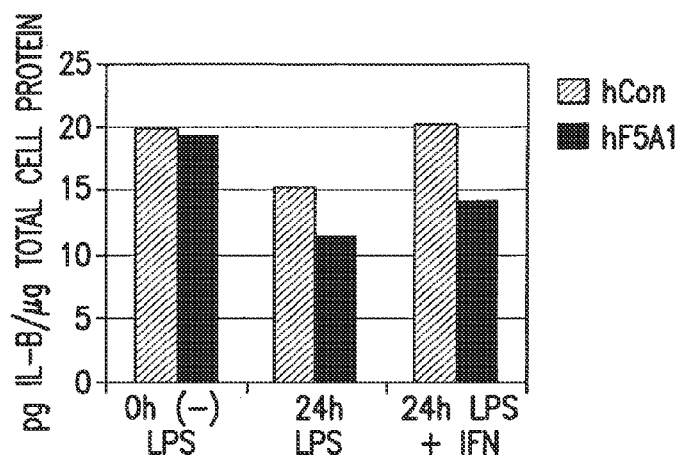

siRNA-MEDIATED DOWNREGULATION OF (APOPTOSIS-SPECIFIC eIF-5A "eIF5A1") COINCIDES WITH A REDUCTION IN IL-8 PRODUCTION IN U937. U937 CELLS WERE ELECTROPORATED WITH eIF5A1 OR CONTROL siRNA. 16h LATER, PMA (100 ng/ml) WAS ADDED AND THE CELLS DIFFERENTIATED INTO ADHERENT MACROPHAGES AND MADE QUIESCENT BEFORE LPS (100 ng/ml) AND/OR IFNγ (100 UNITS/ml) ADDITION. SAMPLES WERE COLLECTED BEFORE AND 24 h AFTER LPS OR LPS AND IFNγ ADDITION. REFER TO THE TIME COURSE SCHEME IN FIGURE 108 FOR CLARIFICATION. SECRETED IL-8 WAS QUANTIFIED BY LIQUID-PHASE ELECTROCHEMILUMINESCENCE (ECL) AND CORRECTED FOR TOTAL CELLULAR PROTEIN.

FIG. 114

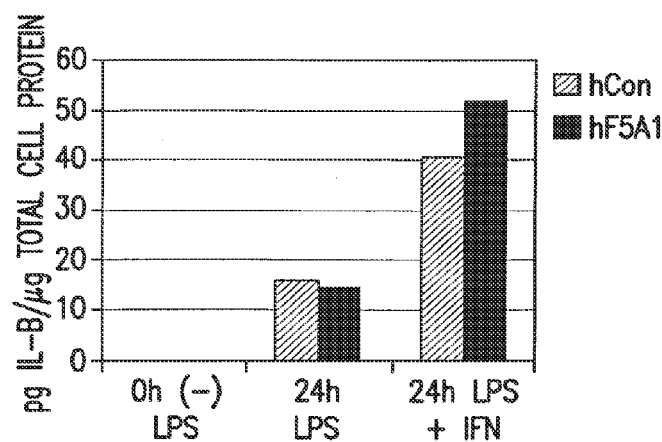

IL-6 PRODUCTION IS INDEPENDENT OF siRNA-MEDIATED DOWNREGULATION OF (APOPTOSIS-SPECIFIC eIF-5A "eIF5A1") IN U937. U937 CELLS WERE ELECTROPORATED WITH eIF5A1 OR CONTROL siRNA. 16h LATER, PMA (100 ng/ml) WAS ADDED AND THE CELLS DIFFERENTIATED INTO ADHERENT MACROPHAGES AND MADE QUIESCENT BEFORE LPS (100 ng/ml) AND/OR IFNγ (100 UNITS/ml) ADDITION. SAMPLES WERE COLLECTED BEFORE AND 24 h AFTER LPS OR LPS AND IFNγ ADDITION. REFER TO THE TIME COURSE SCHEME IN FIGURE 105 FOR CLARIFICATION. SECRETED IL-6 WAS QUANTIFIED BY LIQUID-PHASE ELECTROCHEMILUMINESCENCE (ECL) AND CORRECTED FOR TOTAL CELLULAR PROTEIN.

FIG.115

INHIBITION OF APOPTOSIS-SPECIFIC EIF-5A(EIF-5A1") WITH ANTISENSE OLIGONUCLEOTIDES AND SIRNA AS ANTI-INFLAMMATORY THERAPEUTICS

RELATED APPLICATIONS

This application is a continuation application of U.S. application Ser No. 11/134,445 (filed May 23, 2005) which is a continuation application of U.S. application Ser. No. 10/861, 980 (filed Jun. 6, 2004) which claims the benefit of U.S. Provisional Application 60/476,194 (filed Jun. 6, 2003), U.S. Provisional Application 60/504,731 (filed Sep. 22, 2003), U.S. Provisional Application 60/528,249 (filed Dec. 10, 2003), U.S. Provisional Application 60/557,671 (filed Mar. 31, 2004), and U.S. Provisional Application No. 60/575,814 (filed Jun. 2, 2004), all of which are herein incorporated by reference in their entirety.

FIELD OF THE INVENTION

The present invention relates to apoptosis-specific eucaryotic initiation factor ("eIF-5A") or referred to as "apoptosis-specific eIF-5A" or"eIF-5A 1" and deoxyhypusine synthase (DHS). The present invention relates to apoptosis-specific eIF-5A and DHS nucleic acids and polypeptides and methods for inhibiting expression of apoptosis-specific eIF-5A and DHS.

BACKGROUND OF THE INVENTION

Apoptosis is a genetically programmed cellular event that is characterized by well-defined morphological features, such as cell shrinkage, chromatin condensation, nuclear fragmentation, and membrane blebbing. Kerr et al. (1972) Br. J. Cancer, 26, 239-257; Wylie et al. (1980) hit. Rev. Cytol., 68, 251-306. It plays an important role in normal tissue development and homeostasis, and defects in the apoptotic program are thought to contribute to a wide range of human disorders ranging from neurodegenerative and autoimmunity disorders to neoplasms. Thompson (1995) Science, 267, 1456-1462; Mullauer et al. (2001) Mutat. Res, 488, 211-231. Although the morphological characteristics of apoptotic cells are well characterized, the molecular pathways that regulate this process have only begun to be elucidated.

One group of proteins that is thought to play a key role in apoptosis is a family of cysteine proteases, termed caspases, which appear to be required for most pathways of apoptosis. Creagh & Martin (2001) Biochem. Soc. Trans, 29, 696-701; Dales et al. (2001) Leuk. Lymphoma, 41, 247-253. Caspases trigger apoptosis in response to apoptotic stimuli by cleaving various cellular proteins, which results in classic manifestations of apoptosis, including cell shrinkage, membrane blebbing and DNA fragmentation. Chang & Yang (2000) Microbiol. Mol. Biol. Rev., 64, 821-846.

Pro-apoptotic proteins, such as Bax or Bak, also play a key role in the apoptotic pathway by releasing caspase-activating molecules, such as mitochondrial cytochrome c, thereby promoting cell death through apoptosis. Martinou & Green (2001) Nat. Rev. Mol. Cell. Biol., 2, 63-67; Zou et al. (1997) Cell, 90, 405-413. Anti-apoptotic proteins, such as Bcl-2, promote cell survival by antagonizing the activity of the pro-apoptotic proteins, Bax and Bak. Tsujimoto (1998) Genes Cells, 3, 697-707; Kroemer (1997) Nature Med., 3, 614-620. The ratio of Bax:Bcl-2 is thought to be one way in which cell fate is determined; an excess of Bax promotes apoptosis and an excess of Bcl-2 promotes cell survival. Salomons et al. (1997) Int. J. Cancer, 71, 959-965; Wallace-Brodeur & Lowe (1999) Cell Mol. Life. Sci., 55, 64-75.

Another key protein involved in apoptosis is a protein that encoded by the tumor suppressor gene p53. This protein is a transcription factor that regulates cell growth and induces apoptosis in cells that are damaged and genetically unstable, presumably through up-regulation of Bax. Bold et al. (1997) Surgical Oncology, 6, 133-142; Ronen et al., 1996; Schuler & Green (2001) Biochem. Soc. Trans., 29, 684-688; Ryan et al. (2001) Curr. Opin. Cell Biol., 13, 332-337; Zörnig et al. (2001) Biochem. Biophys. Acta, 1551, F1-F37.

Alterations in the apoptotic pathways are believed to play a key role in a number of disease processes, including cancer. Wyllie et al. (1980) Int. Rev. Cytol., 68, 251-306; Thompson (1995) Science, 267, 1456-1462; Sen & D'Incalci (1992) FEBS Letters, 307, 122-127; McDonnell et al. (1995) Seminars in Cancer and Biology, 6, 53-60. Investigations into cancer development and progression have traditionally been focused on cellular proliferation. However, the important role that apoptosis plays in tumorigenesis has recently become apparent. In fact, much of what is now known about apoptosis has been learned using tumor models, since the control of apoptosis is invariably altered in some way in tumor cells. Bold et al. (1997) Surgical Oncology, 6, 133-142.

Cytokines also have been implicated in the apoptotic pathway. Biological systems require cellular interactions for their regulation, and cross-talk between cells generally involves a large variety of cytokines. Cytokines are mediators that are produced in response to a wide variety of stimuli by many different cell types. Cytokines are pleiotropic molecules that can exert many different effects on many different cell types, but are especially important in regulation of the immune response and hematopoietic cell proliferation and differentiation. The actions of cytokines on target cells can promote cell survival, proliferation, activation, differentiation, or apoptosis depending on the particular cytokine, relative concentration, and presence of other mediators.

The use of anti-cytokines to treat autoimmune disorders such as psoriasis, rheumatoid arthritis, and Crohn's disease is gaining popularity. The pro-inflammatory cytokines IL-1 and TNT play a large role in the pathology of these chronic disorders. Anti-cytokine therapies that reduce the biological activities of these two cytokines can provide therapeutic benefits (Dinarello and Abraham, 2002).

Interleukin 1 (IL-1) is an important cytokine that mediates local and systemic inflammatory reactions and which can synergize with TNF in the pathogenesis of many disorders, including vasculitis, osteoporosis, neurodegenerative disorders, diabetes, lupus nephritis, and autoimmune disorders such as rheumatoid arthritis. The importance of IL-1β in tumour angiogenesis and invasiveness was also recently demonstrated by the resistance of IL-1β knockout mice to metastases and angiogenesis when injected with melanoma cells (Voronov et al., 2003).

Interleukin 18 (IL-18) is a recently discovered member of the IL-1 family and is related by structure, receptors, and function to IL-1. IL-18 is a central cytokine involved in inflammatory and autoimmune disorders as a result of its ability to induce interferon-gamma (IFN-γ), TNF-α, and IL-1. IL-1β and IL-18 are both Capable of inducing production of TNF-α, a cytokine known to contribute to cardiac dysfunction during myocardial ischemia (Maekawa et al., 2002). Inhibition of IL-18 by neutralization with an IL-18 binding protein was found to reduce ischemia-induced myocardial dysfunction in an ischemia/reperfusion model of suprafused human atrial myocardium (Dinarello, 2001). Neutralization of IL-18 using a mouse IL-18 binding protein was also able to decrease IFN-γ, TNF-α, and IL-1β transcript levels and reduce joint damage in a collagen-induced arthritis mouse model (Banda et al., 2003). A reduction of IL-18 production or availability may also prove beneficial to control metastatic cancer as injection of IL-18 binding protein in a mouse melanoma model successfully inhibited metastases (Carrascal et al., 2003). As a further indication of its importance as a pro-inflammatory cytokine, plasma levels of IL-18 were elevated in patients with chronic liver disease and increased levels were correlated with the severity of the disease (Ludwiczek et al., 2002). Similarly, IL-18 and TNF-α were elevated in the serum of diabetes mellitus patients with nephropathy (Moriwaki et al., 2003). Neuroinflammation following traumatic brain injury is also mediated by pro-inflammatory cytokines and inhibition of IL-18 by the IL-18 binding protein improved neurological recovery in mice following brain trauma (Yatsiv et al., 2002).

TNF-α, a member of the TNF family of cytokines, is a pro-inflammatory cytokine with pleiotropic effects ranging from co-mitogenic effects on hematopoietic cells, induction of inflammatory responses, and induction of cell death in many cell types. TNF-α is normally induced by bacterial lipopolysaccharides, parasites, viruses, malignant cells and cytokines and usually acts beneficially to protect cells from infection and cancer. However, inappropriate induction of TNF-α is a major contributor to disorders resulting from acute and chronic inflammation such as autoimmune disorders and can also contribute to cancer, AIDS, heart disease, and sepsis (reviewed by Aggarwal and Natarajan, 1996; Sharma and Anker, 2002). Experimental animal models of disease (i.e. septic shock and rheumatoid arthritis) as well as human disorders (i.e. inflammatory bowel diseases and acute graft-versus-host disease) have demonstrated the beneficial effects of blocking TNF-α (Wallach et al., 1999). Inhibition of TNF-α has also been effective in providing relief to patients suffering autoimmune disorders such as Crohn's disease (van Deventer, 1999) and rheumatoid arthritis (Richard-Miceli and Dougados, 2001). The ability of TNF-α to promote the survival and growth of B lymphocytes is also thought to play a role in the pathogenesis of B-cell chronic lymphocytic leukemia (B-CLL) and the levels of TNF-α being expressed by T cells in B-CLL was positively correlated with tumour mass and stage of the disease (Bojarska-Junak et al., 2002). Interleukin-1β (IL-1β) is a cytokine known to induce TNF-α production.

Thus, since the accumulation of excess cytokines and TNF-α can lead to deleterious consequences on the body, including cell death, there is a need for a method to reduce the levels of cytokines in the body as well as inhibiting or reducing apoptosis. The present invention fulfills these needs.

Deoxyhymisine synthase (DHS) and hypusine-containing eucaryotic translation initiation Factor-5A (eIF-5A) are known to play important roles in many cellular processes including cell growth and differentiation. Hypusine, a unique amino acid, is found in all examined eucaryotes and archaebacteria, but not in eubacteria, and eIF-5A is the only known hypusine-containing protein. Park (1988) J. Biol. Chem., 263, 7447-7449; Schümann & Klink (1989) System: Appl. Microbiol., 11, 103-107; Bartig et al. (1990) System. Appl. Microbiol., 13, 112-116; Gordon et al. (1987a) J. Biol., Chem., 262, 16585-16589. Active eIF-5A is formed in two post-translational steps: the first step is the formation of a deoxyhypusine residue by the transfer of the 4-aminobutyl moiety of spermidine to the α-amino group of a specific lysine of the precursor eIF-5A catalyzed by deoxyhypusine synthase; the second step involves the hydroxylation of this 4-aminobutyl moiety by deoxyhypusine hydroxylase to form hypusine.

The amino acid sequence of eIF-5A is well conserved between species, and there is strict conservation of the amino acid sequence surrounding the hypusine residue in eIF-5A, which suggests that this modification may be important for survival. Park et al. (1993) Biofactors, 4, 95-104. This assumption is further supported by the observation that inactivation of both isoforms of eIF-5A found to date in yeast, or inactivation of the DHS gene, which catalyzes the first step in their activation, blocks cell division. Schnier et al. (1991) Mol. Cell. Biol., 11, 3105-3114; Sasaki et al. (1996) FEBS Lett., 384, 151-154; Park et al. (1998) J. Biol. Chem., 273, 1677-1683. However, depletion of eIF-5A protein in yeast resulted in only a small decrease in total protein synthesis suggesting that eIF-5A may be required for the translation of specific subsets of mRNA's rather than for protein global synthesis. Kang et al. (1993), "Effect of initiation factor eIF-5A depletion on cell proliferation and protein synthesis," in Tuite, M. (ed.), Protein Synthesis and Targeting in Yeast, NATO Series H. The recent finding that ligands that bind eIF-5A share highly conserved motifs also supports the importance of eIF-5A. Xu & Chen (2001) J. Biol. Chem., 276, 2555-2561. In addition, the hypusine residue of modified eIF-5A was found to be essential for sequence-specific binding to RNA, and binding did not provide protection from ribonucleases.

In addition, intracellular depletion of eIF-5A results in a significant accumulation of specific in mRNAs in the nucleus, indicating that eIF-5A may be responsible for shuttling specific classes of mRNAs from the nucleus to the cytoplasm. Liu & Tartakoff (1997) Supplement to Molecular Biology of the Cell, 8, 426a. Abstract No. 2476, 37th American Society for Cell Biology Annual Meeting. The accumulation of eIF-5A at nuclear pore-associated intranuclear filaments and its interaction with a general nuclear export receptor further suggest that eIF-5A is a nucleocytoplasmic shuttle protein, rather than a component of polysomes. Rosorius et al. (1999) J. Cell Science, 112, 2369-2380.

The first cDNA for eIF-5A was cloned from human in 1989 by Smit-McBride et al., and since then cDNAs or genes for eIF-5A have been cloned from various eukaryotes including yeast, rat, chick embryo, alfalfa, and tomato. Smit-McBride et al. (1989) J. Biol. Chem., 264, 1578-1583; Schiller et al. (1991) (yeast); Sano, A. (1995) in Imahori, M. et al. (eds), Polyamines, Basic and Clinical Aspects, VNU Science Press, The Netherlands, 81-88 (rat); Rinaudo & Park (1992) FASEB J., 6, A453 (chick embryo); Pay et al. (1991) Plant Mol. Biol., 17, 927-929 (alfalfa); Wang et al. (2001) J. Biol. Chem., 276, 17541-17549 (tomato).

Expression of eIF-5A mRNA has been explored in various human tissues and mammalian cell lines. For example, changes in eIF-5A expression have been observed in human fibroblast cells after addition of serum following serum deprivation. Pang & Chen (1994) J. Cell Physiol., 160, 531-538. Age-related decreases in deoxyhypusine synthase activity and abundance of precursor eIF-5A have also been observed in senescing fibroblast cells, although the possibility that this reflects averaging of differential changes in isoforms was not determined. Chen & Chen (1997) J. Cell Physiol., 170, 248-254.

Studies have shown that eIF-5A may be the cellular target of viral proteins such as the human immunodeficiency virus type 1 Rev protein and human T cell leukemia virus type 1 Rex protein. Ruhl et al. (1993) J. Cell Biol., 123, 1309-1320; Katahira et al. (1995) J. Virol., 69, 3125-3133. Preliminary studies indicate that eIF-5A may target RNA by interacting with other RNA-binding proteins such as Rev, suggesting that these viral proteins may recruit eIF-5A for viral RNA processing. Liu et al. (1997) Biol. Signals, 6, 166-174.

Thus, although eIF5A and DHS are known, there remains a need in understanding how these proteins are involved in apoptotic pathways as well as cytokine stimulation to be able to modulate apoptosis and cytokine expression. The present invention fulfills this need.

SUMMARY OF INVENTION

The present invention relates to apoptosis specific eucaryotic initiation factor 5A (eIF-5A), referred to as "apoptosis specific eIF-5A" or "eIF-5A1." The present invention also relates to apoptosis-specific eIF-5A nucleic acids and polypeptides and methods for inhibiting or suppressing apoptosis in cells using antisense nucleotides or siRNAs to inhibit expression of apoptosis-specific eIF-5A. The present invention relates to a method of delivering siRNA to mammalian lung cells in vivo. The invention also relates to suppressing or inhibiting expression of pro-inflammatory cytokines by inhibiting expression of apoptosis-specific eIF-5A. Further, the present invention relates to inhibiting or suppressing expression of p53 by inhibiting expression of apoptosis-specific eIF-5A. The present invention also relates to a method of increasing Bcl-2 expression by inhibiting or suppression expression of apoptosis factor 5A using antisense nucleotides or siRNAs. The present invention also provides a method of inhibiting production of cytokines, especially TNF-α in human epithelial cells. In another embodiment of the present invention, suppressing expression of apoptosis-specific eIF-5A by the use of antisense oligonucleotides targeted at apoptosis-specific eIF-5A provides methods of preventing retinal ganglion cell death in a glaucomatous eye.

BRIEF DESCRIPTION OF THE DRAWINGS

FIG. 1 depicts the nucleotide sequence (SEQ ID NO: 11) and derived amino acid sequence (SEQ ID NO: 12) of the 3' end of rat apoptosis-specific eIF-5A.

FIG. 2 depicts the nucleotide sequence (SEQ ID NO: 15) and derived amino acid sequence (SEQ ID NO: 16) of the 5' end of rat apoptosis-specific eIF-5A cDNA.

FIG. 3 depicts the nucleotide sequence of rat corpus luteum apoptosis-specific eIF-5A full-length cDNA (SEQ ID NO: 1). The amino acid sequence is shown in SEQ ID NO: 2.

FIG. 4 depicts the nucleotide sequence (SEQ ID NO: 6) and derived amino acid sequence (SEQ ID NO: 7) of the 3' end of rat apoptosis-specific DHS cDNA.

FIG. 5 is an alignment of the full-length nucleotide sequence of rat corpus luteum apoptosis-specific eIF-5A cDNA (SEQ ID NO: 20) with the nucleotide sequence of human eIF-5A (SEQ ID NO: 3) (Accession number BC000751 or NM_001970, SEQ ID NO:3).

FIG. 6 is an alignment of the full-length nucleotide sequence of rat corpus luteum apoptosis-specific eIF-5A cDNA (SEQ ID NO: 20) with the nucleotide sequence of human eIF-5A (SEQ ID NO: 4) (Accession number NM-020390, SEQ ID NO:4).

FIG. 7 is an alignment of the full-length nucleotide sequence of rat corpus luteum apoptosis-specific eIF-5A cDNA (SEQ ID NO: 20) with the nucleotide sequence of mouse eIF-5A (Accession number BC003889). Mouse nucleotide sequence (Accession number BC003889) is SEQ ID NO:5.

FIG. 8 is an alignment of the derived full-length amino acid sequence of rat corpus luteum apoptosis-specific eIF-5A (SEQ ID NO: 2) with the derived amino acid sequence of human eIF-5A (SEQ ID NO: 21) (Accession number BC000751 or NM_001970).

FIG. 9 is an alignment of the derived full-length amino acid sequence of rat corpus luteum apoptosis-specific eIF-5A (SEQ ID NO: 2) with the derived amino acid sequence of human eIF-5A (SEQ ID NO: 22) (Accession number NM_20390).

FIG. 10 is an alignment of the derived full-length amino acid sequence of rat corpus luteum apoptosis-specific eIF-5A. (SEQ ID NO: 2) with the derived amino acid sequence of mouse eIF-5A (SEQ ID NO: 23) (Accession number BC003889).

FIG. 11 is an alignment of the partial-length nucleotide sequence of rat corpus luteum apoptosis-specific DHS cDNA. (residues 1-453 of SEQ ID NO: 6) with the nucleotide sequence of human DHS (SEQ ID NO: 8) (Accession number BC000333, SEQ ID) NO:8).

FIG. 27 illustrates detection of apoptosis as reflected by increased nuclear fragmentation when COS-7 cells were transiently transfected with pHM6 containing full-length rat apoptosis-specific eIF-5A in the sense orientation.

FIG. 38 is an alignment of human eIF5A2 isolated from RKO cells (SEQ ID NO: 24) with the sequence of human eIF5A2 (SEQ D NO: 22) (Genbank accession number XM_113401). The consensus sequence is shown in SEQ ID NO: 28.

FIG. 42A provides the results of a flow cytometry analysis of RKO cell apoptosis following transient transfection. RKO cells were either left untransfected or were transiently transfected with pHM6-LacZ, pHM6-apoptosis-specific eIF-5A, pHM6-eIF5A2, or pHM6-truncated apoptosis-specific eIF-5A. The FIG. 42B is table depicting the percentage of cells undergoing apoptosis calculated based on the area under the peak of each gate. After correction for background apoptosis in untransfected cells and for transfection efficiency, 80% of cells transfected with pHM6-apoptosis-specific eIF-5A exhibited apoptosis. Cells transfected with pHM6-LacZ, pHM6-eiF5A2 or pHM6-truncated apoptosis-specific eIF-5A exhibited only background levels of apoptosis.

FIGS. 50A-F report patient data where the levels of apoptosis-specific eIF-5A are correlated with levels of IL-1β and IL-18. FIG. 50A is a chart of data obtained from coronary artery bypass graft (CABG) patients. FIG. 50B is a chart of data obtained from valve replacement patients. FIG. 50C is a graph depicting the correlation of apoptosis-specific eIF-5A to IL-18 in CABG patients. FIG. 50D is a graph depicting the correlation of proliferating eIF-5A to IL-18 in CABG patients. FIG. 50E is a graph depicting the correlation of apoptosis-specific eIF-5A to IL-18 in valve replacement patients. FIG. 50F is a graph depicting the correlation of proliferating eIF-5A to IL-18 in valve replacement patients.

FIG. 51A-D is a chart of the patient's data from which patients data used in FIGS. 50A-F was obtained.

FIGS. 60 and 61 shows a decrease in the percentage of cells undergoing apoptosis in the cells having being treated with antisense apoptosis-specific eIF-5A oligonucleotides as compared to cells not having been transfected with the antisense apoptosis-specific eIF-5A oligonucleotides.

FIG. 69 shows that IL-1 exposed HepG2 cells transfected with apoptosis-specific eIF-5A cells secreted less TNF-α than non-transfected cells.

FIG. 70 shows the sequence of human apoptosis-specific eIF-5A (SEQ ID NO:29) and the sequences of 5 siRNAs of the present invention (SEQ ID NO:30, 31, 32, 33 and 34).

FIG. 71 shows the sequence of human apoptosis-specific eIF-5A (SEQ ID NO: 29) and the sequences of 3 antisense oligonucleotides of the present invention (SEQ ID NO:35, 37, and 39, respectively in order of appearance).

FIG. 72 shows the binding position of three antisense oligonucleotides (SEQ ID NO:25-27, respectively in order of appearance) targeted against human apoptosis-specific eIF-5A. The full-length nucleotide sequence is SEQ ID NO: 19.

FIG. 73a and b shows the nucleotide alignment (SEQ ID NO: 41 and 42, respectively in order of appearance) and amino acid alignment (SEQ ID NO: 43 and 22, respectively in order of appearance) of human apoptosis-specific eIF-5A against human proliferating eIF-5A.

FIG. 88 shows TUNEL-labeling of lamina cribosa cell line #506 cells transfected with apoptosis-specific eIF-5A siRNA #1 and treated with TNF-α and camptothecin. Lamina cribrosa cell line #506 cells were seeded at 7500 cells per well onto an 8-well culture slide. Three days later the LC cells were transfected with either apoptosis-specific eIF-5A siRNA #1 (SEQ ID NO:30) or control siRNA #5 (SEQ ID NO:34). 72 hours after transfection, the transfected cells were treated with 10 ng/ml TNF-α plus 50 µM camptothecin. Twenty-four hours later the cells were stained with Hoescht 33258 and DNA fragmentation was evaluated in situ using the terminal deoxynucleotidyl transferase-mediated dUTP-digoxigenin nick end labeling (TUNEL) method. Panel A represents the slide observed by fluorescence microscopy using a fluorescein filter to visualize TUNEL-labeling of the fragmented DNA of apoptotic cells. Panel B represents the same slide observed by through a UV filter to visualize the Hoescht-stained nuclei. The results are representative of two independent experiments. All pictures were taken at 400 times magnification.

FIG. 89A-B depicts the design of siRNAs against apoptosis-specific eIF-5A. The siRNAs have the SEQ ID NO: 45, 48, 51, 54 and 57. The full-length nucleotide sequence is shown in SEQ ID NO: 29.

FIG. 94 demonstrates that PBMCs respond to LPS without PMA differentiation.

FIG. 95 shows that PBMCs transfected with apoptosis-specific eIF-5A siRNAs demonstrate suppression of expression of apoptosis-specific eIF-5A.

FIG. 99 shows that HT-29 cells transfected with apoptosis-specific eIF-5A siRNAs have a reduced level of TNF production.

FIG. 100 shows that HT-29 cells transfected with apoptosis-specific eIF-5A siRNAs exhibit a decreased in apoptosis as compared to control cells. Both control and siRNA-transfected cells were primed with interferon gamma and also treated with TNF-α.

FIG. 101 shows that HT-29 cells transfected with apoptosis-specific eIF-5A siRNAs express less TLR4 protein than control cells.

FIG. 106 shows that apoptosis-specific eIF-5A is upregulated with PMA in U937 cells.

FIG. 108 shows that apoptosis-specific eIF-5A protein expression is still reduced after numerous hours following siRNA treatment.

FIG. 112 shows that siRNA mediated down-regulation of apoptosis-specific eIF-5A coincides with a reduction in LPS-induced TNF-α production in U937 cells.

FIG. 113 shows that siRNA mediated down-regulation of apoptosis-specific eIF-5A coincides with a reduction in LPS-induced IL-1β production in U937 cells.

FIG. 114 shows that siRNA mediated down-regulation of apoptosis-specific eIF-5A coincides with a reduction in LPS-induced IL-8 production in U937 cells.

FIG. 115 shows that IL-6 production is independent of siRNA mediated down-regulation of apoptosis-specific eIF-5A in U937 cells.

DETAILED DESCRIPTION OF THE INVENTION

Figure 12:
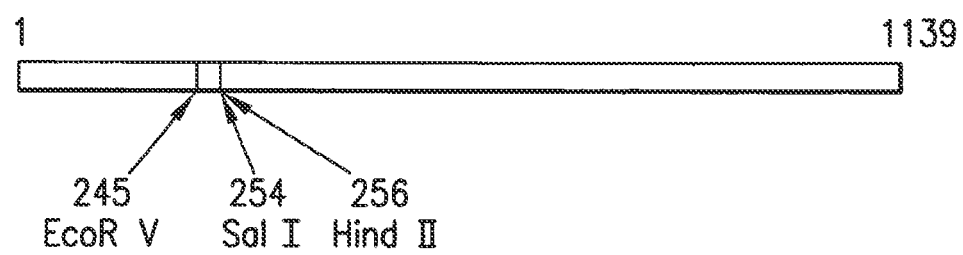
FIG. 12 is a restriction map of rat corpus luteum apoptosis-specific eIF-5A cDNA.
Figure 13:
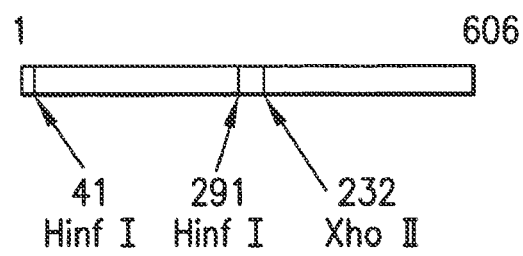
FIG. 13 is a restriction map of the partial-length rat apoptosis-specific DHS cDNA.

Several isoforms of eukaryotic initiation factor 5A ("eIF-5A") have been isolated and present in published databanks. It was thought that these isoforms were functionally redundant. The present inventors have discovered that one isoform is upregulated immediately before the induction of apoptosis, which they have designated apoptosis-specific eIF-5A or eIF-5A1. The subject of the present invention is apoptosis-specific eIF-5A and DHS, which is involved in the activation of eIF-5A.

Apoptosis-specific eIF-5A is likely to be a suitable target for intervention in apoptosis-causing disease states since it appears to act at the level of post-transcriptional regulation of downstream effectors and transcription factors involved in the apoptotic pathway. Specifically, apoptosis-specific eIF-5A appears to selectively facilitate the translocation of mRNAs encoding downstream effectors and transcription factors of apoptosis from the nucleus to the cytoplasm, where they are subsequently translated. The ultimate decision to initiate apoptosis appears to stem from a complex interaction between internal and external pro- and anti-apoptotic signals. Lowe & Lin (2000) Carcinogenesis, 21, 485-495. Through its ability to facilitate the translation of downstream apoptosis effectors and transcription factors, apoptosis-specific eIF-5A appears to tip the balance between these signals in favor of apoptosis.

Accordingly, the present invention provides a method of suppressing or reducing apoptosis in a cell by administering an agent that inhibits or reduces expression of either apoptosis-specific eIF-5A or DHS. By reducing expression of DHS, there is less DHS protein to be available to activate apoptosis-specific eIF-5A. One agent that can inhibit or reduce expression of apoptosis-specific eIF-5A or DHS are antisense oligonucleotides of apoptosis-specific eIF-5A or DHS. By reducing activation of apoptosis-specific eIF-5A or by reducing or inhibiting expression of apoptosis-specific eIF-5A, cellular apoptosis can be delayed or inhibited.

Antisense oligonucleotides have been successfully used to accomplish both in vitro as well as in vivo gene-specific suppression. Antisense oligonucleotides are short, synthetic strands of DNA (or DNA analogs), RNA (or RNA analogs), or DNA/RNA hybrids that are antisense (or complimentary) to a specific DNA or RNA target. Antisense oligonucleotides are designed to block expression of the protein encoded by the DNA or RNA target by binding to the target mRNA and halting expression at the level of transcription, translation, or splicing. By using modified backbones that resist degradation (Blake et al., 1985), such as replacement of the phosphodiester bonds in the oligonucleotides with phosphorothioate linkages to retard nuclease degradation (Matzura and Eckstein, 1968), antisense oligonucleotides have been used successfully both in cell cultures and animal models of disease (Hogrefe, 1999). Other modifications to the antisense oligonucleotide to render the oligonucleotide more stable and resistant to degradation are known and understand by one skilled in the art. Antisense oligonucleotide as used herein encompasses double stranded or single stranded DNA, double stranded or single stranded RNA, DNA/RNA hybrids, DNA and RNA analogs, and oligonucleotides having base, sugar, or backbone modifications. The oligonucleotides may be modified by methods known in the art to increase stability, increase resistance to nuclease degradation or the like. These modifications are known in the art and include, but are not limited to modifying the backbone of the oligonucleotide, modifying the sugar moieties, or modifying the base.

Preferably, the antisense oligonucleotides of the present invention have a nucleotide sequence encoding a portion or the entire coding sequence of an apoptosis-specific eIF-5A polypeptide or a DHS polypeptide. The inventors have transfected various cell lines with antisense nucleotides encoding a portion of an apoptosis-specific eIF-5A polypeptide as described below and measured the number of cells undergoing apoptosis. The cell populations that were transfected with the antisense oligonucleotides showed a decrease in the number of cells undergoing apoptosis as compared to like cell populations not having been transfected with the antisense oligos. FIGS. 54-58 show a decrease in the percentage of cells undergoing apoptosis in the cells having being treated with antisense apoptosis-specific eIF-5A oligonucleotides as compared to cells not having been transfected with the antisense apoptosis-specific eIF-5A oligonucleotides.

The present invention contemplates the use of many suitable nucleic acid sequences encoding an apoptosis-specific eIF-5A polypeptide or DHS polypeptide. For example, the present invention provides antisense oligonucleotides of the following apoptosis-specific eIF-5A nucleic acid sequences (SEQ ID NOS:1, 3, 4, 5, 11, 12, 15, 16, 19, 20, and 21) and DHS sequences (SEQ ID NOS:6, 7, 8). Antisense oligonucleotides of the present invention need not be the entire length of the provided SEQ ID NOs. They need only be long enough to be able to bind to the mRNA and inhibit expression of such mRNA. "Inhibition or reduction of expression" or "suppression of expression" refers to the absence or detectable decrease in the level of protein and/or mRNA product from a target gene, such as apoptosis-specific eIF-5A.

Exemplary antisense oligonucleotides of apoptosis-specific eIF-5A that do not comprise the entire coding sequence are antisense oligonucleotides of apoptosis-specific eIF-5A having the following SEQ ID NO: 35, 37, and 39.

"Antisense oligonucleotide of apoptosis-specific eIF-5A" includes oligonucleotides having substantial sequence identity or substantial homology to apoptosis-specific eIF-5A. Additional antisense oligonucleotides of apoptosis-specific eIF-5A of the present invention include those that have substantial sequence identity to those enumerated above (i.e. 90% homology) or those having sequences that hybridize under highly stringent conditions to the enumerated SEQ ID NOs. As used herein, the term "substantial sequence identity" or "substantial homology" is used to indicate that a sequence exhibits substantial structural or functional equivalence with another sequence. Any structural or functional differences between sequences having substantial sequence identity or substantial homology will be de minimus; that is, they will not affect the ability of the sequence to function as indicated in the desired application. Differences may be due to inherent variations in codon usage among different species, for example. Structural differences are considered de minimus if there is a significant amount of sequence overlap or similarity between two or more different sequences or if the different sequences exhibit similar physical characteristics even if the sequences differ in length or structure. Such characteristics include, for example, the ability to hybridize under defined conditions, or in the case of proteins, immunological cross-reactivity, similar enzymatic activity, etc. The skilled practitioner can readily determine each of these characteristics by art known methods.

Additionally, two nucleotide sequences are "substantially complementary" if the sequences have at least about 70 percent or greater, more preferably 80 percent or greater, even more preferably about 90 percent or greater, and most preferably about 95 percent or greater sequence similarity between them. Two amino acid sequences are substantially homologous if they have at least 70%, more preferably at least 80%, even more preferably at least 90%, and most preferably at least 95% similarity between the active, or functionally relevant, portions of the polypeptides.

To determine the percent identity of two sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (1990) *J. Mol Biol.* 215:403-10. BLAST nucleotide searches can be performed with the NBLAST program. BLAST protein searches can be performed with the XBLAST program to obtain amino acid sequences homologous to the proteins of the invention. To obtain gapped alignments for comparison purposes, Gapped BLAST can be utilized as described in Altschul et al. (1997) *Nucleic Acids Res.* 25(17):3389-3402. When utilizing BLAST and gapped BLAST programs, the default parameters of the respective programs (e.g., XBLAST and NBLAST) can be used.

The term "apoptosis-specific eIF-5A"includes functional derivatives thereof. The term "functional derivative" of a nucleic acid is used herein to mean a homolog or analog of the gene or nucleotide sequence. A functional derivative may retain the function of the given gene, which permits its utility in accordance with the invention. "Functional derivatives" of the apoptosis-specific eIF-5A polypeptide or functional derivatives of antisense oligonucleotides of apoptosis-specific eIF-5A as described herein are fragments, variants, analogs, or chemical derivatives of apoptosis-specific eIF-5A that retain Apoptosis-specific eIF-5A activity or immunological cross reactivity with an antibody specific for apoptosis-specific eIF-5A. A fragment of the apoptosis-specific eIF-5A polypeptide refers to any subset of the molecule.

Functional variants can also contain substitutions of similar amino acids that result in no change or an insignificant change in function. Amino acids that are essential for function can be identified by methods known in the art, such as site-directed mutagenesis or alanine-scanning mutagenesis (Cunningham et al. (1989) Science 244:1081-1085). The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al. (1992) J. Mol. Biol. 224:899-904; de Vos et al. (1992) Science 255:306-312).

A "variant" refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. A "homolog" refers to a fragment or variant sequence from a different animal genus or species. An "analog" refers to a non-natural molecule substantially similar to or functioning in relation to the entire molecule, a variant or a fragment thereof.

Variant peptides include naturally occurring variants as well as those manufactured by methods well known in the art. Such variants can readily be identified/made using molecular techniques and the sequence information disclosed herein. Further, such variants can readily be distinguished from other proteins based on sequence and/or structural homology to the eIF-5A or DHS proteins of the present invention. The degree of homology/identity present will be based primarily on whether the protein is a functional variant or non-functional variant, the amount of divergence present in the paralog family and the evolutionary distance between the orthologs.

Non-naturally occurring variants of the eIF-5A or DHS polynucleotides, antisense oligonucleotides, or proteins of the present invention can readily be generated using recombinant techniques. Such variants include, but are not limited to deletions, additions and substitutions in the nucleotide or amino acid sequence. For example, one class of substitutions are conserved amino acid substitutions. Such substitutions are those that substitute a given amino acid in a protein by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306-1310 (1990).

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, e.g. Sambrook, J. et. al., Molecular Cloning: A Laboratory Manual, $2^{nd}$ edition, Cold Spring Harbour Press, Cold Spring Harbor, N.Y., 1989.

The choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. High stringency conditions means that the hybridization solution contains 6×S.S.C., 0.01 M EDTA, 1×Denhardt's solution and 0.5% SDS. Hybridization is carried out at about 68° C. for about 3 to 4 hours for fragments of cloned DNA and for about 12 to 16 hours for total eucaryotic DNA. For lower stringencies, the temperature of hybridization is reduced to about 42° C. below the melting temperature ($T_m$) of the duplex. The $T_m$ is known to be a function of the G-C content and duplex length as well as the ionic strength of the solution.

As used herein, the phrase "hybridizes to a corresponding portion" of a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridization under appropriate conditions. For example, a 100 nucleotide long sense molecule will recognize and hybridize to an approximately 100 nucleotide portion of a nucleotide sequence, so long as there is about 70% or more sequence similarity between the two sequences. It is to be understood that the size of the "corresponding portion" will allow for some mismatches in hybridization such that the "corresponding portion" may be smaller or larger than the molecule which hybridizes to it, for example 20-30% larger or smaller, preferably no more than about 12-15% larger or smaller.

In addition, functional variants of polypeptides can also contain substitution of similar amino acids that result in no change or an insignificant change in function. Amino acids that are essential for function can be identified by methods known in the art, such as site-directed mutagenesis or alanine-scanning mutagenesis (Cunningham et al., Science 244: 1081-1085 (1989)). The latter procedure introduces single alanine mutations at every residue in the molecule. The resulting mutant molecules are then tested for biological activity or in assays.

The present invention also provides other agents that can inhibit or reduce expression of apoptosis-specific eIF-5A or DHS. One such agent includes small inhibitory RNAs ("siRNA"). siRNA technology has been emerging as a viable alternative to antisense oligonucleotides since lower concentrations are required to achieve levels of suppression that are equivalent or superior to those achieved with antisense oligonucleotides (Thompson, 2002). Long double-stranded RNAs have been used to silence the expression of specific genes in a variety of organisms such as plants, nematodes, and fruit flies. An RNase-III family enzyme called Dicer processes these long double stranded RNAs into 21-23 nucleotide small interfering RNAs which are then incorporated into an RNA-induced silencing complex (RISC). Unwinding of the siRNA activates RISC and allows the single-stranded siRNA to guide the complex to the endogenous mRNA by base pairing. Recognition of the endogenous mRNA by RISC results in its cleavage and consequently makes it unavailable for translation. Introduction of long double stranded RNA into mammalian cells results in a potent antiviral response, which can be bypassed by use of siRNAs. (Elbashir et al., 2001). siRNA has been widely used in cell cultures and routinely achieves a reduction in specific gene expression of 90% or more.

The use of siRNAs has also been gaining popularity in inhibiting gene expression in animal models of disease. A recent study demonstrated that an siRNA against luciferase was able to block luciferase expression from a co-transfected plasmid in a wide variety of organs in post-natal mice. (Lewis et al., 2002). An siRNA against Fas, a receptor in the TNF family, injected hydrodynamically into the tail vein of mice was able to transfect greater than 80% of hepatocytes and decrease Fas expression in the liver by 90% for up to 10 days after the last injection (Song et al., 2003). The Fas siRNA was also able to protect mice from liver fibrosis and fulminant hepatitis. The development of sepsis in mice treated with a lethal dose of lipopolysaccharide was inhibited by the use of an siRNA directed against TNF-α (Sørensen et al., 2003). SiRNA has the potential to be a very potent drug for the inhibition of specific gene expression in vitro in light of their long-lasting effectiveness in cell cultures and their ability to transfect cells in vivo and their resistance to degradation in serum in vivo (Bertrand et al., 2002) in vivo.

Figure 64:
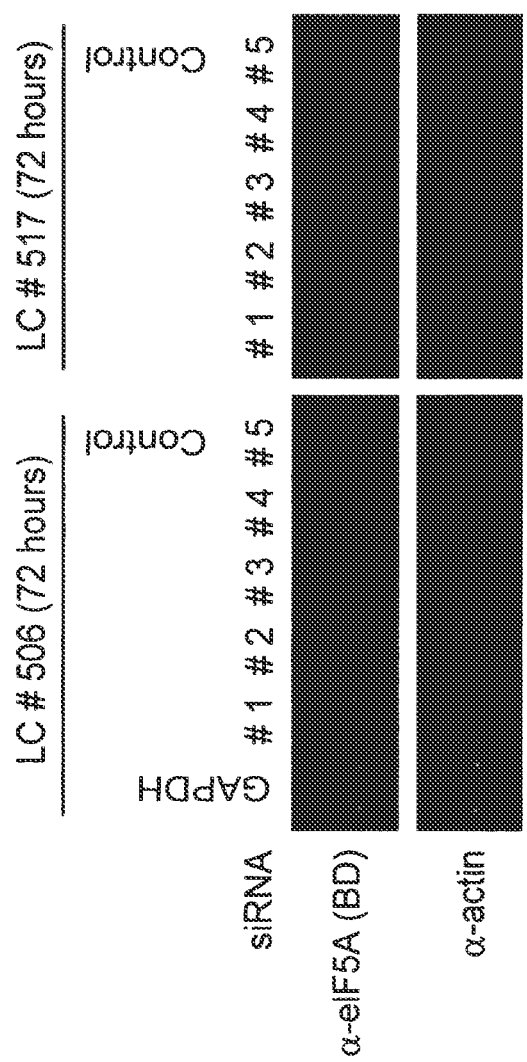
FIG. 64 shows that cells transfected with apoptosis-specific eIF-5A siRNA produced less apoptosis factor 5a protein.
Figure 65:
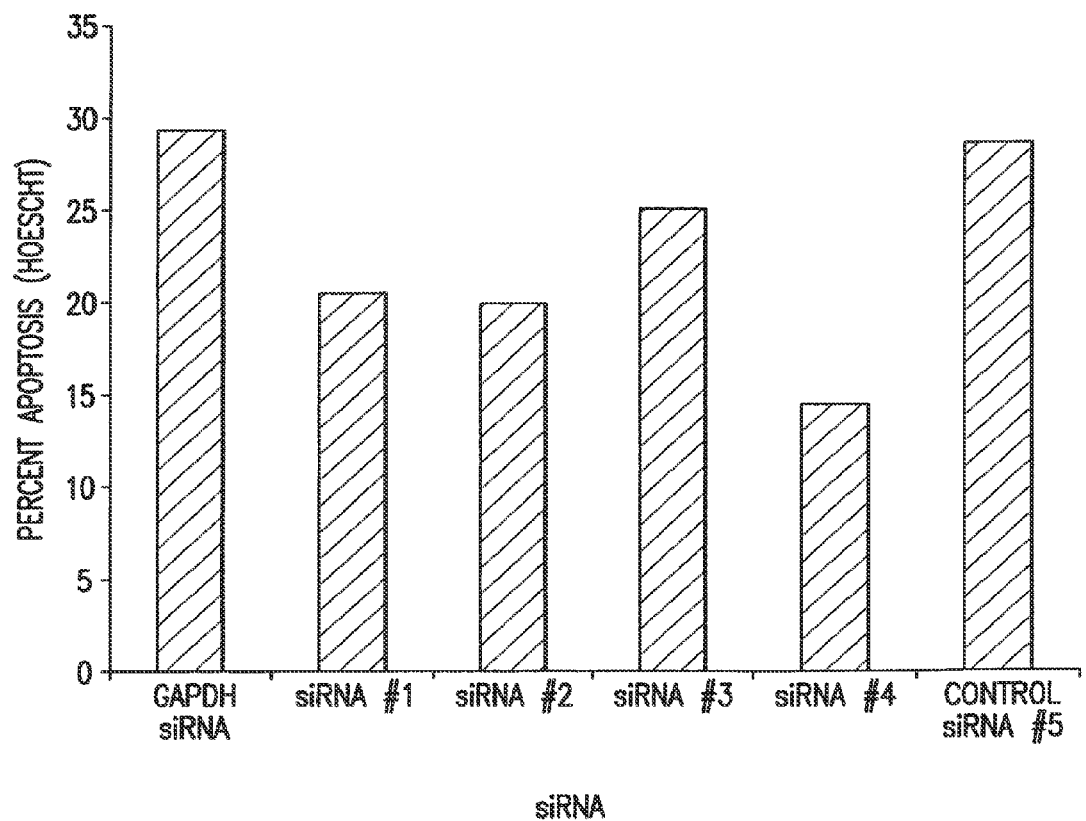
FIGS. 65-67 shows that cells transfected with apoptosis-specific eIF-5A siRNA had a lower percentage of cells undergoing apoptosis after exposure to amptothecin and TNF-α than untransfected cells.
Figure 66:
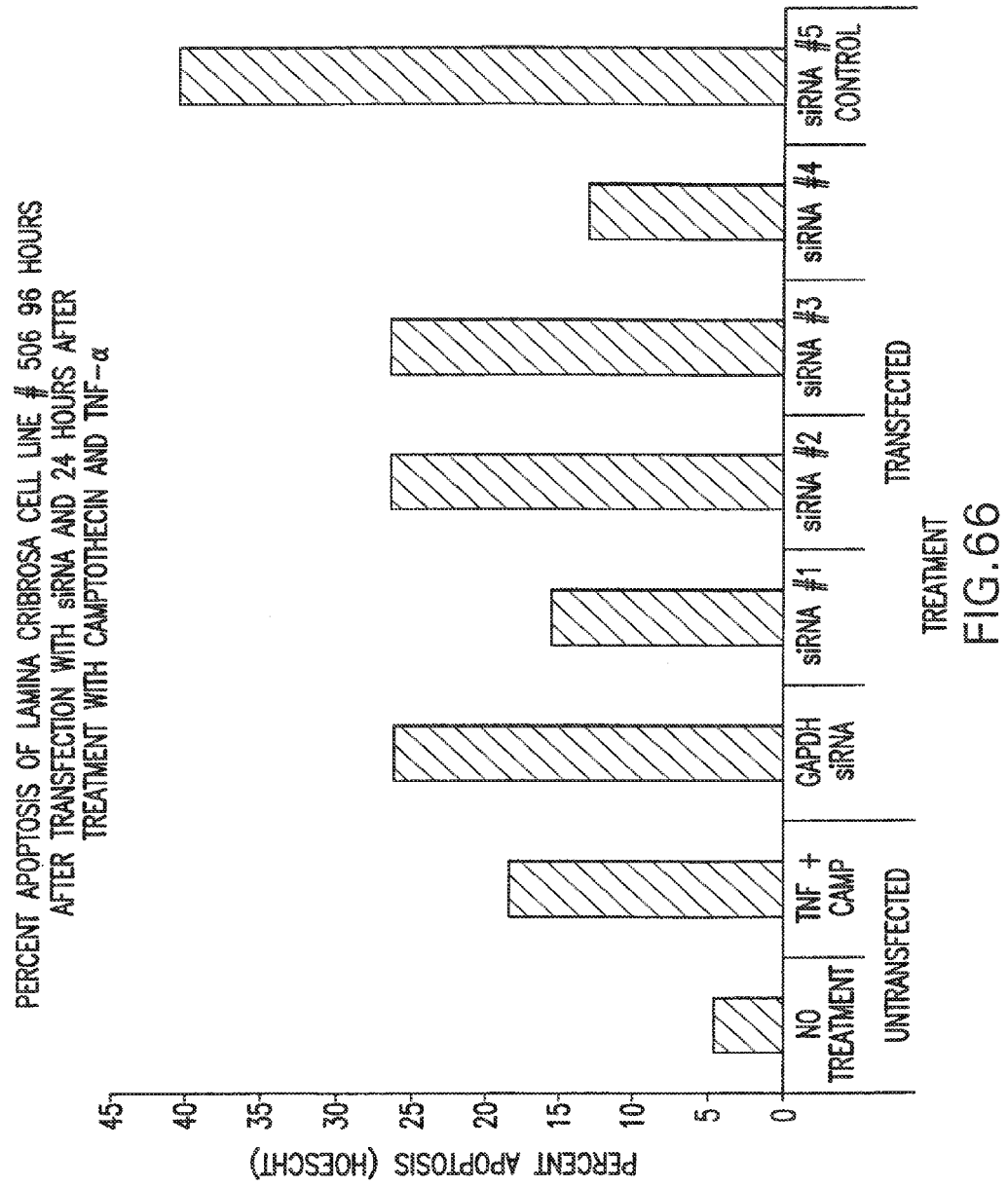
Figure 67:
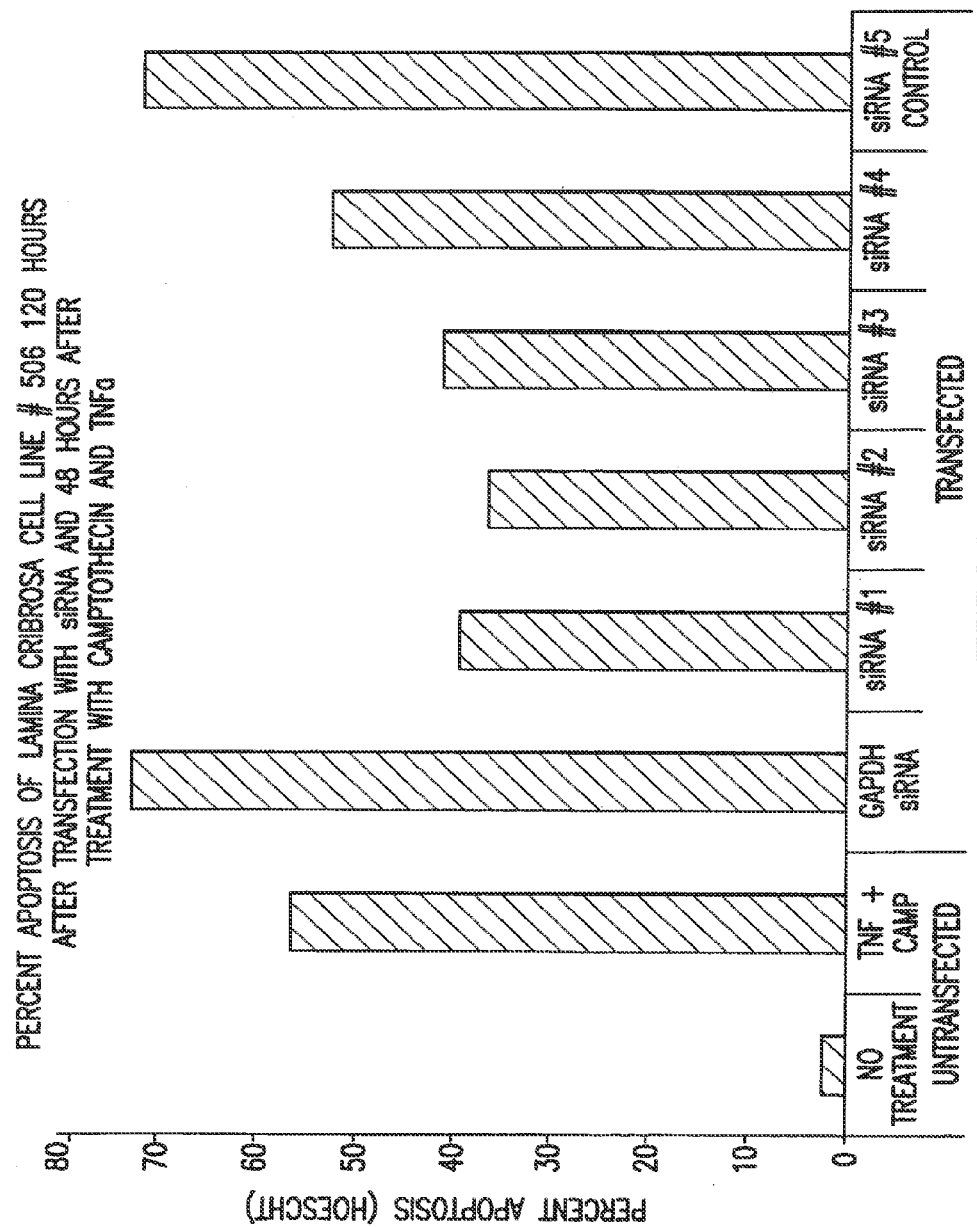

The present inventors have transfected cells with siRNAs of apoptosis-specific eIF-5A and studied the effects on expression of apoptosis-specific eIF-5A. FIG. 64 shows that cells transfected with apoptosis-specific eIF-5A siRNA produced less apoptosis-specific eIF-5A protein. FIGS. 65-67 show that cell populations transfected with apoptosis-specific eIF-5A siRNAs have a lower percentage of cells undergoing apoptosis after exposure to amptothecin and TNF-α as compared to cells not having been transfected with apoptosis-specific eIF-5A siRNAs. Thus, one embodiment of the present invention provides for inhibiting expression of apoptosis-specific eIF-5A in cells by transfecting the cells with a vector comprising a siRNAs of apoptosis-specific eIF-5A.

Preferred siRNAs of apoptosis-specific eIF-5A include those that have SEQ ID NO: 31, 31, 32, and 33. Additional siRNAs include those that have substantial sequence identity to those enumerated (i.e. 90% homology) or those having sequences that hybridize under highly stringent conditions to the enumerated SEQ NOs. What is meant by substantial sequence identity and homology is described above with respect to antisense oligonucleotides of the present invention. The term "siRNAs of apoptosis-specific eIF-5A" include functional variants or derivatives as described above with respect to antisense oligonucleotides of the present invention.

Delivery of siRNA and expression constructs/vectors comprising siRNA are known by those skilled in the art. U.S. applications 2004/106567 and 2004/0086884, which are herein incorporated by reference in their entirety, provide numerous expression constructs/vectors as well as delivery mechanism including viral vectors, non viral vectors, liposomal delivery vehicles, plasmid injection systems, artificial viral envelopes and poly-lysine conjugates to name a few.

One skilled in the art would understand regulatory sequences useful in expression constructs/vectors with antisense oligonucleotides or siRNA. For example, regulatory sequences may be a constitutive promoter, an inducible promoter, a tissue-specific promoter, or a combination thereof.

Many important human diseases are caused by abnormalities in the control of apoptosis. These abnormalities can result in either a pathological increase in cell number (e.g. cancer) or a damaging loss of cells (e.g. degenerative diseases). As non-limiting examples, the methods and compositions of the present invention can be used to prevent or treat the following apoptosis-associated diseases and disorders: neurological/neurodegenerative disorders (e.g., Alzheimer's, Parkinson's, Huntington's, Amyotrophic Lateral Sclerosis (Lou Gehrig's Disease), autoimmune disorders (e.g., rheumatoid arthritis, systemic lupus erythematosus (SLE), multiple sclerosis), Duchenne Muscular Dystrophy (DMD), motor neuron disorders, ischemia, heart ischemia, chronic heart failure, stroke, infantile spinal muscular atrophy, cardiac arrest, renal failure, atopic dermatitis, sepsis and septic shock; AIDS, hepatitis, glaucoma, diabetes (type 1 and type 2), asthma, retinitis pigmentosa, osteoporosis, xenograft rejection, and burn injury.

One such disease caused by abnormalities in the control of apoptosis is glaucoma. Apoptosis in various optical tissues is a critical factor-leading to blindness in glaucoma patients. Glaucoma is a group of eye conditions arising from damage to the optic nerve that results in progressive blindness. Apoptosis has been shown to be a direct cause of this optic nerve damage.

Early work in the field of glaucoma research has indicated that elevated intra-ocular pressure ("IOP") leads to interference in axonal transport at the level of the lamina cribosa (a perforated, collagenous connective tissue) that is followed by the death of retinal ganglion cells. Quigley and Anderson (1976) *Invest. Ophthalmol, Vis. Sci.,* 15, 606-16; Minckler. Bunt, and Klock, (1978) *Invest. Ophthalmol. Vis. Sci.,* 17, 33-50; Anderson and Hendrickson, (1974) *Invest. Ophthalmol. Vis, Sci.,* 13, 771-83; Quigley et al., (1980) *Invest. Ophthalmol. Vis. Sci.,* 19, 505-17. Studies of animal models of glaucoma and post-mortem human tissues indicate that the death of retinal ganglion cells in glaucoma occurs by apoptosis. Garcia-Valenzuela et. al., (1995) *Exp. Eye Res.,* 61, 33-44; Quigley et al., (1995) *Invest. Ophthalmol. Vis. Sci.,* 36, 774-786; Monard, (1998) In: Haefliger IO, Flammer J (eds) *Nitric oxide and Endothelin in the Pathogenesis of Glaucoma,* New York, N.Y., Lippincott-Raven, 213-220. The interruption of axonal transport as a result of increased LOP may contribute to retinal ganglion cell death by deprivation of trophic factors. Quigley, (1995) *Aust NZJ Ophthalmol,* 23(2), 85-91. Optic nerve head astrocytes in glaucomatous eyes have also been found to produce increased levels of some neurotoxic substances. For example, increased production of tumor necrosis factor-α (TNF-α) (Yan et al., (2000) *Arch. Ophthalmol.,* 118, 666-673), and nitric oxide synthase (Neufeld et al., (1997) *Arch. Ophthalmol.,* 115, 497-503), the enzyme which gives rise to nitric oxide, has been found in the optic nerve head of glaucomatous eyes. Furthermore, increased expression of the inducible form of nitric oxide synthase (iNOS) and TNF-α by activated retinal glial cells have been observed in rat models of hereditary retinal diseases. Cotinet et al., (1997) *Glia,* 20, 59-69; de Kozak et al., (1997) *Ocul. Immunoi. Inflamm.,* 5, 85-94; Goureau et al., (1999) *J. Neurochem,* 72, 2506-2515. In the glaucomatous optic nerve head, excessive nitric oxide has been linked to the degeneration of axons of retinal ganglion cells. Arthur and Neufeld, (1999) *Surv Ophthalmol,* 43 (Suppl 1), S129-S135. Finally, increased production of TNF-α by retinal glial cells in response to simulated ischemia or elevated hydrostatic pressure has been shown to induce apoptosis in co-cultured retinal ganglion cells. Tezel and Wax, (2000) *J. Neurosci.,* 20(23), 8693-8700.

Protecting retinal ganglion cells from degeneration by apoptosis is under study as a potential new treatment for blindness due to glaucoma. Antisense oligonucleotides have been used successfully in animal models of eye disease. In a model of transient global retinal ischemia, expression of caspase 2 was increased during ischemia, primarily in the inner nuclear and ganglion cell layers of the retina. Suppression of caspase using an antisense oligonucleotide led to significant histopathologic and functional improvement as determined by electroretinogram. Singh et al., (2001) *J. Neurochem.,* 77(2), 466-75. Another study demonstrated that, upon transfection of the optic nerve, retinal ganglion cells upregulate the pro-apoptotic protein Bax and undergo apoptosis. Repeated injections of a Bax antisense oligonucleotide into the temporal superior retina of rats inhibited the local expression of Bax and increased the number of surviving retinal ganglion cells following transaction of the optic nerve. Isenmann et al., (1999) *Cell Death Differ.,* 6(7). 673-82.

Delivery of antisense oligonucleotides to retinal ganglion cells has been improved by encapsulating the oligonucleotides in liposomes, which were then coated with the envelope of inactivated hemagglutinating virus of Japan (HVJ; Sendai virus) by fusion (HVJ liposomes). Intravitreal injection into mice of FITC-labeled antisense oligonucleotides encapsulated in HVJ liposomes resulted in high fluorescence within 44% of the cells in the ganglion layer which lasted three days while fluorescence with naked FITC-labeled antisense oligonucleotide disappeared after one day. Hangai et al., (1998) *Arch Ophthalmol,* 116(7), 976.

One method of preventing or reducing apoptosis of the present invention is directed to preventing or reducing apoptosis in cells and tissues of the eye, such as but not limited to, astrocytes, retinal ganglion., retinal glial cells and lamina cribosa. Death of retinal ganglion cells in glaucoma occurs by apoptosis and which leads to blindness. Thus, providing a method of inhibiting or reducing apoptosis in retinal ganglion cells or by protecting retinal ganglion cells from degeneration by apoptosis provides a novel treatment for prevention of blindness due to glaucoma.

The present invention provides a method for preventing or inhibiting retinal ganglion cell death in a glaucomatous eye, by suppressing expression of apoptosis-specific eIF-5A. Inhibiting the expression of apoptosis-specific eIF-5A reduces apoptosis. Apoptosis-specific eIF-5A is a powerful gene that appears to regulate the entire apoptotic process. Thus, controlling apoptosis in the optic nerve head indicates that blocking expression of apoptosis-specific eIF-5A provides a treatment for glaucoma.

Suppression of expression of apoptosis-specific eIF-5A is accomplished by administering an antisense oligonucleotides or a siRNA of human apoptosis-specific eIF-5A to cells of the eye such as, but not limited to lamina cribrosa, astrocytes, retinal ganglion, or retinal glial cells. Antisense oligonucleotides and siRNAs are as defined above, i.e. have a nucleotide sequence encoding at least a portion of an apoptosis-specific eIF-5A polypeptide. Exemplary antisense oligonucleotides useful in this aspect of the invention comprise SEQ ID NO:26 or 27 or oligonucleotides that bind to a sequence complementary to SEQ ID NO:26 or 27 under high stringency conditions and which inhibit expression of apoptosis-specific eIF-5A.

Another embodiment of the invention provides a method of suppressing expression of apoptosis-specific eIF-5A in lamina cribosa cells, astrocyte cells, retinal ganglion cells or retinal glial cells. Antisense oligonucleotides or siRNAs, such as but not limited to, SEQ ID NO:26 and 27, targeted against human apoptosis-specific eIF-5A are administered to lamina cribosa cells, astrocyte cells, retinal ganglion cells or retinal glial cells. The cells may be of human origin.

In addition to having a role in apoptosis, eIF5A may also play a role in the immune response. The present inventors have discovered that apoptosis-specific eIF-5A levels correlate with elevated levels of two cytokines (Interleukin 1-beta "IL-1β" and interleukin 18 "IL-18") in ischemic heart tissue, thus further proving that apoptosis-specific eIF-5A is involved in cell death as it is present in ischemic heart tissue. This apoptosis-specific eIF-5A/interleukin correlation is not seen in non-ischemic heart tissue. See FIGS. 50A-F and 51. Using PCR measurements, levels of apoptosis-specific eIF-5A, and proliferating eIF-5A ("eIF-5A2")—another isoform), IL-1β, and IL-18 were measured and compared in various ischemic heart tissue (from coronary bypass graft and valve (mitral and atrial valve) replacement patients).

The correlation of apoptosis-specific eIF-5A to these potent interleukins further suggests that the inflammation and apoptosis pathways in ischemia may be controlled via controlling levels of apoptosis-specific eIF-5A. Further evidence that apoptosis-specific eIF-5A is involved in the immune response is suggested by the fact that human peripheral blood mononuclear cells (PBMCs) normally express very low levels of eIF-5A, but upon stimulation with T-lymphocyte-specific stimuli expression of apoptosis-specific eIF-5A increases dramatically (Bevec et al., 1994). This suggests a role for apoptosis-specific eIF-5A in T-cell proliferation and/or activation. Since activated T cells are capable of producing a wide variety of cytokines; it is also possible that apoptosis-specific eIF-5A may be required as a nucleocytoplasmic shuttle for cytokine mRNAs. The authors of the above referenced article also found elevated levels of eIF5A in the PBMCs of HIV-1 patients which may contribute to efficient HIV replication in these cells as eIF5A has been demonstrated to be a cellular binding factor for the HIV Rev protein and required for HIV replication (Ruhl et al., 1993).

More recently, eIF-5A expression was found to be elevated during dendritic cell maturation (Kruse et al., 2000). Dendritic cells are antigen-presenting cells that sensitize helper and killer T cells to induce T cell-mediated immunity (Steinman, 1991). Immature dendritic cells lack the ability to stimulate T cells and require appropriate stimuli (i.e. inflammatory cytokines and/or microbial products) to mature into cells capable of activating T cells. An inhibitor of deoxyhypusine synthase, the enzyme required to activate eIF5A, was found to inhibit T lymphocyte activation by dendritic cells by preventing CD83 surface expression (Kruse et al., 2000). Thus, eIF5A may facilitate dendritic cell maturation by acting as a nucleocytoplasmic shuttle for CD83 mRNA.

In both of these studies (Bevec et al., 1994; Kruse et al., 2000) implicating a role for eIF5A in the immune system, the authors did not specify nor identify which isoform of eIF5A they were examining, nor did they have a reason to. As discussed above, humans are known to have two isoforms of eIF5A, apoptosis-specific eIF-5A ("eIF5A1") and proliferating eIF-5A ("eIF-5A2"), both encoded on separate chromosomes. Prior to the present inventors discoveries it was believed that both of these isoforms were functional redundant. The oligonucleotide described by Bevec et al., that was used to detect eIf5A mRNA in stimulated PBMCs had 100% homology to human apoptosis-specific eIF-5A and the study pre-dates the cloning of proliferating &IF-5A. Similarly, the primers described by Kruse et al. that were used to detect eIF5A by reverse transcription polymerase chain reaction during dendritic cell maturation had 100% homology to human apoptosis-specific eIF-5A.

Figure 78:
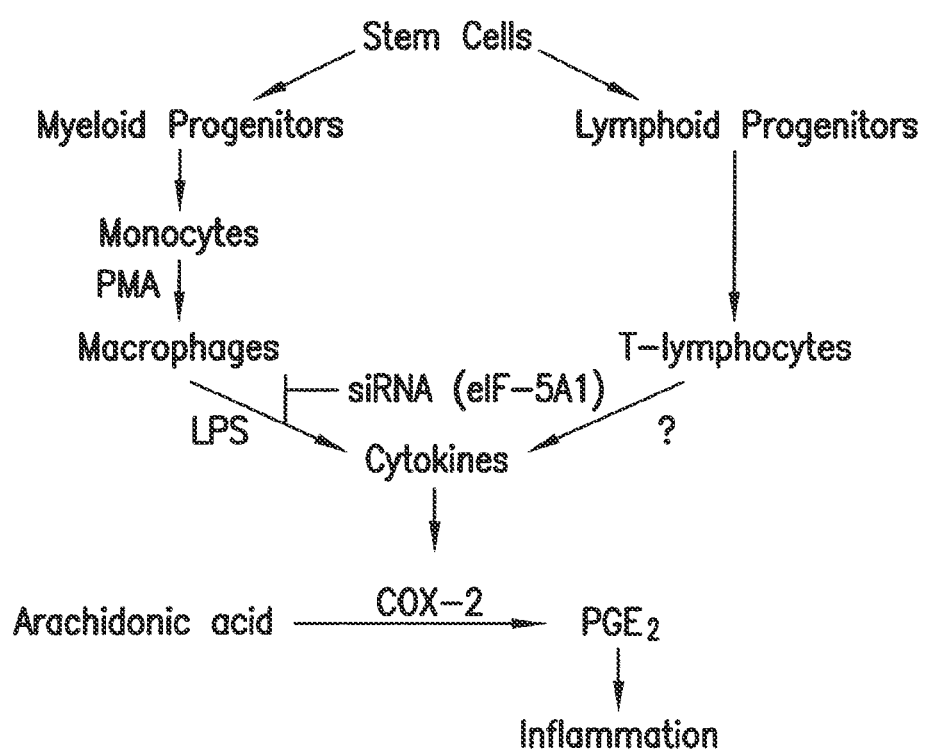
FIG. 78 depicts stem cell differentiation and the use of siRNAs against apoptosis-specific eIF-5A to inhibit cytokine production.

The present invention relates to controlling the expression of apoptosis-specific eIF-5A to control the rate of dendritic cell maturation and PBMC activation, which in turn may control the rate of T cell-mediated immunity. The present inventors studied the role of apoptosis-specific eIF-5A in the differentiation of monocytes into adherent macrophages using the U-937 cell line, as U-937 is known to express eIF-5A mRNA (Bevec et al., 1994). U-937 is a human monocyte cell line that grows in suspension and will become adherent and differentiate into macrophages upon stimulation with PMA. When PMA is removed by changing the media, the cells become quiescent and are then capable of producing cytokines (Barrios-Rodiles et al., J. Immunol., 163:963-969 (1999)). In response to lipopolysaccharide (LPS), a factor found on the outer membrane of many bacteria known to induce a general inflammatory response, the macrophages produce both TNF-α and IL-1β (Barrios-Rodiles et al., 1999). See FIG. 78 showing a chart of stem cell differentiation and the resultant production of cytokines. The U-937 cells also produce IL-6 and IL-10 following LPS-stimulation (Izeboud et al., J. Receptor & Signal Transduction Research, 19(1-4): 191-202. (1999)).

Using U-937 cells, it was shown that apoptosis-specific eIF-5A is upregulated during monocyte differentiation and TNF-α secretion. See FIG. 77. Accordingly, one aspect of the invention provides for a method of inhibiting or delaying maturation of macrophages to inhibit or reduce the production of cytokines. This method involves providing an agent that is capable of reducing the expression of either DHS or apoptosis-specific eIF-5A. By reducing or eliminating expression of DHS, apoptosis-specific eIF-5A activation will be reduced or eliminated. Since, apoptosis-specific eIF-5A is upregulated during monocyte differentiation and TNF-α secretion, it is believed that it is necessary for these events to occur. Thus, by reducing or eliminating activation of apoptosis-specific eIF-5A or by directly reducing or eliminating apoptosis-specific eIF-5A expression, monocyte differentiation and TNF-α secretion can be reduced or eliminated. Any agent capable of reducing the expression of DHS or apoptosis-specific eIF-5A may be used and includes, but is not limited to antisense oligonucleotides or siRNAs as described herein.

The present inventors have studied the ability of human apoptosis-specific eIF-5A to promote translation of cytokines by acting as a nucleocytoplasmic shuttle for cytokine mRNAs in vitro using a cell line known to predictably produce cytokine(s) in response to a specific stimulus. Some recent studies have found that human liver cell lines can respond to cytokine stimulation by inducing production of other cytokines. HepG2 is a well characterized human hepatocellular carcinoma cell line found to be sensitive to cytokines. In response to IL-1β, HepG2 cells rapidly produce TNF-α mRNA and protein in a dose-dependent manner (Frede et al., 1996; Rowell et al., 1997; Wordemann et al., 1998). Thus, HepG2 cells were used as a model system to study the regulation of TNF-α production. The present inventors have shown that inhibition of human apoptosis-specific eIF-5A expression in HepG2 cells caused the cells to produce less TNF-α after having been transfected with antisense oligonucleotide of directed toward apoptosis factor 5A.

Thus one embodiment of the present invention provides a method for reducing levels of a cytokine. The method involves administering an agent capable of reducing expression of apoptosis factor 5A1. Reducing expression of apoptosis factor 5A1 also reduces expression of the cytokine and thus leads to a decreased amount of the cytokine produced by cell. The cytokine is a preferably a pro-inflammatory cytokine, including, but not limited to IL-1, IL-18, IL-6 and TNF-α.

Antisense oligonucleotides are as discussed above. Exemplary antisense oligonucleotides of human apoptosis-specific eIF-5A are selected from the group consisting of SEQ ID NO: 35, 37, and 39 or is an antisense nucleotide that hybridizes under highly stringent conditions to a sequence selected from the group consisting of SEQ ID NO: 35, 37, and 39.

An agent may also comprise a siRNA of human apoptosis-specific eIF-5A and are as discussed above. Exemplary siRNAs have a sequence selected from the group consisting of SEQ ID NO: 30, 31, 32 and 33 or is a siRNA that hybridizes under highly stringent conditions to a sequence selected from the group consisting of SEQ ID NO: 30, 31, 32 and 33. FIGS. 65-67 show that cells transfected with human apoptosis-specific eIF-5A siRNAs have a lower percentage of cells undergoing apoptosis after exposure to amptothecin and TNF-α.

Figure 52:
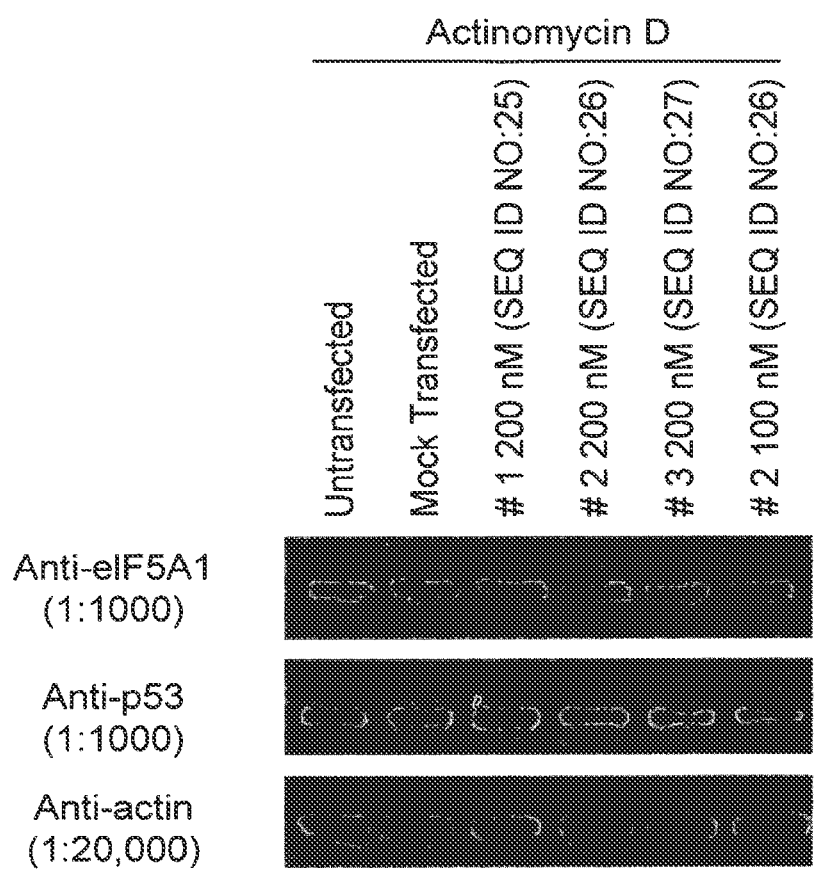
FIG. 52 shows the levels of protein produced by RKO cells after being treated with antisense oligo 1, 2 and 3 (of apoptosis-specific eIF-5A) (SEQ ID NO: 35, 37 and 39, respectively). The RKO cells produced less apoptosis-specific eIF-5A as well as less p53 after having been transfected with the antisense apoptosis-specific eIF-5A oligonucleotides.

The present invention is also directed to a method for reducing the expression of p53. This method involves administering an agent capable of reducing expression of apoptosis factor 5A, such as the antisense oligonucleotides or the siRNAs described above. Reducing expression of apoptosis-specific eIF-5A reduces expression of p53 as shown in FIG. 52 and example 10.

Figure 63:
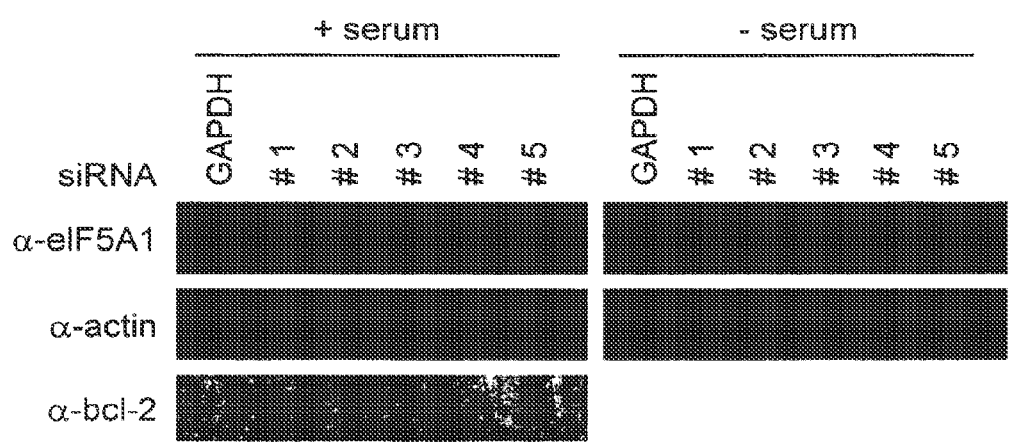
FIG. 63 shows that cells transfected with apoptosis-specific eIF-5A siRNA produced less apoptosis-specific eIF-5A protein and in addition, produced more Bcl-2 protein. A decrease in apoptosis-specific eIF-5A expression correlates with an increase in BCL-2 expression.

The present invention is also directed to a method for increasing the expression of Bcl-2. This method entails administering an agent capable of reducing expression of human apoptosis-specific eIF-5A. Preferred agents include antisense oligonucleotides and siRNAs described above. Reducing expression of apoptosis-specific eIF-5A increases expression of Bcl-2 as shown in FIG. 63 and example 13. FIG. 63 shows that cells transfected with apoptosis-specific eIF-5A siRNA produced less apoptosis-specific eIF-5A protein and in addition, produced more Bcl-2 protein. A decrease in apoptosis-specific eIF-5A expression correlates with an increase in BCL-2 expression.

The present invention also provides a method for reducing levels of TNF-alpha in a patient in need thereof comprising administering to said patient either antisense oligonucleotide or siRNAs of apoptosis-specific eIF-5A as described above. As demonstrated in FIG. 69 and example 14, cells transfected with antisense apoptosis-specific eIF-5A oligonucleotides of the present invention produced less TNF-α after induction with IL-1 than cells not transfected with such antisense oligonucleotides.

Further, the present invention provides a method of treating pathological conditions characterized by an increased IL-1, TNF-alpha, IL-61 or IL-18 level comprising administering to a mammal having said pathological condition, agents to reduce expression of apoptosis-specific eIF-5A as described above (antisense oligonucleotides and siRNA).

Known pathological conditions characterized by an increase in IL-1, TNF-alpha, or Il-6 levels include, but are not limited to arthritis-rheumatoid and osteo arthritis, asthma, allergies, arterial inflammation, crohn's disease, inflammatory bowel disease, (ibd), ulcerative colitis, coronary heart disease, cystic fibrosis, diabetes, lupus, multiple sclerosis, graves disease, periodontitis, glaucoma & macular degeneration, ocular surface diseases including keratoconus, organ ischemia-heart, kidney, repurfusion injury, sepsis, multiple myeloma, organ transplant rejection, psoriasis and eczema. Thus, reducing expression of apoptosis-specific eIF-5A with the antisense oligonucleotides, siRNAs and methods of the present invention, may provide relief from these pathological conditions.

The present invention also provides a method of delivering siRNA to mammalian lung cells in vivo. siRNAs directed against apoptosis-specific eIF-5A were administered intranasally (mixed with water) to mice. 24 hours after administration of the siRNA against apoptosis-specific eIF-5A, lipopolysaccharide (LPS) was administered intranasally to the mice. After another 24 hours, the right lung was removed and myeloperoxidase was measured. The mouse apoptosis-specific eIF-5A siRNA suppressed myeloperoxidase by nearly 90% as compared to the control siRNA. In the study, there were 5 mice in each group. The results of this study show that siRNA can be delivered successfully in vivo to lung tissue in mammals, and that siRNA directed against apoptosis-specific eIF-5A inhibits the expression of apoptosis-specific eIF-5A resulting in a suppression of myeloperoxidase production. Myeloperoxidase ("MPO") is a lysosomal enzyme that is found in neutrophils. The myeloperoxidase is an enzyme that uses hydrogen peroxidase to convert chloride to hypochlorous acid. The hypochlorous acid reacts with and destroys bacteria. Myeloperoxidase is also produced when arteries are inflamed. Thus, it is clear that myeloperoxidase is associated with neutrophils and the inflammation response. The present inventors have shown that by down regulating apoptosis-specific eIF-5A with siRNAs shows a marked decrease in the myeloperoxidase in lung tissue after exposed to LPS (which normally produces an inflammatory response involving the production of myeloperoxidase). Thus, the present inventors have shown that using siRNAs against apoptosis-specific eIF-5A can decrease or suppress the amount of myeloperoxidase in lung tissue and thus decrease or suppress the inflammation response.

LPS is a macromolecular cell surface antigen of bacteria that when applied in vivo triggers a network of inflammatory responses. Intranasally delivering LPS causes an increase in the number of neutrophils in the lungs. One of the primary events is the activation of mononuclear phagocytes through a receptor-mediated process, leading to the release of a number of cytokines, including TNF-α. In turn, the increased adherence of neutrophils to endothelial cells induced by TNF-α leads to massive infiltration in the pulmonary space.

Thus, not only have the present inventors shown the correlation between apoptosis-specific eIF-5A and the immune response, as well as shown that siRNAs against apoptosis-specific eIF-5A an suppress the production of myeloperoxidase (i.e. part of the inflammation response). The inventors have also shown that it is possible to deliver siRNAs in vivo to lung tissue by simple intranasal delivery. The siRNAs were mixed only in water. This presents a major breakthrough and discovery as others skilled in the art have attempted to design acceptable delivery methods for siRNA.

The ability to reduce inflammation is of direct importance in many diseases. MPO levels are a critical predictor of heart attacks and cytokine-induced inflammation caused by autoimmune disorders. This ability to decrease or suppress the inflammation response may serve useful in treating inflammation related disorders such as auto immune disorders. In addition, the ability to lower MPO could be a means of protecting patients from ischemic events and heart attacks.

In another experiment, mice were similarly treated with siRNAs directed against apoptosis-specific eIF-5A. Lipopolysaccharide (LPS) was administered to the mice to induce inflammation and an immune system response. Under control conditions, LPS kills thymocytes, which are important immune system precursor cells created in the thymus to fend off infection. However, using the siRNAs directed against apoptosis-specific eIF-5A allowed approximately 90% survivability of the thymocytes in the presence of LPS. When thymocytes are destroyed, since they are precursors to T cells, the body's natural immunity is compromised by not being able to produce T cells and thus can't ward off bacterial infections and such. Thus, using the siRNAs against apoptosis-specific eIF-5A can be used to reduce inflammation (as shown by a lower level of MPO in the first example) without destroying the body's natural immune defense system.

One embodiment of the present invention relates to reducing NFk beta ("NFkB") levels by inhibiting apoptosis-specific eIF-5A with siRNAs targeted at apoptosis-specific eIF-5A. NFk beta is a major cell-signaling molecule for inflammation—its activation induces the expression of COX-2, which leads to tissue inflammation. The expression of the COX-2-encoding gene, believed to be responsible for the massive production of prostaglandins at inflammatory sites, is transcriptionally regulated by NFkB. NFkB resides in the cytoplasm of the cell and is bound to its inhibitor. Injurious and inflammatory stimuli release NFkB from the inhibitor. NFkB moves into the nucleus and activates the genes responsible for expressing COX-2. Thus, by reducing levels of NFk beta., inflammation can be reduced.

Figure 74A:
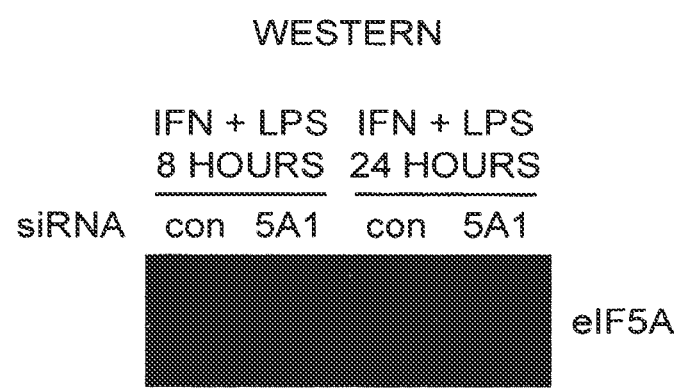
FIG. 74A provides a picture of a Western blot where siRNAs against apoptosis-specific eIF-5A have reduced if not inhibited the production of TNF-α in transfected HT-29 cells.
Figure 74B:
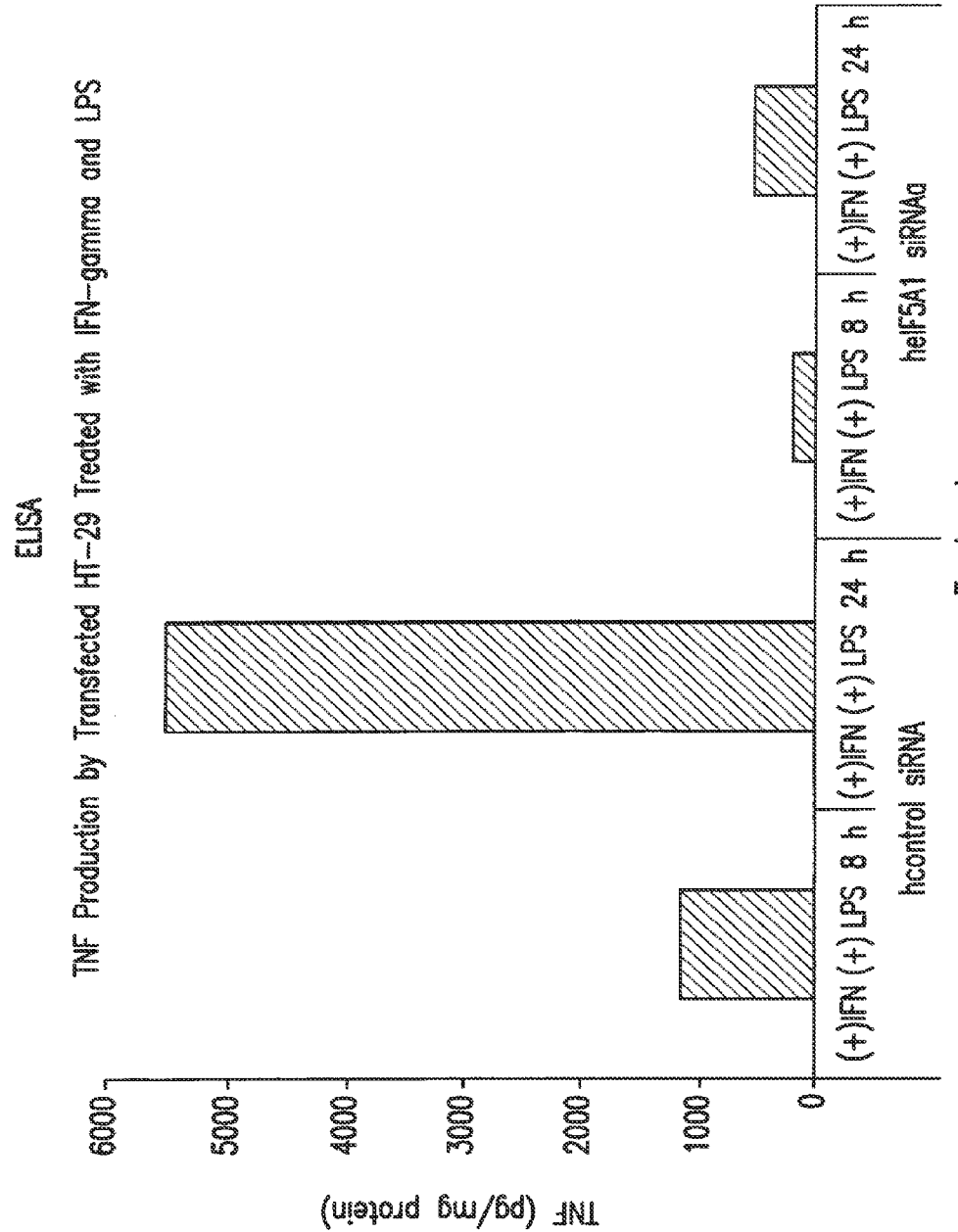
FIG. 74B provides the results of an ELISA.

In one experiment human epithelial cells (HT-29 cells) were treated with siRNA targeted at apoptosis-specific eIF-5A. Inflammation was then induced by NFkB by addition of TINT or interferon gamma and LPS for one hour. The results of this experiment show that inhibiting the expression of apoptosis-specific eIF-5A with siRNAs provided for a reduction in the levels of NFkB that were activated by the gamma interferon and LPS. See FIG. 74.

Figure 109:
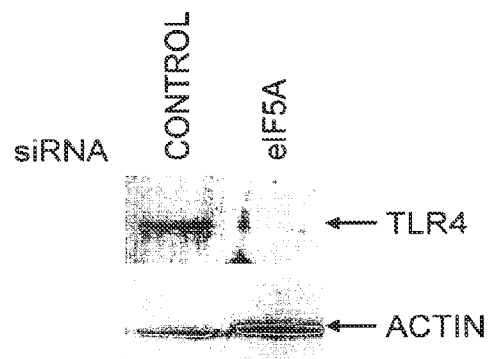
FIG. 109 shows that siRNA mediated down-regulation of apoptosis-specific eIF-5A coincides with a reduction of TLR4.
Figure 110:
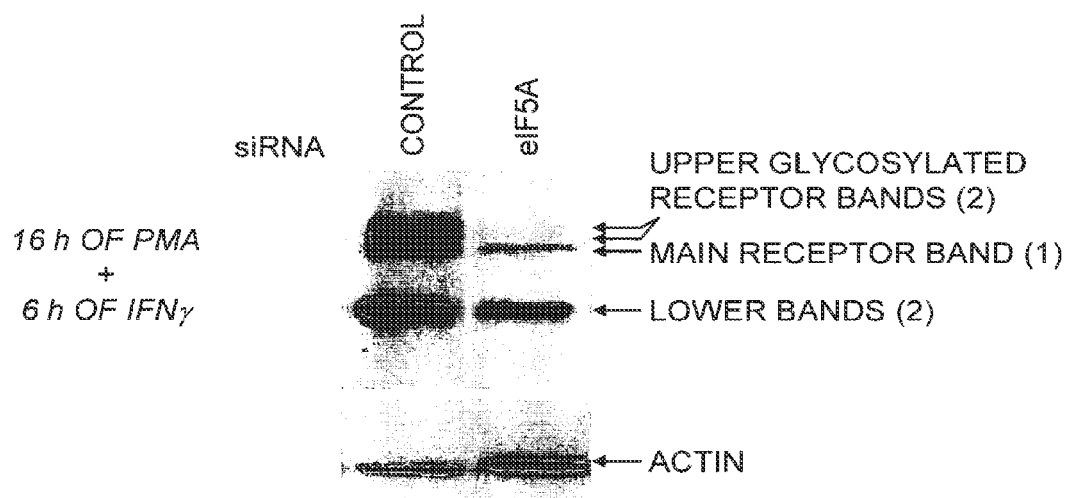
FIG. 110 shows that siRNA mediated down-regulation of apoptosis-specific eIF-5A coincides with fewer glycosylated forms of the interferon gamma receptor in U937 cells.
Figure 111:
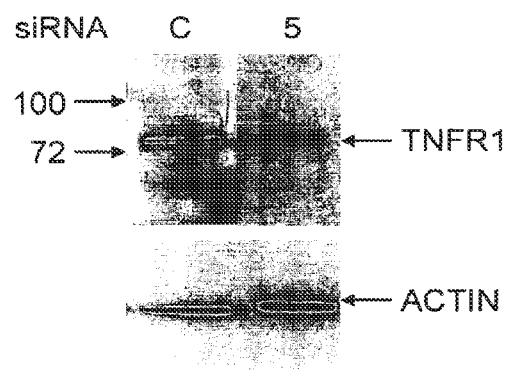
FIG. 111 shows that siRNA mediated down-regulation of apoptosis-specific eIF-5A coincides with a reduction in TNFR1 in U937 cells.

One embodiment of the present invention provides methods of inhibition expression of endogenous apoptosis-specific eIF-5A in a cell. Inhibiting expression is preferably carried out by the use of antisense polynucleotides or siRNAs of apoptosis-specific eIF-5A of the present invention described previously. When expression of endogenous apoptosis-specific eIF-5A occurs various effects on the cell result. For example, a reduction in expression of the various proteins, factors, receptors, cytokines are seen: p53; pro-inflammatory cytokines (See FIG. 112, 113, 114); myeloperoxidase; active NFk beta; TLR4 (See FIG. 109); TNFR-1 (See FIG. 111) and iNOS. A reduction in expression of endogenous apoptosis-specific eIF-5A increases levels expression of Bcl-2 in the cell.

It is understood that the antisense nucleic acids siRNAs of the present invention, where used in an animal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The compositions of this invention can be in a variety of forms. These include, for example, solid, semi-solid and liquid dosage forms, such as tablets, pills, powders, liquid solutions, dispersions or suspensions, liposomes, suppositories, injectable and infusible solutions. The preferred form depends on the intended mode of administration and therapeutic application.

Such compositions can be prepared in a manner well known in the pharmaceutical art. In making the composition the active ingredient will usually be mixed with a carrier, or diluted by a carrier, and/or enclosed within a carrier which can, for example, be in the form of a capsule, sachet, paper or other container. When the carrier serves as a diluent, it can be a solid, semi-solid, or liquid material, which acts as a vehicle, excipient or medium for the active ingredient. Thus, the composition can be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions, suspensions, sterile packaged powders and as a topical patch.

Having now generally described the invention, the same will be more readily understood through reference to the following examples, which are provided by way of illustration. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Detailed descriptions of conventional methods, such as those employed in the construction of vectors and plasmids, the insertion of nucleic acids encoding polypeptides into such vectors and plasmids, the introduction of plasmids into host cells, and the expression and determination thereof of genes and gene products can be obtained from numerous publication, including Sambrook, J. et al., (1989) Molecular Cloning: A Laboratory Manual, $2^{nd}$ ed., Cold Spring Harbor Laboratory Press. All references mentioned herein are incorporated in their entirety.

EXAMPLES

Example 1

Visualization of Apoptosis in Rat Corpus Luteum by DNA Laddering

The degree of apoptosis was determined by DNA laddering. Genomic DNA was isolated from dispersed corpus lineal cells or from excised corpus luteum tissue using the QIAamp DNA Blood Kit (Qiagen) according to the manufacturer's instructions. Corpus luteum tissue was excised before the induction of apoptosis by treatment with PGF-2α, 1 hour and 24 hours after induction of apoptosis. The isolated DNA was end-labeled by incubating 500 ng of DNA with 0.2 µCi [α-$^{32}$P]dCTP, 1 mM Tris, 0.5 mM EDTA, 3 units of Klenow enzyme, and 0.2 pM each of dATP, dGTP, and dTTP at room temperature for 30 minutes. Unincorporated nucleotides were removed by passing the sample through a 1 ml Sepadex G-50 column according to Sambrook et al. The samples were then resolved by Tris-acetate-EDTA (1.8%) gel electrophoresis. The gel was dried for 30 minutes at room temperature under vacuum and exposed to x-ray film at −80° C. for 24 hours.

Figure 16:
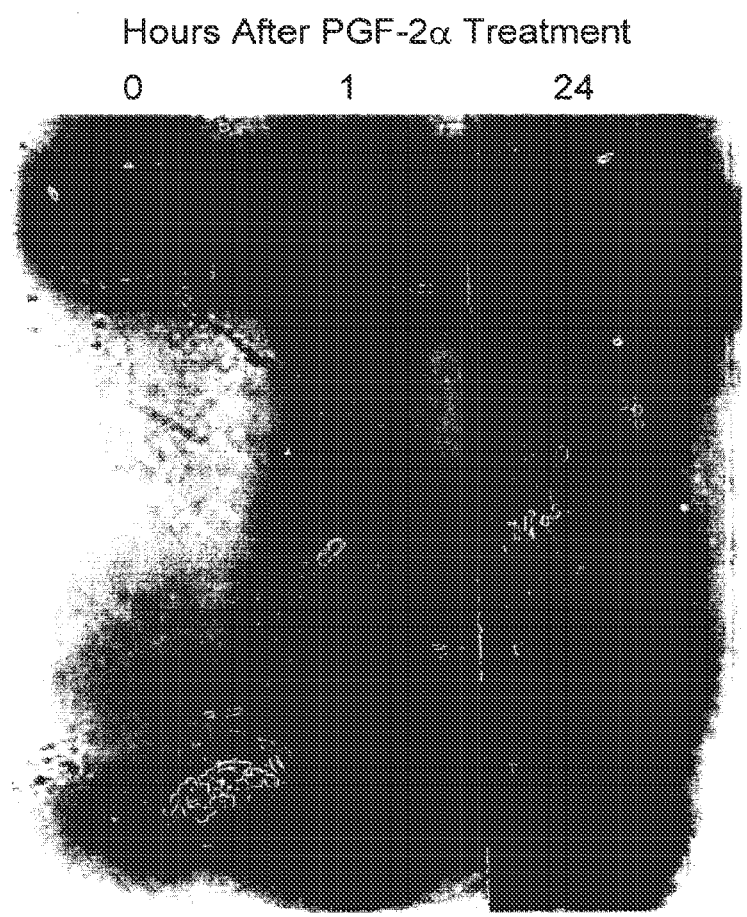
FIG. 16 depicts a DNA laddering experiment in which the degree of apoptosis in superovulated rat corpus lutea was examined after injection with PGF-2α.

In one experiment, the degree of apoptosis in superovulated rat corpus lutea was examined either 0, 1, or 24 hours after injection with PGF-2α. In the 0 hour control, the ovaries were removed without PGF-2α injection. Laddering of low molecular weight DNA fragments reflecting nuclease activity associated with apoptosis is not evident in control corpus luteum tissue excised before treatment with PGF-2α, but is discernible within 1 hour after induction of apoptosis and is pronounced by 24 hours after induction of apoptosis, which is shown in FIG. 16. In this figure, the top panel is an autoradiograph of the Northern blot probed with the $^{32}$P-dCTP-labeled 3'-untranslated region of rat corpus luteum apoptosis-specific DHS cDNA. The lower panel is the ethidium bromide stained gel of total RNA. Each lane contains 10 µg RNA. The data indicate that there is down-regulation of apoptosis-specific transcript following serum withdrawal.

Figure 17:
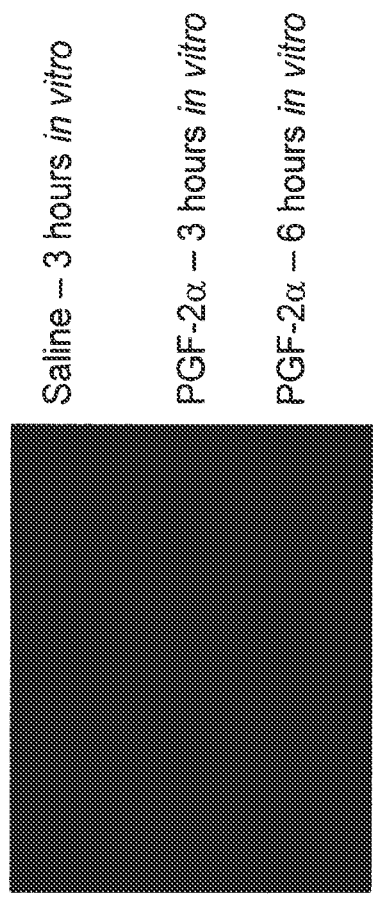
FIG. 17 is an agarose gel of genomic DNA isolated from apoptosing rat corpus luteum showing DNA laddering after treatment of rats with PGF F-2α.

In another experiment, the corresponding control animals were treated with saline instead of PGF-2α. Fifteen minutes after treatment with saline or PGF-2α, corpora lutea were removed from the animals. Genomic DNA was isolated from the corpora lutea at 3 hours and 6 hours after removal of the tissue from the animals. DNA laddering and increased end labeling of genomic DNA are evident 6 hours after removal of the tissue from the PGF-2α-treated animals, but not at 3 hours after removal of the tissue. See FIG. 17. DNA laddering reflecting apoptosis is also evident when corpora lutea are excised 15 minutes after treatment with PGF-2α and maintained for 6 hours under in vitro conditions in EBSS (Gibco). Nuclease activity associated with apoptosis is also evident from more extensive end labeling of genomic DNA.

Figure 18:
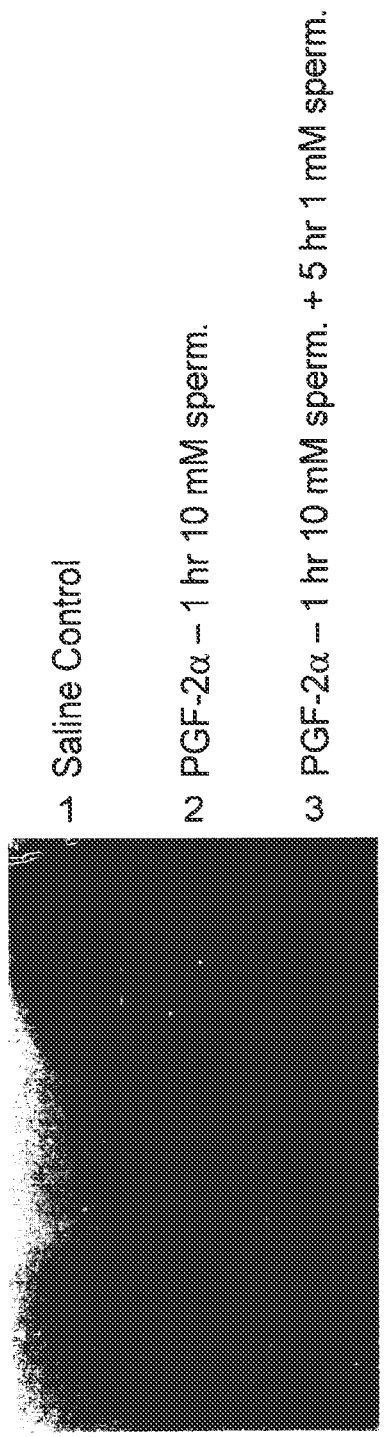
FIG. 18 depicts a DNA laddering experiment in which the degree of apoptosis in dispersed cells of superovulated rat corpora lutea was examined in rats treated with spermidine prior to exposure to PGF-2α.

In another experiment, superovulation was induced by subcutaneous injection with 500 µg of PGF-2α. Control rats were treated with an equivalent volume of saline solution. Fifteen to thirty minutes later, the ovaries were removed and minced with collagenase. The dispersed cells from rats treated with PGF-2α and were incubated in 10 mm glutamine+10 mm spermidine for 1 hour and for a further 5 hours in 10 min glutamine without spermidine (lane 2) or in 10 mm glutamine+10 mm spermidine for 1 hour and for a further 5 hours in 10 mm glutamine+1 mm spermidine (lane 3). Control cells from rats treated with saline were dispersed with collagenase and incubated for 1 hour and a thither 5 hours in glutamine only (lane 1). Five hundred nanograms of DNA from each sample was labeled with [α-$^{32}$P]-dCTP using klenow enzyme, separated on a 1.8% agarose gel, and exposed to film for 24 hours. Results are shown in FIG. 18.

Figure 19:
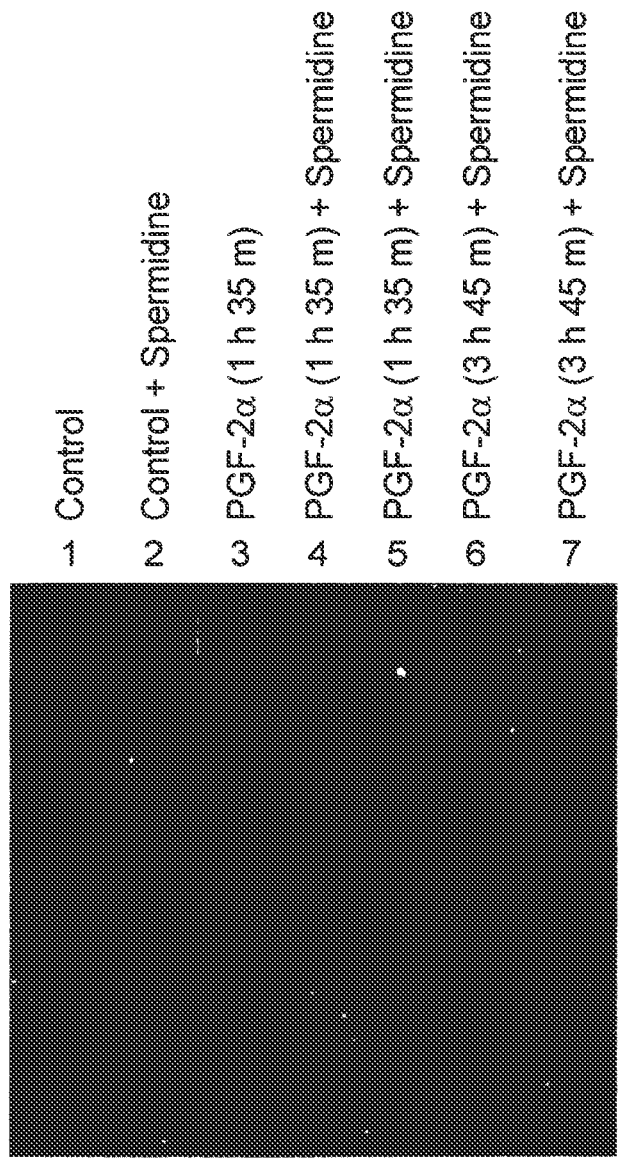
FIG. 19 depicts a DNA laddering experiment in which the degree of apoptosis in superovulated rat corpus lutea was examined in rats treated with spermidine and/or PGF-2α.

In yet another experiment, superovulated rats were injected subcutaneously with 1 mg/100 g body weight of spermidine, delivered in three equal doses of 0.333 mg/100 g body weight, 24, 12, and 2 hours prior to a subcutaneous injection with 500 µg PGF-2α. Control rats were divided into three sets: no injections, three injections of spermidine but no PGF-2α; and three injections with an equivalent volume of saline prior to PGF-2α, treatment. Ovaries were removed front the rats either 1 hour and 35 minutes or 3 hours and 45 minutes after prostaglandin treatment and used for the isolation of DNA. Five hundred nanograms of DNA from each sample was labeled with [α-$^{32}$P]-dCTP using Klenow enzyme, separated on a 1.8% agarose gel, and exposed to film for 24 hours: lane 1, no injections (animals were sacrificed at the same time as for lanes 3-5); lane 2, three injections with spermidine (animals were sacrificed at the same time as for lanes 3-5); lane 3, three injections with saline followed by injection with PGF-2α (animals were sacrificed 1 h and 35 min after treatment with PGF-2α); lane 4, three injections with spermidine followed by injection with PGF-2α (animals were sacrificed 1 h and 35 min after treatment with PGF-2α); lane 5, three injections with spermidine followed by injection with PGF-2α (animals were sacrificed 1 h and 35 min after treatment with PGF-2α); lane 6, three injections with spermidine followed by injection with PGF-2α (animals were sacrificed 3 h and 45 min after treatment with PGF-2α); lane 7, three injections with spermidine followed by injection with PGF-2α (animals were sacrificed 3 h and 45 min after treatment with PGF-2α). Results are shown in FIG. 19.

RNA Isolation

Total RNA was isolated from corpus luteum tissue removed from rats at various times after PGF-2α induction of apoptosis. Briefly, the tissue (5 g) was ground in liquid nitrogen. The ground powder was mixed with 30 ml guanidinium buffer (4 M guanidinium isothiocyanate, 2.5 mM NaOAc pH 8.5, 0.8% β-mercaptoethanol). The mixture was filtered through four layers of Miracloth and centrifuged at 10,000 g at 4° C. for 30 minutes. The supernatant was then subjected to cesium chloride density gradient centrifugation at 11,200 g for 20 hours. The pelleted RNA was rinsed with 75% ethanol, resuspended in 600 ml DEPC-treated water and the RNA precipitated at −70° C. with 1.5 ml 95% ethanol and 60 ml of 3M NaOAc.

Genomic DNA Isolation and Laddering

Genomic DNA was isolated from extracted corpus luteum tissue or dispersed corpus luteal cells using the QIAamp DNA Blood Kit (Qiagen) according to the manufacturer's instructions. The DNA was end-labeled by incubating 500 ng of DNA with 0.2 µCi [α-$^{32}$P]dCTP, 1 mM Tris, 0.5 mM EDTA, 3 units of Klenow enzyme, and 0.2 pM each of dATP, dGTP, and dTTP, at room temperature for 30 minutes. Unincorporated nucleotides were removed by passing the sample through a 1-ml Sephadex G-50 column according to the method described by Maniatis et al. The samples were then resolved by Tris-acetate-EDTA (2%) gel electrophoresis. The gel was dried for 30 minutes at room temperature under vacuum and exposed to x-ray film at −80° C. for 24 hours.

Plasmid DNA Isolation, DNA Sequencing

The alkaline lysis method described by Sambrook et al., supra, was used to isolate plasmid DNA. The full-length positive cDNA clone was sequenced using the dideoxy sequencing method. Sanger et al., Proc. Natl. Acad. Sci. USA, 74:5463-5467. The open reading frame was compiled and analyzed using BLAST search (GenBank, Bethesda, Md.) and sequence alignment was achieved using a BCM Search Launcher: Multiple Sequence Alignments Pattern-Induced Multiple Alignment Method (see F. Corpet, Nuc. Acids Res., 16:10881-10890, (1987). Sequences and sequence alignments are shown in FIGS. 5-11.

Northern Blot Hybridization of Rat Corpus Luteum RNA

Twenty milligrams of total RNA isolated from rat corpus luteum at various stages of apoptosis were separated on 1% denatured formaldehyde agarose gels and immobilized on nylon membranes. The full-length rat apoptosis-specific eIF- 5A cDNA (SEQ ID NO:1) labeled with $^{32}$P-dCTP using a random primer kit (Boehringer) was used to probe the membranes 7×10$^7$. Alternatively, full length rat DHS cDNA (SEQ ID NO:6) labeled with $^{32}$P-dCTP using a random primer kit (Boehringer) was used to probe the membranes (7×10$^7$ cpm). The membranes were washed once with 1×SSC, 0.1% SDS at room temperature and three times with 0.2×SSC, 0.1% SDS at 65° C. The membranes were dried and exposed to X-ray film overnight at −70° C.

Figure 14:
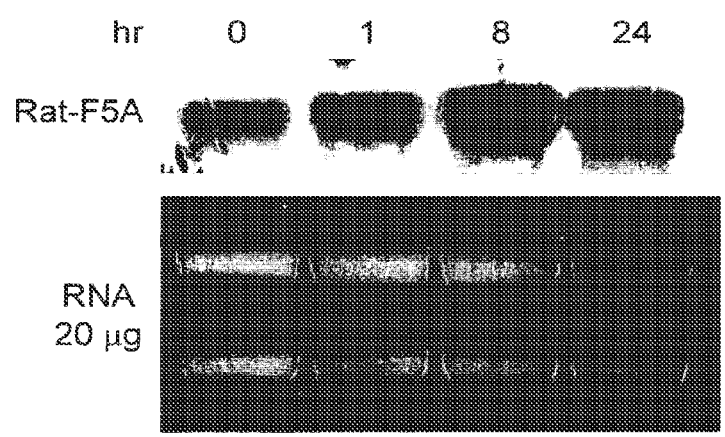
FIG. 14 is a Northern blot (top) and an ethidium bromide stained gel (bottom) of total RNA probed with the $^{32}$P-dCTP-labeled 3'-end of rat corpus luteum apoptosis-specific eIF-5A cDNA.
Figure 15:
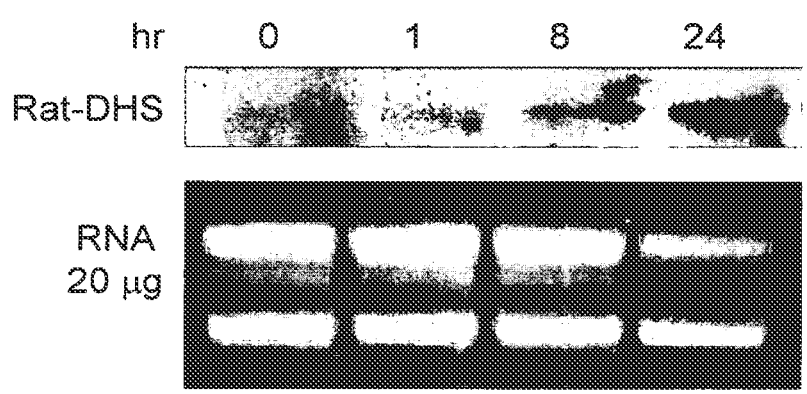
FIG. 15 is a Northern blot (top) and an ethidium bromide stained gel (bottom) of total RNA probed with the $^{32}$P-dCTP-labeled 3'-end of rat corpus luteum apoptosis-specific DHS cDNA.

As can be seen, apoptosis-specific eIF-5A and DHS are both upregulated in apoptosing corpus luteum tissue. Expression of apoptosis-specific eIF-5A is significantly enhanced after induction of apoptosis by treatment with PGF-2α—low at time zero, increased substantially within 1 hour of treatment, increased still more within 8 hours of treatment and increased slightly within 24 hours of treatment (FIG. 14). Expression of DHS was low at time zero, increased substantially within 1 hour of treatment, increased still more within 8 hours of treatment and increased again slightly within 24 hours of treatment (FIG. 15).

Generation of an Apoptosing Rat Corpus Luteum RT-PCR Product Using Primers Based on Yeast, Fungal and Human eIF-5A Sequences A partial-length apoptosis-specific eIF-5A sequence (SEQ ID NO:11) corresponding to the 3' end of the gene was generated from apoptosing rat corpus luteum RNA template by RT-PCR using a pair of oligonucleotide primers designed from yeast, fungal and human apoptosis-specific eIF-5A sequences. The upstream primer used to isolate the 3' end of the rat apoptosis-specific eIF-5A gene is a 20 nucleotide degenerate primer: 5' TCSAARACHGGNAAGCAYGG 3' (SEQ ID NO:9), wherein S is selected from C and G; R is selected from A and G; H is selected from A, T, and C; Y is selected from C and T; and N is any nucleic acid. The downstream primer used to isolate the 3' end of the rat eIF-5A gene contains 42 nucleotides: 5' GCGAAGCTTCCATGG CTCGAGTTTTTTTTTTTTTTTTTTTTT 3' (SEQ ID NO:10). A reverse transcriptase polymerase chain reaction (RT-PCR) was carried put. Briefly, using 5 mg of the downstream primer, a first strand of cDNA was synthesized. The first strand was then used as a template in a RT-PCR using both the upstream and downstream primers.

Separation of the RT-PCR products on an agarose gel revealed the presence a 900 by fragment, which was subcloned into pBluescript™ (Stratagene Cloning Systems, LaJolla, Calif.) using blunt end ligation and sequenced (SEQ ID NO:11). The cDNA sequence of the 3' end is SEQ ID NO:11 and the amino acid sequence of the 3' end is SEQ ID NO:12. See FIGS. 1-2.

A partial-length apoptosis-specific eIF-5A sequence (SEQ ID NO:15) corresponding to the 5 end of the gene and overlapping with the 3' end was generated from apoptosing rat corpus luteum RNA template by RT-PCR. The 5' primer is a 24-mer having the sequence, 5' CAGGTCTAGAGTTG-GAATCGAAGC 3' (SEQ ID NO:13), that was designed from human eIF-5A sequences. The 3' primer is a 30-mer having the sequence, 5' ATATCTCGAGCCTT GATTGCAA-CAGCTGCC 3' (SEQ ID NO:14) that was designed according to the 3' end RT-PCR fragment. A reverse transcriptase-polymerase chain reaction (RT-PCR) was carried out. Briefly, using 5 mg of the downstream primer, a first strand of cDNA was synthesized. The first strand was then used as a template in a RT-PCR using both the upstream and downstream primers.

Separation of the RT-PCR products on an agarose gel revealed the presence a 500 by fragment, which was subcloned into pBluescript™ (Stratagene Cloning Systems, LaJolla, Calif.) using XbaI and XhoI cloning sites present in the upstream and downstream primers, respectively, and sequenced (SEQ ID NO:15). The cDNA sequence of the 5' end is SEQ ID NO:15, and the amino acid sequence of the 5' end is SEQ ID NO:16. See FIG. 2.

The sequences of the 3' and 5' ends of the rat apoptosis-specific eIF-5A (SEQ ID NO:11 and SEQ ID NO:15, respectively) overlapped and gave rise to the full-length cDNA sequence (SEQ ID NO:1). This full-length sequence was aligned and compared with sequences in the GeneBank data base. See FIGS. 1-2. The cDNA clone encodes a 154 amino acid polypeptide (SEQ ID NO:2) having a calculated molecular mass of 16.8 KDa. The nucleotide sequence, SEQ ID NO:1, for the full length cDNA of the rat apoptosis-specific corpus luteum eIF-5A gene obtained by RT-PCR is depicted in FIG. 3 and the corresponding derived amino acid sequence is SEQ ID NO:9. The derived full-length amino acid sequence of eIF-5A was aligned with human and mouse eIF-5a sequences. See FIG. 7-9.

Generation of an Apoptosing Rat Corpus Luteum RT-PCR Product Using Primers Based on a Human DHS Sequence A partial-length DHS sequence (SEQ ID NO:6) corresponding to the 3' end of the gene was generated from apoptosing rat corpus luteum RNA template by RT-PCR using a pair of oligonucleotide primers designed from a human DHS sequence. The 5' primer is a 20-mer having the sequence, 5' GTCTGTGTATTATTGGGCCC 3' (SEQ ID NO. 17).; the 3' primer is a 42-mer having the sequence, 5' GCGAAGCTTC-CATGGC TCGAGTTTTTTTTTTTTTTTTTTTTTT 3' (SEQ ID NO:18). A reverse transcriptase polymerase chain reaction (RT-PCR) was carried out. Briefly, using 5 mg of the downstream primer, a first strand of cDNA was synthesized. The first strand was then used as a template in a RT-PCR using both the upstream and downstream primers.

Separation of the RT-PCR products on an agarose gel revealed the presence a 606 by fragment, which was subcloned into pBluescript™ (Stratagene Cloning Systems, LaJolla, Calif.) using blunt end ligation and sequenced (SEQ ID NO:6). The nucleotide sequence (SEQ ID NO:6) for the partial length cDNA of the rat apoptosis-specific corpus luteum DHS gene obtained by RT-PCR is depicted in FIG. 4 and the corresponding derived amino acid sequence is SEQ ID NO.7.

Isolation of Genomic DNA and Southern Analysis

Genomic DNA for southern blotting was isolated from excised rat ovaries. Approximately 100 mg of ovary tissue was divided into small pieces and placed into a 15 ml tube. The tissue was washed twice with 1 ml of PBS by gently shaking the tissue suspension and then removing the PBS using a pipette. The tissue was resuspended in 2.06 ml of DNA-buffer (0.2 M Tris-HCl pH 8.0 and 0.1 mM EDTA) and 240 µl of 10% SDS and 100 µl of proteinase K (Boehringer Martheim; 10 mg/ml) was added. The tissue was placed in a shaking water bath at 45° C. overnight. The following day another 100 µl of proteinase K (10 mg/ml) was added and the tissue suspension was incubated in a water-bath at 45° C. for an additional 4 hours. After the incubation the tissue suspension was extracted once with an equal volume of phenol:chloroform:iso-amyl alcohol (25:24:1) and once with an equal volume of chloroform:iso-amyl alcohol (24:1). Following the extractions ¹⁄₁₀th volume of 3M sodium acetate (pH 5.2) and 2 volumes of ethanol were added. A glass pipette sealed and formed into a hook using a Bunsen burner was used to pull the DNA threads out of solution and to transfer the DNA into a clean microcentrifuge tube. The DNA was washed once in 70% ethanol and air-dried for 10 minutes. The DNA pellet was dissolved in 500 µl of 10 mM Tris-HCl (pH 8.0), 10 μl of RNase A (10 mg/ml) was added, and the DNA was incubated for 1 hour at 37° C. The DNA was extracted once with phenol:chloroform:iso-amyl alcohol (25:24:1) and the DNA was precipitated by adding 1/10th volume of 3 M sodium acetate (pH 5.2) and 2 volumes of ethanol. The DNA was pelleted by centrifugation for 10 minutes at 13,000×g at 4° C. The DNA pellet was washed once in 70% ethanol and dissolved in 200 μl 10 mM Tris-HCl (pH 8.0) by rotating the DNA at 4° C. overnight.

For Southern blot analysis, genomic DNA isolated from rat ovaries was digested with various restriction enzymes that either do not cut in the endogenous gene or cut only once. To achieve this, 10 μg genomic DNA, 20 μl 10× reaction buffer and 100 U restriction enzyme were reacted for five to six hours in a total reaction volume of 200 μl. Digested DNA was loaded onto a 0.7% agarose gel and subjected to electrophoresis for 6 hours at 40 volts or overnight at 15 volts. After electrophoresis, the gel was depurinated for 10 minutes in 0.2 N HCl followed by two 15-minute washes in denaturing solution (0.5 M NaOH, 1.5 M NaCl) and two 15 minute washes in neutralizing buffer (1.5 M NaCl, 0.5 M Tris-HCl pH 7.4). The DNA was transferred to a nylon membrane, and the membrane was prehybridized in hybridization solution (40% formamide, 6×SSC, 5× Denhardt's, solution (1× Denhardt's solution is 0.02% Ficoli, 0.02% PVP, and 0.02% BSA), 0.5% SDS, and 1.5 mg of denatured salmon sperm DNA). A 700 by PCR fragment of the 3' UTR of rat eIF-5A cDNA (650 by of 3' UTR and 50 by of coding) was labeled with [a-32P]-dCTP by random priming and added to the membrane at 1×106 cpm/ml.

Similarly, a 606 by PCR fragment of the rat DHS cDNA (450 by coding and 156 bp 3' UTR) was random prime labeled with $[\alpha-^{32}P]$-dCTP and added at 1×10 6 cpm/ml to a second identical membrane. The blots were hybridized overnight at 42° C. and then washed twice with 2×SSC and 0.1% SDS at 42° C. and twice with 1×SSC and 0.1% SDS at 42° C. The blots were then exposed to film for 3-10 days.

Figure 20:
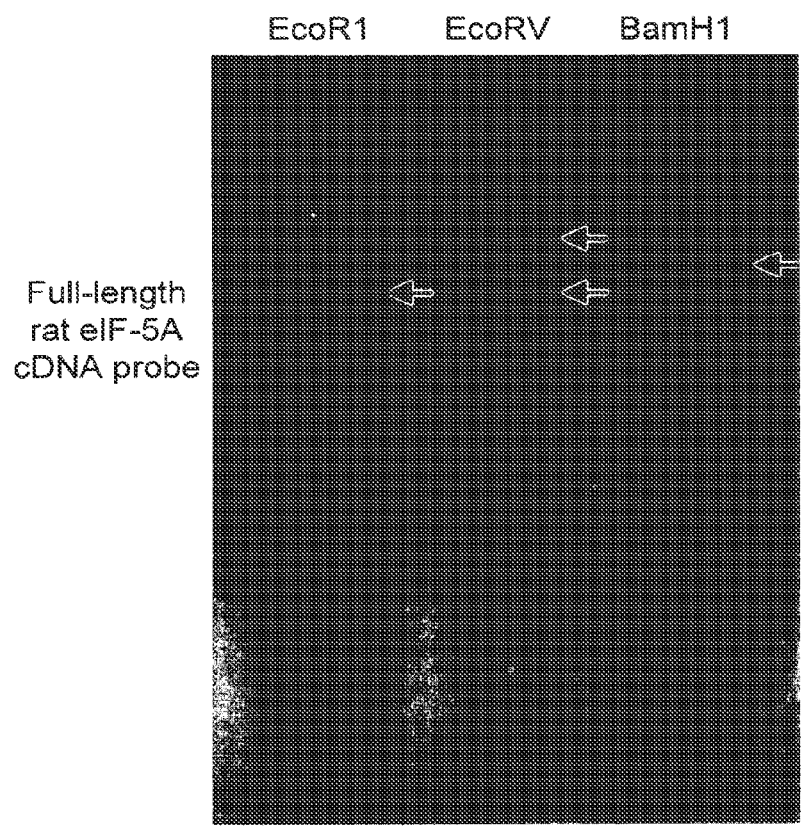
FIG. 20 is a Southern blot of rat genomic DNA probed with $^{32}$P-dCTP-labeled partial-length rat corpus luteum apoptosis-specific eIF-5A cDNA.

Rat corpus genomic DNA was cut with restriction enzymes as indicated on FIG. 20 and probed with $^{32}$P-dCTP-labeled full-length eIF-5A cDNA. Hybridization under high stringency conditions revealed hybridization of the full-length cDNA probe to several restriction fragments for each restriction enzyme digested DNA sample, indicating the presence of several isoforms of eIF-5A. Of particular note, when rat genomic DNA was digested with EcoRV, which has a restriction site within the open reading frame of apoptosis-specific eIF-5A, two restriction fragments of the apoptosis-specific isoform of eIF-5A were detectable in the Southern blot. The two fragments are indicated with double arrows in FIG. 20. The restriction fragment corresponding to the apoptosis-specific isoform of eIF-5A is indicated by a single arrow in the lanes labeled EcoR1 and BamH1, restriction enzymes for which there are no cut sites within the open reading frame. These results suggest that the apoptosis-specific eIF-5A is a single copy gene in rat. As shown in FIGS. 5 through 13, the eIF-5A gene is highly conserved across species, and so it would be expected that there is a significant amount of conservation between isoforms within any species.

Figure 21:
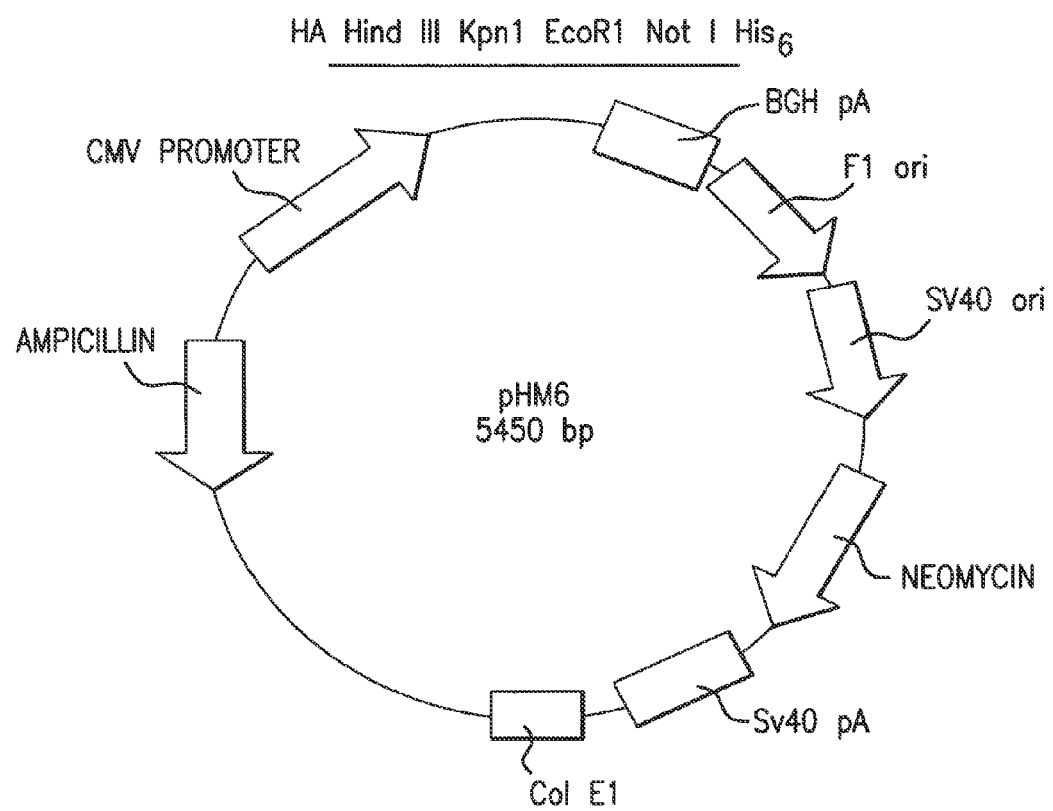
FIG. 21 depicts pHM6, a mammalian epitope tag expression vector (Roche Molecular Biochemicals).

FIG. 21 shows a Southern blot of rat genomic DNA probed with $^{32}$P-dCTP-labeled partial-length rat corpus luteum DHS cDNA. The genomic DNA was cut with EcoRV, a restriction enzyme that does not cut the partial-length cDNA used as a probe. Two restriction fragments are evident indicating that there are two copies of the gene or that the gene contains an intron with an EcoRV site.

Example 2

The present example demonstrates modulation of apoptosis apoptosis-specific eIF-5A (increasing apoptosis with apoptosis-specific eIF-5A in sense orientation)

Culturing of COS-7 Cells and Isolation of RNA

COS-7, an African green monkey kidney fibroblast-like cell line transformed with a mutant of SV40 that codes for wild-type T antigen, was used for all transfection-based experiments. COS-7 cells were cultured in Dulbecco's Modified Eagle's medium (MEM) with 0.584 grams per liter of L-glutamine, 4.5 g of glucose per liter, and 0.37% sodium bicarbonate. The culture media was supplemented with 10% fetal bovine serum (FBS) and 100 units of penicillin/streptomycin. The cells were grown at 37° C. in a humidified environment of 5% $CO_2$ and 95% air. The cells were subcultured every 3 to 4 days by detaching the adherent cells with a solution of 0.25% trypsin and 1 mM EDTA. The detached cells were dispensed at a split ratio of 1:10 in a new culture dish with fresh media.

COS-7 cells to be used for isolation of RNA were grown in 150-mm tissue culture treated dishes (Corning). The cells were harvested by detaching them with a solution of trypsin-EDTA. The detached cells were collected in a centrifuge tube, and the cells were pelleted by centrifugation at 3000 rpm for 5 minutes. The supernatant was removed, and the cell pellet was flash-frozen in liquid nitrogen. RNA was isolated from the frozen cells using the GenElute Mammalian Total RNA Miniprep kit (Sigma) according to the manufacturer's instructions.

Construction of Recombinant Plasmids and Transfection of COS-7 Cells

Recombinant plasmids carrying the full-length coding sequence of rat apoptosis-specific eIF-5A in the sense orientation and the 3' untranslated region (UTR) of rat apoptosis-specific eIF-5A in the antisense orientation were constructed using the mammalian epitope tag expression vector, pHM6 (Roche Molecular Biochemicals), which is illustrated in FIG. 21. The vector contains the following: CMV promoter—human cytomegalovirus immediate-early promoter/enhancer; HA—nonapeptide epitope tag from influenza hemagglutinin; BGH pA—Bovine growth hormone polyadenylation signal; f1 ori—f1 origin; SV40 on SV40 early promoter and origin; Neomycin—Neomycin resistance (G418) gene; SV40 pA SV40 polyadenylation signal; Col E1—ColE1 origin; Ampicillin—Ampicillin resistance gene. The full-length coding sequence of rat apoptosis-specific eIF-5A and the 3' UTR of rat apoptosis-specific eIF-5A were amplified by PCR from the original rat eIF-5A RT-PCR fragment in pBluescript (SEQ ID NO:1). To amplify the full-length eIF-5A the primers used were as follows: Forward 5' GCCAAGCTTAATGGCAGATGATTT GG 3' (SEQ ID NO: 59) (Hind3) and Reverse 5' CT GAATTCCAGTTATTTGCCATGG 3' (SEQ ID NO:60) (EcoR1). To amplify the 3' UTR rat apoptosis-specific eIF-5A the primers used were as follows: forward 5' AAT GAATTCCGCCATGACAGAGGAGGC 3' (SEQ ID NO: 61) (EcoR1) and reverse 5' GCGAAGCTTCCATGG CTCGAGTTTTTTTTTTTTTTTTTTTTT 3' (SEQ ID NO: 62) (Hind3).

The full-length rat apoptosis-specific eIF-5A PCR product isolated after agarose gel electrophoresis was 430 by in length while the 3' UTR rat apoptosis-specific PCR product was 697 by in length. Both PCR products were subcloned into the Hind 3 and EcoR1 sites of pHM6 to create pHM6-full-length apoptosis-specific eIF-5A and pHM6-antisense 3'UTReIF-5A. The full-length rat apoptosis-specific eIF-5A PCR product was subcloned in frame with the nonapeptide epitope tag from influenza hemagglutinin (HA) present upstream of the multiple cloning site to allow for detection of the recombinant protein using an anti-[HA]-peroxidase antibody. Expression is driven by the human cytomegalovirus immediate-early promoter/enhancer to ensure high level expression in mammalian cell lines. The plasmid also features a neomycin-resistance (G418) gene, which allows for selection of stable transfectants, and a SV40 early promoter and origin, which allows episomal replication in cells expressing SV40 large antigen, such as COS-7.

COS-7 cells to be used in transfection experiments were cultured in either 24 well cell culture plates (Corning) for cells to be used for protein extraction, or 4 chamber culture slides (Falcon) for cells to be used for staining. The cells were grown in DMEM media supplemented with 10% FBS, but lacking penicillin/streptomycin, to 50 to 70% confluency. Transfection medium sufficient for one well of a 24-well plate or culture slide was prepared by diluting 0.32 µg of plasmid DNA in 42.5 µl of serum-free DMEM and incubating the mixture at room temperature for 15 minutes. 1.6 µl of the transfection reagent, LipofectAMINE (Gibco, BRL), was diluted in 42.5 µl of serum-free DMEM and incubated fix 5 minutes at room temperature. After 5 minutes the LipofectAMINE mixture was added to the DNA mixture and incubated together at room temperature for 30 to 60 minutes. The cells to be transfected were washed once with serum-free DMEM before overlaying the transfection medium and the cells were placed back in the growth chamber for 4 hours.

After the incubation, 0.17 ml of DMEM+20% FBS was added to the cells. The cells were the cultured for a further 40 hours before either being induced to undergo apoptosis prior to staining or harvested for Western blot analysis. As a control, mock transfections were also performed in which the plasmid DNA was omitted from the transfection medium.

Protein Extraction and Western Blotting

Protein was isolated for Western blotting from transfected cells by washing the cells twice in PBS (8 g/L NaCl, 0.2 g/L KCl, 1.44 g/L $Na_2HPO_4$, and 0.24 g/L $KH_2PO_4$) and then adding 150 µl of hot SDS gel-loading buffer (50 mM Tris-HCl pH 6.8, 100 mM dithiothreitol, 2% SDS, 0.1% bromophenol blue, and 10% glycerol). The cell lysate was collected in a microcentrifuge tube, heated at 95° C. for 10 minutes, and then centrifuged at 13,000×g for 10 minutes. The supernatant was transferred to a fresh microcentrifuge tube and stored at −20° C. until ready for use.

For Western blotting, 2.5 or 5 µg of total protein was separated on a 12% SDS-polyacrylamide gel. The separated proteins were transferred to a polyvinylidene difluoride membrane. The membrane was then incubated for one hour in blocking solution (5% skim milk powder, 0.02% sodium azide in PBS) and washed three times for 15 minutes in PBS-T (PBS+0.05% Tween-20). The membrane was stored overnight in PBS-T at 4° C. After being warmed to room temperature the next day, the membrane was blocked for 30 seconds in 1 µg/ml polyvinyl alcohol. The membrane was rinsed 5 times in deionized water and then blocked for 30 minutes in a solution of 5% milk in PBS. The primary antibody was preincubated for 30 minutes in a solution of 5% milk in PBS prior to incubation with the membrane.

Several primary antibodies were used. An anti-[HA]-peroxidase antibody (Roche Molecular Biochemicals) was used at a dilution of 1:5000 to detect expression of the recombinant proteins. Since this antibody is conjugated to peroxidase, no secondary antibody was necessary, and the blot was washed and developed by chemiluminescence. The other primary antibodies that were used are monoclonal antibodies from Oncogene that recognize p53 (Ab-6), Bcl-2 (Ab-1), and c-Myc (Ab-2). The monoclonal antibody to p53 was used at a dilution of 0.1 µg/ml, and the monoclonal antibodies to Bcl-2 and c-Myc were both used at a dilution of 0.83 µg/ml. After incubation with primary antibody for 60 to 90 minutes, the membrane was washed 3 times for 15 minutes in PBS-T. Secondary antibody was then diluted in 1% milk in PBS and incubated with the membrane for 60 to 90 minutes. When p53 (Ab-6) was used as the primary antibody, the secondary antibody used was a goat anti-mouse IgG conjugated to alkaline phosphatase (Rockland) at a dilution of 1:1000. When Bcl-2 (Ab-1) and c-Myc (Ab-2) were used as the primary antibody, a rabbit anti-mouse IgG conjugated to peroxidase (Signia) was used at a dilution of 1:5000. After incubation with the secondary antibody, the membrane was washed 3 times in PBS-T.

Two detection methods were used to develop the blots, a colorimetric method and a chemiluminescent method. The colorimetric method was used only when p53 (Ab-6) was used as the primary antibody in conjunction with the alkaline phosphatase-conjugated secondary antibody. Bound antibody was visualized by incubating the blot in the dark in a solution of 0.33 mg/mL nitro blue tetrazolium, 0.165 mg/mL 5-bromo-4-chloro-3-indolyl phosphate, 100 mM NaCl, 5 mM $MgCl_2$, and 100 mM Tris-HCl (pH 9.5). The color reaction was stopped by incubating the blot in 2 mM EDTA in PBS. A chemiluminescent detection method was used for all other primary antibodies, including anti-[HA]-peroxidase, Bcl-2 (Ab-1), and c-Myc (Ab-2). The ECL Plus Western blotting detection kit (Amersham Pharmacia Biotech) was used to detect peroxidase-conjugated bound antibodies. In brief, the membrane was lightly blotted dry and then incubated in the dark with a 40:1 mix of reagent A and reagent B for 5 minutes. The membrane was blotted dry, placed between sheets of acetate, and exposed to X-ray film for time periods varying from 10 seconds to 10 minutes.

Induction of Apoptosis in COS 7 Cells

Figure 22:
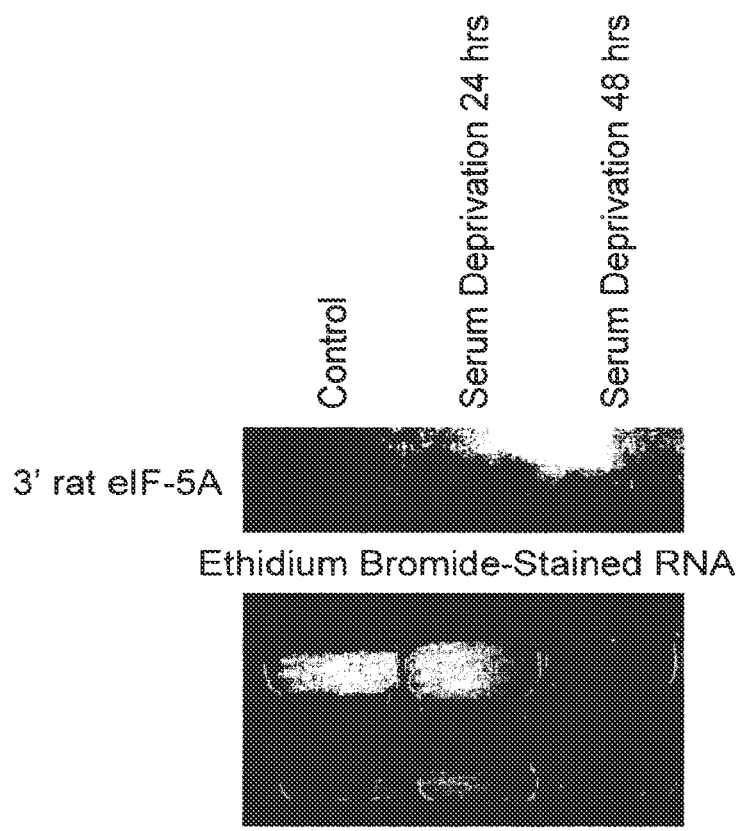
FIG. 22 is a Northern blot (top) and ethidium bromide stained gel (bottom) of total RNA isolated from COS-7 cells after induction of apoptosis by withdrawal of serum probed with the $^{32}$P-dCTP-labeled 3'-untranslated region of rat corpus luteum apoptosis-specific DHS cDNA.

Two methods were used to induce apoptosis in transfected COS-7 cells, serum deprivation and treatment with Actinomycin D, *streptomyces* sp (Calbiochem). For both treatments, the medium was removed 40 hours post-transfection. For serum starvation experiments, the media was replaced with serum- and antibiotic-free DMEM. Cells grown in antibiotic-free DMEM supplemented with 10% FBS were used as a control. For Actinomycin D induction of apoptosis, the media was replaced with antibiotic-free DMEM supplemented with 10% FBS and 1 µg/ml Actinomycin D dissolved in methanol. Control cells were grown in antibiotic-free DMEM supplemented with 10% FBS and an equivalent volume of methanol. For both methods, the percentage of apoptotic cells was determined 48 hours later by staining with either Hoescht or Annexin V-Cy3. Induction of apoptosis was also confirmed by Northern blot analyses, as shown in FIG. 22

Hoescht Staining

The nuclear stain, Hoescht, was used to label the nuclei of transfected COS-7 cells in order to identify apoptotic cells based on morphological features such as nuclear fragmentation and condensation. A fixative, consisting of a 3:1 mixture of absolute methanol and glacial acetic acid, was prepared immediately before use. An equal volume of fixative was added to the media of COS-7 cells growing on a culture slide and incubated for 2 minutes. The media/fixative mixture was removed from the cells and discarded, and 1 ml of fixative was added to the cells. After 5 minutes the fixative was discarded, and 1 ml of fresh fixative was added to the cells and incubated for 5 minutes. The fixative was discarded, and the cells were air-dried for 4 minutes before adding 1 ml of Hoescht stain (0.5 μg/ml Hoescht 33258 in PBS). After a 10-minute incubation in the dark, the staining solution was discarded and the slide was washed 3 times for 1 minute with deionized water. After washing, 1 ml of Mcilvaine's buffer (0.021 M citric acid, 0.058 M $Na_2HPO_4 \cdot 7H_2O$; pH 5.6) was added to the cells, and they were incubated in the dark for 20 minutes. The buffer was discarded, the cells were air-dried for 5 minutes in the dark and the chambers separating the wells of the culture slide were removed. A few drops of Vectashield mounting media for fluorescence (Vector Laboratories) was added to the slide and overlaid with a coverslip. The stained cells were viewed under a fluorescence microscope using a UV filter. Cells with brightly stained or fragmented nuclei were scored as apoptotic.

Annexin F-Cy3 Staining

An Annexin V-Cy3 apoptosis detection kit (Sigma) was used to fluorescently label externalized phosphatidylserine on apoptotic cells. The kit was used according to the manufacturer's protocol with the following modifications, in brief, transfected COS-7 cells growing on four chamber culture slides were washed twice with PBS and three times with 1× Binding Buffer, 150 μl of staining solution (1 μg/ml AnnCy3 in 1×Binding Buffer) was added, and the cells were incubated in the dark for 10 minutes. The staining solution was then removed, and the cells were washed 5 times with 1× Binding Buffer. The chamber walls were removed from the culture slide, and several drops of 1× Binding Buffer were placed on the cells and overlaid with a coverslip. The stained cells were analyzed by fluorescence microscopy using a green filter to visualize the red fluorescence of positively stained (apoptotic) cells. The total cell population was determined by counting the cell number under visible light.

Example 3

The present example demonstrates modulation of apoptosis apoptosis-specific eIF-5A.

Figure 23:
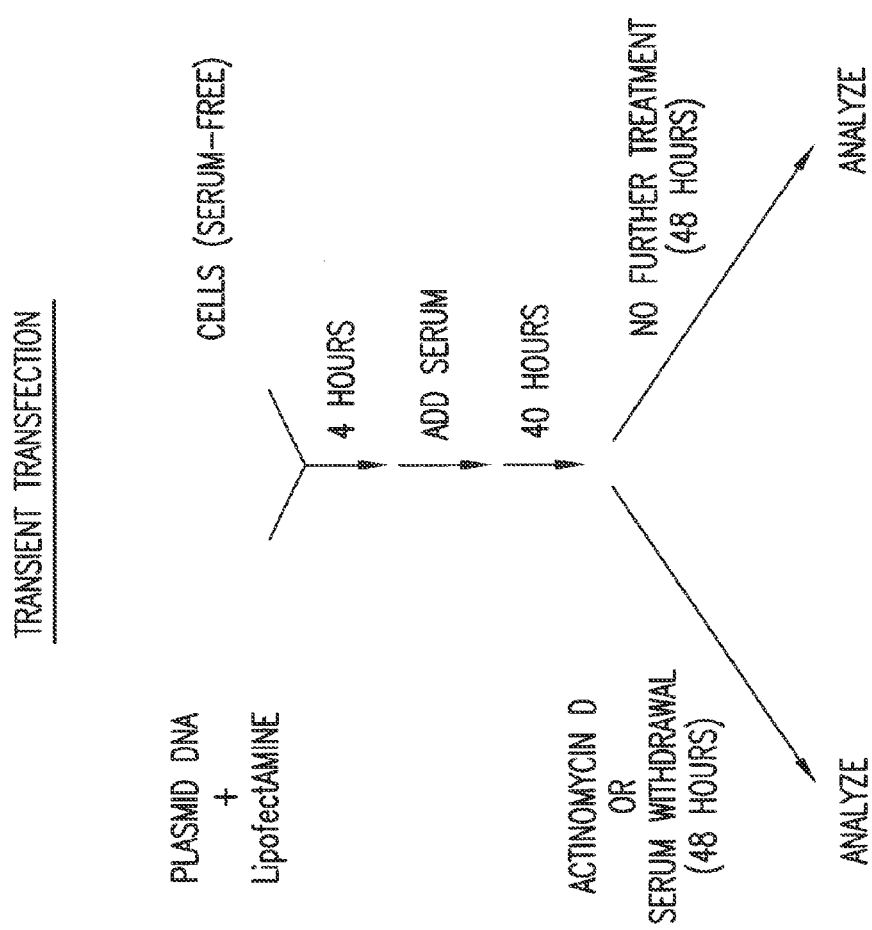
FIG. 23 is a flow chart illustrating the procedure for transient transfection of COS-7 cells.
Figure 24:
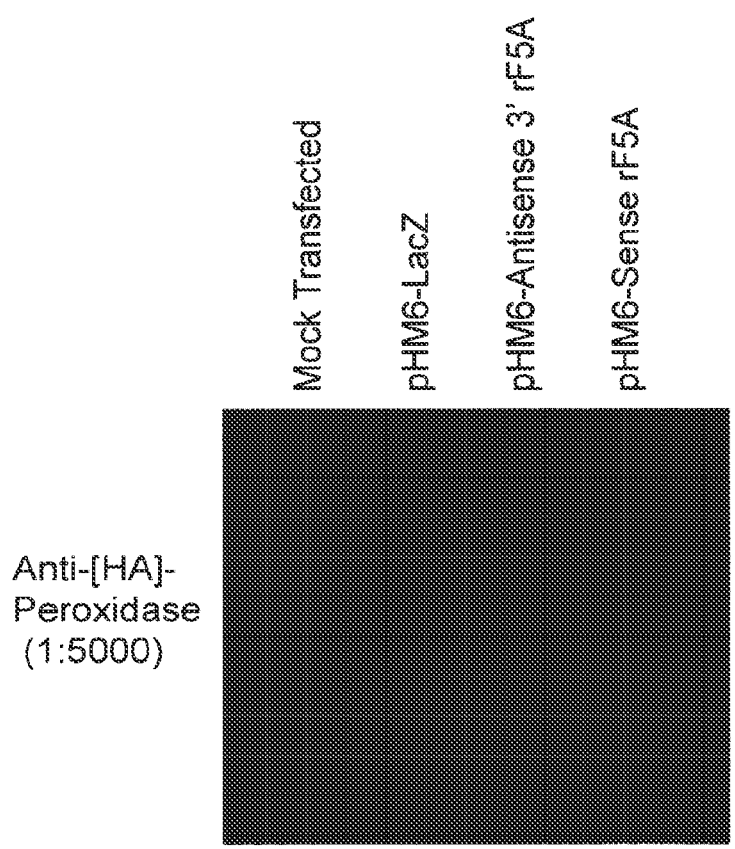
FIG. 24 is a Western blot of transient expression of foreign proteins in COS-7 cells following transfection with pHM6.

Using the general procedures and methods described in the previous examples, FIG. 23 is a flow chart illustrating the procedure for transient transfection of COS-7 cells, in which cells in serum-free medium were incubated in plasmid DNA in lipofectAMINE for 4 hours, serum was added, and the cells were incubated for a further 40 hours. The cells were then either incubated in regular medium containing serum for a further 48 hours before analysis (i.e. no further treatment), deprived of serum for 48 hours to induce apoptosis before analysis, or treated with actinomycin D for 48 hours to induce apoptosis before analysis.

FIG. 22 is a Western blot illustrating transient expression of foreign proteins in COS-7 cells following transfection with pHM6. Protein was isolated from COS-7 cells 48 hours after either mock transfection, or transfection with pHM6-LacZ, pHM6-Antisense 3' rF5A (pHM6-Antisense 3' UTR rat apoptosis-specific eIF-5A), or pHM6-Sense rF5A (pHM6-Full length rat apoptosis-specific eIF-5A. Five μg of protein from each sample was fractionated by SDS-PAGE, transferred to a PVDF membrane, and Western blotted with anti-[HA]-peroxidase. The bound antibody was detected by chemiluminescence and exposed to x-ray film for 30 seconds. Expression of LacZ (lane 2) and of sense rat apoptosis-specific eIF-5A (lane 4) is clearly visible.

As described above, COS-7 cells were either mock transfected or transfected with pHM6-Sense rF5A (pHM6-Full length rat apoptosis-specific eIF-5A). Forty hours after transfection, the cells were induced to undergo apoptosis by withdrawal of serum for 48 hours. The caspase proteolytic activity in the transfected cell extract was measured using a fluorometric homogenous easpase assay kit (Roche Diagnostics). DNA fragmentation was also measured using the FragEL DNA Fragmentation Apoptosis Detection kit (Oncogene) which labels the exposed 3'-OH ends of DNA fragments with fluorescein-labeled deoxynucleotides.

Additional COS-7 cells were either mock transfected or transfected with pHM6-Sense rF5A (pHM6-Full length rat apoptosis-specific eIF-5A). Forty hours after transfection, the cells were either grown for an additional 48 hours in regular medium containing serum (no further treatment), induced to undergo apoptosis by withdrawal of serum for 48 hours or induced to undergo apoptosis by treatment with 0.5 μg/ml of Actinomycin D for 48 hours. The cells were either stained with Hoescht 33258, which depicts nuclear fragmentation accompanying apoptosis, or stained with Annexin V-Cy3, which depicts phosphatidylserine exposure accompanying apoptosis. Stained cells were also viewed by fluorescence microscopy using a green filter and counted to determine the percentage of cells Undergoing apoptosis. The total cell population was counted under visible light.

Figure 25:
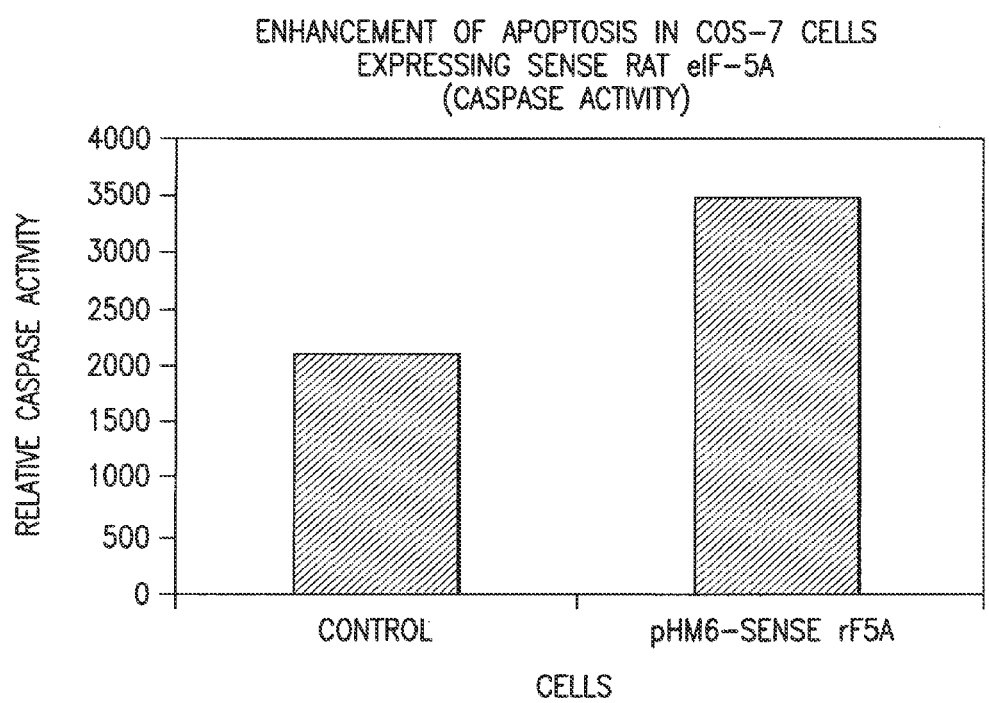
FIG. 25 illustrates enhanced apoptosis as reflected by increased caspase activity when COS-7 cells were transiently transfected with pHM6 containing full-length rat apoptosis-specific eIF-5A in the sense orientation.

FIG. 25 illustrates enhanced apoptosis as reflected by increased caspase activity when COS-7 cells were transiently transfected with pHM6 containing full-length rat apoptosis-specific eIF-5A in the sense orientation. Expression of rat apoptosis-specific eIF-5A resulted in a 60% increase in caspase activity.

Figure 26:
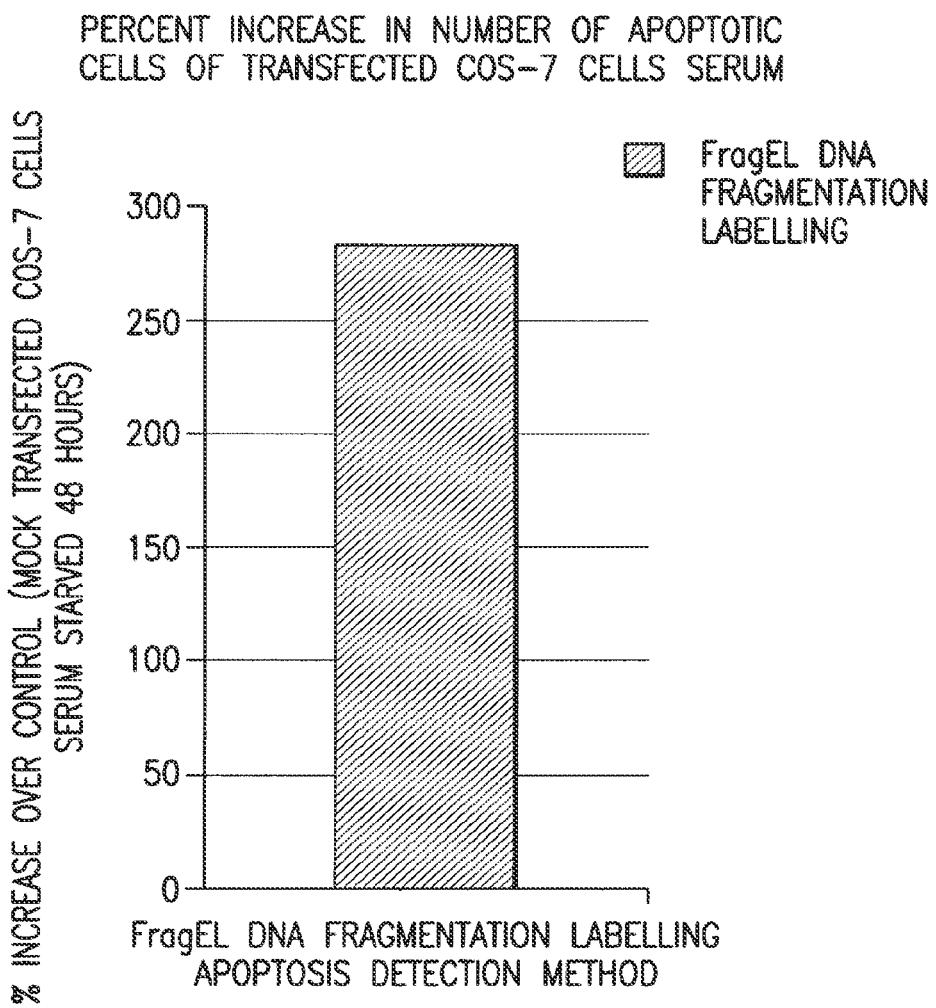
FIG. 26 illustrates enhanced apoptosis as reflected by increased DNA fragmentation when COS-7 cells were transiently transfected with pHM6 containing full-length rat apoptosis-specific eIF-5A in the sense orientation.
Figure 28:
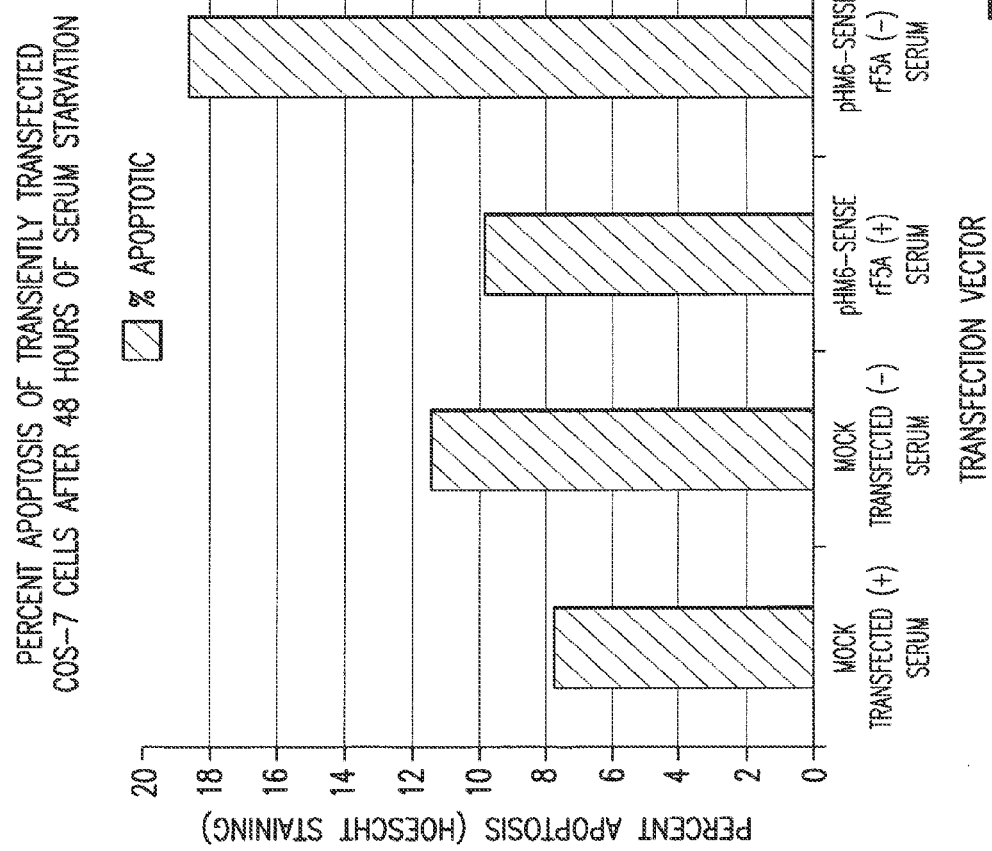
FIG. 28 illustrates enhanced apoptosis as reflected by increased nuclear fragmentation when COS-7 cells were transiently transfected with pHM6 containing full-length rat apoptosis-specific eIF-5A in the sense orientation.

FIG. 26 illustrates enhanced apoptosis as reflected by increased DNA fragmentation when COS-7 cells were transiently transfected with pHM6 containing full-length rat apoptosis-specific eIF-5A in the sense orientation. Expression of rat apoptosis-specific eIF-5A resulted in a 273% increase in DNA fragmentation. FIG. 27 illustrates detection of apoptosis as reflected by increased nuclear fragmentation when COS-7 cells were transiently transfected with pHM6 containing full-length rat apoptosis-specific eIF-5A in the sense orientation. There is a greater incidence of fragmented nuclei in cells expressing rat apoptosis-specific eIF-5A. FIG. 28 illustrates enhanced apoptosis as reflected by increased nuclear fragmentation when COS-7 cells were transiently transfected with pHM6 containing full-length rat apoptosis-specific eIF-5A in the sense orientation. Expression of rat apoptosis-specific eIF-5A resulted in a 27% and 63% increase in nuclear fragmentation over control in non-serum starved and serum starved samples, respectively.

Figure 29:
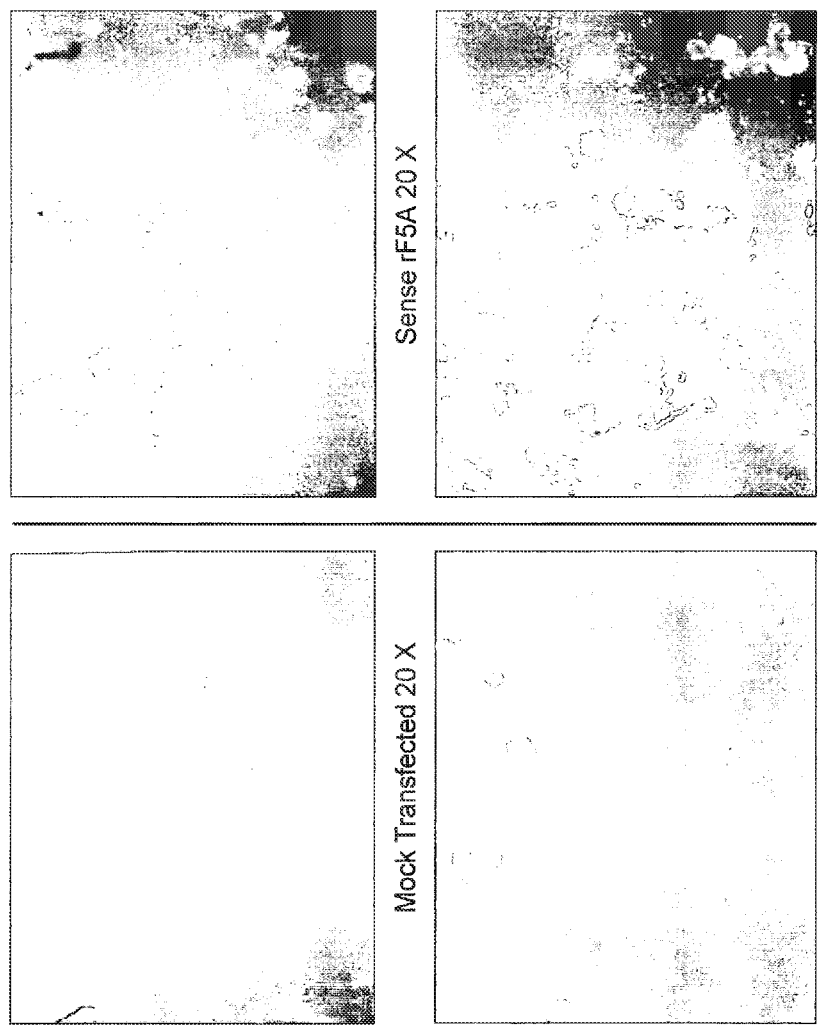
FIG. 29 illustrates detection of apoptosis as reflected by phosphatidylserine exposure when COS-7 cells were transiently transfected with pHM6 containing full-length rat apoptosis-specific eIF-5A in the sense orientation.
Figure 30:
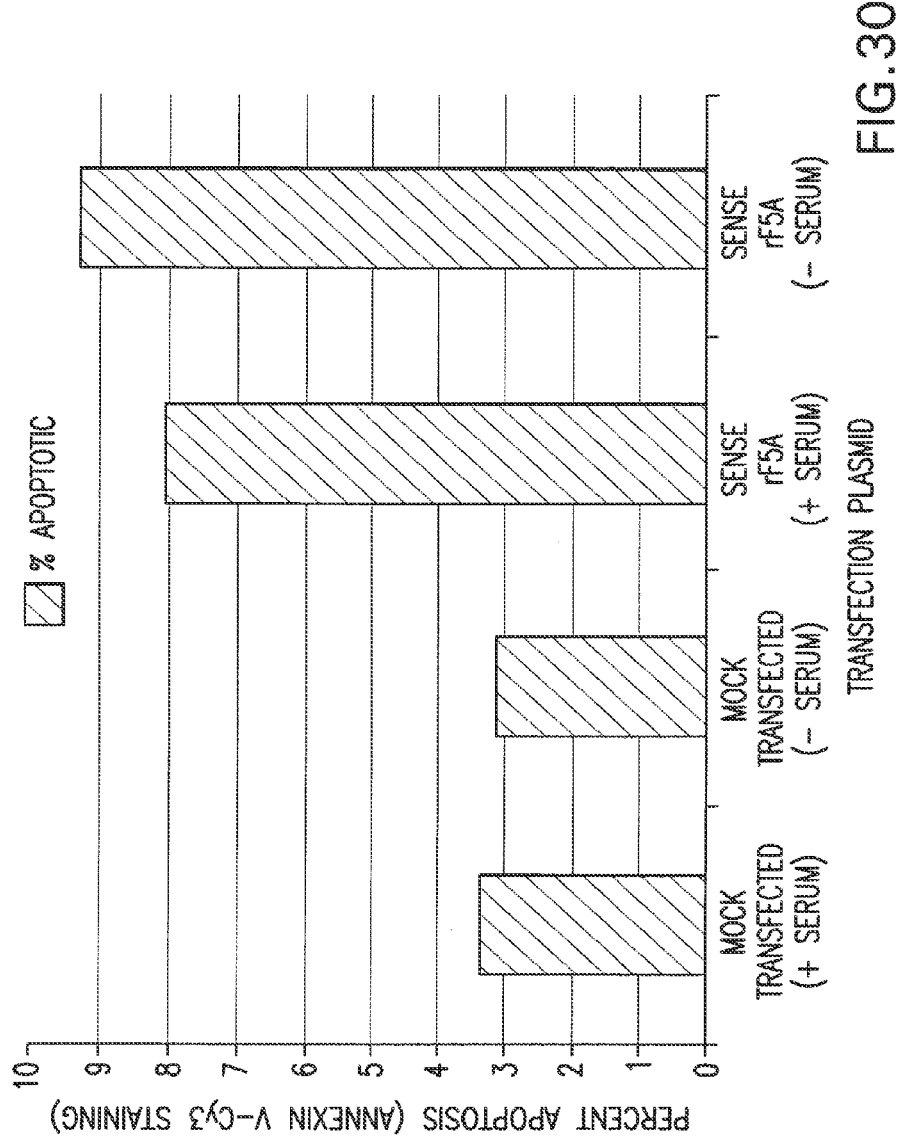
FIG. 30 illustrates enhanced apoptosis as reflected by increased phosphatidylserine exposure when COS-7 cells were transiently transfected with pHM6 containing full-length rat apoptosis-specific eIF-5A in the sense orientation.

FIG. 29 illustrates detection of apoptosis as reflected by phosphatidylserine exposure when COS-7 cells were transiently transfected with pHM6 containing full-length rat apoptosis-specific eIF-5A in the sense orientation. FIG. 30 illustrates enhanced apoptosis as reflected by increased phosphatidylserine exposure when COS-7 cells were transiently transfected with pHM6 containing full-length rat apoptosis-specific eIF-5A in the sense orientation. Expression of rat apoptosis-specific eIF-5A resulted in a 140% and 198% increase in phosphatidylserine exposure over control, in non-serum starved and serum starved samples, respectively.

Figure 31:
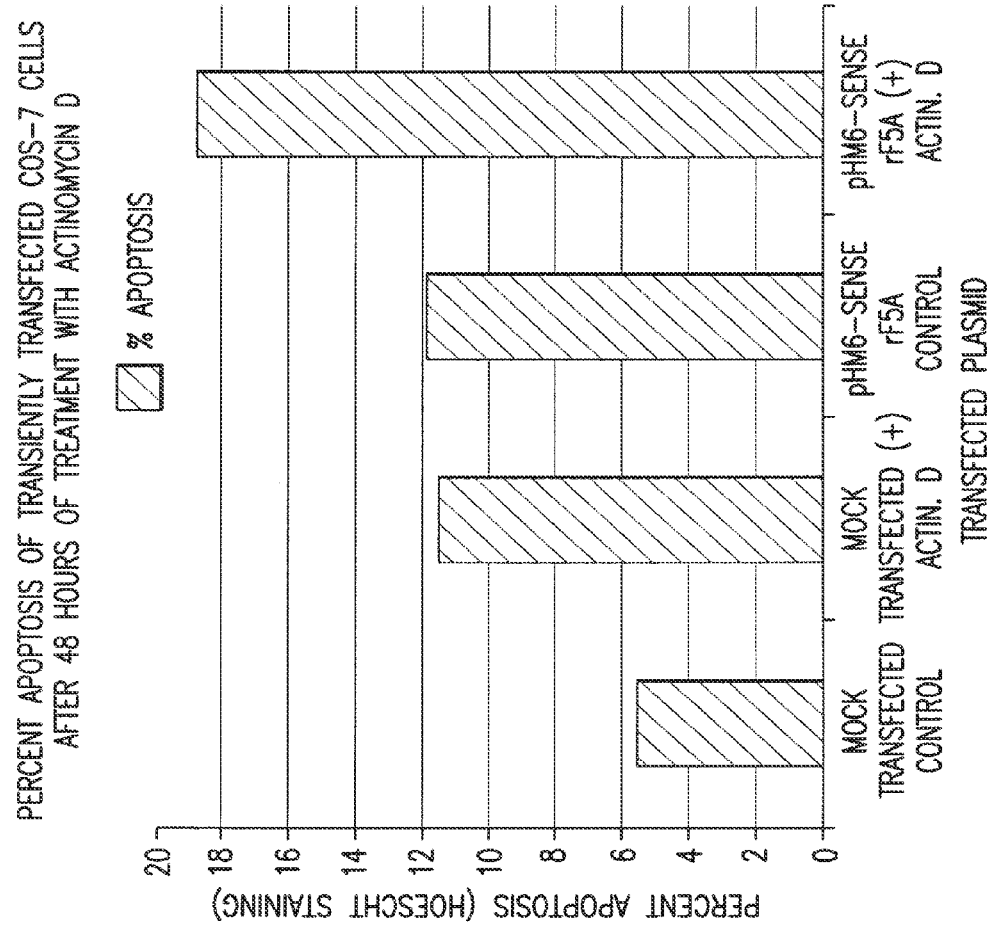
FIG. 31 illustrates enhanced apoptosis as reflected by increased nuclear fragmentation when COS-7 cells were transiently transfected with pHM6 containing full-length rat apoptosis-specific eIF-5A in the sense orientation.
Figure 32:
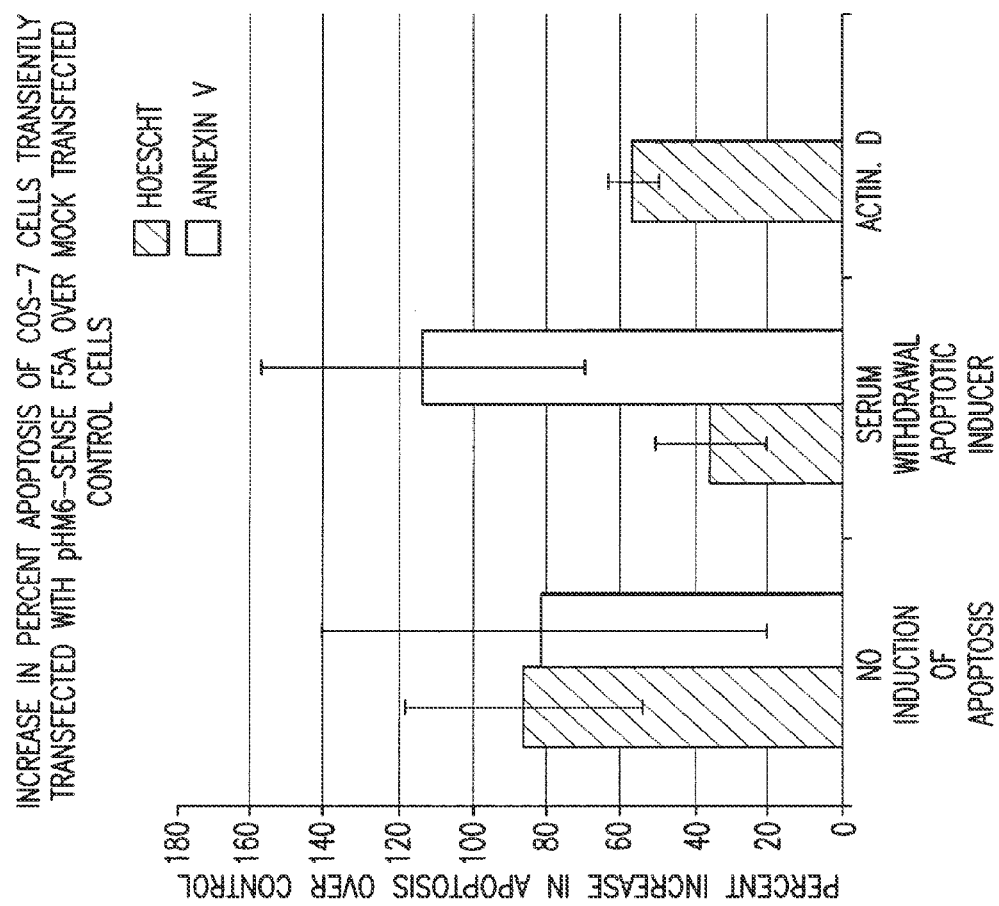
FIG. 32 illustrates enhanced apoptosis when COS-7 cells were transiently transfected with pHM6 containing full-length rat apoptosis-specific eIF-5A in the sense orientation.

FIG. 31 illustrates enhanced apoptosis as reflected by increased nuclear fragmentation when COS-7 cells were transiently transfected with pHM6 containing full-length rat apoptosis-specific eIF-5A in the sense orientation. Expression of rat apoptosis-specific eIF-5A resulted in a 115% and 62% increase in nuclear fragmentation over control in untreated and treated samples, respectively. FIG. 32 illustrates a comparison of enhanced apoptosis under conditions in which COS-7 cells transiently transfected with pHM6 containing full-length rat apoptosis-specific eIF-5A in the sense orientation were either given no further treatment or treatment to induce apoptosis.

Example 4

The present example demonstrates modulation of apoptotic activity following administration of apoptosis-specific eIF-5A.

Figure 33:
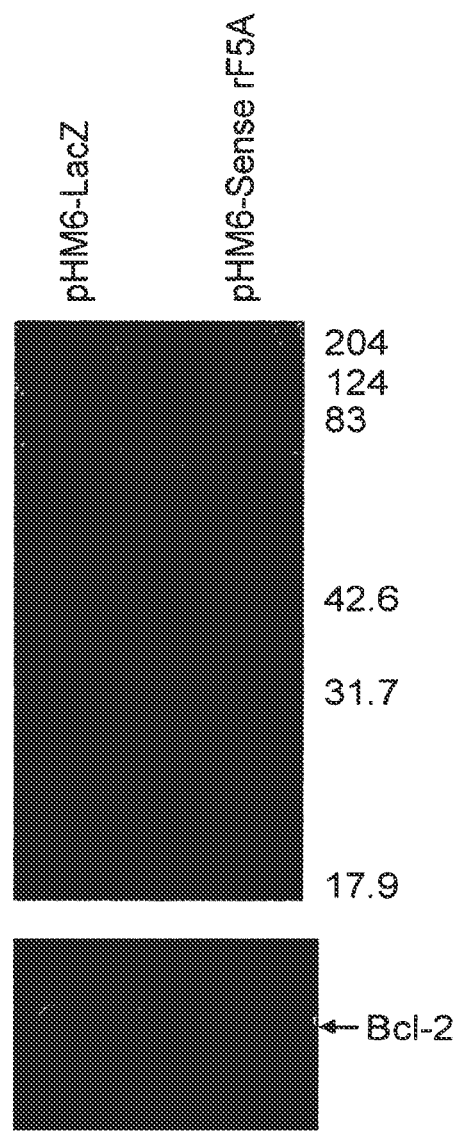
FIG. 33 illustrates down-regulation of Bcl-2 when COS-7 cells were transiently transfected with pHM6 containing full-length rat apoptosis-specific eIF-5A in the sense orientation. The top photo is the Coomassie-blue-stained protein blot; the bottom photo is the corresponding Western blot.

COS-7 cells were either mock transfected, transfected with pHM6-LacZ or transfected with pHM6-Sense rF5A (pHM6-Full length rat apoptosis-specific eIF-5A) and incubated for 40 hours. Five μg samples of protein extract from each sample were fractionated by SDS-PAGE, transferred to a PVDF membrane, and Western blotted with a monoclonal antibody that recognizes Bcl-2. Rabbit anti-mouse IgG conjugated to peroxidase was used as a secondary antibody, and bound antibody was detected by chemiluminescence and exposure to x-ray film. Results are shown in FIG. 33. Less Bcl-2 is detectable in cells transfected with pHM6-Sense rF5A than in those transfected with pHM6-LacZ; thus showing that Bcl-2 is down-regulated with the pHM6-sense rF5A construct.

Additional COS-7 cells were either mock transfected, transfected with pHM6-antisense 3' rF5A. (pHM6-antisense 3'UTR of rat apoptosis-specific eIF-5A) or transfected with pHM6-Sense rF5A (pHM6-Full length rat apoptosis-specific eIF-5A). Forty hours after transfection, the cells were induced to undergo apoptosis by withdrawal of serum for 48 hours. Five μg samples of protein extract from each sample were fractionated by SDS-PAGE, transferred to a PVDF membrane, and Western blotted with a monoclonal antibody that recognizes Bcl-2. Rabbit anti-mouse IgG conjugated to peroxidase was used as a secondary antibody, and bound antibody was detected by chemiluminescence and exposure to x-ray film.

Also additionally, COS-7 cells were either mock transfected, transfected with pHM6-LacZ or transfected with pHM6-Sense rF5A (pHM6-Full length rat apoptosis-specific eIF-5A) and incubated for 40 hours. Five μg samples of protein extract from each sample were fractionated by SDS-PAGE, transferred to a PVDF membrane, and Western blotted with a monoclonal antibody that recognizes p53. Goat anti-mouse IgG conjugated to alkaline phosphatase was used as a secondary antibody, and bound antibody was detected a colorimetrically.

Finally, COS-7 cells were either mock transfected, transfected with pHM6-LacZ or transfected with pHM6-Sense rF5A (pHM6-Full length rat apoptosis-specific eIF-5A) and incubated for 40 hours. Five μg samples of protein extract from each sample were fractionated by SDS-PAGE, transferred to a PVDF membrane, and probed with a monoclonal antibody that recognizes p53. Corresponding protein blots were probed with anti-[HA]-peroxidase to determine the level of rat apoptosis-specific eIF-5A expression. Goat anti-mouse IgG conjugated to alkaline phosphatase was used as a secondary antibody, and bound antibody was detected by chemiluminescence.

FIG. 33 illustrates downregulation of Bcl-2 when COS-7 cells were transiently transfected with pHM6 containing frill-length rat apoptosis-specific eIF-5A in the sense orientation. The upper panel illustrates the Coomassie-blue-stained protein blot; the lower panel illustrates the corresponding Western blot. Less Bcl-2 is detectable in cells transfected with pHM6-Sense rF5A than in those transfected with pHM6-LacZ.

Figure 34:
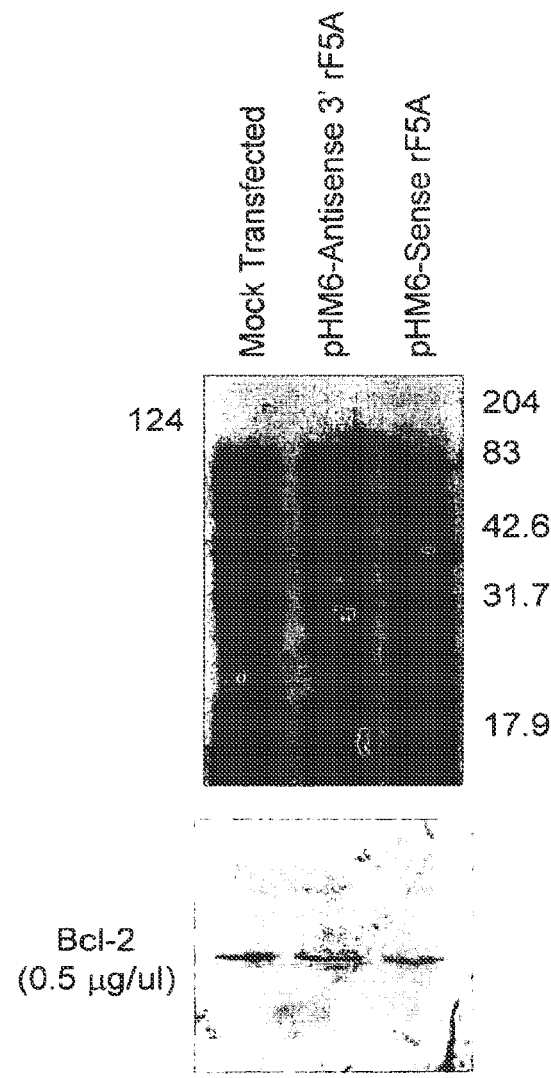
FIG. 34 is a Coomassie-blue-stained protein blot and the corresponding Western blot of COS-7 cells transiently transfected with pHM6 containing full-length rat apoptosis-specific eIF-5A in the antisense orientation using Bcl-2 as a probe.

FIG. 34 illustrates upregulation of Bcl-2 when COS-7 cells were transiently transfected with pHM6 containing the 3' end of apoptosis-specific eIF-5A in the antisense orientation. The upper panel illustrates the Coomassie-blue-stained protein blot; the lower panel illustrates the corresponding Western blot. More Bcl-2 is detectable in cells transfected with pHM6-antisense 3' rF5A than in those mock transfected or transfected with pHM6-Sense rF5A.

Figure 35:
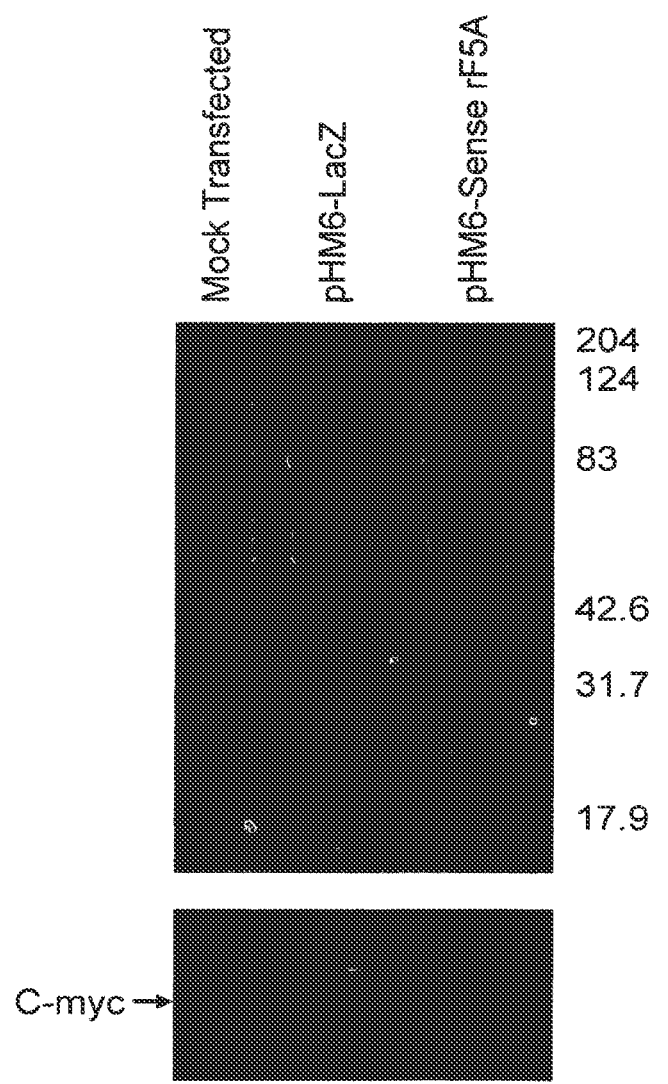
FIG. 35 is a Coomassie-blue-stained protein blot and the corresponding Western blot of COS-7 cells transiently transfected with pHM6 containing full-length rat apoptosis-specific eIF-5A in the sense orientation using c-Myc as a probe.

FIG. 35 illustrates upregulation of c-Myc when COS-7 cells were transiently transfected with pHM6 containing full-length rat apoptosis-specific eIF-5A in the sense orientation. The upper panel illustrates the Coomassie-blue-stained protein blot; the lower panel illustrates the corresponding Western blot. Higher levels of c-Myc is detected in cells transfected with pHM6-Sense rF5A than in those transfected with pHM6-LacZ or the mock control.

Figure 36:
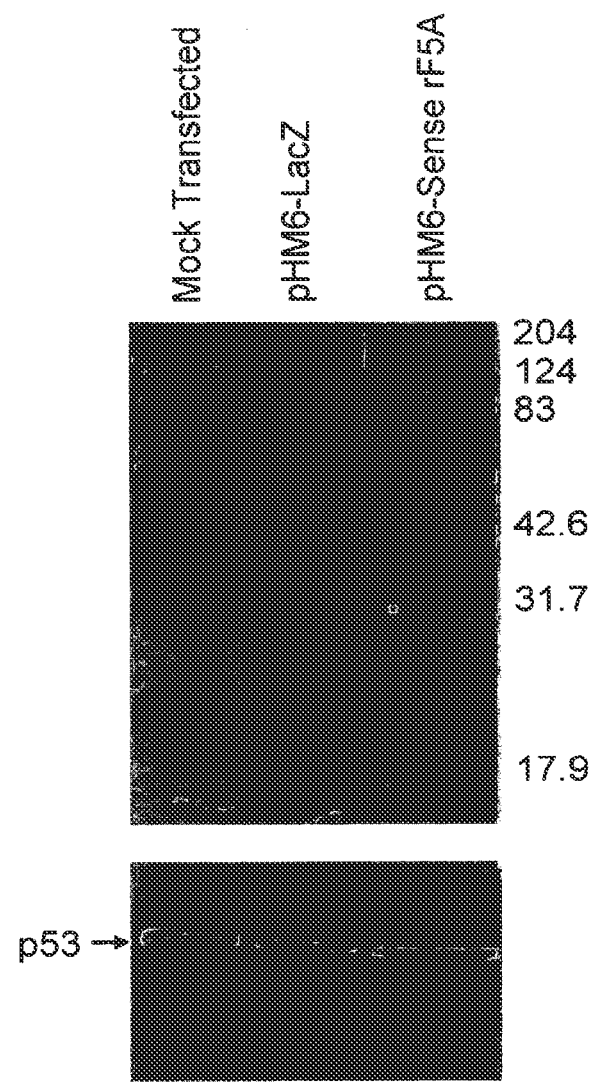
FIG. 36 is a Coomassie-blue-stained protein blot and the corresponding Western blot of COS-7 cells transiently transfected with pHM6 containing full-length rat apoptosis-specific eIF-5A in the sense orientation when p53 is used as a probe.

FIG. 36 illustrates upregulation of p53 when COS-7 cells were transiently transfected with pHM6 containing full-length rat apoptosis-specific eIF-5A in the sense orientation. The upper panel illustrates the Coomassie-blue-stained protein blot; the lower panel illustrates the corresponding Western blot. Higher levels of p53 is detected in cells transfected with pHM6-Sense rF5A than in those transfected with pHM6-LacZ or the mock control.

Figure 37A:
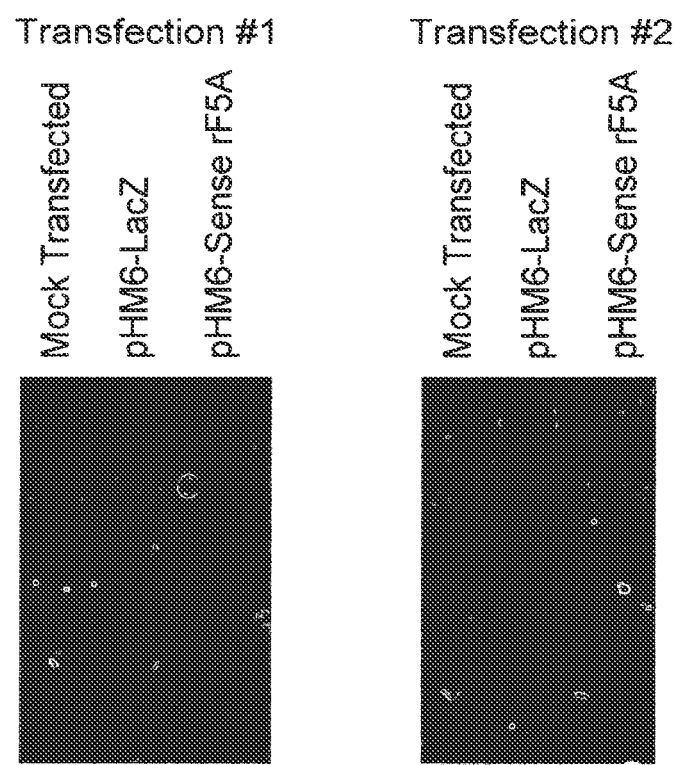
FIG. 37A-C is a Coomassie-blue-stained protein blot and the corresponding Western blot of expression of pHM6-full-length rat apoptosis-specific eIF-5A in COS-7 cells using an anti-[HA]-peroxidase probe and a Coomassie-blue-stained protein blot and the corresponding Western blot of expression of pHM6-full-length rat apoptosis-specific eIF-5A in COS-7 cells when a p53 probe is used.
Figure 37B:
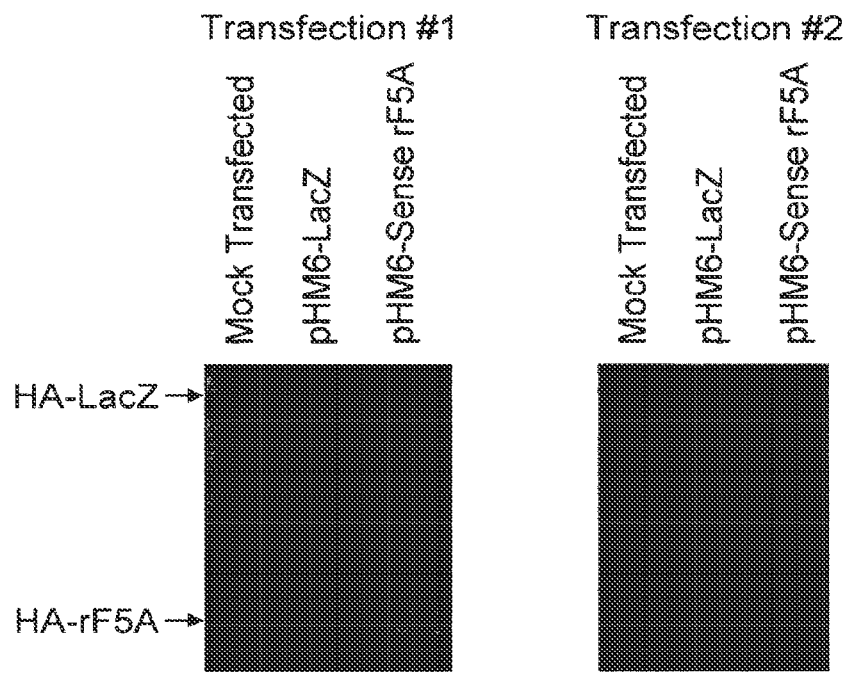
Figure 37C:
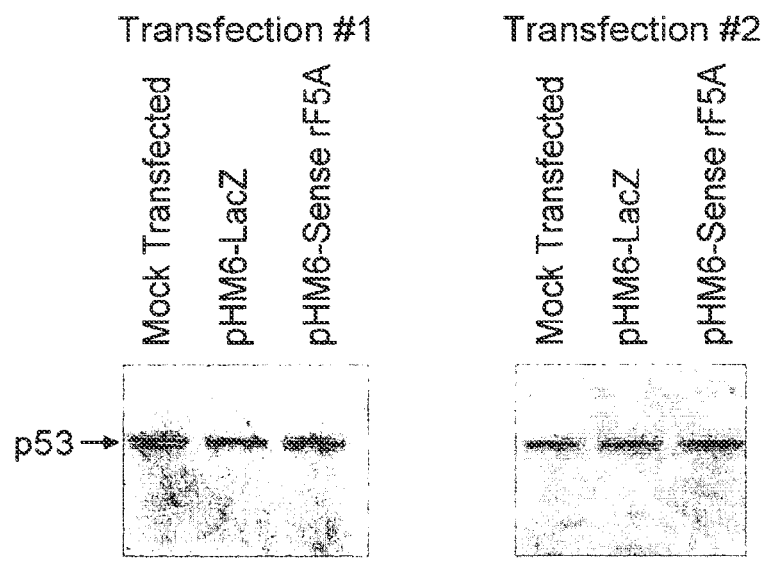
Figure 39:
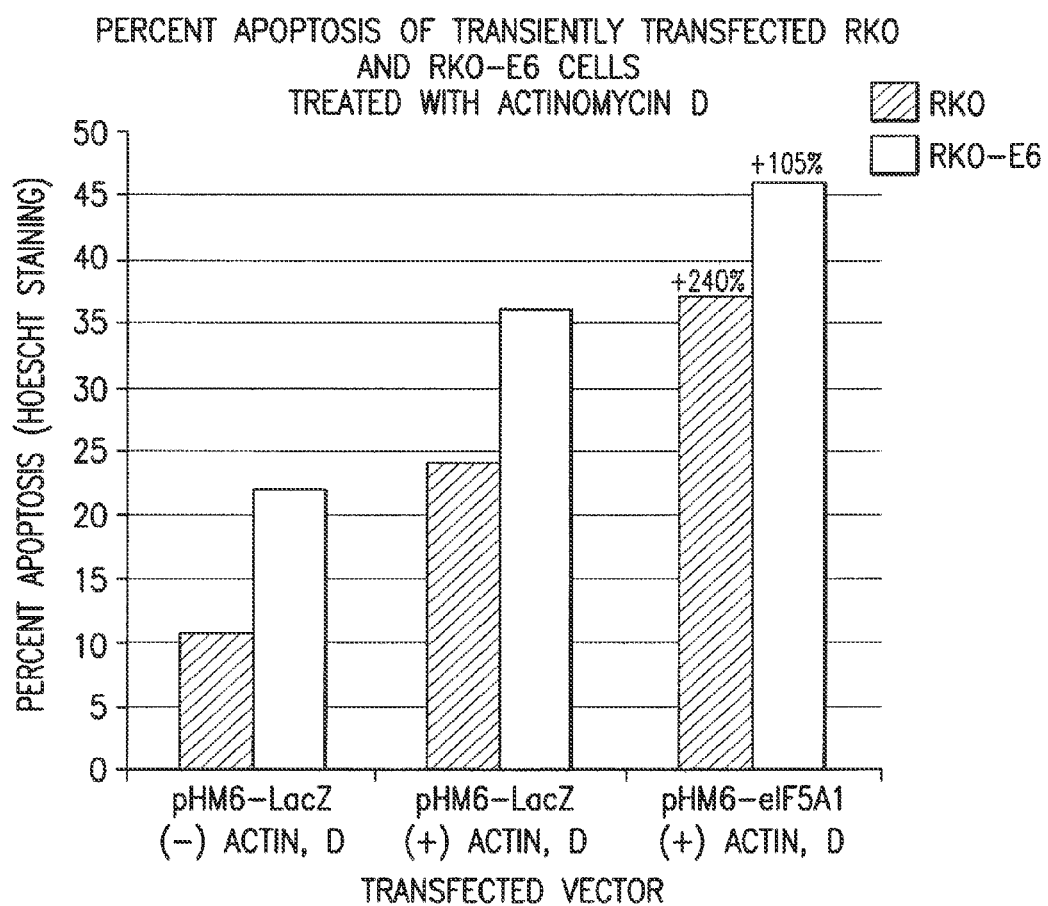
FIG. 39 is a graph depicting the percentage of apoptosis occurring in RKO and RKO-E6 cells following transient transfection. RKO and RKO-E6 cells were transiently transfected with pHM6-LacZ or pHM6-apoptosis-specific eIF-5A. RKO cells treated with Actinomycin D and transfected with pHM6-apoptosis-specific eIF-5A showed a 240% increase in apoptosis relative to cells transfected with pHM6-LacZ that were not treated with Actinomycin D. RKO-E6 cells treated with Actinomycin D and transfected with pHM6-apoptosis-specific eIF-5A showed a 105% increase in apoptosis relative to cells transfected with pHM6-LacZ that were not treated with Actinomycin D.
Figure 40:
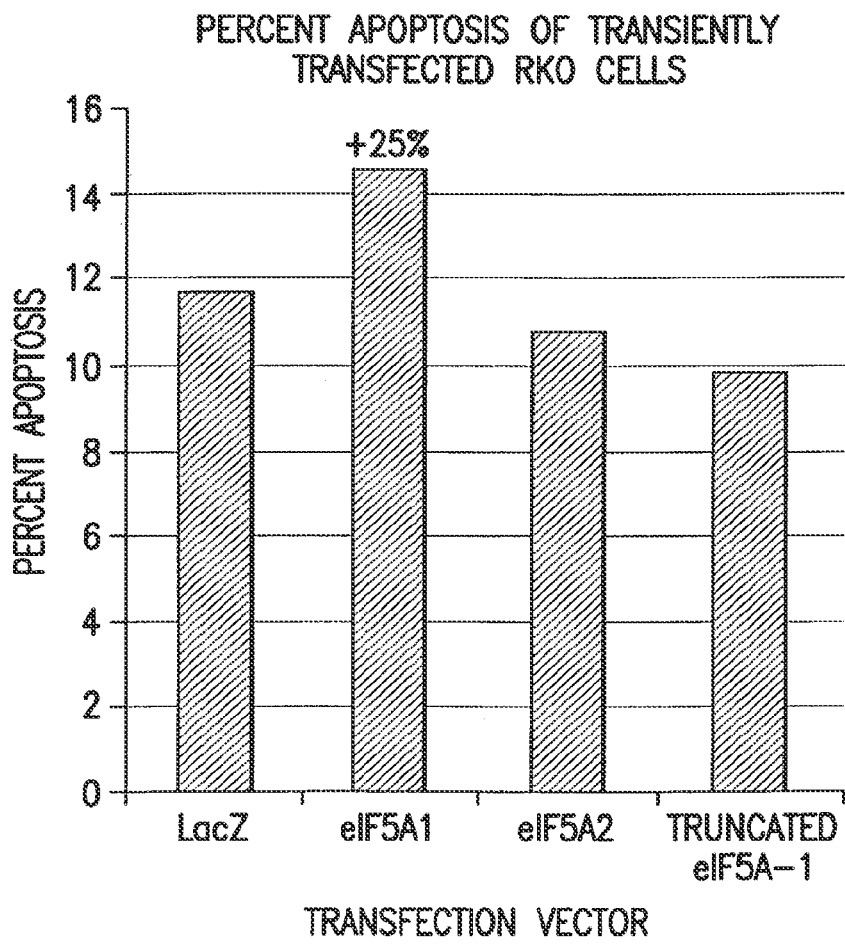
FIG. 40 is a graph depicting the percentage of apoptosis occurring in RKO cells following transient transfection. RKO cells were transiently transfected with pHM6-LacZ, pHM6-apoptosis-specific eIF-5A, pHM6-eIF5A2, or pHM6-truncated apoptosis-specific eIF-5A. Cells transfected with pHM6-apoptosis-specific eIF-5A showed a 25% increase in apoptosis relative to control cells transfected with pHM6-LacZ. This increase was not apparent for cells transfected with pHM6-eIF5A2 or pHM6-truncated apoptosis-specific eIF-5A.
Figure 41:
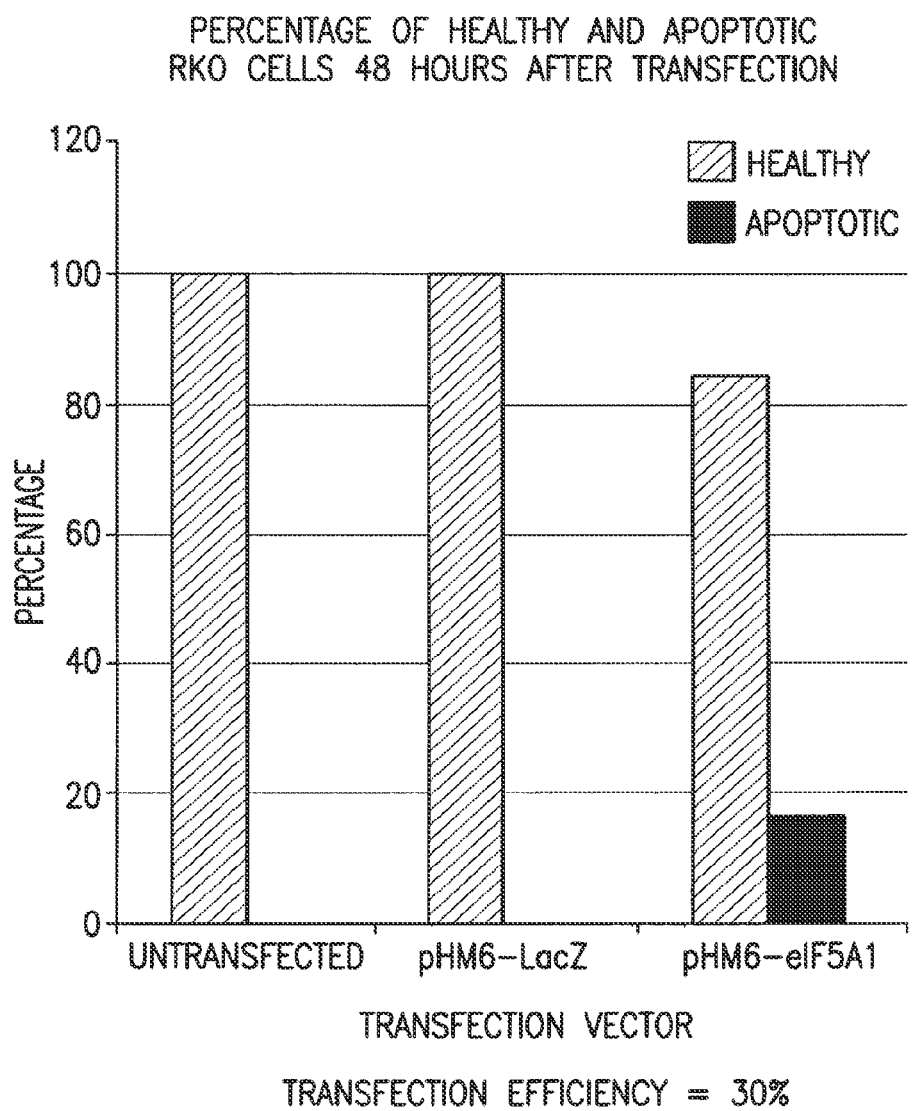
FIG. 41 is a graph depicting the percentage of apoptosis occurring in RKO cells following transient transfection. RKO cells were either left untransfected or were transiently transfected with pHM6-LacZ or pHM6-apoptosis-specific eIF-5A. After correction for transfection efficiency, 60% of the cells transfected with pHM6-apoptosis-specific eIF-5A were apoptotic.
Figures 42A, 42B:
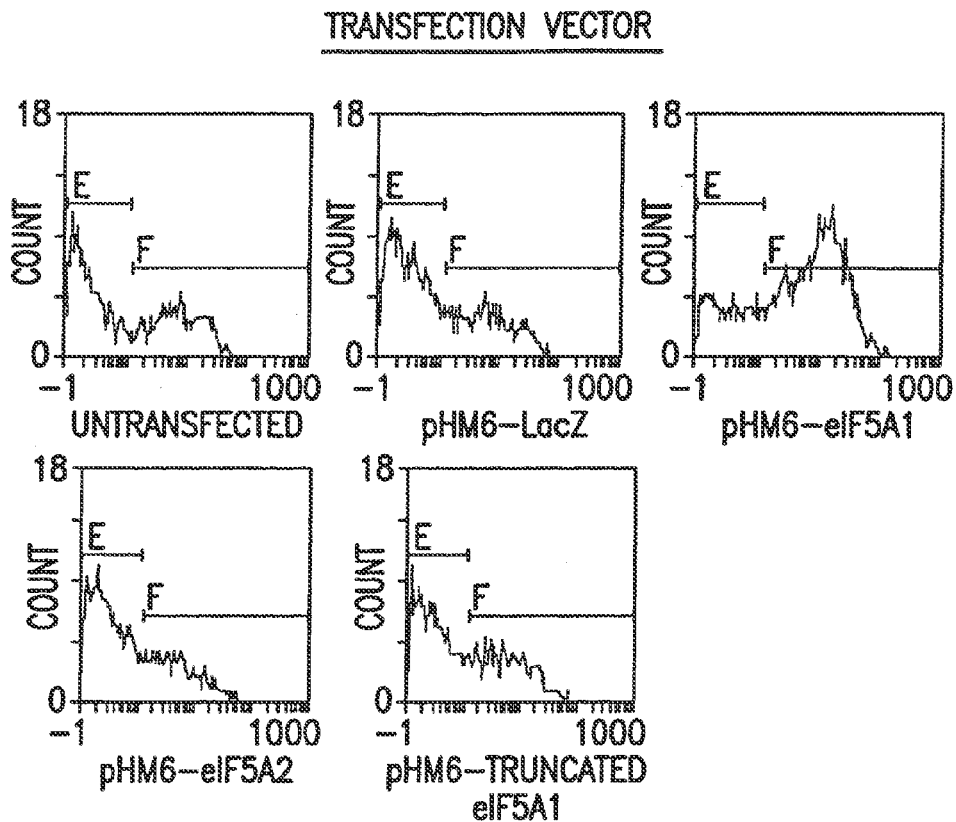
FIG. 42A-B.
Figure 43:
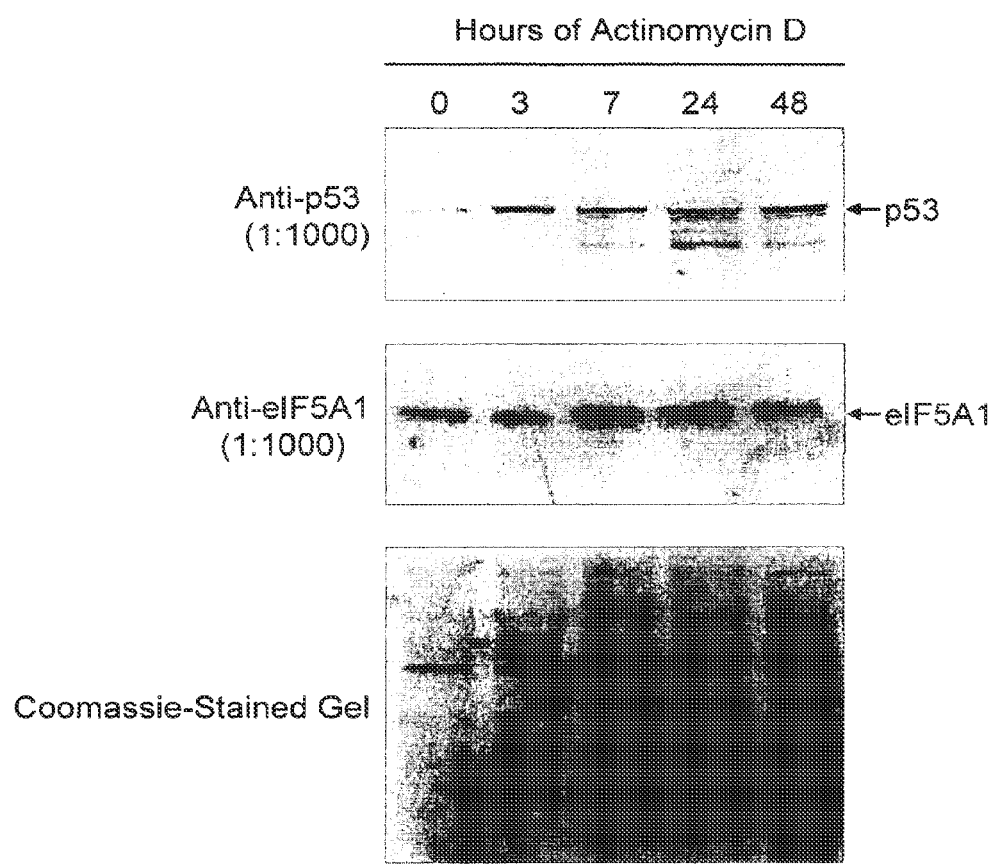
FIG. 43 provides Western blots of protein extracted from RKO cells treated with 0.25 µg/ml Actinomycin D for 0, 3, 7, 24, and 48 hours. The top panel depicts a Western blot using anti-p53 as the primary antibody. The middle panel depicts a Western blot using anti-apoptosis-specific eIF-5A as the primary antibody. The bottom panel depicts the membrane used for the anti-apoptosis-specific eIF-5A blot stained with Coomassie blue following chemiluminescent detection to demonstrate equal loading. p53 and apoptosis-specific eIF-5A are both upregulated by treatment with Actinomycin D.
Figure 44:
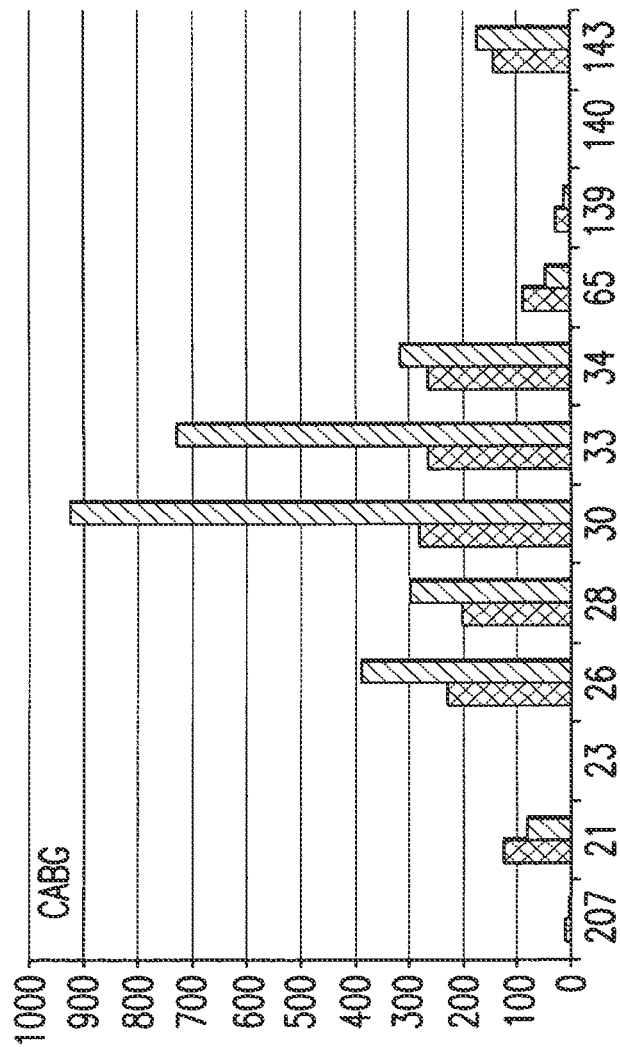
FIG. 44 is a bar graph showing that both apoptosis-specific eIF-5A and proliferation eIF-5A are expressed in heart tissue. The heart tissue was taken from patients receiving coronary artery bypass grafts ("CABG"). Gene expression levels apoptosis-specific eIF-5A (light gray bar) are compared to proliferation eIF-5A (dark gray bar). The X-axis is patient identifier numbers. The Y-axis is pg/ng of 18s (picograms of message RNA over nanograms of ribosomal RNA 18S).
Figure 45:
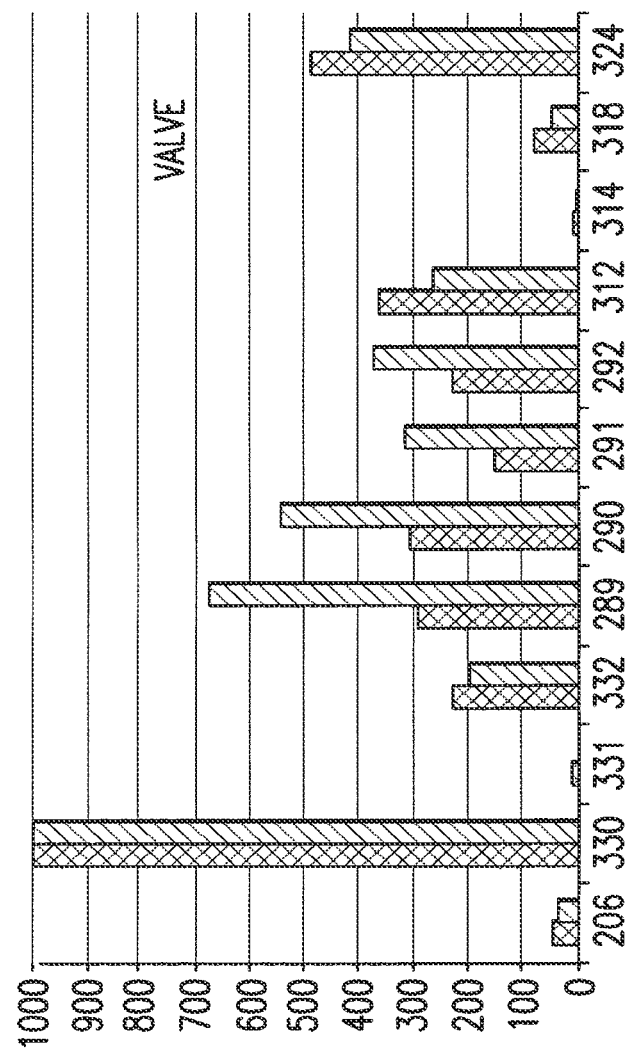
FIG. 45 is a bar graph showing that both apoptosis-specific eIF-5A and proliferation eIF-5A are expressed in heart tissue. The heart tissue was taken from patients receiving valve replacements. Gene expression levels of apoptosis-specific eIF-5A (light gray bar) are compared to proliferation eIF-5A (dark gray bar). The X-axis is patient identifier numbers. The Y-axis is pg/ng of 18s (picograms of message RNA over nanograms of ribosomal RNA 18S).

FIG. 37 illustrates the dependence of p53 upregulation upon the expression of pHM6-full length rat apoptosis-specific eIF-5A in COS-7 cells. More rat apoptosis-specific eIF-5A is detectable in the first transfection than in the second transfection. In the Western blot probed with anti-p53, the panel illustrates a corresponding Coomassie-blue-stained protein blot and the panel illustrates the Western blot with p53. For the first transfection, more p53 is detectable in cells transfected with pHM6-Sense rF5A than in those transfected with pHM6-LacZ or the mock control. For the second transfection in which there was less expression of rat apoptosis-specific eIF-5A, there was no detectable difference in levels of p53 between cells transfected with pHM6-Sense rF5A, pHM6-LacZ or the mock control.

Example 5

Figure 46:
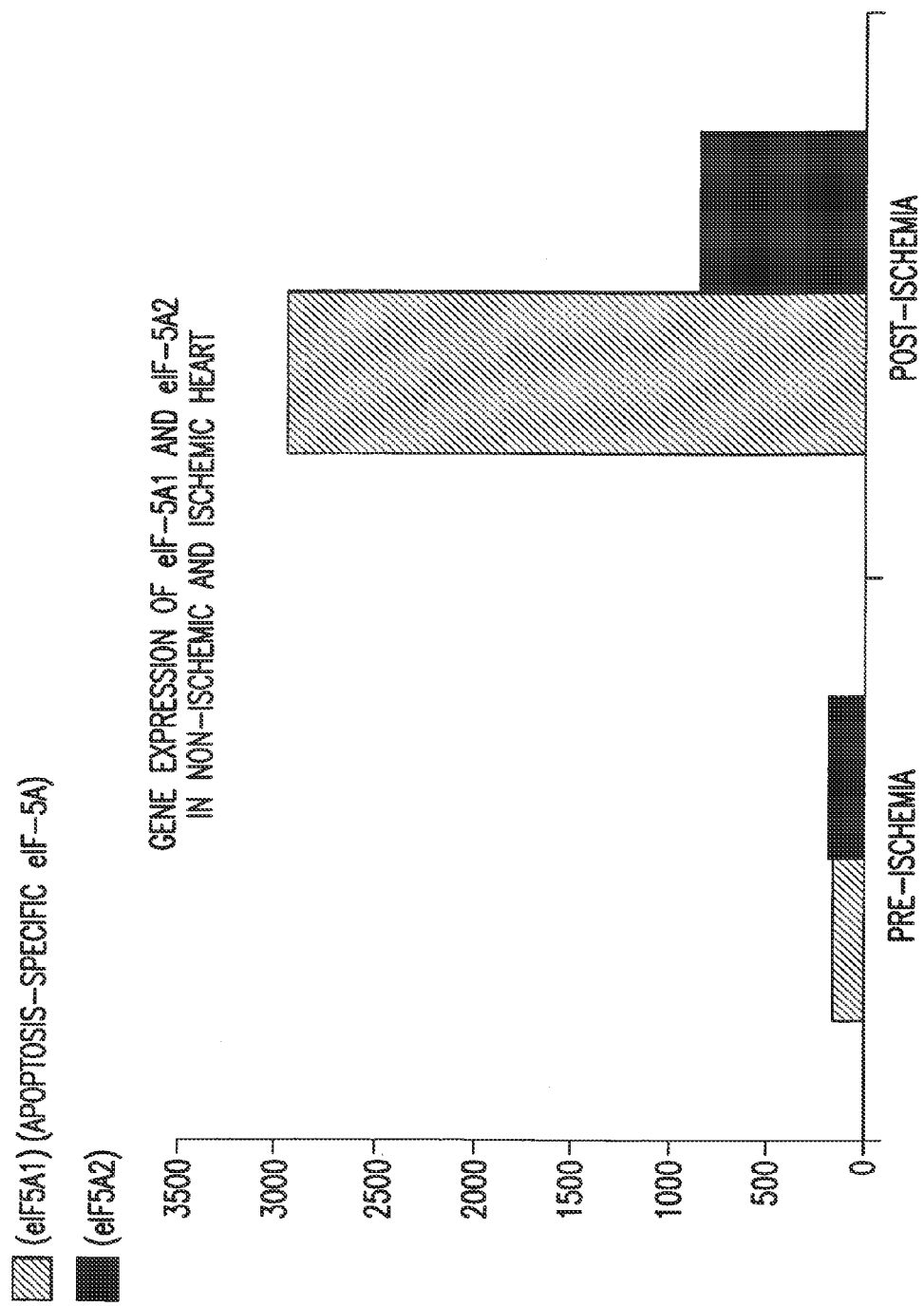
FIG. 46 is a bar graph showing the gene expression levels measured by real-time PCR of apoptosis-specific eIF-5A (eIf5a) versus proliferation eIF-5A (eIF5b) in pre-ischemia heart tissue and post ischemia heart tissue. The Y-axis is pg/ng of 18s (picograms of message RNA over nanograms of ribosomal RNA 18S).
Figure 47:
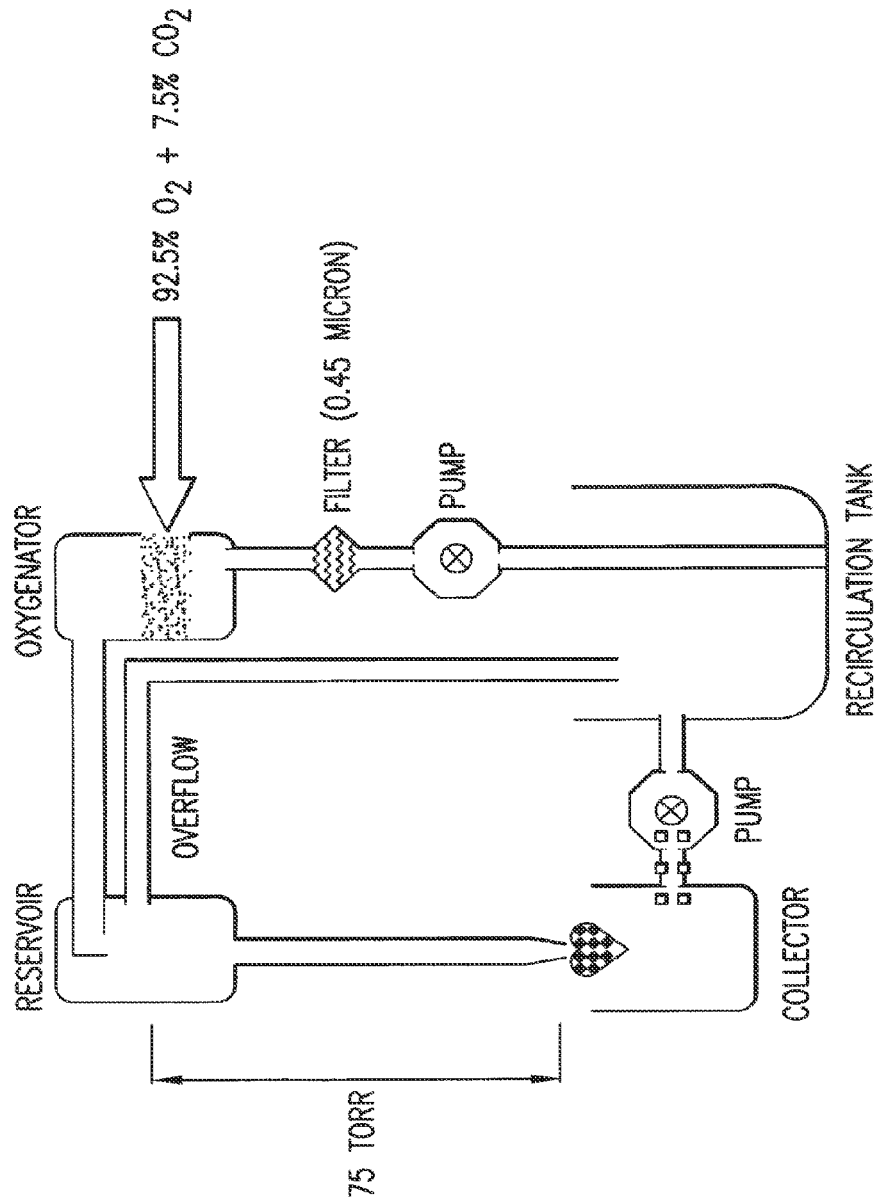
FIG. 47 depicts schematically an experiment performed on heart tissue. The heart tissue was exposed to normal oxygen levels and the expression levels apoptosis-specific eIF-5A and proliferating eIF-5A measured. Later, the amount of oxygen delivered to the heart tissue was lowered, thus inducing hypoxia and ischemia, and ultimately, a heart attack in the heart tissue. The expression levels of apoptosis-specific eIF-5A and proliferating eIF-5A were measured and compared to the expression levels of the heart tissue before it was damaged by ischemia.
Figure 49:
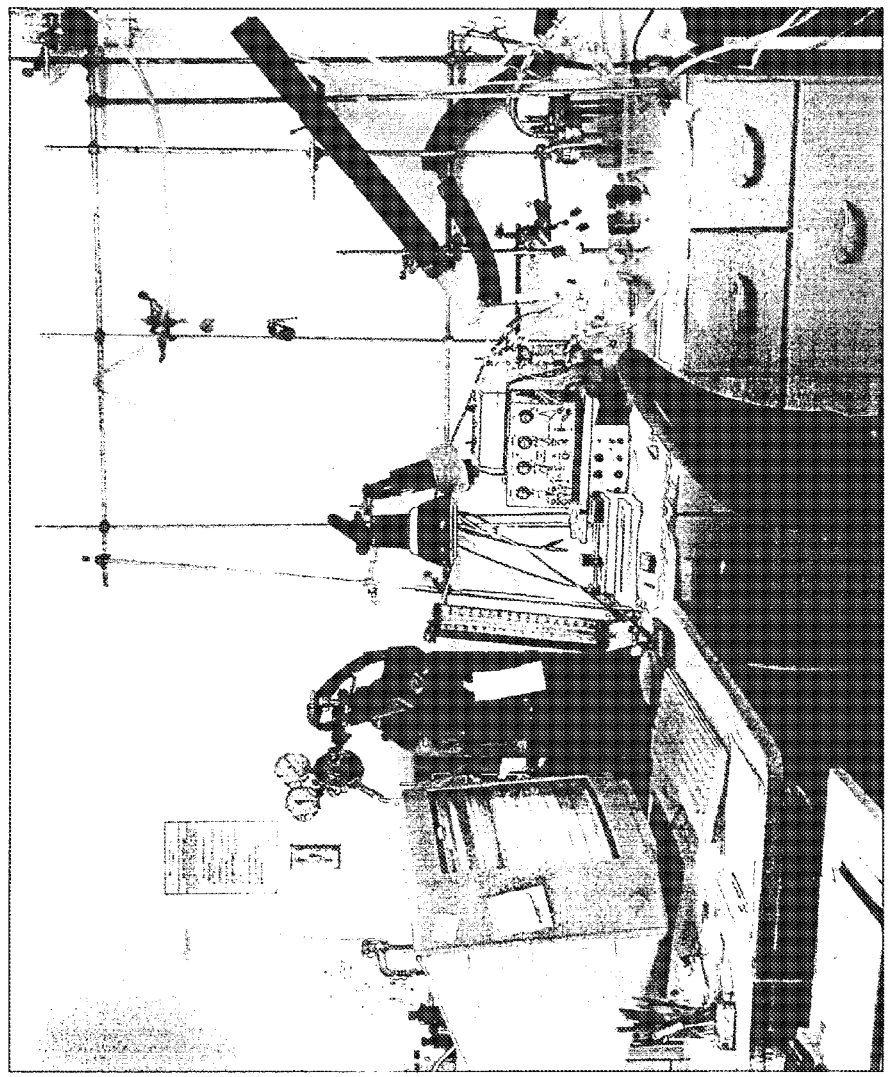
FIG. 49 shows the lab bench with the set up of the experiment depicted in FIG. 47.
Figure 50D:
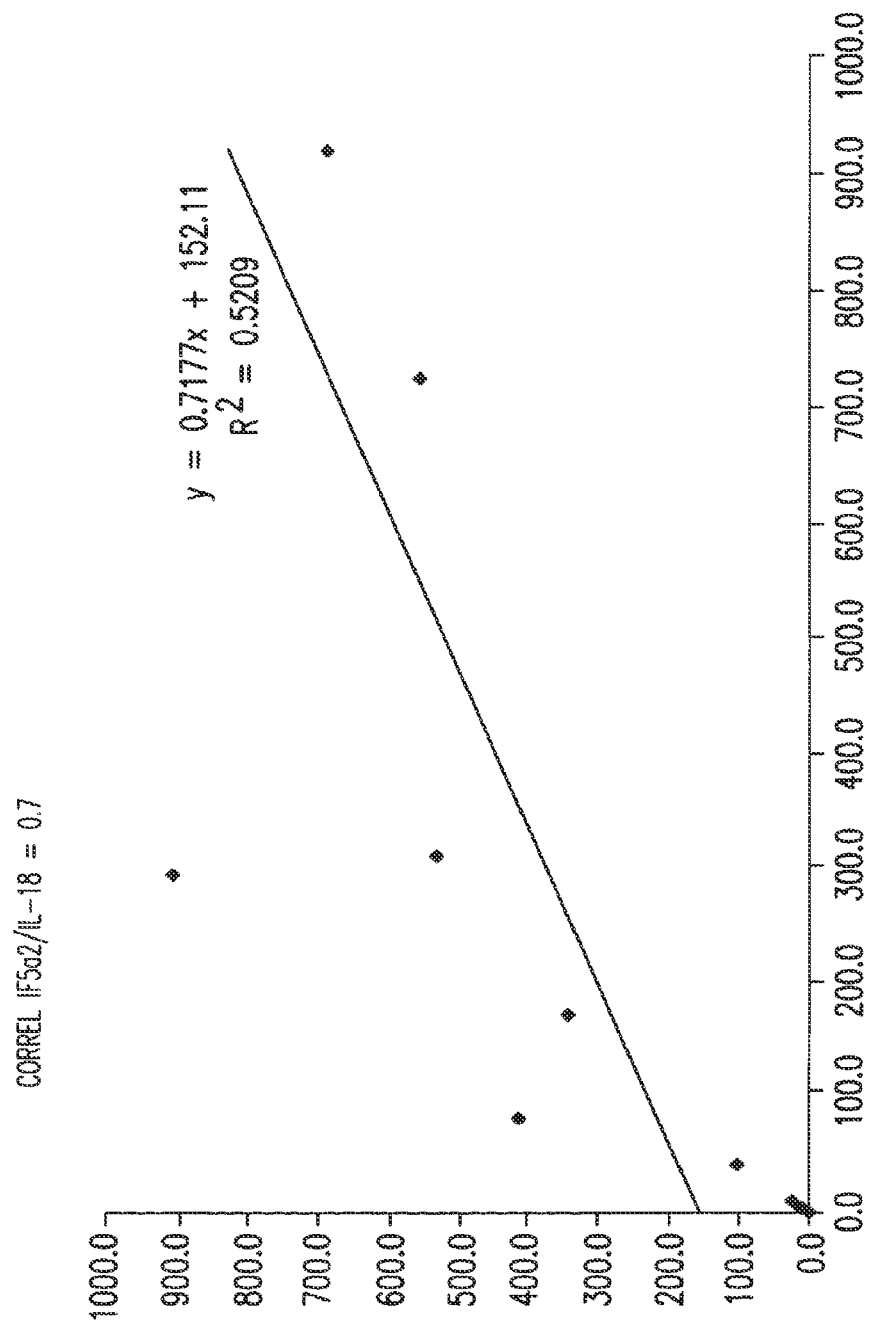
Figure 50E:
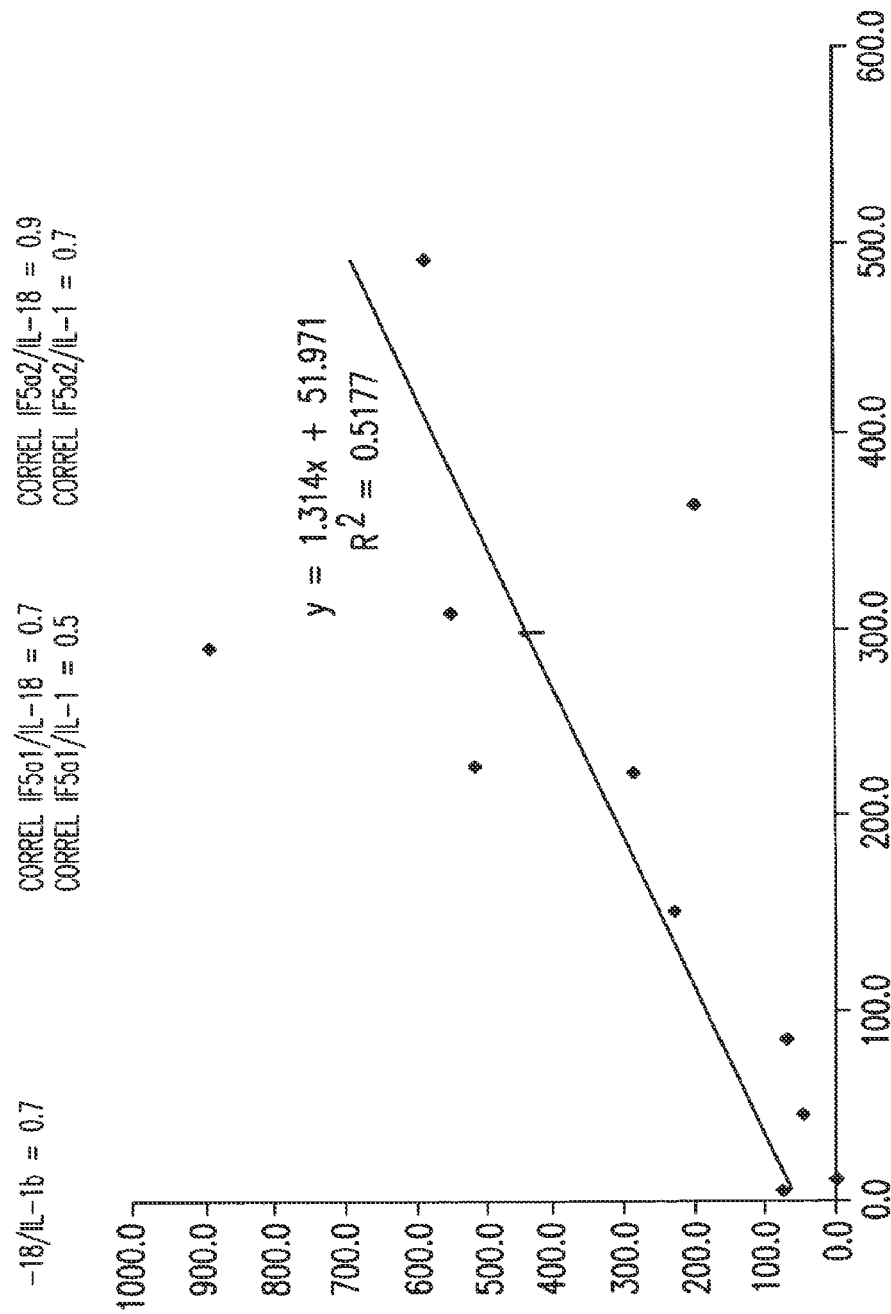
Figure 50F:
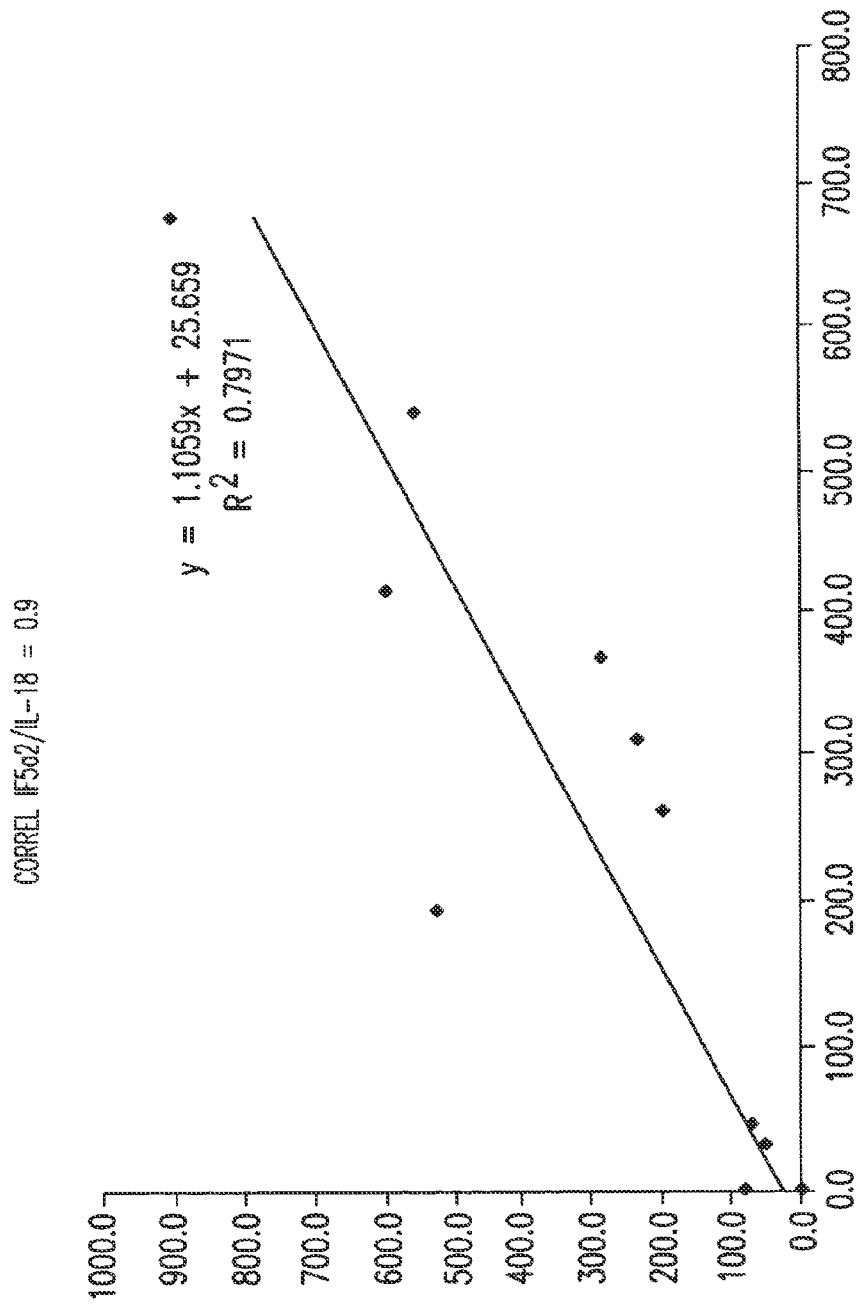

FIG. 47 depicts an experiment run on heart tissue to mimic the beating of a human heart and the subsequent induced heart attack. FIG. 49 shows the laboratory bench set up. A slice of human heart tissue removed during valve replacement surgery was hooked up to electrodes. A small weight as attached to the heart tissue to ease in measuring the strength of the heart beats. The electrodes provided an electrical stimulus to get the tissue to start beating. The levels of gene expression for both apoptosis-specific eIF-5A and proliferating eIF-5A were measured in the heart tissue before ischemia was induced. See FIG. 46. In the pre-ischemic heart tissue low levels both apoptosis-specific eIF-5A and proliferating eIF-5A were produced and their levels were in relative balance. During this time, oxygen and carbon dioxide were delivered in a buffer to the heart at 92.5% and 7.5%, respectively. Later, the oxygen levels was reduced and the nitrogen levels was increased, to induce ischemia and finally a "heart attack." The heart tissue stopped beating. The oxygen levels were then returned to normal, the heart tissue was pulsed again with an electrical stimulus to start the heart beating again. After the "heart attack" the expression levels of apoptosis-specific eIF-5A and proliferating eIF-5A were again measured. This time, there was a significant increase in the level of expression of the apoptosis-specific eIF-5A levels, whereas the increase in the level of expression of proliferating eIF-5A was noticeably less. See FIG. 46.

After the "heart attack" the heart did not beat as strong, as indicated by less compression/movement of the attached weight, thus indicating that the heart tissue cells were being killed rapidly due to the presence of apoptosis-specific eIF-5A.

Figure 48:
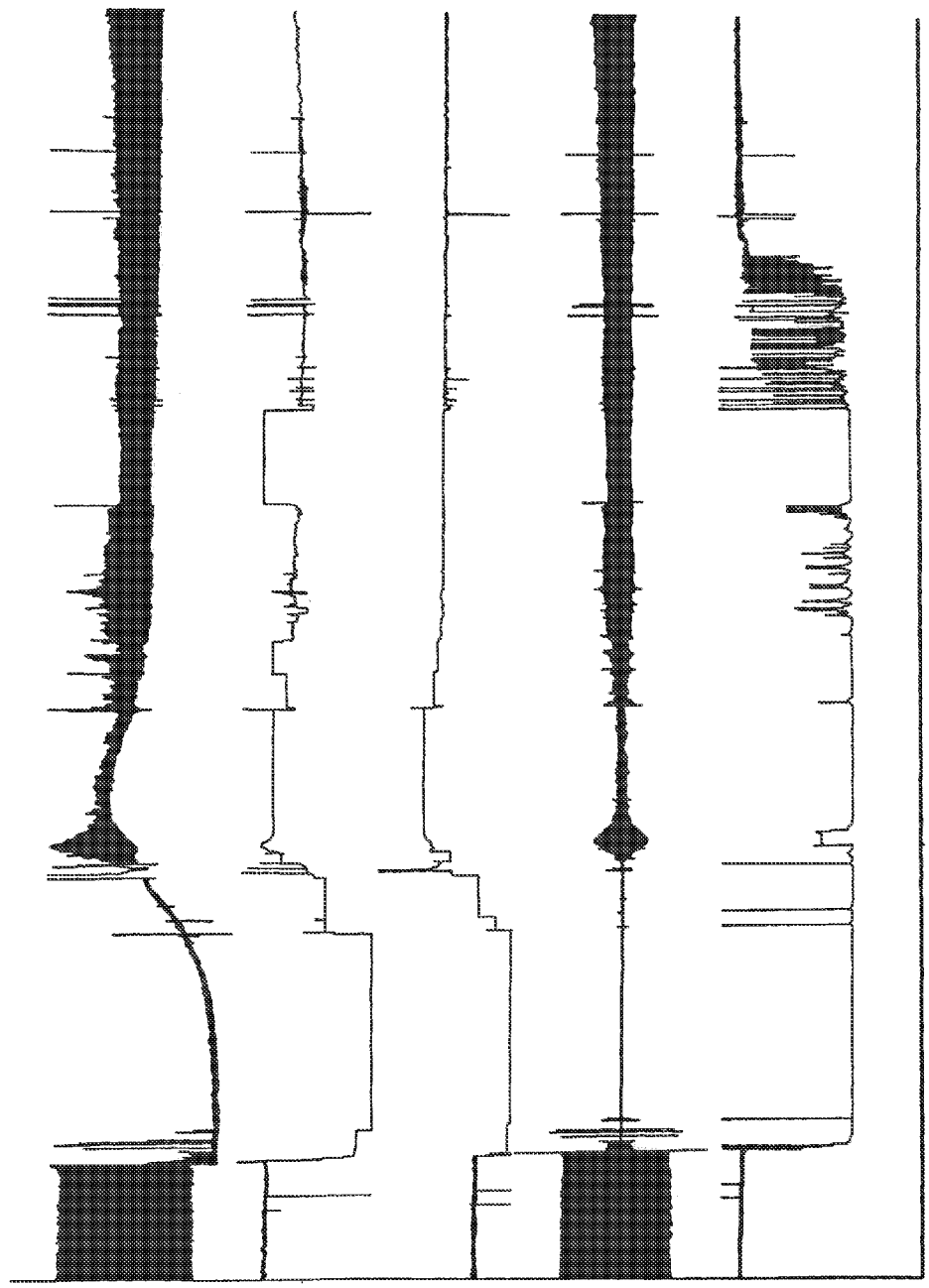
FIG. 48 shows EKGs of heart tissue before and after the ischemia was induced.

The EKG results are depicted in FIG. 48. On the left side of the panels a normal heart beat is shown (the pre-ischemic heart tissue). After the "heart attack" (straight line), and the re-initiation of the heart beat, the EKG shows decreased activity due to muscle cell death. The EKG shows relative loss in strength of heart beat.

Example 6

The following examples provide cell culture conditions.
Human Lamina Cribrosa and Astrocyte Culture Paired human eyes were obtained within 48 hours post mortem from the Eye Bank of Canada, Ontario Division. Optic nerve heads (with attached pole) were removed and placed in Dulbecco's modified Eagle's medium (DIVIEM) supplemented with antibiotic/antimycotic, glutamine, and 10% FBS for 3 hours. The optic nerve head (ONH) button was retrieved from each tissue sample and minced with fine dissecting scissors into four small pieces. Explants were cultured in 12.5 cm$^2$ plastic culture flasks in DMEM medium. Growth was observed within one month in viable explants. Once the cells reached 90% confluence, they were trypsinized and subjected to differential subculturing to produce lamina cribrosa (LC) and astrocyte cell populations. Specifically, LC cells were subcultured in 25 cm$^2$ flasks in DMEM supplemented with gentamycin, glutamine, and 10% FBS, whereas astrocytes were expanded in 25 cm$^2$ flasks containing EBM complete medium (Clonetics) with no FBS. FBS was added to astrocyte cultures following 10 days of subculture. Cells were maintained and subcultured as per this protocol.

Cell populations obtained by differential subculturing were characterized for identity and population purity using differential fluorescent antibody staining on 8 well culture slides. Cells were fixed in 10% formalin solution and washed three times with Dulbecco's Phosphate Buffered Saline (DPBS). Following blocking with 2% nonfat milk in DPBS, antibodies were diluted in 1% BSA in DPBS and applied to the cells in 6 of the wells. The remaining two wells were treated with only 1% bovine serum albumin (BSA) solution and no primary antibody as controls. Cells were incubated with the primary antibodies for one hour at room temperature and then washed three times with DPBS. Appropriate secondary antibodies were diluted in 1% BSA in DPBS, added to each well and incubated for 1 hour. Following washing with DPBS, the chambers separating the wells of the culture slide were removed from the slide, and the slide was immersed in double distilled water and then allowed to air-dry. Fluoromount (Vector Laboratories) was applied to each slide and overlayed by 22×60 mm coverglass slips.

Immunofluorescent staining was viewed under a fluorescent microscope with appropriate filters and compared to the control wells that were not treated with primary antibody. All primary antibodies were obtained from Sigma unless otherwise stated. All secondary antibodies were purchased from Molecular Probes. Primary antibodies used to identify LC cells were: anti-collagen I, anti-collagen IV, anti-laminin, anti-cellular fibronectin. Primary antibodies used to identify astrocytes were: anti-galactocerebroside (Chemicon International), anti-A2B5 (Chemicon International), anti-NCAM, anti-human Von willebrand Factor. Additional antibodies used for both cell populations included anti-glial fibrillary (GFAP) and anti-alpha-smooth muscle actin. Cell populations were determined to be comprised of LC cells if they stained positively for collagen I, collagen IV, laminin, cellular fibronectin, alpha smooth muscle actin and negatively for glial fibrillary (GFAP). Cell populations were determined to be comprised of astrocytes if they stained positively for NCAM, glial fibrillary (GFAP), and negatively for galactocerebroside, A2B5, human Von willebrand Factor, and alpha smooth muscle actin.

In this preliminary study, three sets of human eyes were used to initiate cultures. LC cell lines #506, #517, and #524 were established from the optic nerve heads of and 83-Year old male, a 17-year old male, and a 26-year old female, respectively. All LC cell lines have been fully characterized and found to contain greater than 90% LC cells.
RKO Cell Culture RKO (American Type Culture Collection CRL-2577), a human colon carcinoma cell line expressing wild-type p53, was used to test the antisense oligonucleotides for the ability to suppress apoptosis-specific eIF-5A protein expression. RKO were cultured in Minimum Essential Medium Eagle (MEM) with non-essential amino acids, Earle's salts, and L-glutamine. The culture media was supplemented with 10% fetal bovine serum (FBS) and 100 units of penicillin/streptomycin. The cells were grown at 37° C. in a humidified environment of 5% $CO_2$ and 95% air. The cells were subcultured every 3 to 4 days by detaching the adherent cells with a solution of 0.25% trypsin and 1 mM EDTA. The detached cells were dispensed at a split ratio of 1:10 to 1:12 into a new culture dish with fresh media.
HepG2 Cell Culture HepG2, a human hepatocellular carcinoma cell line, was used to test the ability of an antisense oligo directed against human apoptosis-specific eIF-5A to block production of TNF-α in response to treatment with IL-1β. HepG2 cells were cultured in DMEM supplemented with gentamycin, glutamine, and 10% FBS and grown at 37° C. in a humidified environment of 5% $CO_2$ and 95% air.

Example 7

Induction of Apoptosis

Apoptosis was induced in RKO and lamina cribrosa cells using Actinomycin D, an RNA polymerase inhibitor, and camptothecin, a topoisomerase inhibitor, respectively. Actinomycin D was used at a concentration of 0.25 μg/ml and camptothecin was used at a concentration of 20, 40, or 50 μM. Apoptosis was also induced in lamina cribrosa cells using a combination of camptothecin (50 μM) and TNF-α (10 ng/ml). The combination of camptothecin and TNF-α was found to be more effective at inducing apoptosis than either camptothecin or TNF-α alone.
Antisense Oligonucleotides A set of three antisense oligonucleotides targeted against human apoptosis-specific eIF-5A were designed by, and purchased from, Molecula Research Labs. The sequence of the first antisense oligonucleotide targeted against human apoptosis-specific eIF-5A (#1) was 5' CCT GTC TCG AAG TCC AAG TC 3' (SEQ ID NO: 63). The sequence of the second antisense oligonucleotide targeted against human apoptosis-specific eIF-5A (#2) was 5' GGA CCT TGG CGT GGC CGT GC 3' (SEQ ID NO: 64). The sequence of the third antisense oligonucleotide targeted against human apoptosis-specific eIF-5A (#3) was 5' CTC GTA CCT CCC CGC TCT CC 3' (SEQ ID NO: 65). The control oligonucleotide had the sequence 5' CGT ACC GGT ACG GTT CCA GG 3' (SEQ ID NO: 66). A fluorescein isothiocyanate (FITC)-labeled antisense oligonucleotide (Molecula Research Labs) was used to monitor transfection efficiency and had the sequence 5' GGA CCT TGG CGT GGC CGT GCX 3' (SEQ ID NO: 67), where X is the FITC label. All antisense oligonucleotides were hilly phosphorothioated.

Transfection of Antisense Oligonucleotides

The ability of the apoptosis-specific eIF-5A antisense oligonucleotides to block apoptosis-specific eIF-5A protein expression was tested in RKO cells. RKO cells were transfected with antisense oligonucleotides using the transfection reagent, Oligofectamine (Invitrogen). Twenty four hours prior to transfection, the cells were split onto a 24 well plate at 157,000 per well in MEM media supplemented with 10% FBS but lacking penicillin/streptomycin. Twenty four hours later the cells had generally reached a confluency of approximately 50%. RKO cells were either mock transfected, or transfected with 100 nM or 200 nM of antisense oligonucleotide. Transfection medium sufficient for one well of a 24 well plate was prepared by diluting 0, 1.25, or 2.5 µl of a 20 µM stock of antisense oligonucleotide with serum-free MEM to a final volume of 42.5 µl and incubating the mixture at room temperature for 15 minutes. 1.5 µl of Oligofectamine was diluted in 6 µl of serum-free MEM and incubated for 7.5 minutes at room temperature. After 5 minutes the diluted Oligofectamine mixture was added to the DNA mixture and incubated together at room temperature for 20 minutes. The cells were washed once with serum-free MEM before adding 200 µl of MEM to the cells and overlaying 50 µl of transfection medium. The cells were placed back in the growth chamber for 4 hours. After the incubation, 125 µl of MEM+30% FBS was added to the cells. The cells were then cultured for a further 48 hours, treated with 0.25 µg/ml Actinomycin D for 24 hours, and then cell extract was harvested for Western blot analysis.

Transfection of lamina cribrosa cells was also tested using 100 and 200 nM antisense oligonucleotide and Oligofectamine using the same procedure described for RKO cells. However, effective transfection of lamina cribrosa cells was achieved by simply adding antisense oligonucleotide, diluted from 1 µM to 10 µM in serum-free media, to the cells for 24 hours and thereafter replacing the media with fresh antisense oligonucleotides diluted in serum-containing media every 24 hours for a total of two to five days.

The efficiency of antisense oligonucleotide transfection was optimized and monitored by performing transfections with an FITC-labeled antisense oligonucleotide having the same sequence as apoptosis-specific eIF-5A antisense oligonucleotide #2 (SEQ ID NO:64) but conjugated to FITC at the 3' end. RKO and lamina cribrosa cells were transfected with the FITC-labeled antisense oligonucleotide on an 8-well culture slide. Forty-eight hours later the cells were washed with PBS and fixed for 10 minutes in 3.7% formaldehyde in PBS. The wells were removed and mounting media (Vectashield) was added, followed by a coverslip. The cells were then visualized under UV light on a fluorescent microscope nucleus using a fluorescein filter (Green H546, filter set 48915) and cells fluorescing bright green were determined to have taken up the oligonucleotide.

Detection of Apoptosis

Following transfection of lamina cribosa cells with antisense oligonucleotides and induction of apoptosis with camptothecin, the percentage of cells undergoing apoptosis in cells treated with either control antisense oligonucleotide or antisense oligonucleotide apoptosis-specific eIF-5A SEQ ID NO:26 was determined. Two methods were used to detect apoptotic lamina cribosa cells—Hoescht staining and DeadEnd™ Fluorometric TUNEL. The nuclear stain, Hoescht, was used to label the nuclei of lamina cribosa cells in order to identify apoptotic cells based on morphological features such as nuclear fragmentation and condensation. A fixative, consisting of a 3:1 mixture of absolute methanol and glacial acetic acid, was prepared immediately before use. An equal volume of fixative was added to the media of cells growing on a culture slide and incubated for 2 minutes. The media/fixative mixture was removed from the cells and discarded and 1 ml of fixative was added to the cells. After 5 minutes the fixative was discarded and 1 ml of fresh fixative was added to the cells and incubated for 5 minutes. The fixative was discarded and the cells were air-dried for 4 minutes before adding 1 ml of Hoescht stain (0.5 µg/ml Hoescht 33258 in PBS). After a 10 minute incubation in the dark, the staining solution was discarded, the chambers separating the wells of the culture slide were removed, and the slide was washed 3 times for 1 minute with deionized water. After washing, a few drops of McIlvaine's buffer (0.021 M citric acid, 0.058 M $Na_2HPO_4.7H_2O$; pH 5.6) was added to the cells and overlaid with a coverslip. The stained cells were viewed under a fluorescent microscope using a UV filter. Cells with brightly stained or fragmented nuclei were scored as apoptotic. A minimum of 200 cells were counted per well.

The DeadEnd™ Fluorometric TUNEL, (Promega) was used to detect the DNA fragmentation that is a characteristic feature of apoptotic cells. Following Hoescht staining, the culture slide was washed briefly with distilled water, and further washed by immersing the slide twice for 5 minutes in PBS (137 mM NaCl, 2.68 mM KCl, 1.47 mM $KH_2PO_4$, 8.1 mM.$Na_2HPO_4$), blotting the slide on paper towel between washes. The cells were permeabilized by immersing them in 0.2% Triton X-100 in PBS for 5 minutes. The cells were then washed again by immersing the slide twice for 5 minutes in PBS and blotting the slide on paper towel between washes. 25 µl of equilibration buffer [200 mM potassium cacodylate (pH 6.6), 25 mM Tris-HCl (pH 6.6), 0.2 mM dithiothreitol, 0.25 mg/ml bovine serum albumin, and 2.5 mM cobalt chloride] was added per well and incubated for 5 to 10 minutes. During equilibration, 30 µl of reaction mixture was prepared for each well by mixing in a ratio of 45:5:1, respectively, equilibration buffer, nucleotide mix [50 µM fluorescein-12-dUTP, 100 µM dATP, 10 mM Tris-HCl (pH 7.6), and 1 mM EDTA], and terminal deoxynucleotidyl transferase enzyme (Tdt, 25 U/µl). After the incubation in equilibration buffer, 30 µl of reaction mixture was added per well and overlayed with a coverslip. The reaction was allowed to proceed in the dark at 37° C. for 1 hour. The reaction was terminated by immersing the slide in 2×SSC [0.3 M NaCl, and 30 mM sodium citrate (pH 7.0)] and incubating for 15 minutes. The slide was then washed by immersion in PBS three times for 5 minutes. The PBS was removed by sponging around the wells with a Kim wipe, a drop of mounting media (Oncogene research project, JA1750-4 ML) was added to each well, and the slide was overlayed with a coverslip. The cells were viewed under a fluorescent microscope using a UV filter (UV-G 365, filter set 487902) in order to count the Hoescht-stained nuclei. Any cells with brightly stained or fragmented nuclei were scored as apoptotic. Using the same field of view, the cells were then viewed using a fluorescein filter (Green H546, filter set 48915) and any nuclei fluorescing bright green were scored as apoptotic. The percentage of apoptotic cells in the field of view was calculated by dividing the number of bright green nuclei counted using the fluorescein filter by the total number of nuclei counted under the UV filter. A minimum of 200 cells were counted per well.

FIGS. 54-57 depict the results of these studies. The percentage of apoptotic cells in samples having been transfected with apoptosis-specific eIF-5A is clearly much less than seen in cells having been transfected with the control oligonucleotide.

Protein Extraction and Western Blotting

Protein from transfected RKO cells was harvested for Western blot analysis by washing the cells with PBS, adding 40 µl of hot lysis buffer [0.5% SDS, 1 mM dithiothreitol, 50 mM Tris-HCl (pH 8.0)] per well. The cells were scraped and the resulting extract was transferred to a microfuge tube, boiled for 5 minutes, and stored at −20° C. The protein was quantitated using the Bio-Rad Protein Assay (Bio-Rad) according to the manufacturer's instructions.

For Western blotting 5 µg of total protein was separated on a 12% SDS-polyacrylamide gel. The separated proteins were transferred to a polyvinylidene difluoride membrane. The membrane was then incubated thr one hour in blocking solution (5% skim milk powder in PBS) and washed three times for 15 minutes in 0.05% Tween-20/PBS. The membrane was stored overnight in PBS-T at 4° C. After being warmed to room temperature the next day, the membrane was blocked for 30 seconds in 1 µg/ml polyvinyl alcohol. The membrane was rinsed 5 times in deionized water and then blocked for 30 minutes in a solution of 5% milk in 0.025% Tween-20/PBS. The primary antibody was preincubated for 30 minutes in a solution of 5% milk in 0.025% Tween-20/PBS prior to incubation with the membrane.

Several primary antibodies were used. A monoclonal antibody from Oncogene which recognizes p53 (Ab-6) and a polyclonal antibody directed against a synthetic peptide (amino-CRLPEGDLGKEIEQKYD-carboxy) (SEQ ID NO:68) homologous to the c-terminal end of human apoptosis-specific eIF-5A that was raised in chickens (Gallus Immunotech). An anti-β-actin antibody (Oncogene) was also used to demonstrate equal loading of protein. The monoclonal antibody to p53 was used at a dilution of 0.05 µg/ml, the antibody against apoptosis-specific eIF-5A was used at a dilution of 1:1000, and the antibody against actin was used at a dilution of 1:20,000. After incubation with primary antibody for 60 to 90 minutes, the membrane was washed 3 times for 15 minutes in 0.05% Tween-20PBS. Secondary antibody was then diluted in 1% milk in 0.025% Tween-20/PBS and incubated with the membrane for 60 to 90 minutes. When p53 (Ab-6) was used as the primary antibody, the secondary antibody used was a rabbit anti-mouse IgG conjugated to peroxidase (Sigma) at a dilution of 1:5000. When anti-apoptosis-specific eIF-5A was used as the primary antibody, a rabbit anti-chicken IgY conjugated to peroxidase (Gallus Immunotech) was used at a dilution of 1:5000. The secondary antibody used with actin was a goat anti-mouse IgM conjugated to peroxidase (Calbiochem) used at a dilution of 1:5000. After incubation with the secondary antibody, the membrane was washed 3 times in PBS-T.

The ECL Plus Western blotting detection kit (Amersham Pharmacia Biotech) was used to detect peroxidase-conjugated bound antibodies. In brief, the membrane was lightly blotted dry and then incubated in the dark with a 40:1 mix of reagent A and reagent B for 5 minutes. The membrane was blotted dry, placed between sheets of acetate, and exposed to X-ray film for time periods varying from 10 seconds to 30 minutes. The membrane was stripped by submerging the membrane in stripping buffer [100 mM 2-Mercaptoethanol, 2% SDS, and 62.5 mM Tris-HCl (pH 6.7)], and incubating at 50° C. for 30 minutes. The membrane was then rinsed in deionized water and washed twice for 10 minutes in large volumes of 0.05% Tween-20/PBS. Membranes were stripped and re-blotted up to three times.

Example 8

Construction of siRNA

Small inhibitory RNAs (siRNAs) directed against human apoptosis-specific eIF-5A were used to specifically suppress expression of apoptosis-specific eIF-5A in RKO and lamina cribrosa cells. Six siRNAs were generated by in vitro transcription using the Silencer™ siRNA Construction Kit (Ambion Inc.). Four siRNAs were generated against human apoptosis-specific eIF-5A (siRNAs #1 to #4) (SEQ ID NO:30-33). Two siRNAs were used as controls; an siRNA directed against GAPDH provided in the kit, and an siRNA (siRNA #5) (SEQ ID NO: 34) which had the reverse sequence of the apoptosis-specific eIF-5A siRNA #1 (SEQ ID NO:30) but does not itself target apoptosis-specific eIF-5A. The siRNAs were generated according to the manufacturer's protocol. In brief, DNA oligonucleotides encoding the desired siRNA strands were used as templates for T7 RNA polymerase to generate individual strands of the siRNA following annealing of a T7 promoter primer and a fill-in reaction with Klenow fragment. Following transcription reactions for both the sense and antisense strands, the reactions were combined and the two siRNA strands were annealed, treated with DNase and RNase, and then column purified. The sequence of the DNA oligonucleotides (T7 primer annealing site underlined) used to generate the siRNAs were: siRNA #1 antisense 5' AAAG-GAATGACTTCCAGCTGACCTGTCTC 3' (SEQ ID NO:69) and siRNA #1 sense 5' AATCAGCTGGAAGTCAT-TCCTCCTGTCTC 3' (SEQ ID NO:70); siRNA #2 antisense 5' AAGATCGTCGAGATGTCTACTCCTGTCTC 3' (SEQ ID NO:71) and siRNA #2 sense 5' AAAGTAGACATCTC-GACGATCCCTGTCTC 3' (SEQ ID NO:72); siRNA. #3 antisense 5' AAGGTCCATCTGGTTGGTATTCCTGTCTC 3' (SEQ ID NO:73) and siRNA #3 sense 5' AAAATAC-CAACCAGATGGACCCCTGTCTC 3' (SEQ ID NO:74) siRNA #4 antisense 5' AAGCTGGACTCCTCCTACACA CCTGTCTC 3' (SEQ ID NO:75) and siRNA #4 sense 5' AATGTGTAGGAGGAGTCCAGCCCTGTCTC 3' (SEQ ID NO:76); siRNA 5 antisense 5' AAAGTCGACCTTCAG-TAAGGACCTGTCTC 3' (SEQ ID NO:77) and siRNA #5 sense 5' AATCCTTACTGAAGGTCGACTCCTGTCTC 3' (SEQ ID NO:78).

The Silencer™ siRNA Labeling Kit—FAM (Ambion) was used to label GAPDH siRNA with FAM in order to monitor the uptake of siRNA into RKO and lamina cribrosa cells. After transfection on 8-well culture slides, cells were washed with PBS and fixed for 10 minutes in 3.7% formaldehyde in PBS. The wells were removed and mounting media (Vectashield) was added, followed by a coverslip. Uptake of the FAM-labeled siRNA was visualized under a fluorescent microscope under UV light using a fluorescein filter. The GAPDH siRNA was labeled according to the manufacturer's protocol.

Transfection of siRNA

RKO cells and lamina cribrosa cells were transfected with siRNA using the same transfection protocol. RKO cells were seeded the day before transfection onto 8-well culture slides or 24-well plates at a density of 46,000 and 105,800 cells per well, respectively. Lamina cribrosa cells were transfected when cell confluence was at 40 to 70% and were generally seeded onto 8-well culture slides at 7500 to 10,000 cells per well three days prior to transfection. Transfection medium sufficient for one well of an 8-well culture slide was prepared by diluting 25.5 pmoles of siRNA stock to a final volume of 21.2 µl in Opti-Mem (Sigma). 0.425 µl of Lipofectamine 2000 was diluted to a final volume of 21.2 µl in Opti-Mem and incubated for 7 to 10 minutes at room temperature. The diluted Lipofectamine 2000 mixture was then added to the diluted siRNA mixture and incubated together at room temperature for 20 to 30 minutes. The cells were washed once with serum-free media before adding 135 µl of serum-free media to the cells and overlaying the 42.4 µl of transfection medium. The cells were placed back in the growth chamber for 4 hours. After the incubation, 65 µl it of serum-free media +30% FBS was added to the cells. Transfection of siRNA into cells to be used for Western blot analysis were performed in 24-well plates using the same conditions as the transfections in 8-well slides except that the volumes were increased by 2.3 fold.

Following transfection, RKO and lamina cribrosa cells were incubated for 72 hours prior to collection of cellular extract for Western blot analysis. In order to determine the effectiveness of the siRNAs directed against apoptosis-specific eIF-5A to block apoptosis, lamina cribrosa cells were treated with 50 µM of camptothecin (Sigma) and 10 ng/ml of TNF-α (Leinco Technologies) to induce apoptosis either 48 or 72 hours after transfection. The cells were stained with Hoescht either 24 or 48 hours later in order to determine the percentage of cells undergoing apoptosis.

Example 9

Quantification of HepG2 TNF-α Production

HepG2 cells were plated at 20,000 cells per well onto 48-well plates. Seventy two hours later the media was removed and fresh media containing either 2.5 µM control antisense oligonucleotide or 2.5 µM antisense oligonucleotide apoptosis-specific eIF-5A #2 was added to the cells. Fresh media containing antisense oligonucleotides was added after twenty four hours. After a total of 48 hours incubation with the oligonucleotides, the media was replaced with media containing interleukin 1β (IL-1β, 1000 pg/ml; Leinco Technologies) and incubated for 6 hours. The media was collected and frozen (20° C.) for TNF-α quantification. Additional parallel incubations with untreated cells (without antisense oligonucleotide and IL-1β) and cells treated with only IL-1β were used for controls. All treatments were done in duplicate. TNF-α released into the media was measured by ELISA assays (Assay Designs Inc.) according to the manufacturer's protocol.

Example 10

The following experiments show that antisense apoptosis-specific eIF-5A nucleotides were able to inhibit expression of apoptosis-specific eIF-5A as well as p53.

RKO cells were either left untransfected, mock transfected, or transfected with 200 nM of antisense oligonucleotides apoptosis-specific eIF-5A #1, #2, or #3 (SEQ ID NO: 25, 26, and 27). RKO cells were also transfected with 100 nM of antisense oligonucleotide apoptosis-specific eIF-5A #2 (SEQ ID NO:26). Forty-eight hours after transfection, the cells were treated with 0.25 µg/ml Actinomycin D. Twenty-four hours later, the cell extract was harvested and 5 µg of protein from each sample was separated on an SDS-PAGE gel, transferred to a PVDF membrane, and Western blotted with an antibody against apoptosis-specific eIF-5A. After chemiluminescent detection, the membrane was stripped and reprobed with an antibody against p53. After chemiluminescent detection, the membrane was stripped again and reprobed with an antibody against actin. FIG. 52 which shows the levels of protein produced by RKO cells after being treated with antisense oligo 1, 2 and 3 (to apoptosis-specific eIF-5a) (SEQ ID NO:25, 26, and 27, respectively). The RKO cells produced less apoptosis-specific eIF-5A as well as less p53 after having been transfected with the antisense apoptosis-specific eIF-5A nucleotides.

Example 11

The following experiments show that apoptosis-specific eIF-5A nucleotides were able to reduce apoptosis.

Figure 53A:
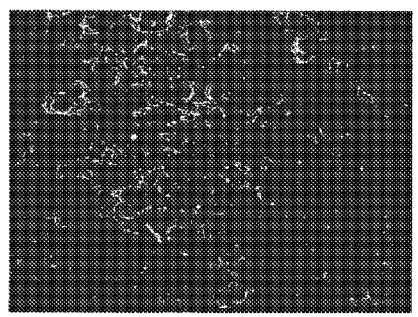
FIG. 53A-B shows uptake of the fluorescently labeled antisense oligonucleotide.
Figure 53B:
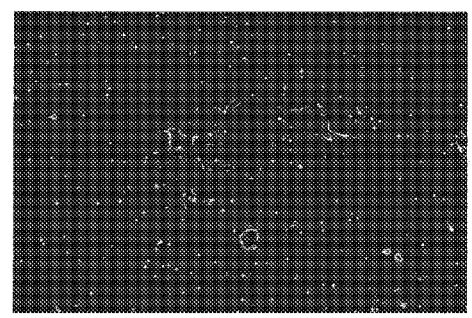
Figure 54:
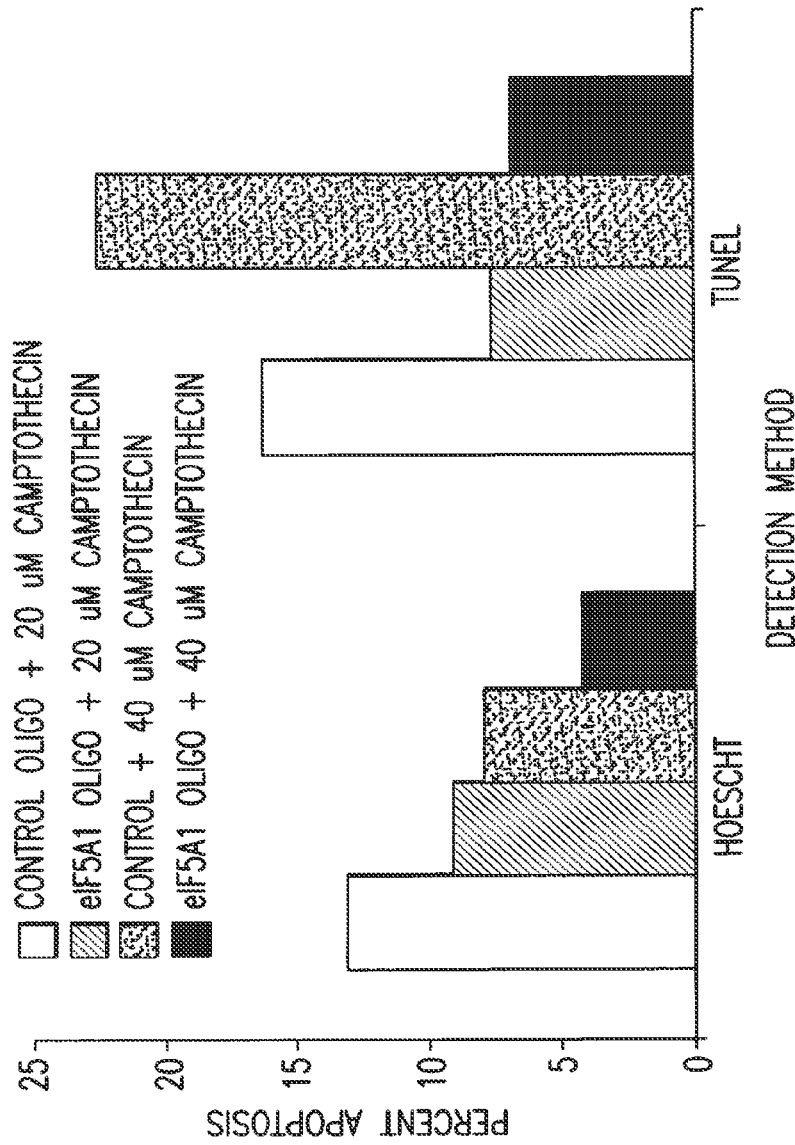
FIGS. 54-58 show a decrease in the percentage of cells undergoing apoptosis in the cells having being treated with antisense apoptosis-specific eIF-5A oligonucleotides as compared to cells not having been transfected with the antisense apoptosis-specific eIF-5A oligonucleotides.
Figure 55:
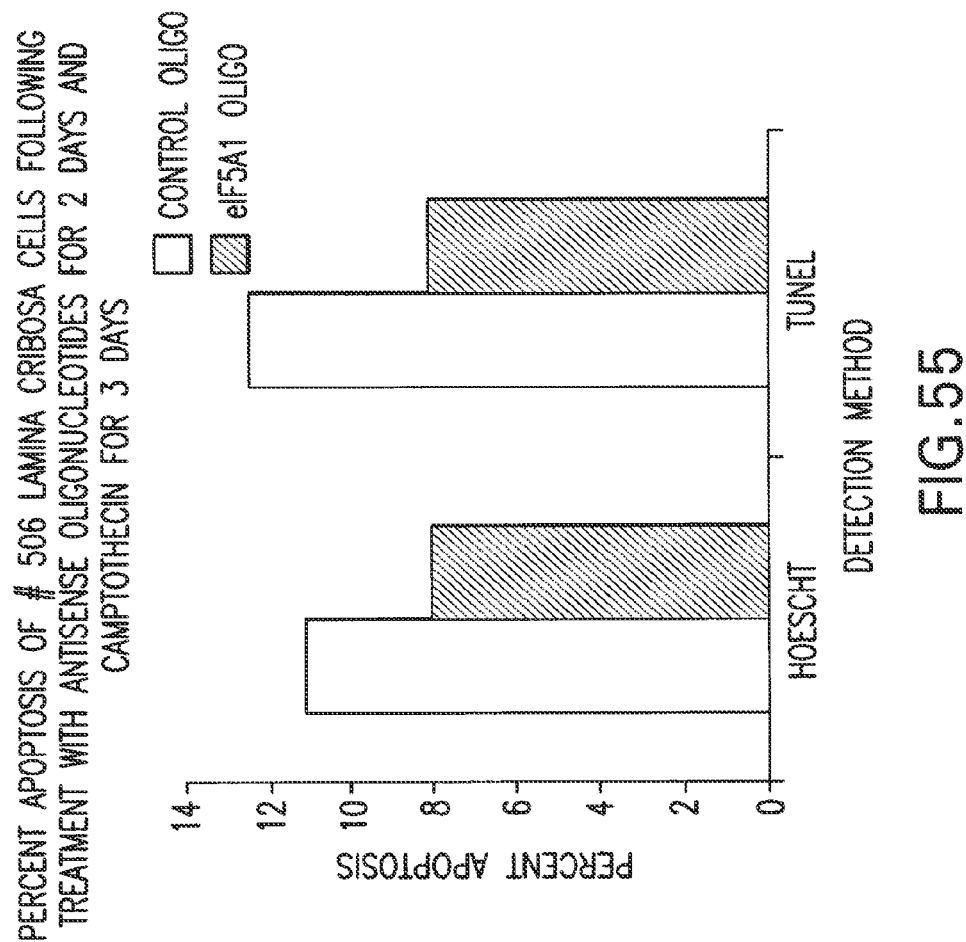
Figure 56:
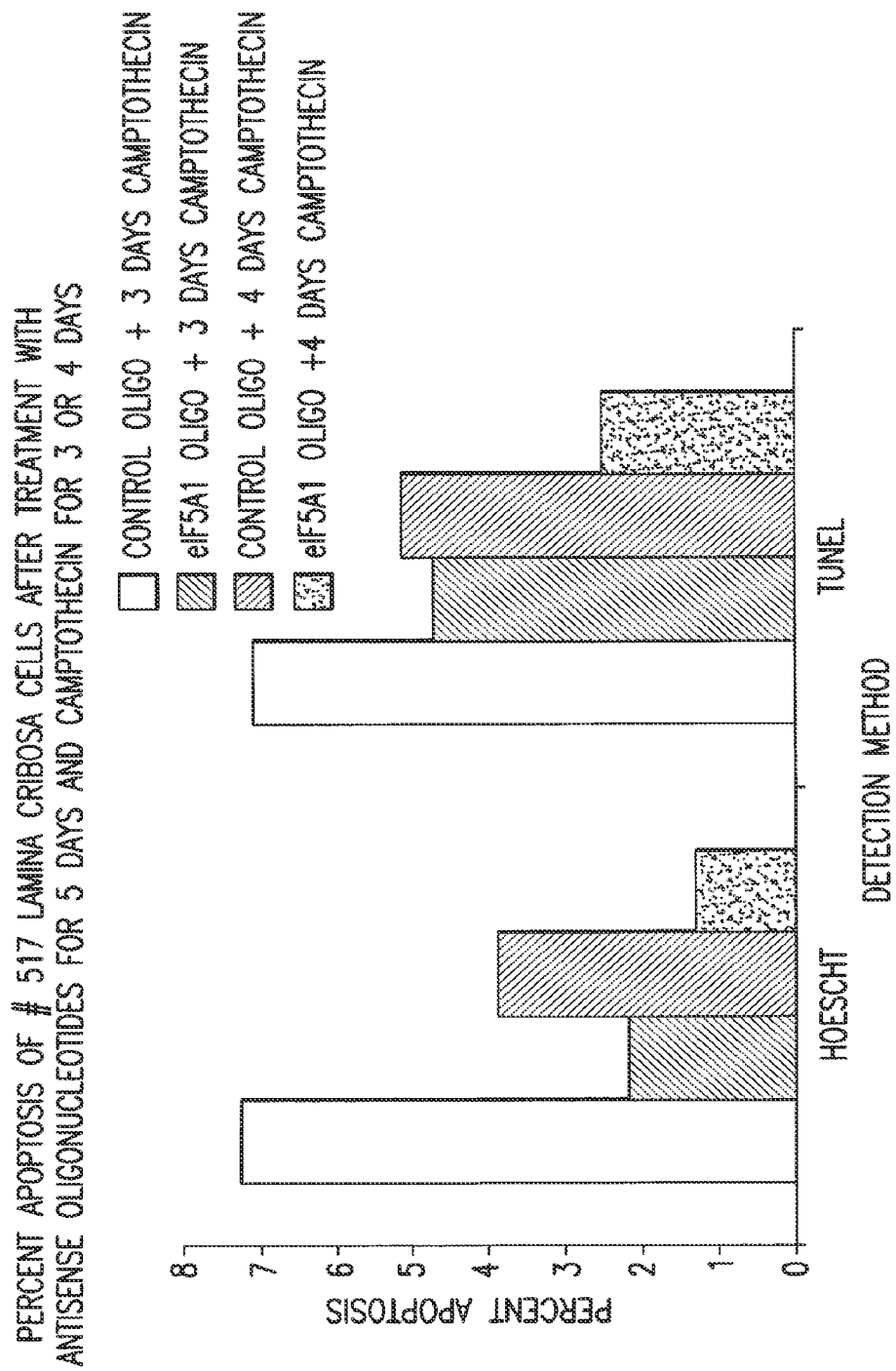
Figure 57:
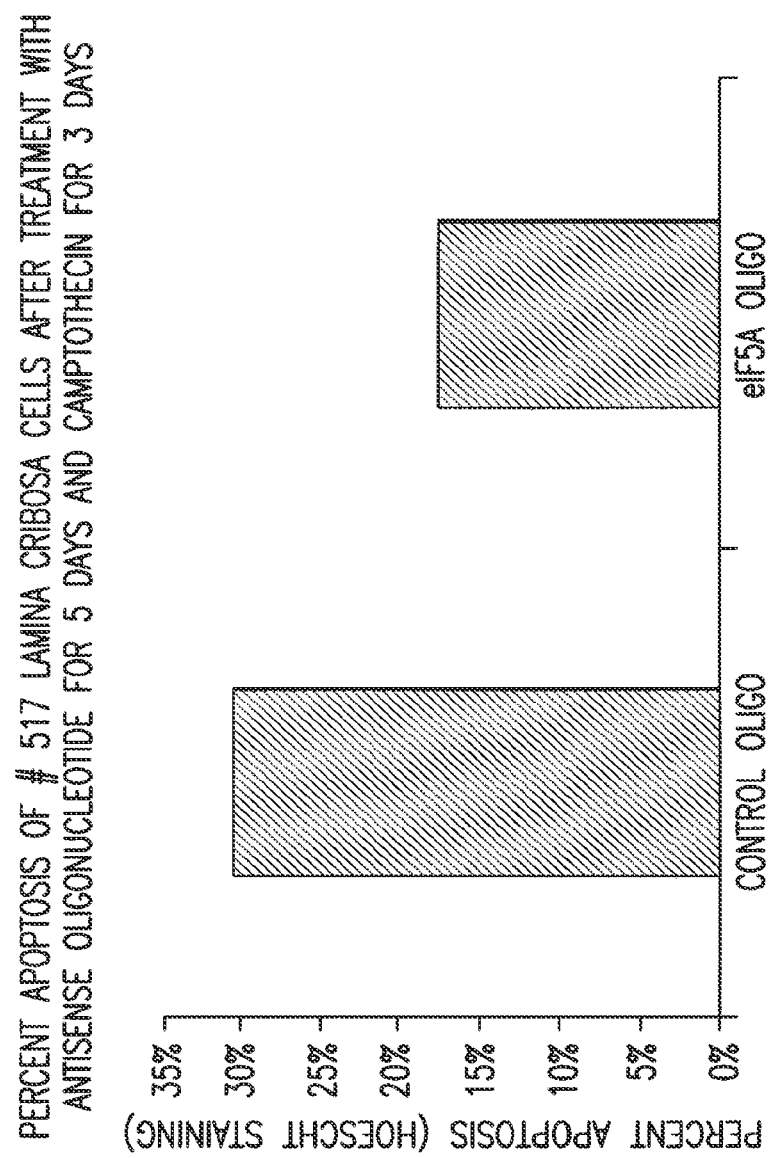
Figure 58:
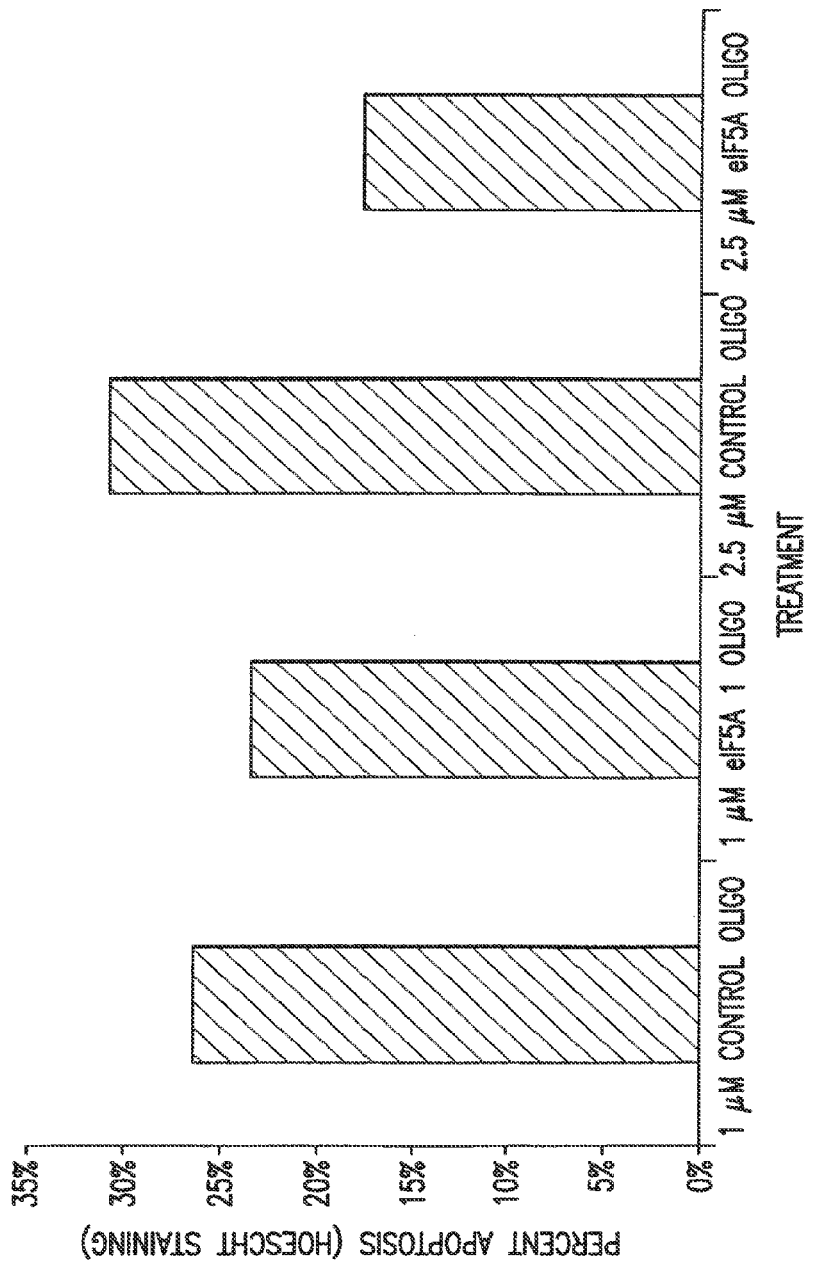

In one experiment, the lamina cribrosa cell line #506 was either (A) transfected with 100 nM of FITC-labeled antisense oligonucleotide using Oligofectamine transfection reagent or (B) transfected with 10 µM of naked FITC-labeled antisense oligonucleotide diluted directly in serum-free media. After 24 hours fresh media containing 10% FBS and fresh antisense oligonucleotide diluted to 10 µM was added to the cells. The cells, (A) and (B), were fixed after a total of 48 hours and visualized on a fluorescent microscope under UV light using a fluorescein filter. FIG. 53 shows uptake of the fluorescently labeled antisense oligonucleotide.

In another experiment, the lamina cribrosa cell line #506 was transfected with 10 µM of either the control antisense oligonucleotide or antisense oligonucleotide apoptosis-specific eIF-5A #2 (SEQ ID NO:26) for a total of 4 days. Forty-eight, hours after beginning antisense oligonucleotide treatment, the cells were treated with either 20 µM or 40 µM camptothecin for 48 hours. Antisense oligonucleotide and camptothecin-containing media was changed daily. The percentage of apoptotic cells was determined by labeling the cells with Hoescht and TUNEL. See FIG. 54.

In another experiment, the lamina cribrosa cell line #506 was transfected with 10 µM of either the control antisense oligonucleotide or antisense oligonucleotide apoptosis-specific eIF-5A #2 (SEQ ID NO:26). Twenty-four hours later the media was changed and fresh antisense oligonucleotides were added. Forty-eight hours after beginning antisense oligonucleotide treatment, the antisense-oligonucleotides were removed and the cells were treated with 20 µM camptothecin for 3 days. The camptothecin-containing media was changed daily. The percentage of apoptotic cells was determined by labeling the cells with Hoescht and TUNEL. See FIG. 55.

In yet another experiment, the lamina cribrosa cell line #517 was transfected with 1 µM of either the control antisense oligonucleotide or antisense oligonucleotide apoptosis-specific eIF-5A #2 (SEQ ID NO:26) for a total of five days. Forty-eight hours after beginning antisense oligonucleotide treatment, the cells were treated with 20 µM camptothecin thr either 3 or 4 days. Antisense oligonucleotide and camptothecin-containing media was changed daily. The percentage of apoptotic cells was determined by labeling the cells with Hoescht and TUNEL. See FIG. 56.

In another experiment, the lamina cribrosa cell line #517 was transfected with 2.5 µM of either the control antisense oligonucleotide or antisense oligonucleotide apoptosis-specific eIF-5A #2 (SEQ ID NO:26) for a total of five days. Forty-eight hours after beginning antisense oligonucleotide treatment, the cells were treated with 40 µM camptothecin for 3 days, Antisense oligonucleotide and camptothecin-containing media was changed daily. The percentage of apoptotic cells was determined by labeling the cells with Hoescht. See FIG. 57.

In another experiment, the lamina cribrosa cell line #517 was transfected with either 1 µM or 2.5 µM of either the control antisense oligonucleotide or antisense oligonucleotide apoptosis-specific eIF-5A #2 (SEQ ID NO:26) for a total of five days. Forty-eight hours after beginning antisense oligonucleotide treatment, the cells were treated with 40 µM camptothecin for 3 days. Antisense oligonucleotide and camptothecin-containing media was changed daily. The percentage of apoptotic cells was determined by labeling the cells with Hoescht. See FIG. 58.

Figure 59:
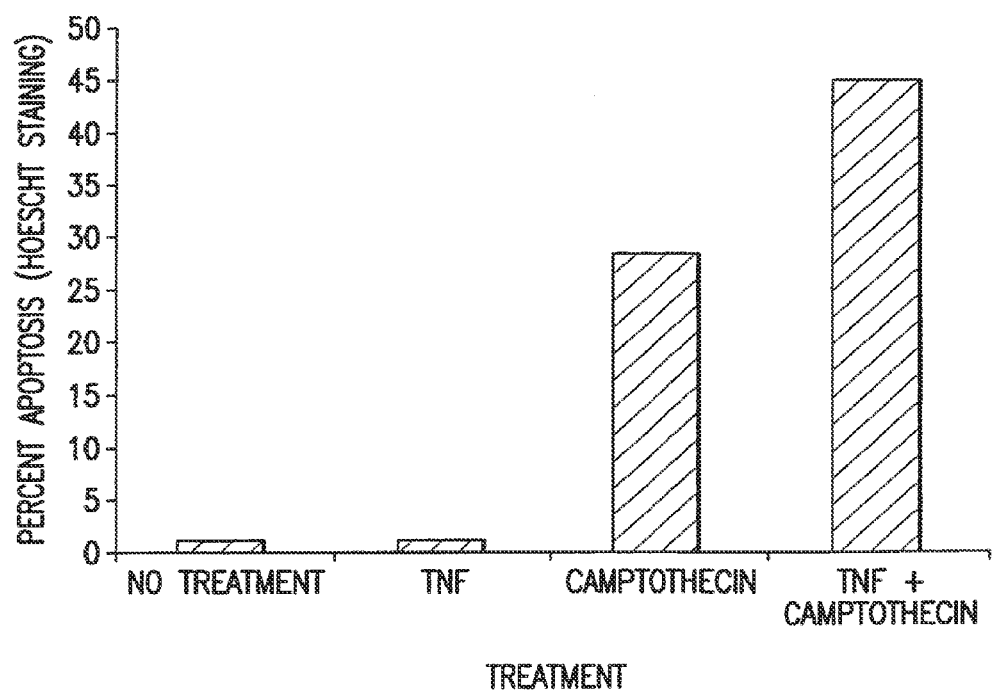
FIG. 59 shows that treating lamina cribrosa cells with TNF-α and/or camptothecin caused an increase in the number of cells undergoing apoptosis.

In another experiment, the lamina cribrosa cell line #517 was left either untreated, or was treated with 10 ng/ml TNF-α, 50 µM camptothecin, or 10 ng/ml TNF-α and 50 µM camptothecin. The percentage of apoptotic cells was determined by labeling the cells with Hoescht. See FIG. 59.

Figure 60:
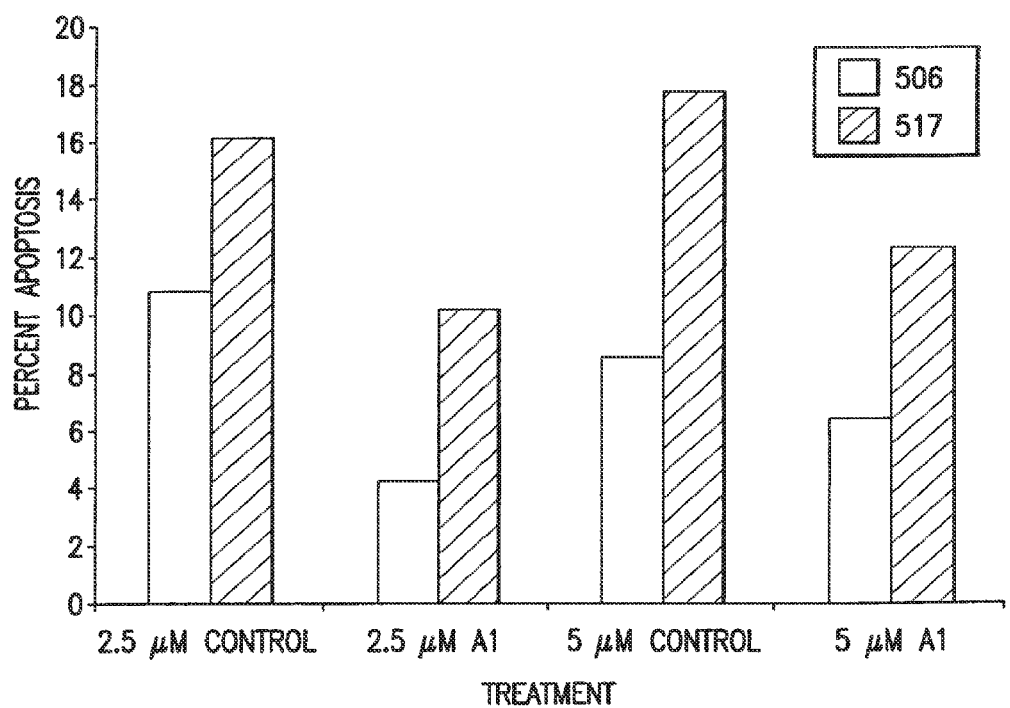

In another experiment, the lamina cribrosa cell lines #506 and #517 were transfected with either 2.5 µM or 5 µM of either the control antisense oligonucleotide or antisense oligonucleotide apoptosis-specific eIF-5A #2 (SEQ ID NO:26) for a total of two days. Fresh media containing antisense oligonucleotides was added after 24 hours. Forty-eight hours after beginning antisense oligonucleotide treatment, the cells were treated with 50 µM camptothecin and 10 ng/ml TNF-α for 2 days. The percentage of apoptotic cells was determined by labeling the cells with Hoescht. See FIG. 60.

In another experiment, the lamina cribrosa cell lines #506, #517, and #524 were transfected with 2.5 µM of either the control antisense oligonucleotide or antisense oligonucleotide apoptosis-specific eIF-5A #2 (SEQ ID NO:26) for a total of two days. Fresh media containing antisense oligonucleotides was added after 24 hours. Forty-eight hours after beginning antisense oligonucleotide treatment, the cells were treated with 50 µM camptothecin and 10 ng/ml TNF-α for 2 days. The percentage of apoptotic cells was determined by labeling the cells with Hoescht. See FIG. 61.

Example 12

The following experiments show that cells transfected with siRNAs targeted against apoptosis-specific eIF-5A expressed less apoptosis-specific eIF-5A. The experiments also show that siRNAs targeted against apoptosis-specific eIF-5A were able to reduce apoptosis.

Figure 62A:
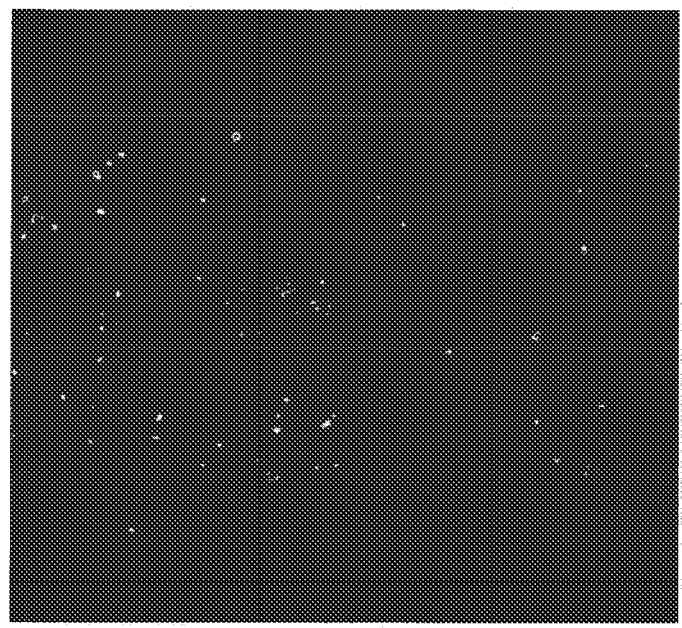
FIG. 62A-B shows that the lamina cribrosa cells uptake the labeled siRNA, either in the presence of serum (FIG. 62A) or without serum (FIG. 62B).
Figure 62B:
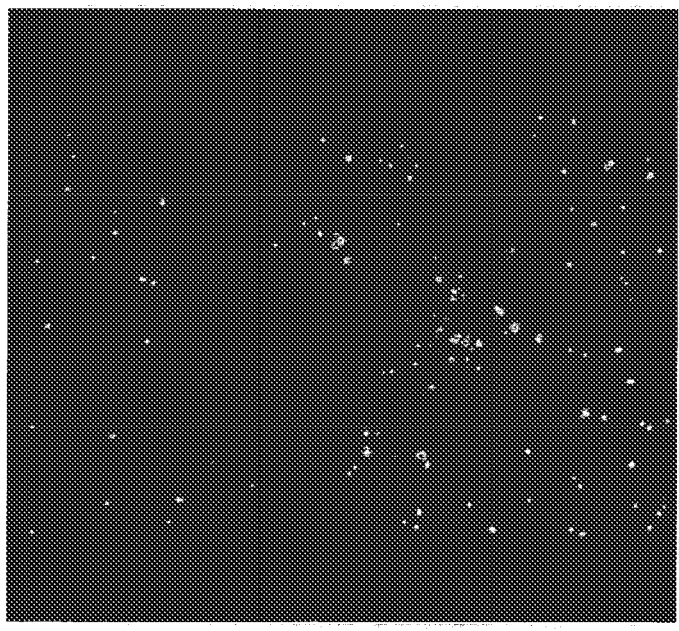

In one experiment, the lamina cribrosa cell line #517 was transfected with 100 nM of FAM-labeled siRNA using Lipofectamine 2000 transfection reagent either with serum (A) or without serum (B) during transfection. The cells. (A) and (B), were fixed after a total of 24 hours and visualized on a fluorescent microscope under UV light using a fluorescein filter. See FIG. 62.

In another experiment., RKO cells were transfected with 100 nM of siRNA either in the presence or absence of serum during the transfection. Six siRNAs were transfected, two control siRNAs (siRNA #5 (SEQ ID NO:34) and one targeted against GAPDH) and four targeted against apoptosis-specific eIF-5A (siRNA #1 to #4) (SEQ ID NO:30-33). Seventy-two hours after transfection, the cell extract was harvested and 5 µg of protein from each sample was separated on an SDS-PAGE gel, transferred to a PVDF membrane, and Western blotted with an antibody against apoptosis-specific eIF-5A. After chemiluminescent detection, the membrane was stripped and re-probed with an antibody against bcl-2. After chemiluminescent detection, the membrane was stripped again and re-probed with an antibody against actin. See FIG. 63.

In another experiment, lamina Cribrosa cell lines #506 and #517 were transfected with 100 nM of siRNA. Six siRNAs were transfected, two control siRNAs (siRNA #5 (SEQ ID NO:34) and one targeted against GAPDH) and four targeted against apoptosis-specific eIF-5A (siRNA #1 to #4) (SEQ ID NO:30-33). Seventy-two hours after transfection, the cell extract was harvested and 5 µg of protein from each sample was separated on an SDS-PAGE gel, transferred to a PVDF membrane, and Western blotted with an antibody against apoptosis-specific eIF-5A. After chemiluminescent detection, the membrane was stripped and re-probed with an antibody against actin. See FIG. 64.

In another experiment, the lamina cribrosa cell #506 was transfected with 100 nm of siRNA. Six siRNAs were transfected, two control siRNAs (siRMA. #5 (SEQ ID NO:34) and one targeted against GAPDH) and four targeted against apoptosis-specific eIF-5A (siRNA #1 to #4) (SEQ ID NO:30-33). Forty-eight hours after transfection, the media was replaced with media containing 50 µM camptothecin and 10 ng/ml TNF-α. Twenty-four hours later, the percentage of apoptotic cells was determined by labeling the cells with Hoescht. See FIG. 65

In another experiment, the lamina cribrosa cell line #506 was transfected with 100 nm of siRNA. Six siRNAs were transfected, two control siRNAs (siRNA #5 (SEQ ID NO:34) and one targeted against GAPDH) and four targeted against apoptosis-specific eIF-5A (siRNA #1 to #4) (SEQ ID NO:30-33). Seventy-two hours after transfection, the media was replaced with media containing 50 µM camptothecin and 10 ng/ml TNF-α. Twenty-four hours later, the percentage of apoptotic cells was determined by labeling the cells with Hoescht. See FIG. 66.

In another experiment, the lamina cribrosa cell line #506 was either left untransfected or was transfected with 100 nm of siRNA. Six siRNAs were transfected, two control siRNAs (siRNA #5 (SEQ ID NO:34) and one targeted against GAPDH) and four targeted against apoptosis-specific eIF-5A (siRNA #1 to #4) (SEQ ID NO:30-33). Seventy-two hours after transfection, the media was replaced with media containing 50 µM camptothecin and 10 ng/ml TNF-α. Fresh media was also added to the untransfected, untreated control cells. Forty-eight hours later, the percentage of apoptotic cells was determined by labeling the cells with Hoescht. See FIG. 67.

Figure 68:
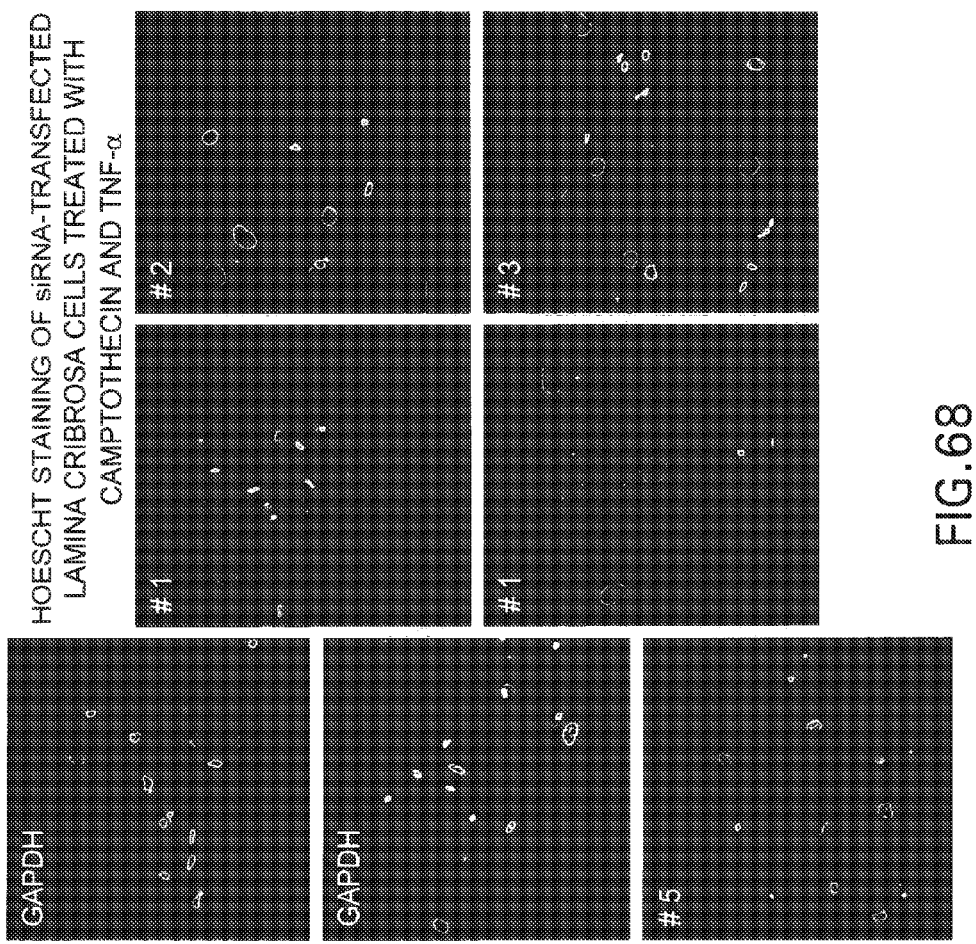
FIG. 68 are photographs of Hoescht-stained lamina cribrosa cell line #506 transfected with siRNA and treated with camptothecin and TNF-α from the experiment described in FIG. 67 and Example 13. The apoptosing cells are seen as more brightly stained cells. They have smaller nucleic because of chromatin condensation and are smaller and irregular in shape.

Photographs of Hoescht-stained lamina cribrosa cell line #506 transfected with siRNA and treated with camptothecin and TNF-α from the experiment described in FIG. 67 and example 13 are provided in FIG. 68.

Example 13

This example shows that treating a human cell line with antisense oligonucleotides directed against apoptosis-specific eIF-5A causes the cells to produce less TNF-α.

HepG2 cells were treated with 2.5 µM of either the control antisense oligonucleotide or antisense oligonucleotide apoptosis-specific eIF-5A #2 for a total of two days. Fresh media containing antisense oligonucleotides was added after 24 hours. Additional cells were left untreated for two days. Forty-eight hours after the beginning of treatment, the cells were treated with IL-1β (1000 pg/ml) in fresh media for 6 hours. At the end of the experiment, the media was collected and frozen (−20° C.) for TNF-α quantification. TNF-α released into the media was measured using ELISA assays purchased from Assay Designs Inc. See FIG. 69. Cells that were transfected with antisense oligonucleotides of apoptosis-specific eIF-5A produced less TNF-α.

Example 14

HT-29 cells (human colon adenocarcinoma) were transfected with either an siRNA against apoptosis-specific eIF-5A or with a control siRNA with the reverse sequence. The siRNA used is as follows:

```
Position 690 (3'UTR) % G/C = 48
5' AAGCUGGACUCCUCCUACACA 3'    (SEQ ID NO: 79)
```

The control siRNA used is as follows:

```
% G/C = 39
5' AAACACAUCCUCCUCAGGUCG 3'  (SEQ ID NO: 80)
```

Figure 75:
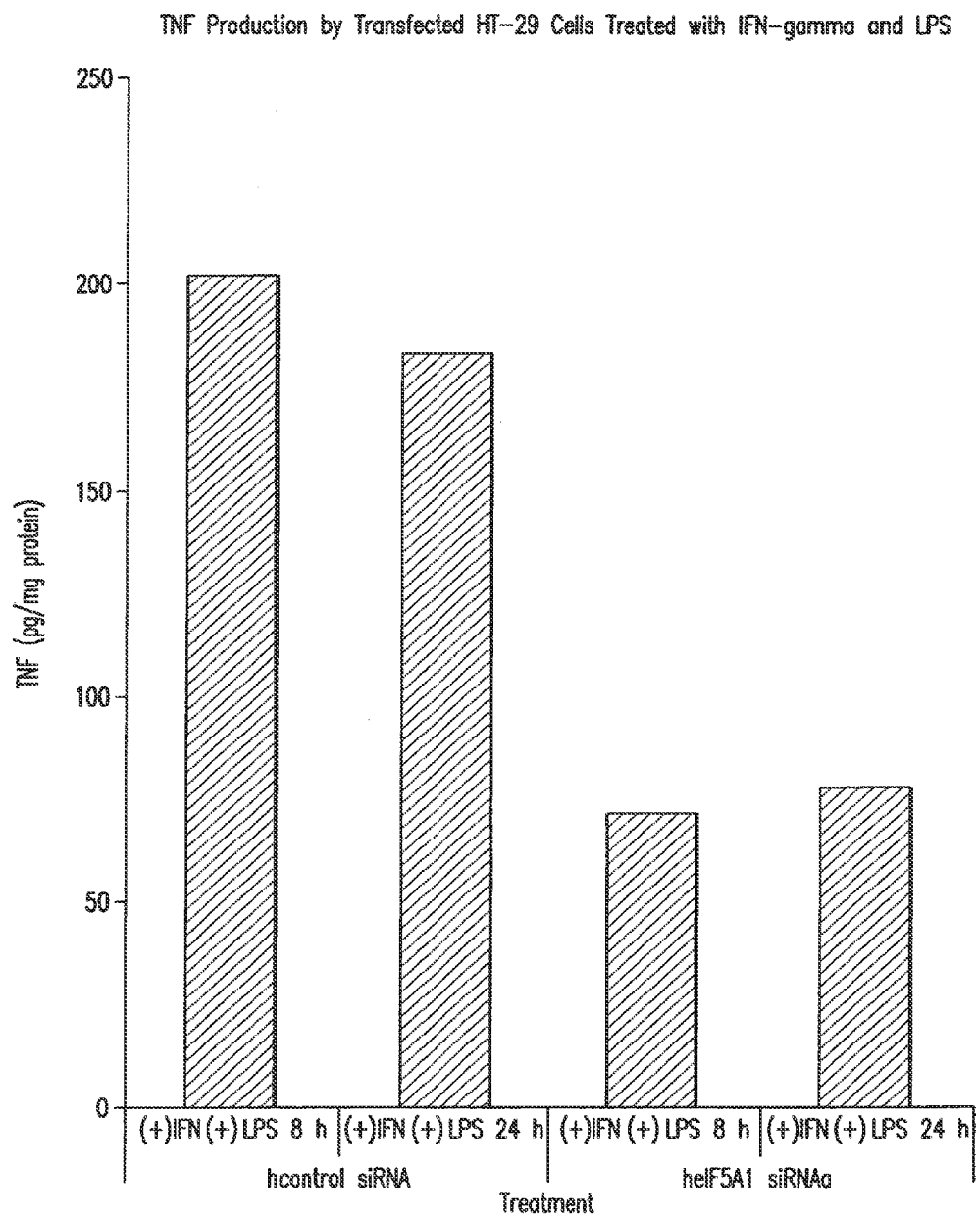
FIG. 75 provides the results of an ELBA. TNF-α production was reduced in cells treated with siRNAs against apoptosis-specific eIF-5A as compared to control cells.

After 48 hours the cells were treated with interferon-gamma (IFN-gamma) for 16 hours. After 16 hours the cells were washed with fresh media and treated with lipopolysaccharide (LPS) for 8 or 24 hours. At each time point (8 or 24 hours) the cell culture media was removed from the cells, frozen, and the TNF-alpha present in the media was quantitated by ELISA. The cell lysate was also harvested, quantitated for protein, and used to adjust the TNF-alpha values to pg/mg protein (to adjust for differences in cell number in different wells). The results of the Western blot and Elisa are provided in FIGS. 74 A and B. FIG. 75 are the results of the same experiment except the cells were at a higher density.

Example 15

Tissue Culture Conditions of U-937 Cell Line

U-937 is a human monocyte cell line that grows in suspension and will become adherent and differentiate into macrophages upon stimulation with PMA (ATCC Number CRL-1593.2) (cells not obtained directly from ATCC). Cells were maintained in RPMI 1640 media with 2 mM L-glutamine, 1.5 g/L, sodium bicarbonate, 4.5 g/L glucose, 10 mM HEPES, 1.0 mM sodium pyruvate and 10% fetal bovine serum in a 37° C. $CO_2$ (5%) incubator. Cells were split into fresh media (1:4 or 1:5 split ratio) twice a week and the cell density was always kept between 105 and $2 \times 10^6$ cells/ml. Cells were cultured in suspension in tissue culture-treated plastic T-25 flasks and experiments were conducted in 24-well plates.

Time Course Experiment

Two days before the start of an experiment, the cell density was adjusted to $3 \times 10^5$ cells/ml media. On the day of the experiment, the cells were harvested in log phase. The cell suspension was transferred to 15 ml tubes and centrifuged at 400×g for 10 mins at room temperature. The supernatant was aspirated and the cell pellet was washed/resuspended with fresh media. The cells were again centrifuged at 400×g for 10 mins, the supernatant was aspirated, and the cell pellet was finally resuspended in fresh Media. Equal volumes of cell suspension and trypan blue solution (0.4% trypan blue dye in PBS) were mixed and the live cells were counted using a haemocytometer and a microscope. The cells were diluted to $4 \times 10^5$ cells/ml.

Figure 76:
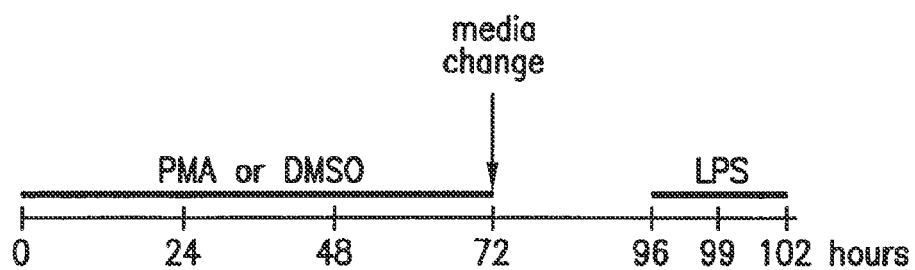
FIG. 76 shows the time course of the U-937 differentiation experiment. See Example 16.

A 24-well plate was prepared by adding either PMA or DMSO (vehicle control) to each well. 1 ml of cell suspension was added to each well so that each well contained 400,000 cells, 0.1% DMSO+/−162 nM PMA. The cells were maintained in a 37° C. $CO_2$ (5%) incubator. Separate wells of cells were harvested at times 0, 24, 48, 72, 96, 99 and 102 h. See FIG. 76 for a summary of the experimental time points and additions.

The media was changed at 72 h. Since some cells were adherent and others were in suspension, care was taken to avoid disrupting the adherent cells. The media from each well was carefully transferred into corresponding microcentrifuge tubes and the tubes were centrifuged at 14,000×g for 3 mm. The tubes were aspirated, the cell pellets were resuspended in fresh media (1 ml, (−) DMSO, (−) PMA), and returned to their original wells. The cells become quiescent in this fresh media without PMA. At 96 h, LPS (100 ng/ml) was added and cells were harvested at 3 h (99 h) and 6 h (102 h) later.

At the time points, the suspension cells and media were transferred from each well into microcentrifuge tubes. The cells were pelleted at 14,000×g for 3 min. The media (supernatant) was transferred to clean tubes and stored (−20° C.) for ELISA/cytokine analysis. The cells remaining in the wells were washed with PBS (1 ml, 37° C.) and this PBS was also used to wash the cell pellets in the corresponding microcentrifuge tubes. The cells were pelleted again at 14,000×g for 3 min. The cells were lysed with boiling lysis buffer (50 mM Tris pH 7.4 and 2% SDS). The adherent cells and the suspension cells from each well were pooled. The samples were boiled and then stored at −20° C.

Western Blotting

The protein concentration in each cell sample was determined by the BCA (bicinchoninic acid) method using BSA (bovine serum albumin) as the standard protein. Protein samples (5 µg total protein) were separated by 12% SDS-PAGE electrophoresis and transferred to PVDF membranes. The membranes were blocked with polyvinyl alcohol (1 µg/ml, 30 sec) and with 5% skim milk in PBS-t (1 h). The membranes were probed with a mouse monoclonal antibody raised against human eIF-5A (BD Biosciences cat #611976; 1:20,000 in 5% skim milk, 1 h). The membranes were washed 3×10 mins PBS-t. The secondary antibody was a horseradish peroxidase-conjugated antimouse antibody (Sigma, 1:5000 in 1% skim milk, 1 h). The membranes were washed 3×10 mins PBS-t. The protein bands were visualized by chemiluminescence (ECL detection system, Amersham Pharmacia Biotech).

To demonstrate that similar amounts of protein were loaded on each gel lane, the membranes were stripped and reprobed for actin. Membranes were stripped (100 mM 2-mercaptoethanol, 2% SDS, 62.5 mM Tris-HCl pH 6.7; 50° C. for 30 mins), washed, and then blocked as above. The membranes were probed with actin primary antibody (actin monoclonal antibody made in mouse; Oncogene, Ab-1; 1:20, 000 in 5% skim milk). The secondary antibody, washing, and detection were the same as above.

Figure 77:
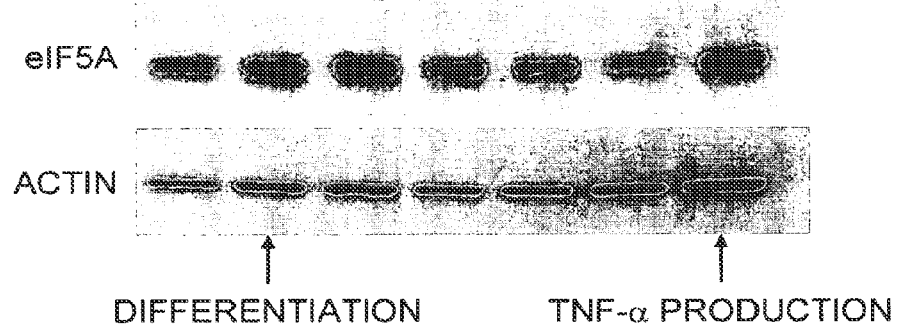
FIG. 77 shows the results of a Western blot showing that apoptosis-specific eIF-5A is up-regulated during monocyte differentiation and subsequence TNF-α secretion.

FIG. 77 shows that eIF5A is upregulated during monocyte (U-397) differentiation and subsequent TNF-α secretion.

Example 16

Suppression of Il-8 Production in Response to Interferon Gamma by Apoptosis-Specific eIF-5A siRNA HT-29 (human colon adenocarcinoma) cells were transfected with siRNA directed to apoptosis-specific eIF-5A. Approximately 48 hours after transfection the media was changed so that some of the test samples had media with interferon gamma and some of the samples had media without interferon gamma. 16 hours after interferon gamma addition, the cells were washed, and the media, with or without TNF-alpha, was placed on the cells. The media (used for ELISA detection of IL-8) and the cell lysate was harvested 8 or 24 hours later.

Figure 79:
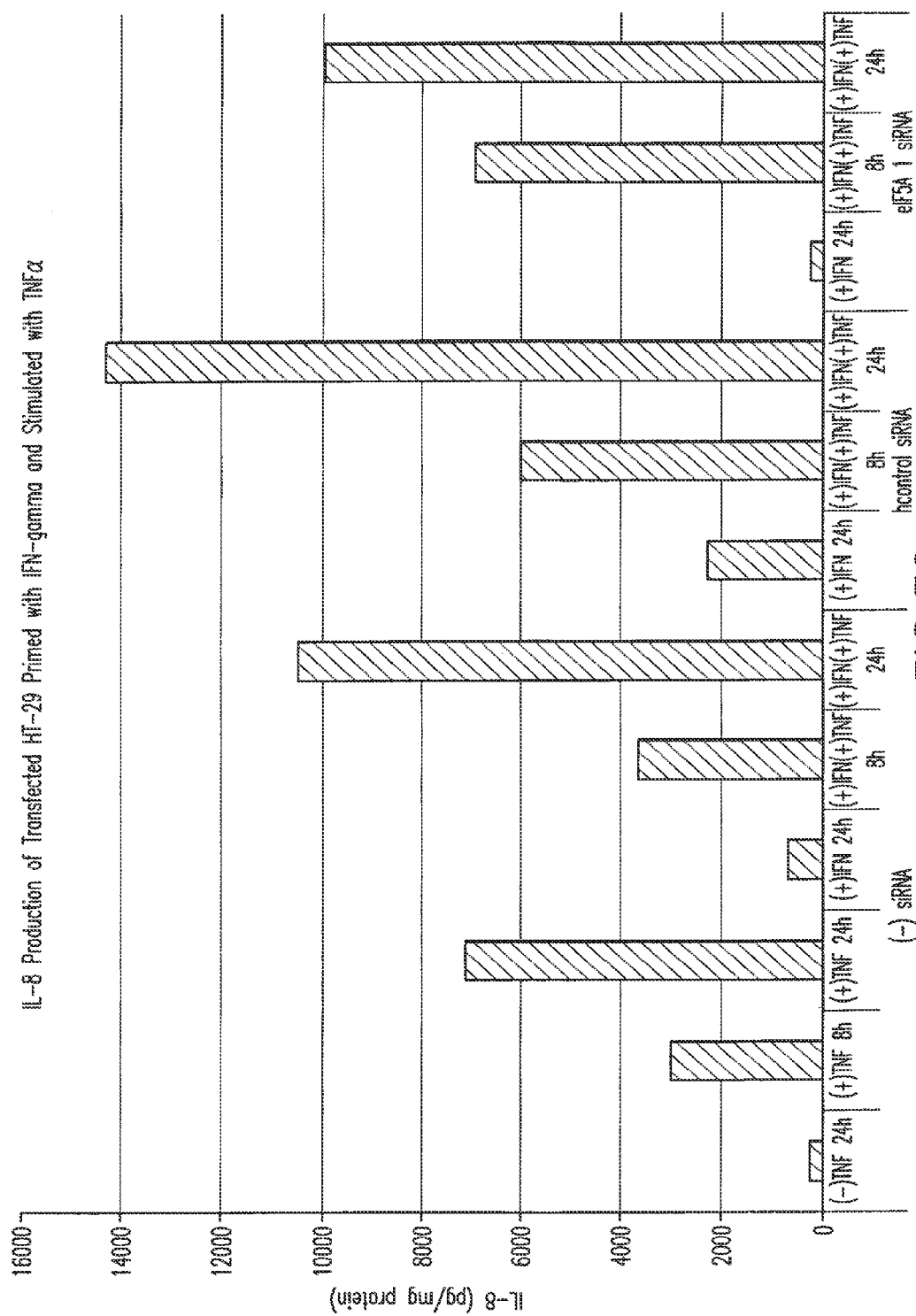
FIG. 79 is a bar graph showing that IL-8 is produced in response to TNF-alpha as well as in response to interferon. This graph shows that siRNA against apoptosis-specific eIF-5A blocked almost all IL-8 produced in response to interferon as well as a significant amount of the IL-8 produced as a result of the combined treatment of interferon and TNF.
Figure 80:
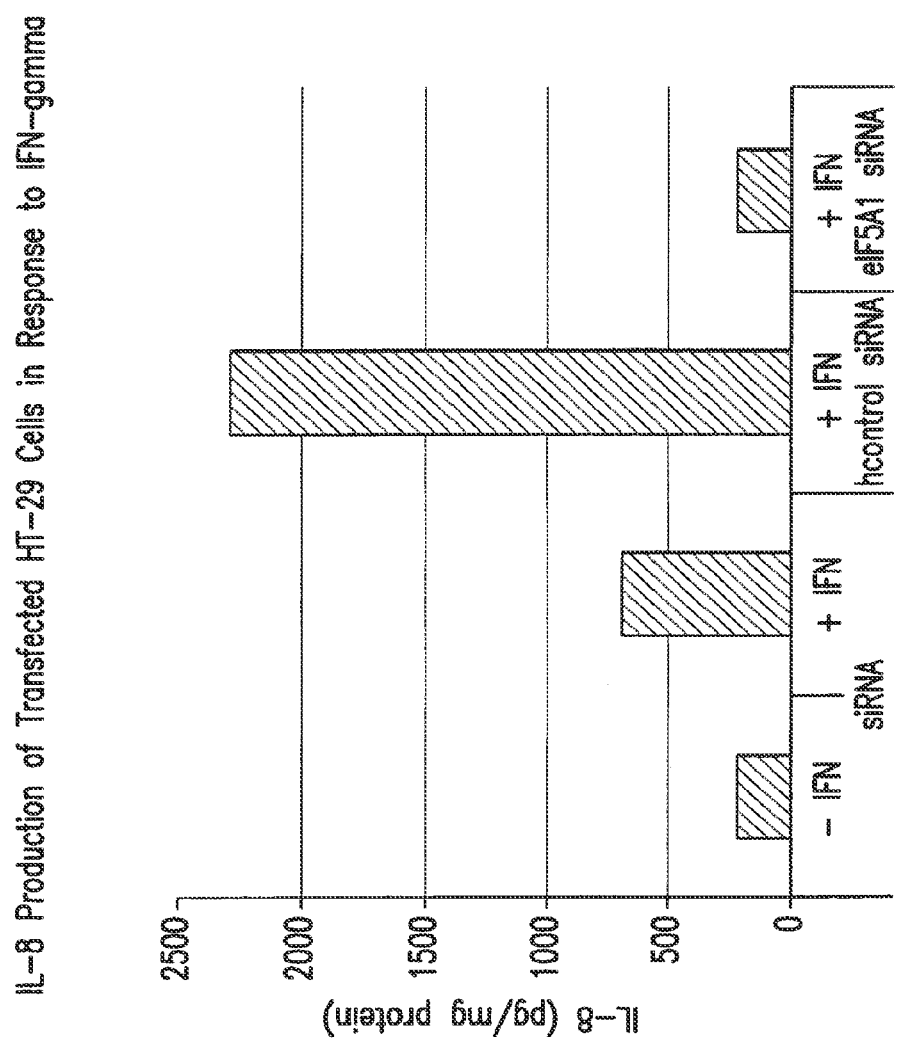
FIG. 80 is another bar graph showing that IL-8 is produced in response to TNF-alpha as well as in response to interferon. This graph shows that siRNA against apoptosis-specific eIF-5A blocked almost all IL-8 produced in response to interferon as well as a significant amount of the IL-8 produced as a result of the combined treatment of interferon and TNF.
Figure 81:
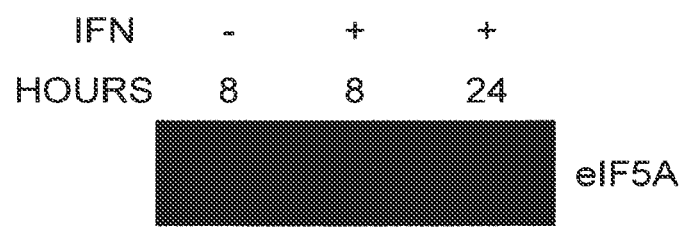
FIG. 81 is a western blot of HT-29 cells treated with IFN gamma for 8 and 24 hours. This blot shows up-regulation in HT-29 cells (4 fold at 8 hours) of against apoptosis-specific eIF-5A in response to interferon gamma.

FIGS. 79 and 80 show that IL-8 is produced in response to TNF-alpha as well as in response to interferon. Priming the cells with interferon gamma prior to TNF treatment causes the cells to produce more IL-8 than either treatment alone. This may be due to the known upregulation of the TNF receptor 1 in response to interferon, so 'priming' the cells with interferon allows them to respond to TNF better since the cells have more receptors. siRNA against apoptosis-specific eIF-5A had no effect on IL-8 production in response to TNF alone (previous experiment) however, the siRNA blocked almost all IL-8 produced in response to interferon as well as a significant amount of the IL-8 produced as a result of the combined treatment of interferon and TNF. These results show that the by using siRNAs directed against apoptosis-specific eIF-5A, the inventors have the interferon signaling pathway leading to IL-8, but not the TNF pathway. FIG. 81 is a western showing up-regulation (4 fold at 8 hours) of apoptosis-specific eIF-5A in response to interferon gamma in HT-29 cells.

Example 17

Human Lamina Cribrosa Culture

Paired human eyes were obtained within 48 hours post mortem from the Eye Bank of Canada, Ontario Division. Optic nerve heads (with attached pole) were removed and placed in Dulbecco's modified Eagle's medium (DMEM) supplemented with antibiotic/antimycotic, glutamine, and 10% FBS for 3 hours. The optic nerve head (ONH) button was retrieved from each tissue sample and minced with fine dissecting scissors into four small pieces. Explants were cultured in 12.5 cm² plastic culture flasks in DMEM medium. Growth was observed within one month in viable explants. Once the cells reached 90% confluence, they were trypsinized and subjected to differential subculturing to produce lamina cribrosa (LC) and astrocyte cell populations. LC cells were enriched by subculture in 25 cm² flasks in DMEM supplemented with gentamycin, glutamine, and 10% FBS. Cells were maintained and subcultured as per this protocol.

The identity and population purity of cells populations obtained by differential subculturing was characterized using differential fluorescent antibody staining on 8 well culture slides. Cells were fixed in 10% formalin solution and washed three times with Dulbecco's Phosphate Buffered Saline (DPBS). Following blocking with 2% nonfat milk in DPBS, antibodies were diluted in 1% BSA in DPBS and applied to the cells in 6 of the wells. The remaining two wells were treated with only 1% bovine serum albumin (BSA) solution and only secondary antibody as controls. Cells were incubated with the primary antibodies for one hour at room temperature and then washed three times with DPBS. Appropriate secondary antibodies were diluted in 1% BSA in DPBS, added to each well and incubated for 1 hour. Following washing with DPBS, the slide was washed in water, air-dried, and overlayed with Fluoromount (Vector Laboratories). Immunofluorescent staining was viewed under a fluorescent microscope with appropriate filters and compared to the control wells that were not treated with primary antibody. All primary antibodies were obtained from Sigma unless otherwise stated. All secondary antibodies were purchased from Molecular Probes. Primary antibodies used to identify LC cells were: anti-collagen I, anti-collagen IV, anti-laminin, anti-cellular fibronectin, anti-glial fibrillary acidic protein (GFAP), and anti-alpha-smooth muscle actin. Cell populations were determined to be comprised of LC cells if they stained positively for collagen I, collagen IV, laminin, cellular fibronectin, alpha smooth muscle actin and negatively for glial fibrillary (GFAP). In this study, two sets of human eyes were used to initiate cultures. LC cell lines #506 and #517 were established from the optic nerve heads of and 83-year old male and a 17-year old male, respectively. All LC cell lines have been fully characterized and found to contain greater than 90% LC cells.

Treatment of LC Cells

Apoptosis was induced in lamina cribrosa cells using a combination of 50 µM camptothecin (Sigma) and 10 ng/ml TNF-α (Leinco Technologies). The combination of camptothecin and TNF-α was found to be more effective at inducing apoptosis than either camptothecin or TNF-α alone.

Construction and Transfection of siRNAs

Small inhibitory RNAs (siRNAs) directed against human apoptosis-specific eIF-5A were used to specifically suppress expression of eIF5A in lamina cribrosa cells. Six siRNAs were generated by in vitro transcription using the Silencer™ siRNA Construction Kit (Ambion Inc.), Four siRNAs were generated against human apoptosis-specific eIF-5A (siRNAs #1 to #4). Two siRNAs were used as controls; an siRNA directed against GAPDH provided in the kit, and an siRNA (siRNA #5), which had the reverse sequence of the apoptosis-specific eIF-5A specific siRNA #1, but does not itself target eIF5A. The siRNAs were generated according to the manufacturer's protocol. The eIF5A and control siRNA targets had the following sequences: siRNA #1 5' AAAGGAATGACTTCCAGCTGA 3' (SEQ ID NO: 81); siRNA #2 5' AAGATCGTCGAGATGTCTACT 3' (SEQ ID NO: 82); siRNA #3 5' AAGGTCCATCTGGTTGGTATT 3' (SEQ ID NO: 83); siRNA #4 5' AAGCTGGACTCCTCCTACACA 3' (SEQ ID NO: 84); siRNA #5' AAAGTCGACCTTCAGTAAGGA 3' (SEQ ID NO: 85). Lamina cribrosa cells were transfected with siRNA using LipofectAMINE 2000.

Lamina cribrosa cells were transfected when cell confluence was at 40 to 70% and were generally seeded onto 8-well culture slides at 7500 cells per well three days prior to transfection. Transfection medium sufficient for one well of an 8-well culture slide was prepared by diluting 25.5 proles of siRNA to a final volume of 21.2 µl in Opti-Mem (Sigma). 0.425 µl of Lipofectamine 2000 was diluted to a final volume of 21.2 µl in Opti-Mem and incubated for 7 to 10 minutes at room temperature. The diluted Lipofectamine 2000 mixture was then added to the diluted siRNA mixture and incubated together at room temperature for 20 to 30 minutes, The cells were washed once with serum-free media before adding 135 µl of serum-free media to the cells and overlaying 42.4 µl of transfection medium. The cells were placed back in the growth chamber for 4 hours. After the incubation, 65 µl of serum-free media plus 30% FBS was added to the cells. Transfection of siRNA into cells to be used for Western blot analysis were performed in 24-well plates using the same conditions as the transfections in 8-well slides except that the volumes were increased by 2.3 fold. Following transfection, lamina cribrosa cells were incubated for 72 hours prior to treatment with 50 µM of camptothecin (Sigma) and 10 ng/ml of TNF-α (Leinco Technologies) to induce apoptosis. Cell lysates were then harvested for Western blotting or the cells were examined for apoptosis Detection of Apoptotic Cells Transfected cells that had been treated with TNF-α and camptothecin for 24 hours were stained with Hoescht 33258 in order to determine the percentage of cells undergoing apoptosis. Briefly, cells were fixed with a 3:1 mixture of absolute methanol and glacial acetic acid and then incubated with Hoescht stain (0.5 µg/ml Hoescht 33258 in PBS). After a 10 minute incubation in the dark, the staining solution was discarded, the chambers separating the wells of the culture slide were removed, and the slide was washed 3 times for 1 minute with deionized water. After washing, a few drops of McIlvaine's buffer (0.021 M citric acid, 0.058 M $Na_2HPO_4.7H_2O$; pH 5.6) was added to the cells and overlaid with a coverslip. The stained cells were viewed under a fluorescent microscope using a UV filter. Cells with brightly stained or fragmented nuclei were scored as apoptotic. A minimum of 200 cells were counted per well. The DeadEnd™ Fluorometric TUNEL (Promega) was also used to detect the DNA fragmentation that is a characteristic feature of apoptotic cells. Following Hoescht staining, the culture slide was washed briefly with distilled water, and further washed by immersing the slide twice for 5 minutes in PBS (137 mM NaCl, 2.68 mM KCl, 1.47 mM $KH_2PO_4$, 8.1 mM $Na_2HPO_4$), blotting the slide on paper towel between washes. The cells were permeabilized by immersing them in 0.2% Triton X-100 in PBS for 5 minutes. The cells were then washed again by immersing the slide twice for 5 minutes in PBS and blotting the slide on paper towel between washes. 25 µl of equilibration buffer [200 mM potassium cacodylate (pH 6.6), 25 mM. Tris-HCl (pH 6.6), 0.2 mM dithiothreitol, 0.25 mg/ml bovine serum albumin, and 2.5 mM cobalt chloride] was added per well and incubated for 5 to 10 minutes. During equilibration, 30 µA of reaction mixture was prepared for each well by mixing in a ratio of 45:5:1, respectively, equilibration buffer, nucleotide mix [50 µM fluorescein-12-dUTP, 100 µM dATP, 10 mM Tris-HCl (pH 7.6), and 1 mM EDTA], and terminal deoxynucleotidyl transferase enzyme (Tdt, 25 U/µl). After the incubation in equilibration buffer, 30 µl of reaction mixture was added per well and overlayed with a coverslip. The reaction was allowed to proceed in the dark at 37° C. for 1 hour. The reaction was terminated by immersing the slide in 2×SSC [0.3 M NaCl, and 30 mM sodium citrate (pH 7.0)] and incubating for 15 minutes. The slide was then washed by immersion in PBS three times for 5 minutes. The PBS was removed by sponging around the wells with a Kim wipe, a drop of mounting media (Oncogene research project, JA1750-4 ML) was added to each well, and the slide was overlayed with a coverslip. The cells were viewed under a fluorescent microscope using a UV filter (UV-G 365, filter set 487902) in order to count the Hoescht-stained nuclei. Any cells with brightly stained or fragmented nuclei were scored as apoptotic. Using the same field of view, the cells were then viewed using a fluorescein filter (Green H546, filter set 48915) and any nuclei fluorescing bright green were scored as apoptotic. The percentage of apoptotic cells in the field of view was calculated by dividing the number of bright green nuclei counted using the fluorescein filter by the total number of nuclei counted under the UV filter. A minimum of 200 cells were counted per well.

Protein Extraction and Western Blot Analysis

Protein was isolated for Western blotting from lamina cribrosa cells growing on 24-well plates by washing the cells twice in PBS (8 g/L NaCl, 0.2 g/L KCl, 1.44 g/L $Na_2HPO_4$, and 0.24 g/L $KH_2PO_4$) and then adding 50 µl of lysis buffer [2% SDS, 50 mM Tris-HCl (pH 7.4)]. The cell lysate was collected in a microcentrifuge tube, boiled for 5 minutes and stored at −20° C. until ready for use. Protein concentrations were determined using the Bicinchoninic Acid Kit (BCA; Sigma). For Western blotting, 5 µg of total protein was separated on a 12 SDS-polyacrylamide gel. The separated proteins were transferred to a polyvinylidene difluoride membrane. The membrane was then incubated for one hour in blocking solution (5% skim milk powder, 0.02% sodium azide in PBS) and washed three times for 15 minutes in PBS-T (PBS+0.05% Tween-20). The membrane was stored overnight in PBS-T at 4°C. After being warmed to room temperature the next day, the membrane was blocked for 30 seconds in 1 µg/ml polyvinyl alcohol. The membrane was rinsed 5 times in deionized water and then blocked for 30 minutes in a solution of 5% milk in PBS. The primary antibody was preincubated for 30 minutes in a solution of 5% milk in PBS prior to incubation with the membrane. The primary antibodies used were anti-eIF5A (BD Transduction Laboratories) at 1:20,000 and anti-β-actin (Oncogene). The membranes were washed three times in PBS-T and incubated for 1 hour with the appropriate HRP-conjugated secondary antibodies diluted in 1% milk in PBS. The blot was washed and the ECL Plus Western blotting detection kit (Amersham Pharmacia Biotech) was used to detect the peroxidase-conjugated bound antibodies.

Results

Figure 82A:
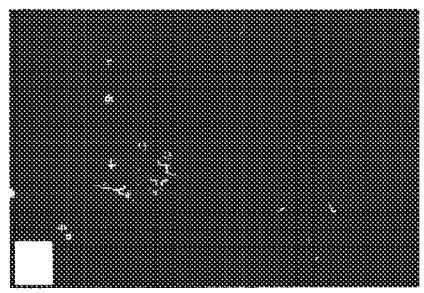
FIG. 82 is a characterization of lamina cribrosa cells by immunofluorescence. Lamina cribrosa cells (#506) isolated from the optic nerve head of an 83-year old male were characterized by immunofluorescence. Primary antibodies were a) actin; b) fibronectin; c) laminin; d) GFAP. All pictures were taken at 400 times magnification.
Figure 82B:
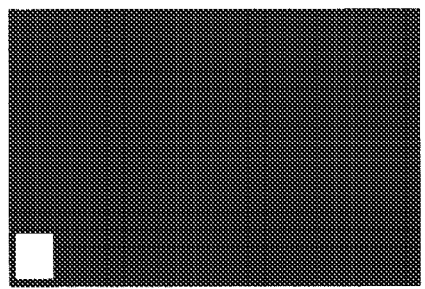
Figure 82C:
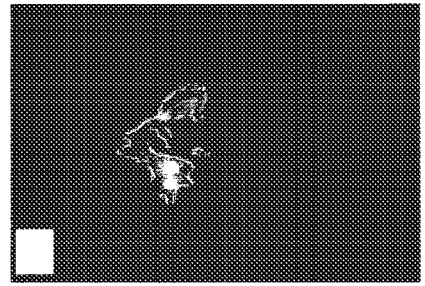
Figure 82D:
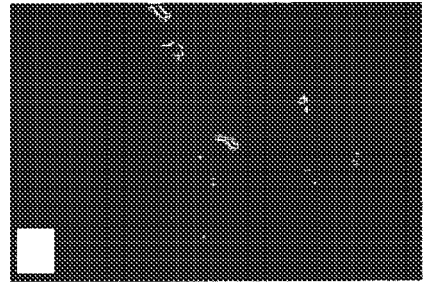

Two lamina cribrosa (LC) cell lines were established from optic nerve heads obtained from male donors ranging in age from 83 years (#506) to 17 years (#517). The cells isolated from the human lamina cribrosa had the same broad, flat morphology with prominent nucleus observed in other studies (Lambert et al., 2001). Consistent with the characterizations of other groups, the LC cells showed immunoreactivity to alpha smooth muscle actin (FIG. 82a) as well as to a number of extracellular matrix proteins including cellular fibronectin (FIG. 82b), laminin (FIG. 82c), collagen I, and collagen IV (data not shown) (Clark et al., 1995; Hernandez et al., 1998; Hernandez and Yang, 2000; Lambert et al.; 2001). Negative immunoreactivity of the LC cells to glial fibrillary acidic protein (GFAP) was also observed consistent with previous findings (FIG. 82d) (Lambert et al., 2001). These findings support the identification of the isolated cells as being LC cells rather than optic nerve head astrocytes.

Figure 83:
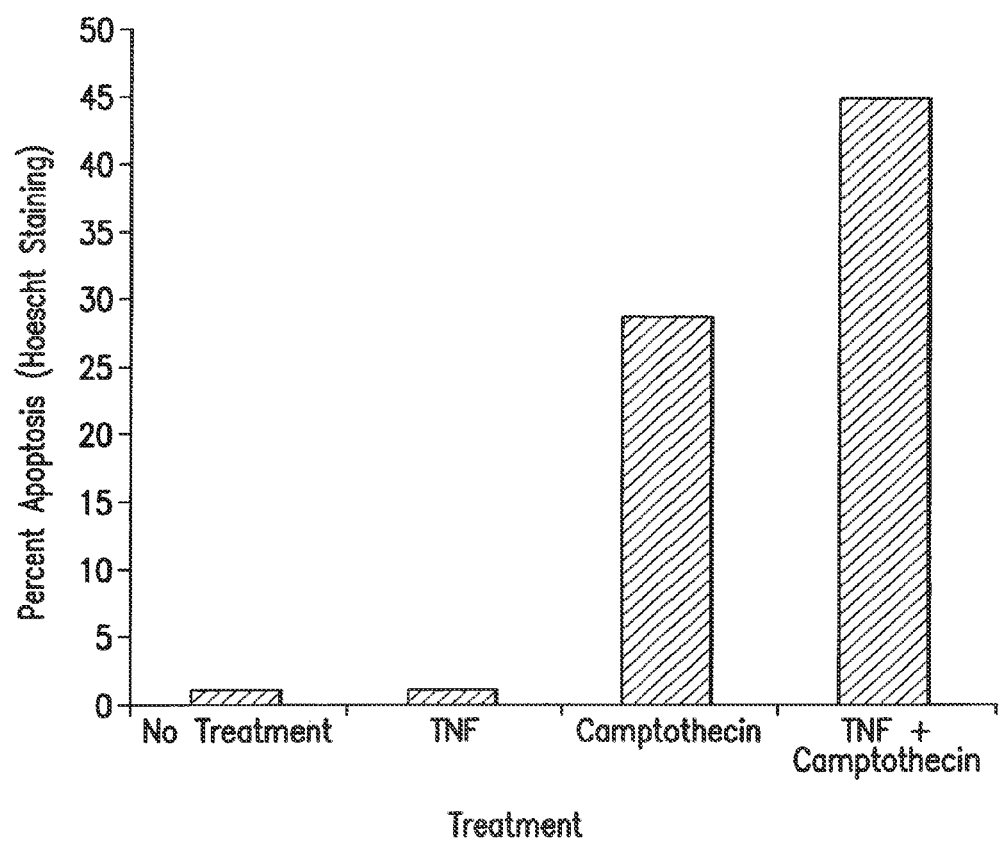
FIG. 83 is a graph showing percent apoptosis of lamina cribrosa cell line #506 in response to treatment with camptothecin and TNF-α. Lamina cribrosa cell line #506 cells were seeded at 40,000 cells per well onto an 8-well culture slide. Three days later the confluent LC cells were treated with either 10 ng/ml TNF-α, 50 μM camptothecin, or 10 ng/ml TNF-α plus 50 μM camptothecin. An equivalent volume of DMSO, a vehicle control for camptothecin, was added to the untreated control cells. The cells were stained with Hoescht 33258 48 hours after treatment and viewed by fluorescence microscopy using a UV filter. Cells with brightly stained condensed or fragmented nuclei were counted as apoptotic.

Since TNF-α is believed to play an important role during the glaucomatous process, the susceptibility of LC cells to the cytotoxic effects of TNF-α was examined. Confluent LC cells were exposed to either camptothecin, TNF-α, or a combination of camptothecin and TNF-α for 48 hours (FIG. 83). Hoescht staining revealed that TNF-α alone was not cytotoxic to LC cells. Treatment with camptothecin resulted in approximately 30% cell death of the LC cells. However, a synergistic increase in apoptosis was observed when LC cells were treated with both camptothecin and TNF-α, a treatment which resulted in the death of 45% of LC cells by 48 hours. These results indicate that LC cells are capable of responding to the cytotoxic effects of TNF-α when primed for apoptosis by camptothecin.

Figure 84A:
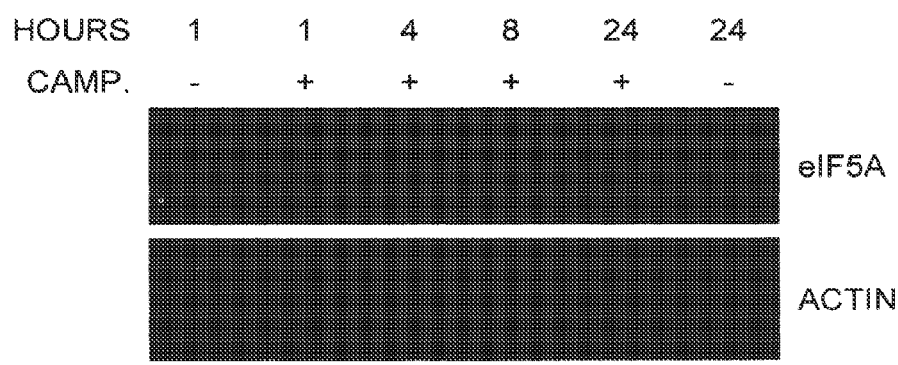
FIG. 84A-B shows expression levels of against apoptosis-specific eIF-5A during camptothecin (FIG. 84A) or TNF-a plus camptothecin (FIG. 84B) treatment. Lamina cribosa cell #506 cells were seeded at 40,000 cells per well onto a 24-well plate. Three days later the LC cells were treated with either 50 µM camptothecin or 10 ng/ml TNF-α plus 50 µM camptothecin and protein lysate was harvested 1, 4, 8, and 24 hours later. An equivalent volume of DMSO was added to control cells as a vehicle control and cell lysate was harvested 1 and 24 hours later. 5 µg of protein from each sample was separated by SDS-PAGE, transferred to a PVDF membrane, and Western blot with anti-apoptosis-specific eIF-5A antibody. The bound antibody was detected by chemiluminescence and exposed to x-ray film. The membrane was then stripped and re-blotted with anti-β-actin as an internal loading control.
Figure 84B:
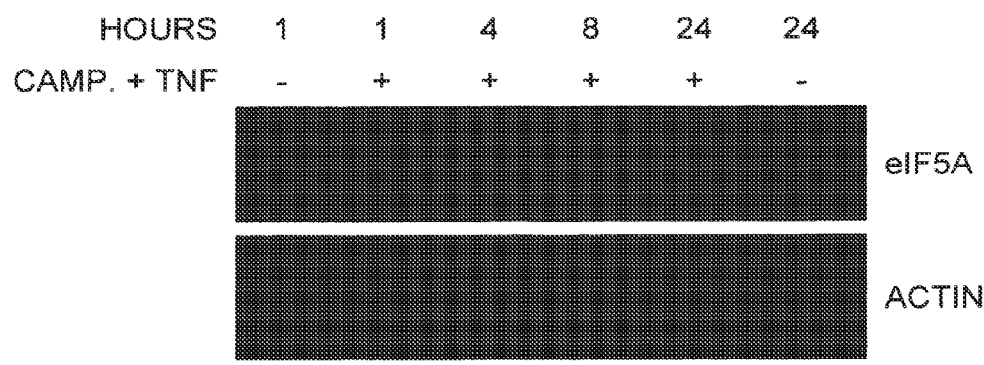

EIF5A is a nucleocytoplasmic shuttle protein known to be necessary for cell division and recently suggested to also be involved during apoptosis. The expression of apoptosis-specific eIF-5A protein in LC cells being induced to undergo apoptosis by either camptothecin, or camptothecin plus TNF-α. The expression of apoptosis-specific eIF-5A did not alter significantly upon treatment with camptothecin except perhaps to decrease slightly (FIG. 84A). However, a significant upregulation of apoptosis-specific eIF-5A protein was observed after 8 and 24 hours of camptothecin plus TNF-α treatment (FIG. 84B). These results indicate that of apoptosis-specific eIF-5A expression is induced specifically by exposure TNF-α and expression correlates to the induction of apoptosis. This points to a role for apoptosis-specific eIF-5A in the apoptotic pathway downstream of TNF-α receptor binding.

Figure 85:
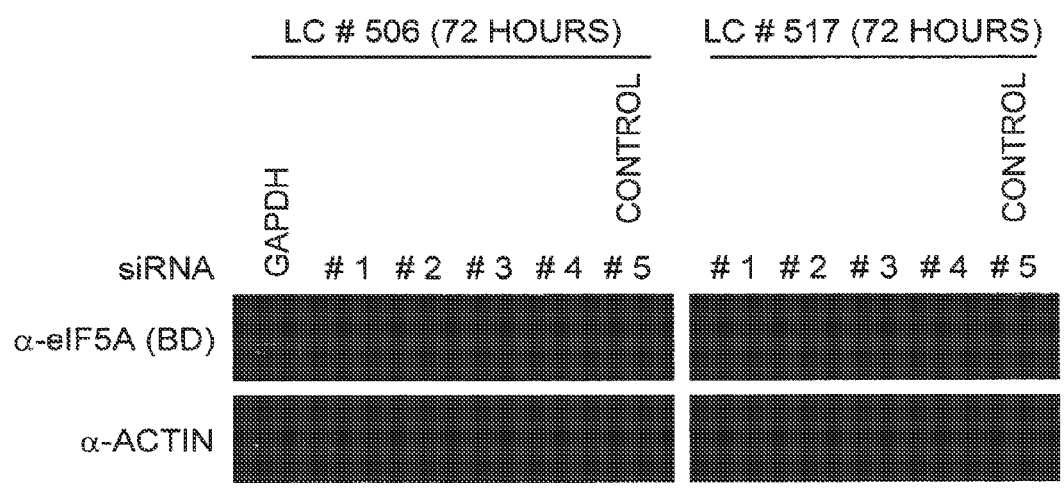
FIG. 85 shows expression levels of apoptosis-specific eIF-5A in lamina cribosa cell lines #506 and #517 following transfection with siRNAs. Lamina cribrosa cell #506 and #517 cells were seeded at 10,000 cells per well onto a 24-well plate. Three days later the LC cells were transfected with either GAPDH siRNA, apoptosis-specific eIF-5A siRNAs #1-4 (SEQ ID NO:30-33) or control siRNA #5 (SEQ. ID NO:34). Three days after transfection the protein lysate was harvested and 5 µg of protein from each sample was separated by SDS-PAGE, transferred to a PVDF membrane, and Western blotted with anti-eIF5A antibody. The bound antibody was detected by chemiluminescence and exposed to x-ray film. The membrane was then stripped and re-blotted with anti-β-actin as an internal loading control. This figure shows that cells treated with siRNAs of apoptosis-specific eIF-5A produce less apoptosis-specific eIF-5A protein.
Figure 86:
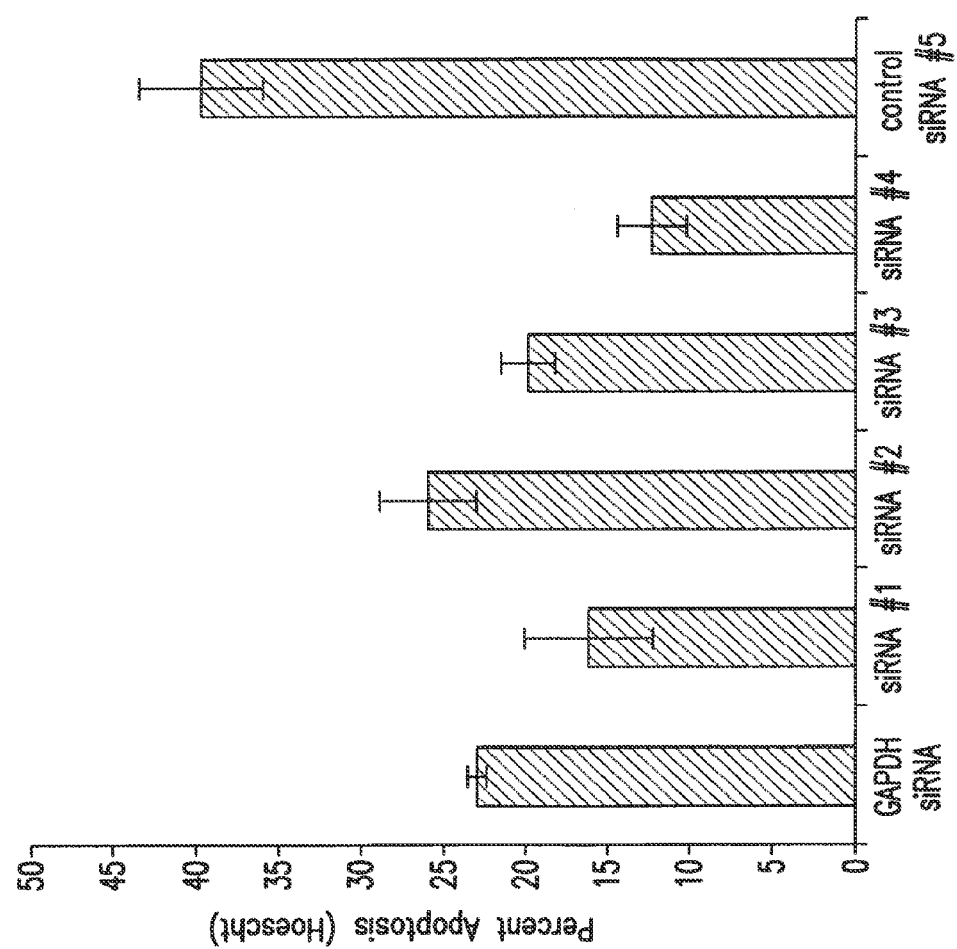
FIG. 86 shows the percent apoptosis of lamina cribosa cell line #506 cells transfected with apoptosis-specific eIF-5A siRNAs and treated with TNF-α and camptothecin. Lamina cribrosa cell line #506 cells were seeded at 7500 cells per well onto an 8-well culture slide. Three days later the LC cells were transfected with either GAPDH siRNA, apoptosis-specific eIF-5A siRNAs #1-4 (SEQ ID NO:30-33), or control siRNA #5 (SEQ ID NO:34). 72 hours after transfection, the transfected cells were treated with 10 ng/ml TNF-α plus 50 µM camptothecin. Twenty-four hours later the cells were stained with Hoescht 33258 and viewed by fluorescence microscopy using a UV filter. Cells with brightly stained condensed or fragmented nuclei were counted as apoptotic. This graph represents the average of n=4 independent experiments. This figure shows that cells treated with siRNAs of apoptosis-specific eIF-5A show a smaller percentage of apoptosis upon treatment with camptothecin and TNF as compared to cells not transfected with siRNAs of apoptosis-specific eIF-5A.
Figure 87:
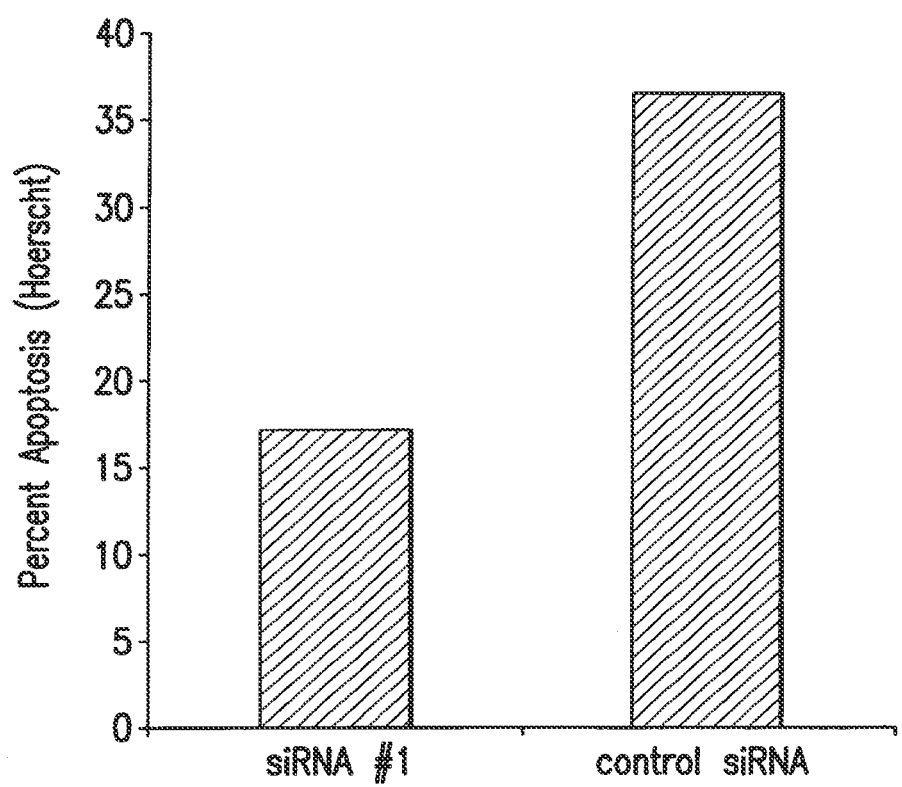
FIG. 87 shows percent apoptosis of lamina cribosa cell line #517 cells transfected with apoptosis-specific eIF-5A siRNA #1 and treated with TNF-α and camptothecin. Lamina cribrosa cell line #517 cells were seeded at 7500 cells per well onto an 8-well culture slide. Three days later the LC cells were transfected with either apoptosis-specific eIF-5A siRNA #1 (SEQ ID NO:30) or control siRNA #5 (SEQ ID NO:34). 72 hours after transfection, the transfected cells were treated with 10 ng/ml TNF-α plus 50 µM camptothecin. Twenty-four hours later the cells were stained with Hoescht 33258 and viewed by fluorescence microscopy using a UV filter. Cells with brightly stained condensed or fragmented nuclei were counted as apoptotic. The results of two independent experiments are represented here. This shows that cells treated with siRNAs had a lower percentage of apoptosis.
Figure 90:
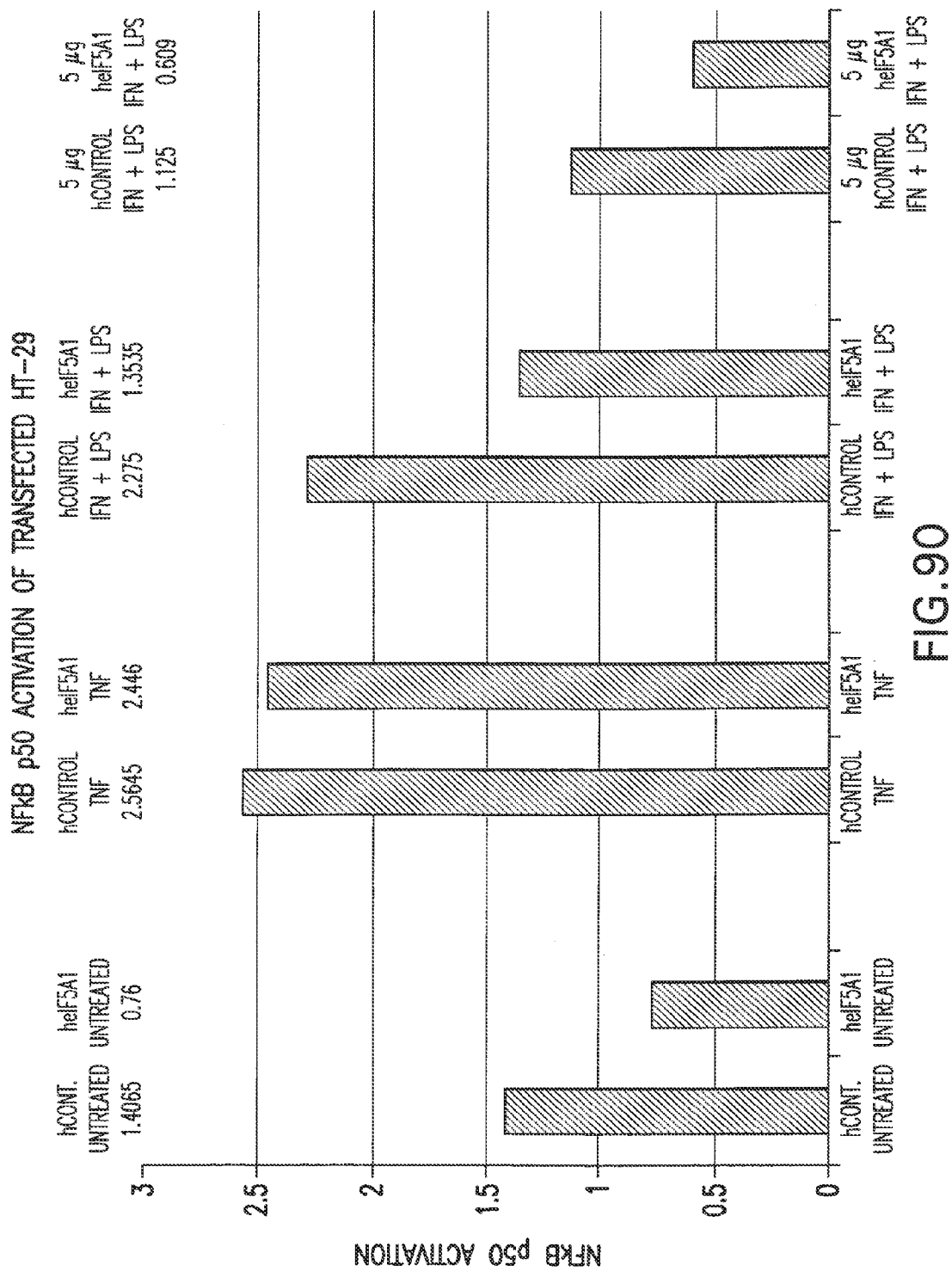
FIG. 90 shows the results of an experiment where siRNAs directed against apoptosis-specific eIF-5A provided for a reduction in NKkB activation in the presence of interferon gamma and LPS.

In order to examine the importance of apoptosis-specific eIF-5A expression during TNF-α-induced apoptosis in LC cells, a series of four siRNAs (siRNAs #1 to #4) targeting apoptosis-specific eIF-5A were designed and synthesized by in vitro transcription. To determine the effectiveness of the siRNAs in suppressing apoptosis-specific eIF-5A protein expression, LC cell lines #506 and #517 were transfected with each of the siRNAs and expression of apoptosis-specific eIF-5A protein in the cell lysate was examined 72 hours later (FIG. 85). For comparison, cells were also transfected with either an siRNA against GAPDH and/or a control siRNA (siRNA #5) having the same chemical composition as siRNA #1 but which does not recognize apoptosis-specific eIF-5A. All siRNAs directed against apoptosis-specific eIF-5A were capable of significantly suppressing apoptosis-specific eIF-5A expression in both LC cell lines (FIG. 85). The GAPDH siRNA was used as an additional control because, unlike the control siRNA #5 which simply has the reverse sequence of siRNA #1 and does not have a cellular target, it is an active siRNA capable of suppressing the expression of it's target protein, GAPDH (data not shown). All four siRNAs against apoptosis-specific eIF-5A were also capable of protecting transfected LC cells (#506) from apoptosis induced by 24 hour treatment with TNF-α and camptothecin (FIG. 86). Using Hoescht staining to detect cell death, the siRNAs (siR-NAs #1 to #4) were found to be able to reduce apoptosis of LC cells by 59% (siRNA #1), 35% (siRNA #2), 50% (siRNA #3), and 69% (siRNA #4). Interestingly, the siRNA against GAPDH was also able to reduce apoptosis of LC cells by 42% (FIG. 86). GAPDH is known to have cellular functions outside of it's role as a glycolytic enzyme, including a proposed function during apoptosis of cerebellar neurons (Ishitani and Chuang, 1996; Ishitani et al., 1996a; Ishitani et al., 1996b). In a similar experiment we also demonstrated that siRNA #1 was able to reduce apoptosis of the LC line #517 by 53% in response to TNF-α and camptothecin indicating that apoptosis-specific eIF-5A. siRNAs are protective for LC cells isolated from different optic nerve heads (FIG. 87). These results indicate that apoptosis-specific eIF-5A does have a function during apoptosis and may be an important intermediate in the pathway leading to TNF-α-induced apoptosis in LC cells.

In order to confirm that LC cells exposed to TNF-a and camptothecin were dying by classical apoptosis, DNA fragmentation was evaluated in situ using the terminal deoxynucleotidyl transferase-mediated dUTP-digoxigenin nick end labeling (TUNEL) method. LC cells (#506) were treated with TNF-α and camptothecin for 24 hours, 3 days after transfection with either an apoptosis-specific eIF-5A siRNA (siRNA #1) or a control siRNA (siRNA #5). The cells were also stained with Hoescht to facilitate visualization of the nuclei. 46% of LC cells transfected with the control siRNA were positive for TUNEL staining while only 8% of LC cells transfected with apoptosis-specific eIF-5A siRNA #1 were positively labeled indicating that the apoptosis-specific eIF-5A siRNA provided greater than 80% protection from apoptosis (FIG. 88). Similar results were obtained with apoptosis-specific eIF-5A siRNA #4 which provided greater than 60% protection from apoptosis relative to the control siRNA (data not shown).

Example 18

Blood Collection and Preparation of PBMCs

Approximately 10 ml of blood was collected from each healthy donor. The blood was collected by venapuncture in a vacutainer containing sodium citrate as the anti-coagulant. The samples were processed within 24 hours of collection.

A 60% SIP (9 parts v/v Percoll with 1 part v/v 1.5M NaCl) was cushioned on the bottom of 1.5 ml conical tubes. The blood was then layered overtop with minimal mixing of the blood and Percoll cushion. The samples were centrifuged for 30 minutes total at 1000×g with slow acceleration in the first 5 minutes and slow deceleration in the last 5 minutes. The pure serum at the very top of the resulting gradient was removed and the white cushion (1-2 ml) of PBMCs was collected and added dropwise to a tube containing 10 ml of warm RPMI plus 15% FBS. The PBMCs were pelleted and counted.

Stimulation to Induce Cytokine Production in PBMCs Over a Time Course

Figure 91:
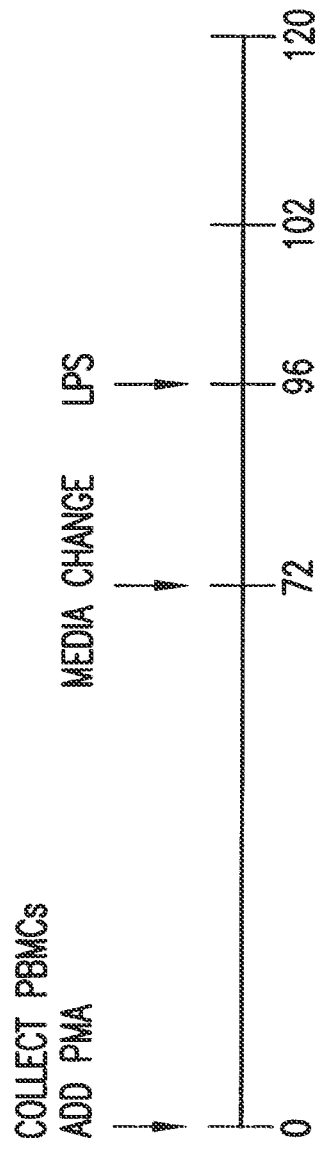
FIG. 91 shows the time course for PBMC experiments (see Example 18).
Figure 92:
FIG. 92 shows a Western blot of a cell lysate from PBMCs collected from two donors over a time course. The PBMCs were treated with PMA and subsequently stimulated with LPS to have an increased apoptosis-specific eIF-5A expression.
Figure 93A:
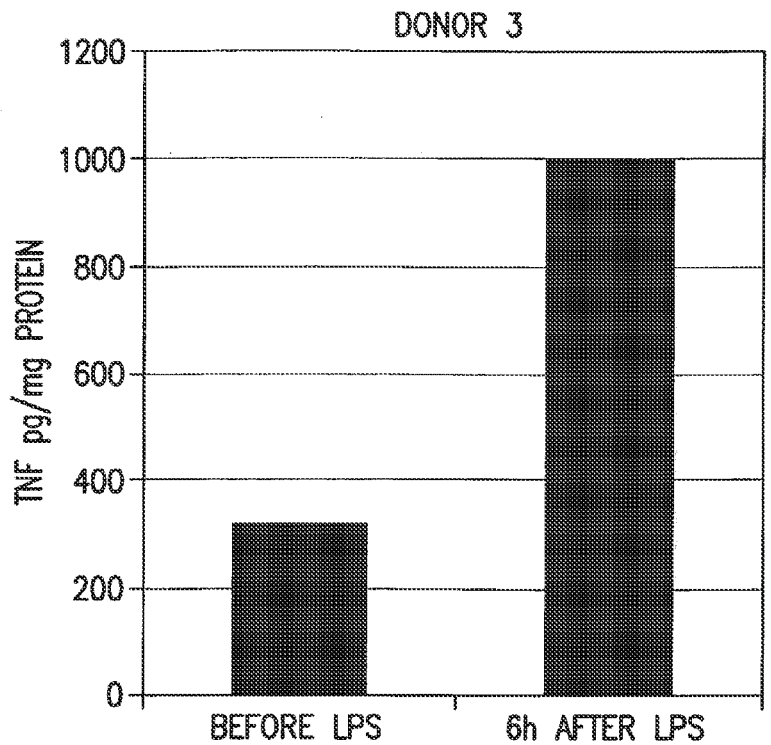
FIG. 93A-B shows that PBMCs treated with PMA and subsequently stimulated with LPS have an increased apoptosis-specific eIF-5A expression, which coincides with increased TNF production.
Figure 93B:
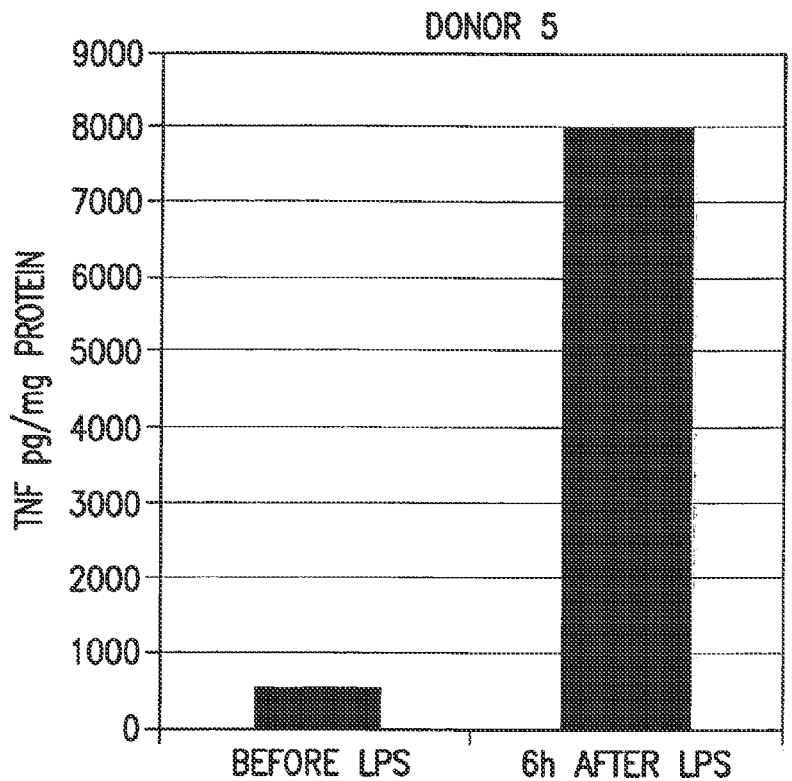
Figure 96A:
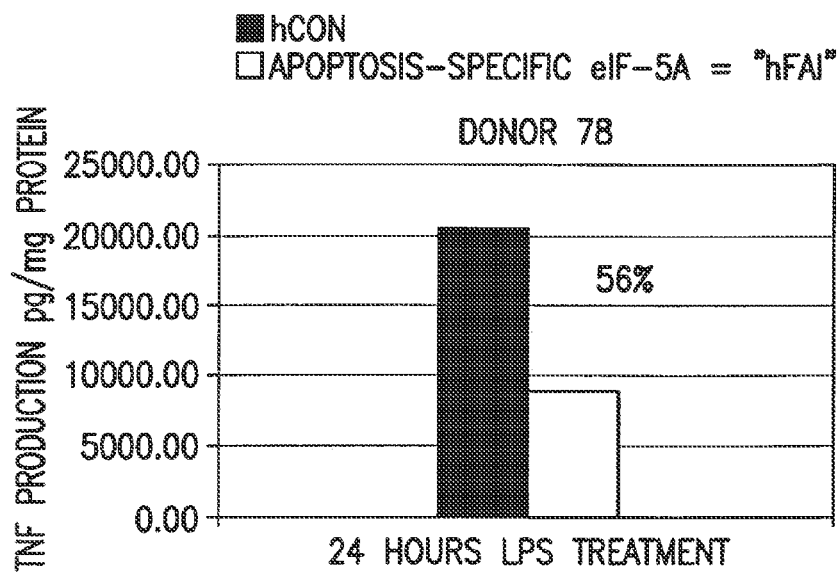
FIG. 96A-D shows that PBMCs transfected with apoptosis-specific eIF-5A siRNAs and stimulated with LPS produce less TNF than PBMCs not transfected with apoptosis-specific eIF-5A siRNAs.
Figure 96B:
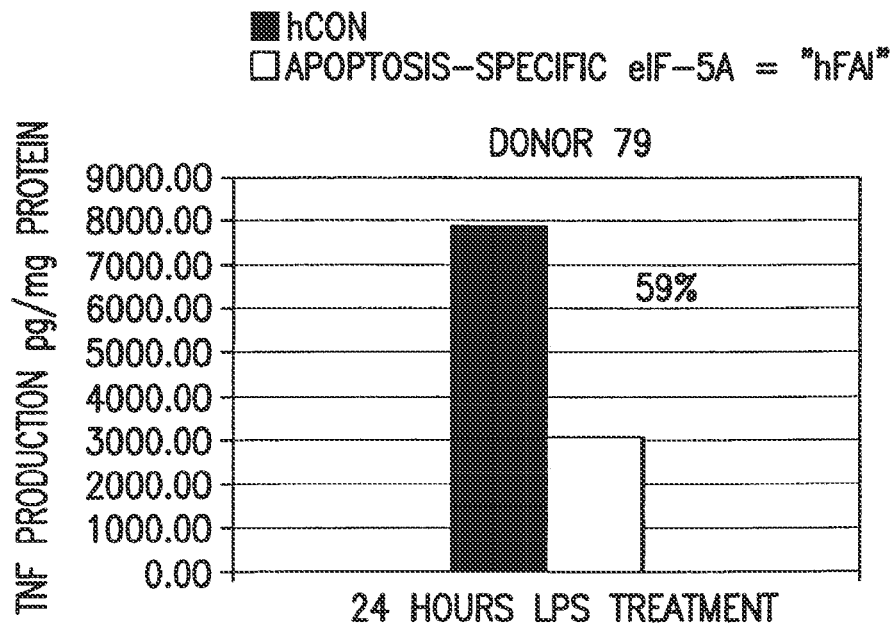
Figure 96C:
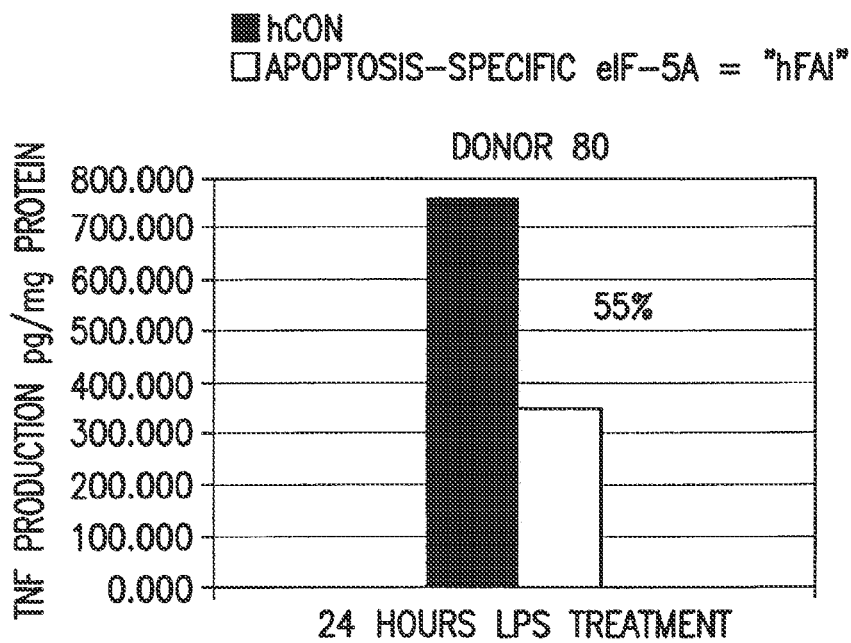
Figure 96D:
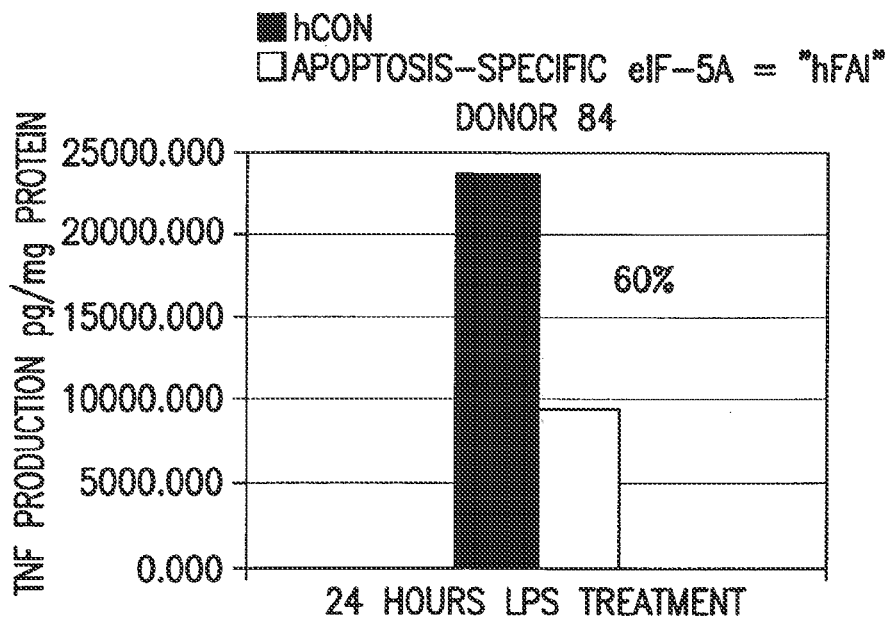
Figure 97:
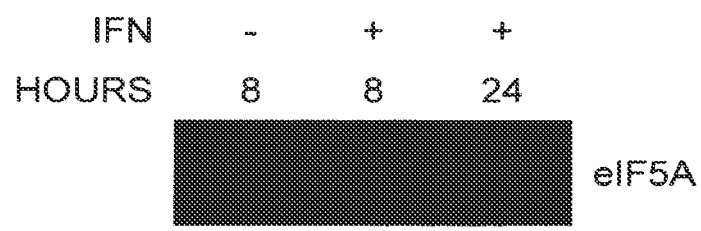
FIG. 97 shows a western blot of cell lysate from HT-29 cells treated with or without gamma interferon.
Figure 98:
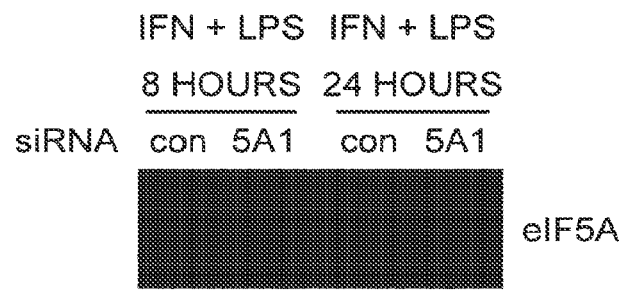
FIG. 98 shows a western blot of cell lysate from HT-29 cells that were transfected with either control siRNA or apoptosis-specific eIF-5A siRNAs. This figure shows that siRNAs of apoptosis-specific eIF-5A inhibit expression of apoptosis-specific eIF-5A.
Figure 102:
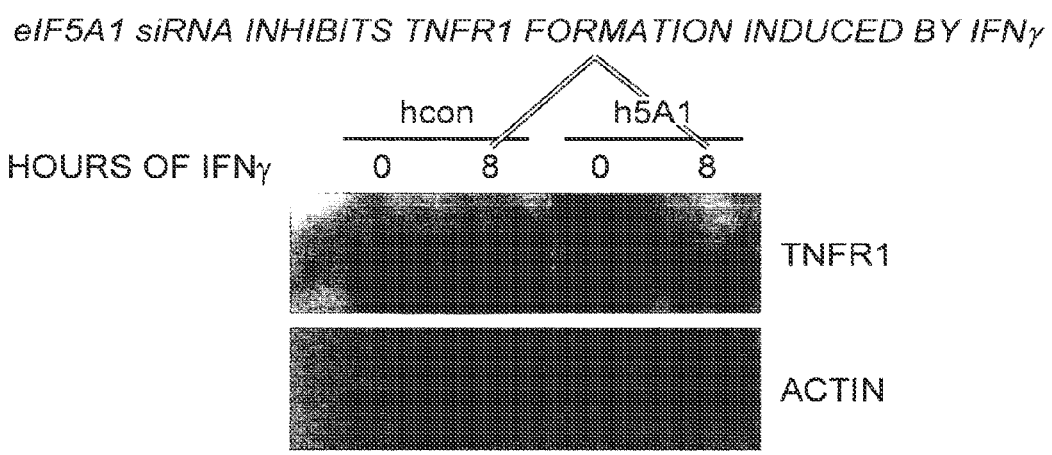
FIG. 102 shows that HT-29 cells transfected with apoptosis-specific eIF-5A siRNAs express less TNFR1 protein than control cells.
Figure 103:
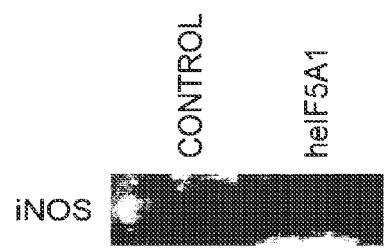
FIG. 103 shows that HT-29 cells transfected with apoptosis-specific eIF-5A siRNAs express less iNOS protein than control cells.
Figure 104:
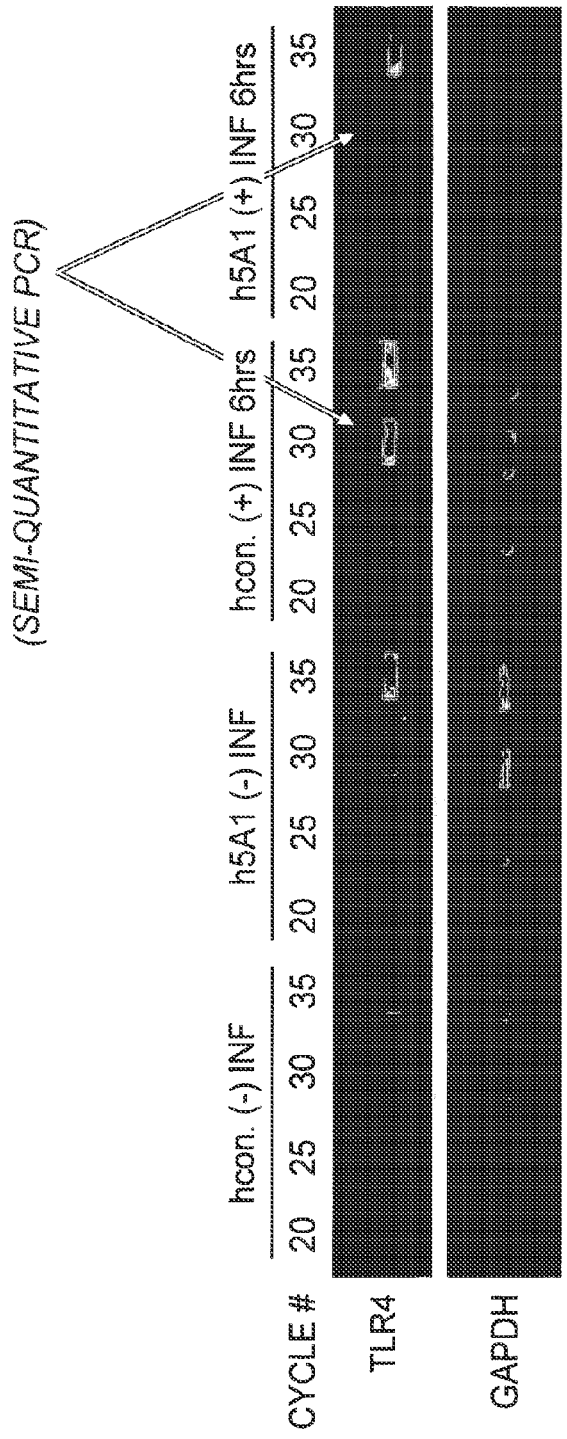
FIG. 104 shows that HT-29 cells transfected with apoptosis-specific eIF-5A siRNAs express less TLR4 mRNA than control cells.
Figure 105:
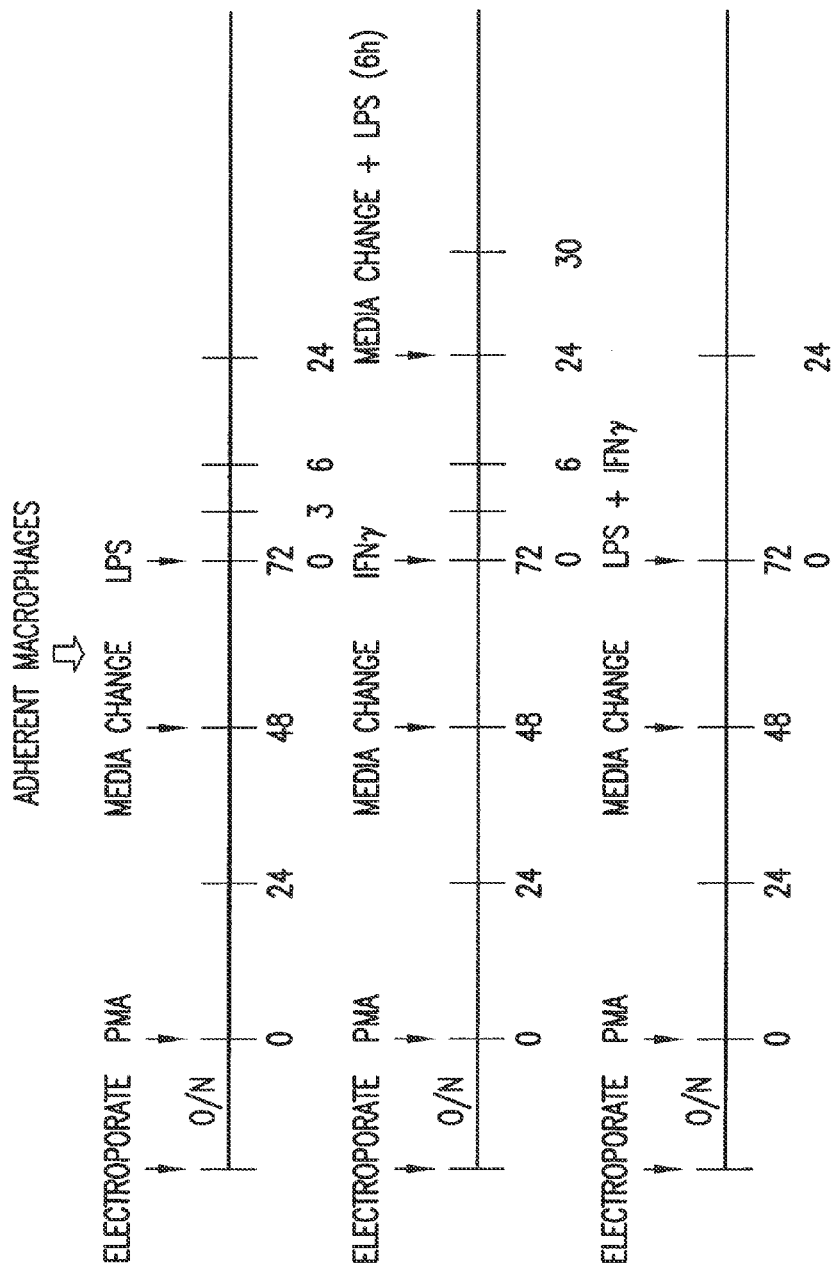
FIG. 105 shows the time course for U937 treatments.
Figure 107:
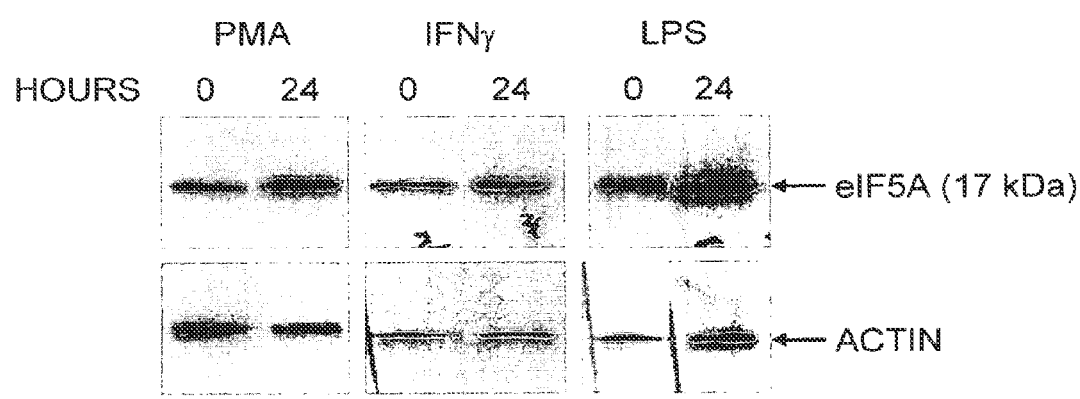
FIG. 107 shows that apoptosis-specific eIF-5A is upregulated with LPS in U937 cells.

PBMCs were isolated and seeded at $2 \times 10^5$ to $5 \times 10^5$ cells/well. The cells were treated with phorbol 12-myristate 13-acetate (PMA; 100 ng/well). At 72 hours the media was replaced and did not contain any stimulating factors. Then at 96 hours after PMA addition to PBMCs, lipopolysaccharide (LPS; 100 ng/well; from E. coli, serotype 0111) was added to the wells. Samples were collected before LPS addition (96 h), and at various times after addition as outlined in FIG. 91. Both adherent cells (likely to be monocytes and macrophages) were collected with the floating cells (likely to be lymphocytes). To collect samples for analysis of cytokine secretion, the media from each well was transferred to clean microcentrifuge tubes and cleared of any debris by centrifugation at 13000×g for 3 minutes. The resulting pellet was collected with the adherent cells. The media was stored at −20° C. in 200-250 µl aliquots prior to analysis. The cells were washed with 1 ml of 37° C. phosphate buffered saline (PBS) and then lysed in boiling lysis buffer (50 mM Tris pH 7, 2% SDS; 100 µl per well). The cell lysates were boiled and stored frozen at −20° C. The Western blot is shown in FIG. 92 and the corresponding ELISA in FIG. 93.

PBMC Stimulation to Induce Apoptosis-Specific eIF-5A Expression

PBMCs were collected and seeded at $2 \times 10^5$ to $5 \times 10^5$ cells/well. To determine which stimulators induce apoptosis-specific eIF-5A; as well as to see if they act synergistically, the PBMCs were stimulated with phytohemagglutinin (PHA; 100 ng/ml), phorbol 12-myristate 13-acetate (PMA; 100 ng/ml), lipopolysaccharide (LPS; 100 ng/ml) or all three (each at 100 ng/ml). The samples were collected 12 and 36 hours after stimulation and analyzed for apoptosis-specific eIF-5A expression (FIG. 94).

Transfection of PBMGs

PBMCs were transfected the day they were prepared. Cells were seeded at $2 \times 10^5$ to $5 \times 10^5$ cells/well (150 µl per well for transfection in a 24-well plate). They were either transfected individually in each well (Donors 77, 78 and 79; FIGS. 95 and 96) or all at once in a conical tube before seeding (Donors 80 and 84; FIG. 96). For each well of cells to be transfected, 15 pmoles of siRNA was diluted in 50 µl of Opti-MEM (Sigma). 1 µl of Lipofectamine 2000 (Invitrogen) was diluted in 49 µl of Opti-MEM, incubated for 7 to 10 minutes, added to the diluted siRNA and incubated 25 minutes. The transfection medium was overlayed onto the cells were placed in the 37° C. growth chamber for 4 hours. The final transfection medium contained 9% serum. After the incubation, 250 µl of serum-free RPMI+21% FBS was added to the cells to make the final serum concentration 15%.

Stimulation to Induce Cytokine Production in PBMCs Post Transfection 72 hours after transfection of the PBMCs, as outlined above, lipopolysaccharide (LPS; 100 rig/well; from E. coli, serotype 0111) was added to the cells in 500 µl of media. The samples were collected at 24 hours post stimulation. Both wells that were treated with LPS and wells that were transfected only (i.e. no stimulation) were collected. To collect samples for analysis of cytokine secretion, the media from each well was transferred to clean microcentrifuge tubes and cleared of any debris by centrifugation at 13000×g for 3 minutes. The resulting pellet was collected with the adherent cells. The media was stored at −20° C. in 200-250 µl aliquots prior to analysis. The cells were washed with 1 ml of 37° C. phosphate buffered saline (PBS) and then lysed in boiling lysis buffer (50 mM Tris pH 7, 2% SDS; 1000µl per well). The cell lysates were boiled and stored frozen at −20° C. for BCA protein quantitation.

Example 19

Cell Culture

HT-29, a human colorectal adenocarcinoma cell line, was maintained in RPMI with 10% fetal bovine serum (FBS). U937, a histiocytic lymphoma cell line, was grown in suspension in RPMI with 10% FBS. Both cell lines were maintained in a humidified environment at 37° C. and 5% CO$_2$. For experiments with U937 cells, cells were counted and adjusted to 3×10$^5$ cells/ml two days before the start of the experiment. On the first day of the experiment, cells were collected by centrifugation at 400×g for 10 ruins, the cell pellet was resuspended in fresh RPMI media with 10% FBS, the centrifugation was repeated, and the repelleted cells were resuspended in fresh RPMI media without FBS. The cells were counted and adjusted to 2×10$^6$ cells/ml.

siRNA siRNA sequences were designed based on the human apoptosis-specific eIF-5A sequence and were synthesized by Dharmacon RNA Technologies. The apoptosis-specific eIF-5A siRNA (h5A1) target sequence was: 5' NNGCUGGACUCCUCCUACACA 3' (SEQ ID No: 86). The corresponding double stranded siRNA sequence was:

```
5' GCUGGACUCCUCCUACACAdTdT 3'    (SEQ ID NO: 87)
3' dTdTCGACCUGAGGAGGAUGUGU 5'    (SEQ ID NO: 88)
```

The control siRNA (hcontrol) sequence was 5' NNACACAUCCUCCUCAGGUCG 3'(SEQ ID No: 89). The corresponding double stranded siRNA sequence was:

```
5' ACACAUCCUCCUCAGGUCGdTdT 3'    (SEQ ID NO: 90)
3' dTdTUGUGUAGGAGGAGUCCAGC 5'    (SEQ ID NO: 91)
```

Transfection of HT-29 Cells

The day before transfection, HT-29 cells were seeded at 105,000 cells per well onto a 24-well plate. For each well of cells to be transfected, 25.5 pmoles of siRNA was diluted in 50 μl of Opti-Mem (Sigma). 1 μdiluted in 49 μl of Opti-Mem, incubated for 7 to 10 minutes and added to the diluted siRNA and incubated 25 minutes. The cells to be transfected were washed once with serum-free RPMI before adding 300 μl of serum-free RPMI and overlaying 100 μl of transfection medium. The cells were placed back in the growth chamber for 4 hours. After the incubation, 300 μl of serum-free RPMI+ 30% FBS was added to the cells.

Electroporation of U937 Cells apoptosis-specific eIF-5A and control siRNA were diluted in Opti-Mem media (Sigma). 400 μl cells (800,000 cells) and 100 pmoles siRNA were mixed in a 0.4 mm electroporation cuvette. The cells were electroporated at 300 V, 10 mSec, 1 pulse with an ECM 830 Electrosquare porator (BTX, San Diego, Calif.). Following electroporation, the cells were gently mixed and added to wells containing RPM and concentrated FBS so that the final FBS concentration was 10%.

Treatment of HT-29 Cells

TNF-α production was induced in HT-29 cells according to the method developed by Suzuki et al. 2003. HT-29 cells were primed with 200 units/ml interferon gamma (Roche Diagnostics) 48 hours after transfection. After 16 hours of interferon gamma (IFNγ) priming the cells were washed with media and lipopolysaccharide (LPS; 100 ng/ml; from E. coli, serotype 0111; Sigma) was added at 100 μg/ml. After 8 or 24 hours of LPS stimulation, the media from each well was transferred to microcentrifuge tubes and stored at −20° C. until assayed for TNFα by ELISA. The cells were washed with 1 ml of phosphate buffered saline (PBS) heated to 37° C. and then lysed in boiling lysis buffer (50 mM Tris pH 7, 2% SDS). The cell lysates were boiled and stored frozen at −20° C. The protein concentration in the cell lysates was determined by bicinchoninic acid assays (BCA) with bovine serum albumin used as the standard.

IL-8 production was induced in HT-29 cells by treatment with IFNγ. HT-29 cells were treated with 200 units/ml IFNγ 48 hours after transfection. After 24 hours of treatment, the media from each well was transferred to microcentrifuge tubes and stored at −20° C. until assayed for IL-8 by liquid-phase electrochemiluminescence (ECL). The cells were washed with 1 ml of phosphate buffered saline (PBS) heated to 37° C. and then lysed in boiling lysis buffer (50 mM Tris pH 7, 2% SDS). The cell lysates were boiled and stored frozen at −20° C. The protein concentration in the cell lysates was determined by bicinchoninic acid assays (BCA) with bovine serum albumin used as the standard.

Induction of Differentiation in U937 Cells

U937 cells were collected and counted 16 hours after electroporation. 200,000 cells in 1 ml of media were added to each well of 24-well plates. Macrophage differentiation was stimulated by adding phorbol 12-myristate 13-acetate (PMA; 100 ng/ml). After 48 h with PMA., >80% of the monocytes had transformed from cells in suspension (monocytes) to adherent cells (macrophages). At 48 hours the media and any non-adherent cells were removed and fresh RPMI media with 10% FBS (1 ml per well) was added. The cells were left for 24 hours in fresh media to become quiescent.

Stimulation to Induce Cytokine Production in U937 Cells 72 hours after PMA addition to U937 cells, lipopolysaccharide (LPS; 100 ng/ml; from E. coli, serotype 0111), interferony (IFNγ; 100 Units/ml), or a combination of LPS and IFNγ were added to the wells. Samples were collected before stimulator addition (72h), and at various times after addition as outlined in FIG. 108. To collect samples for analysis of cytokine secretion, the media from each well was transferred to clean microcentrifuge tubes and cleared of any debris by centrifugation at 13000×g for 3 mins. The media was stored at −20° C. in 200-250 μl aliquots prior to analysis. The cells were washed with 1 ml of 37° C. phosphate buffered saline (PBS) and then lysed in boiling lysis buffer (50 mM Tris pH 7, 2% SDS; 75 μl per well). Like wells were pooled. The cell lysates were boiled and stored frozen at −20° C.

Cytokine Quantification

All media samples were stored frozen at −20° C. TNFα was quantified using ELISA kits from Assay Designs according to the manufacturer's instructions with supplied standards for 0-250 pg TNFα/ml. For U937 experiments media samples for TNFα were diluted 20 fold (0 h, 3 h LPS) or 80 fold (6 h, 24 h, 30 h LPS) with RPMI+10% FBS. IL-1β, IL-8, and IL-6 were quantified by liquid-phase electrochemiluminescence (ECL). Media from HT-29 experiments were not diluted. All cytokine measurement results were corrected for the amount of total cellular protein (mg) per well.

IL-8, IL-1β, and IL-6 were assayed by liquid-phase. Briefly, a purified monoclonal mouse anti-mouse anti-human IL-8, IL-6 or IL-1 p (R & D Systems) were labeled with biotin (Igen, Inc., Gaithersburg, Md.). In addition, the goat anti-human IL-8, IL-6, or IL-1β antibody (R & D) were labeled with ruthenium (Igen) according to the manufacturer's instructions. The biotinylated antibodies were diluted to a final concentration of 1 mg/mL in PBS, pH 7.4, containing 0.25% BSA, 0.5% Tween-20 and 0.01% azide, (ECL buffer). Per assay tube, 25 mL of the biotinylated antibodies were pre-incubated at room temperature with 25 mL of a 1 mg/mL solution of streptavidin-coated paramagnetic beads (Dynal Corp., Lake Success, N.Y.) for 30 min by vigorous shaking, Samples to be tested (25 mL) which had been diluted in RPMI or standards were added to tubes followed by 25 ml, of ruthenylated antibody (final concentration 1 mg/mL, diluted in ECL buffer). The tubes were then shaken for an additional 2 hours. The reaction was quenched by the addition of 200 mL/tube of PBS and the amount of chemiluminescence determined using an Origen Analyzer (Igen).

SDS-PAGE and Western Blotting

The protein concentration in the cell lysates was determined by bicinchoninic acid assays (BCA) with bovine serum albumin used as the standard. 5 μg of total cellular protein was separated by either 10% or 14% SDS-PAGE (sodium dodecyl sulfate polyacrylamide gel electrophoresis). 10% gels were used for analysis of proteins above 50 kDa (TLR4, IFNγ, TNF-R1, iNOS) while 14% gels were used for apoptosis-specific eIF-5A (17 kDa). Gels were transferred to polyvinylidene fluoride (PVDF) membranes with transfer buffer (48 mM Tris, 39 mM glycine, 1.3 mM SDS, pH 9.2; 15V for 18 mins) using a semi-dry transfer unit (Bio-Rad). Membranes were blocked for 1 hour with 5% skim milk in PBS-t (PBS with 0.1% Teen 20). Primary antibodies were diluted in the blocking solution and all blots were incubated at room temperature with shaking. Primary antibodies used were apoptosis-specific eIF-5A (BD Biosciences; 1:20,000; incubate 1 hour; recognizes both apoptosis-specific eIF-5A and eIF5A2), TLR4 (Santa Cruz Biotechnology Inc; TLR4 (H-80): sc-10741; 1:1000; incubate 2 hours), IFN-γRα (Santa Cruz Biotechnology Inc; IFN-γRα (C-20): sc-700; 1:1000; incubate 1 hour), TNF-R1 (Santa Cruz Biotechnology Inc; TNF-R1 (H-5): sc-8436; 1:200; incubate 3 hours), iNOS (BD Transduction Laboratories: 61.0431; 1:10,000; incubate 1 hour) and β-actin (Oncogene; actin (Ab-1); 1:20,000; incubate 1 hour). Following primary antibody incubations, blots were washed 3 times for 5-10 minutes with PBS-t. Horseradish peroxidase-conjugated (HRP) secondary antibodies were diluted in 1% skim milk and incubated with the membrane for 1 hour. Secondary antibodies used were anti-mouse IgG-HRP (Sigma; 1:5000; for apoptosis-specific eIF-5A and TNF-R1), anti-rabbit IgG-HRP (Amersham Pharmacia Biotech; 1:2500; for TLR4 and IFNγ-Rα), anti-mouse IgM-HRP (Calbiochem; 1:5000; for actin). Following secondary antibody incubations, blots were washed 4 times for 5-10 mins with PBS-t. Blots were developed with enhanced chemiluminescent detection reagent (ECL; Amersham Pharmacia Biotech) according to the manufacturers instructions and bands were visualized on X-ray film (Fuji).

RT-PCR

RT-PCR was performed according to Medvedev et al. 2002 in order to observe changes in TLR4 mRNA expression in transfected HT-29 cells in response to IFNγ. Expression of GAPDH was used as a control to show that equal amounts of cDNA were being used between samples. Increasing PCR cycles (20, 25, 30, and 35) were used to determine the optimal cycle number that resulted in detectable amplified products under nonsaturating conditions. PCR products were detected by ethidium bromide—incorporation and were separated by agarose gel electrophoresis. RT-PCR of total mRNA isolated from siRNA-transfected HT-29 cells treated with or without IFNγ for 6 hours was used to detect TLR4 and GAPDH transcripts. HT-29 cells were transfected with siRNA as described above. 48 hours after transfection, the cells were treated with 200 units/ml IFNγ. Control cells which were not treated with IFNγ received only a media change. Total mRNA was isolated using the GenElute Mammalian RNA miniprep kit (Sigma) according to the manufacturer's protocol for adherent cells. The media was removed and the cells were washed twice with warm PBS. Lysis buffer was added to the cells and the lysate was transferred to a microcentrifuge tube and total RNA was isolated according to the manufacturer's protocol.

The primers for TLR4 (NM_003266) were:

```
                                    (SEQ ID NO: 92)
Forward    5' CGGATGGCAACATTTAGAATTAGT 3'

(SEQ ID NO: 93)
Reverse    5' TGATTGAGACTGTAATCAAGAACC 3'
Expected fragment size: 674 bp
```

The primers for GAPDH (BC023632) were:

```
                                    (SEQ ID NO: 94)
Forward    5' CTGATGCCCCCATGTTCGTCAT 3'

(SEQ ID NO: 95)
Reverse    5' CCACCACCCTGTTGCTGTAG 3'
Expected fragment size: 599 bp
```

The total RNA was reverse transcribed using the following conditions:

| Mix: | |
|---|---|
| RNA | 2.5 μg |
| Poly (T) primer | 6.25 μl |
| Depc water | to 13.75 μl |
| | Heat 70° C. 5 min |
| | Chill on ice 5 min |
| Add: | |
| 5X AMV Buffer | 5.0 μl |
| dNTPs (10 mM) | 2.5 μl |
| Rnase Inhibitor | 1.25 μl |
| AMV RT | 2.5 μl |
| | Heat 42° C. 60 min |
| | Heat 70° C. 10 min |

A single PCR reaction was performed using the following conditions:

| | |
|---|---|
| 10X Tsg buffer | 2.0 μl |
| dNTP (10 mM) | 0.4 μl |
| forward primer (25 pmol/μl) | 0.4 μl |
| reverse primer (25 pmol/μl) | 0.4 μl |
| MgCl$_2$ (15 mM) | 2.0 μl |
| cDNA | 0.8 μl |
| H$_2$O | 13.88 μl |
| Tsg polymerase | 0.12 μl |

The PCR conditions for TLR4 were:

Heat to 95° C. 5 min 20, 25, 30, or 35 cycles of: 95° C. 1 min

55° C. 1 min

72° C. 2 min

Extend at 72° C. for 10 min

Sink to 4° C.

The PCR conditions for GAPDH were:

Heat to 95° C. 5 min 20, 25, 30, or 35 cycles of: 95° C. 1 min

57° C. 1 min

72° C. 2 min

Extend at 72° C. for 10 min

Sink to 4° C.

We claim:

1. A method delivering apoptosis-specific elF-5A siRNA having the sequence set forth in SEQ ID NO: 33 to lung cells of a mammal in vivo, the method comprising mixing said siRNA with water and delivering to a mammal intranasally.

2. An siRNA of apoptosis-specific elF-5A wherein said siRNA suppresses endogenous expression of apoptosis-specific elF-5A in a cell and the siRNA has the sequence set forth in SEQ ID NO: 33.

3. The siRNA of claim 2, wherein apoptosis-specific elF-5A is encoded by nucleotide sequence of SEQ ID NO: 20.

4. The siRNA of claim 2, wherein apoptosis-specific elF-5A is encoded by nucleotide sequence of SEQ ID NO: 41.

5. An siRNA of apoptosis-specific elF-5A wherein said siRNA suppresses endogenous expression of apoptosis-specific elF-5A in a cell and the siRNA has the sequence set forth in SEQ ID NO: 30.

6. An siRNA of apoptosis-specific elF-5A wherein said siRNA suppresses endogenous expression of apoptosis-specific elF-5A in a cell and the siRNA has the sequence set forth in SEQ ID NO: 31.

7. An siRNA of apoptosis-specific elF-5A wherein said siRNA suppresses endogenous expression of apoptosis-specific elF-5A in a cell and the siRNA has the sequence set forth in SEQ ID NO: 32.

8. A method of inhibiting expression of apoptosis-specific elF-5A in a cell, the method comprising administering the siRNA of claim 2 to said cell whereby said apoptosis-specific elF-5A siRNA inhibits expression of endogenous apoptosis-specific elF-5A in said cell.

9. A method of inhibiting expression of apoptosis-specific elF-5A in a cell, the method comprising administering the siRNA of claim 5 to said cell whereby said apoptosis-specific elF-5A siRNA inhibits expression of endogenous apoptosis-specific elF-5A in said cell.

10. A method of inhibiting expression of apoptosis-specific elF-5A in a cell, the method comprising administering the siRNA of claim 5 to said cell whereby said apoptosis-specific elF-5A siRNA inhibits expression of endogenous apoptosis-specific elF-5A in said cell.

11. The method of claim 8 wherein said inhibition of expression of endogenous apoptosis-specific elF-5A in said cell has an effect on the cell selected from the group consisting of suppressing apoptosis in said cell, reducing expression of p53 in said cell, reducing levels of cytokine produced in said cell, increasing expression of Bcl-2 in said cell; reducing levels of myeloperoxidase produced in said cell, reducing levels of active NFk beta in said cell, reducing levels of TLR4 in said cell, reducing levels of TNFR-1 in said cell and reducing levels of iNOS in said cell.

12. The method of claim 11 wherein said inhibition of expression of endogenous apoptosis-specific elF-5A in said cell has an effect on the cell selected from the group consisting of suppressing apoptosis in said cell, reducing expression of p53 in said cell, reducing levels of a cytokine produced in said cell, reducing levels of a cytokine produced in said cell, increasing expression of Bcl-2 in said cell; reducing levels of myeloperoxidase produced in said cell, and reducing levels of active NFk beta in said cell, reducing levels of TLR4 in said cell, reducing levels of TNFR-1 in said cell and reducing levels of iNOS in said cell.

\* \* \* \* \*

UNITED STATES PATENT AND TRADEMARK OFFICE
CERTIFICATE OF CORRECTION

| | | Page 1 of 1 |
|---|---|---|
| PATENT NO. | : 8,754,057 B2 | |
| APPLICATION NO. | : 13/099171 | |
| DATED | : June 17, 2014 | |
| INVENTOR(S) | : John E. Thompson et al. | |

It is certified that error appears in the above-identified patent and that said Letters Patent is hereby corrected as shown below:

On the Title page, item (54), and in the Specification, at column 1, line 2, in the title: replace "(EIF-5A1")" with --("EIF-5A1")--

In the claims:

At column 108, line 37, replace "claim 11" with --claim 10--

Signed and Sealed this
Ninth Day of September, 2014

Michelle K. Lee
*Deputy Director of the United States Patent and Trademark Office*

SEQUENCE LISTING

<160> NUMBER OF SEQ ID NOS: 95

<210> SEQ ID NO 1
<211> LENGTH: 1139
<212> TYPE: DNA
<213> ORGANISM: Rattus sp.
<220> FEATURE:
<221> NAME/KEY: CDS
<222> LOCATION: (33)..(494)

<400> SEQUENCE: 1

```
caggtctaga gttggaatcg aagcctctta aa atg gca gat gat ttg gac ttc         53
                                   Met Ala Asp Asp Leu Asp Phe
                                     1               5 gag aca gga gat gca ggg gcc tca gcc acc ttc cca atg cag tgc tca        101
Glu Thr Gly Asp Ala Gly Ala Ser Ala Thr Phe Pro Met Gln Cys Ser
         10                  15                  20 gca tta cgt aag aat ggt ttt gtg gtg ctc aag ggc cgg cca tgt aag        149
Ala Leu Arg Lys Asn Gly Phe Val Val Leu Lys Gly Arg Pro Cys Lys
     25                  30                  35 atc gtc gag atg tct act tcg aag act ggc aag cat ggc cat gcc aag        197
Ile Val Glu Met Ser Thr Ser Lys Thr Gly Lys His Gly His Ala Lys
 40                  45                  50                  55 gtc cat ctg gtt ggt att gat att ttt act ggg aag aaa tat gaa gat        245
Val His Leu Val Gly Ile Asp Ile Phe Thr Gly Lys Lys Tyr Glu Asp
                 60                  65                  70 atc tgc ccg tcg act cat aac atg gat gtc ccc aac atc aaa agg aat        293
Ile Cys Pro Ser Thr His Asn Met Asp Val Pro Asn Ile Lys Arg Asn
             75                  80                  85 gat ttc cag ctg att ggc atc cag gat ggg tac cta tcc ctg ctc cag        341
Asp Phe Gln Leu Ile Gly Ile Gln Asp Gly Tyr Leu Ser Leu Leu Gln
         90                  95                 100 gac agt ggg gag gta cga gag gac ctt cgt ctg cct gag gga gac ctt        389
Asp Ser Gly Glu Val Arg Glu Asp Leu Arg Leu Pro Glu Gly Asp Leu
    105                 110                 115 ggc aag gag att gag cag aag tat gac tgt gga gaa gag atc ctg atc        437
Gly Lys Glu Ile Glu Gln Lys Tyr Asp Cys Gly Glu Glu Ile Leu Ile
120                 125                 130                 135 aca gtg ctg tcc gcc atg aca gag gag gca gct gtt gca atc aag gcc        485
Thr Val Leu Ser Ala Met Thr Glu Glu Ala Ala Val Ala Ile Lys Ala
                140                 145                 150 atg gca aaa taactggctt ccagggtggc ggtggtggca gcagtgatcc                 534
Met Ala Lys atgagcctac agaggcccct cccccagctc tggctgggcc cttggctgga ctcctatcca      594
atttatttga cgttttattt tggttttcct caccccttca aactgtcggg gagaccctgc      654
ccttcaccta gctcccttgg ccaggcatga gggagccatg gccttggtga agctacctgc      714
ctcttctctc gcagccctga tgggggaaag ggagtgggta ctgcctgtgg tttaggttcc      774
cctctccctt tttcttttta attcaatttg gaatcagaaa gctgtggatt ctggcaaatg      834
gtcttgtgtc ctttatccca ctcaaaccca tctggtcccc tgttctccat agtccttcac      894
ccccaagcac cactgacaga ctggggacca gccccttcc ctgcctgtgt ctcttcccaa       954
acccctctat aggggtgaca agaagaggag ggggggaggg gacacgatcc ctcctcaggc      1014
atctgggaag gccttgcccc catgggcttt accctttcct gtgggctttc tccctgacac      1074
atttgttaaa aatcaaacct gaataaaact acaagtttaa tatgaaaaaa aaaaaaaaa       1134 aaaaa                                                                  1139
```

<210> SEQ ID NO 2
<211> LENGTH: 154
<212> TYPE: PRT
<213> ORGANISM: Rattus sp.

<400> SEQUENCE: 2

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 3
<211> LENGTH: 462
<212> TYPE: DNA
<213> ORGANISM: Homo sapiens

<400> SEQUENCE: 3
atggcagatg acttggactt cgagacagga gatgcagggg cctcagccac cttcccaatg     60
cagtgctcag cattacgtaa gaatggcttt gtggtgctca aggccggcc atgtaagatc     120 gtcgagatgt ctacttcgaa gactggcaag cacggccacg ccaaggtcca tctggttggt    180
attgacatct ttactgggaa gaaatatgaa gatatctgcc cgtcaactca taatatggat    240
gtccccaaca tcaaaaggaa tgacttccag ctgattggca tccaggatgg gtacctatca    300
ctgctccagg acagcgggga ggtacgagag gaccttcgtc tccctgaggg agaccttggc    360
aaggagattg agcagaagta cgactgtgga gaagagatcc tgatcacggt gctgtctgcc    420
atgacagagg aggcagctgt tgcaatcaag gccatggcaa aa                        462

<210> SEQ ID NO 4
<211> LENGTH: 460
<212> TYPE: DNA
<213> ORGANISM: Homo sapiens

<400> SEQUENCE: 4
atggcagacg aaattgattt cactactgga gatgccgggg cttccagcac ttaccctatg     60
cagtgctcgg ccttgcgcaa aaacggcttc gtggtgctca aggacgacc atgcaaaata     120 gtggagatgt caacttccaa aactggaaag catggtcatg ccaaggttca ccttgttgga    180
attgatattt tcacgggcaa aaaatatgaa gatatttgtc cttctactca aacatggat    240 gttccaaata ttaagagaaa tgattatcaa ctgatatgca ttcaagatgg ttaccttccc    300

```
ctgctgacag aaactggtga agttcgtgag gatcttaaac tgccagaagg tgaactaggc    360
aaagaaaata gagggaaaata caatgcaggt gaagatgtac aggtgtctgt catgtgtgca    420
atgagtgaag aatatgctgt agccataaaa ccctgcaaat                           460
```

<210> SEQ ID NO 5
<211> LENGTH: 462
<212> TYPE: DNA
<213> ORGANISM: Rattus sp.

<400> SEQUENCE: 5

```
atggcagatg atttggactt cgagacagga gatgcagggg cctcagccac cttcccaatg     60
cagtgctcag cattacgtaa gaatggtttt gtggtgctca aaggccggcc atgtaagatc    120
gtcgagatgt ctacttcgaa gactggcaag catggccatg ccaaggtcca tctggttggc    180
attgacattt ttactgggaa gaaatatgaa gatatctgcc cgtcgactca taatatggat    240
gtccccaaca tcaaacggaa tgacttccag ctgattggca tccaggatgg gtacctatcc    300
ctgctccagg acagtgggga ggtacgagag gaccttcgtc tgcctgaagg agaccttggc    360
aaggagattg agcagaagta tgactgtgga gaagagatcc tgatcacagt gctgtctgcc    420
atgacagagg aggcagctgt tgcaatcaag gccatggcaa aa                       462
```

<210> SEQ ID NO 6
<211> LENGTH: 606
<212> TYPE: DNA
<213> ORGANISM: Rattus sp.
<220> FEATURE:
<221> NAME/KEY: CDS
<222> LOCATION: (1)..(453)

<400> SEQUENCE: 6

```
gct gtg tat tat tgg gcc cat aag aac cac ata cct gtg ctg agt cct      48
Ala Val Tyr Tyr Trp Ala His Lys Asn His Ile Pro Val Leu Ser Pro
  1               5                  10                  15 gca ctc aca gac ggc tca ctg ggt gac atg atc ttt ttc cat tcc tat      96
Ala Leu Thr Asp Gly Ser Leu Gly Asp Met Ile Phe Phe His Ser Tyr
             20                  25                  30 aaa aac cca ggc ttg gtc ctg gac atc gtt gaa gac ctg cgg ctc atc     144
Lys Asn Pro Gly Leu Val Leu Asp Ile Val Glu Asp Leu Arg Leu Ile
         35                  40                  45 aac atg cag gcc att ttc gcc aag cgc act ggg atg atc atc ctg ggt     192
Asn Met Gln Ala Ile Phe Ala Lys Arg Thr Gly Met Ile Ile Leu Gly
     50                  55                  60 gga ggc gtg gtc aag cac cac atc gcc aat gct aac ctc atg cgg aat     240
Gly Gly Val Val Lys His His Ile Ala Asn Ala Asn Leu Met Arg Asn
 65                  70                  75                  80 gga gct gac tac gct gtt tat atc aac aca gcc cag gag ttt gat ggc     288
Gly Ala Asp Tyr Ala Val Tyr Ile Asn Thr Ala Gln Glu Phe Asp Gly
                 85                  90                  95 tca gac tca gga gcc cgg cca gat gag gct gtc tcc tgg ggc aag atc     336
Ser Asp Ser Gly Ala Arg Pro Asp Glu Ala Val Ser Trp Gly Lys Ile
            100                 105                 110 cgg atg gat gca cag cca gta aag gtc tat gct gat gca tct ctg gtt     384
Arg Met Asp Ala Gln Pro Val Lys Val Tyr Ala Asp Ala Ser Leu Val
        115                 120                 125 ttc ccc ttg ctg gtg gct gag aca ttc gcc caa aag gca gat gcc ttc     432
Phe Pro Leu Leu Val Ala Glu Thr Phe Ala Gln Lys Ala Asp Ala Phe
    130                 135                 140 aga gct gag aag aat gag gac tgagcagatg ggtaaagacg gaggcttctg        483
Arg Ala Glu Lys Asn Glu Asp
145                 150
```
ccacaccttt atttattatt tgcataccaa cccctcctgg gccctctcct tggtcagcag    543
catcttgaga ataaatggcc ttttgttgg tttctgtaaa aaaggactt taaaaaaaaa    603 aaa                                                                606

<210> SEQ ID NO 7
<211> LENGTH: 151
<212> TYPE: PRT
<213> ORGANISM: Rattus sp.

<400> SEQUENCE: 7

Ala Val Tyr Tyr Trp Ala His Lys Asn His Ile Pro Val Leu Ser Pro
 1               5                  10                  15

Ala Leu Thr Asp Gly Ser Leu Gly Asp Met Ile Phe Phe His Ser Tyr
            20                  25                  30

Lys Asn Pro Gly Leu Val Leu Asp Ile Val Glu Asp Leu Arg Leu Ile
        35                  40                  45

Asn Met Gln Ala Ile Phe Ala Lys Arg Thr Gly Met Ile Ile Leu Gly
    50                  55                  60

Gly Gly Val Val Lys His His Ile Ala Asn Ala Asn Leu Met Arg Asn
65                  70                  75                  80

Gly Ala Asp Tyr Ala Val Tyr Ile Asn Thr Ala Gln Glu Phe Asp Gly
                85                  90                  95

Ser Asp Ser Gly Ala Arg Pro Asp Glu Ala Val Ser Trp Gly Lys Ile
            100                 105                 110

Arg Met Asp Ala Gln Pro Val Lys Val Tyr Ala Asp Ala Ser Leu Val
        115                 120                 125

Phe Pro Leu Leu Val Ala Glu Thr Phe Ala Gln Lys Ala Asp Ala Phe
    130                 135                 140

Arg Ala Glu Lys Asn Glu Asp
145                 150

<210> SEQ ID NO 8
<211> LENGTH: 453
<212> TYPE: DNA
<213> ORGANISM: Homo sapiens

<400> SEQUENCE: 8
tccgtgtatt actgggccca gaagaaccac atccctgtgt ttagtcccgc acttacagac    60
ggctcgctgg gcgacatgat cttcttccat tcctacaaga cccgggcct ggtcctggac   120 atcgttgagg acctgaggct catcaacaca caggccatct tgccaagtg cactgggatg   180 atcattctgg gcgggggcgt ggtcaagcac acattgcca atgccaacct catgcggaac   240
ggggccgact acgctgttta catcaacaca gcccaggagt tgatggctc tgactcaggt   300 gcccgaccag acgaggctgt ctcctggggc aagatccggg tggatgcaca gcccgtcaag   360
gtctatgctg acgcctccct ggtcttcccc ctgcttgtgg ctgaaacctt tgcccagaag   420
atggatgcct tcatgcatga agaacgag gac                                 453

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (12)

<223> OTHER INFORMATION: a, t, c or g

<400> SEQUENCE: 9
tcsaarachg gnaagcaygg                                                    20

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gcgaagcttc catggctcga gttttttttt tttttttttt tt                           42

<210> SEQ ID NO 11
<211> LENGTH: 972
<212> TYPE: DNA
<213> ORGANISM: Rattus sp.
<220> FEATURE:
<221> NAME/KEY: CDS
<222> LOCATION: (1)..(327)

<400> SEQUENCE: 11

```
tcg aag acc ggt aag cac ggc cat gcc aag gtc cat ctg gtt ggt att          48
Ser Lys Thr Gly Lys His Gly His Ala Lys Val His Leu Val Gly Ile
  1               5                  10                  15 gat att ttt act ggg aag aaa tat gaa gat atc tgc ccg tcg act cat          96
Asp Ile Phe Thr Gly Lys Lys Tyr Glu Asp Ile Cys Pro Ser Thr His
             20                  25                  30 aac atg gat gtc ccc aac atc aaa agg aat gat ttc cag ctg att ggc         144
Asn Met Asp Val Pro Asn Ile Lys Arg Asn Asp Phe Gln Leu Ile Gly
         35                  40                  45 atc cag gat ggg tac cta tcc ctg ctc cag gac agt ggg gag gta cga         192
Ile Gln Asp Gly Tyr Leu Ser Leu Leu Gln Asp Ser Gly Glu Val Arg
     50                  55                  60 gag gac ctt cgt ctg cct gag gga gac ctt ggc aag gag att gag cag         240
Glu Asp Leu Arg Leu Pro Glu Gly Asp Leu Gly Lys Glu Ile Glu Gln
 65                  70                  75                  80 aag tat gac tgt gga gaa gag atc ctg atc aca gtg ctg tcc gcc atg         288
Lys Tyr Asp Cys Gly Glu Glu Ile Leu Ile Thr Val Leu Ser Ala Met
                 85                  90                  95 aca gag gag gca gct gtt gca atc aag gcc atg gca aaa taactggctt         337
Thr Glu Glu Ala Ala Val Ala Ile Lys Ala Met Ala Lys
            100                 105
```
ccagggtggc ggtggtggca gcagtgatcc atgagcctac agaggcccct cccccagctc       397
tggctgggcc cttggctgga ctcctatcca atttatttga cgttttattt tggttttcct       457
caccccttca aactgtcggg gagaccctgc ccttcaccta gctcccttgg ccaggcatga       517
gggagccatg gccttggtga agctacctgc ctcttctctc gcagccctga tgggggaaag       577
ggagtgggta ctgcctgtgg tttaggttcc cctctccctt tttcttttta attcaatttg       637
gaatcagaaa gctgtggatt ctggcaaatg gtcttgtgtc ctttatccca ctcaaaccca       697
tctggtcccc tgttctccat agtccttcac ccccaagcac cactgacaga ctggggacca       757 gccccttcc ctgcctgtgt ctcttcccaa acccctctat aggggtgaca agaagaggag        817
ggggggaggg gacacgatcc ctcctcaggc atctgggaag gccttgcccc catgggcttt       877
accctttcct gtgggctttc tccctgacac atttgttaaa aatcaaacct gaataaaact       937
acaagtttaa tatgaaaaaa aaaaaaaaaa aaaaa                                   972

<210> SEQ ID NO 12
<211> LENGTH: 109
<212> TYPE: PRT
<213> ORGANISM: Rattus sp.

<400> SEQUENCE: 12

```
Ser Lys Thr Gly Lys His Gly His Ala Lys Val His Leu Val Gly Ile
 1               5                  10                  15

Asp Ile Phe Thr Gly Lys Lys Tyr Glu Asp Ile Cys Pro Ser Thr His
             20                  25                  30

Asn Met Asp Val Pro Asn Ile Lys Arg Asn Asp Phe Gln Leu Ile Gly
         35                  40                  45

Ile Gln Asp Gly Tyr Leu Ser Leu Leu Gln Asp Ser Gly Glu Val Arg
     50                  55                  60

Glu Asp Leu Arg Leu Pro Glu Gly Asp Leu Gly Lys Glu Ile Glu Gln
 65                  70                  75                  80

Lys Tyr Asp Cys Gly Glu Glu Ile Leu Ile Thr Val Leu Ser Ala Met
                 85                  90                  95

Thr Glu Glu Ala Ala Val Ala Ile Lys Ala Met Ala Lys
            100                 105
```

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
caggtctaga gttggaatcg aagc                                          24

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
atatctcgag ccttgattgc aacagctgcc                                    30

<210> SEQ ID NO 15
<211> LENGTH: 489
<212> TYPE: DNA
<213> ORGANISM: Rattus sp.
<220> FEATURE:
<221> NAME/KEY: CDS
<222> LOCATION: (33)..(485)

<400> SEQUENCE: 15

```
caggtctaga gttggaatcg aagcctctta aa atg gca gat gat ttg gac ttc      53
                                   Met Ala Asp Asp Leu Asp Phe
                                    1               5 gag aca gga gat gca ggg gcc tca gcc acc ttc cca atg cag tgc tca     101
Glu Thr Gly Asp Ala Gly Ala Ser Ala Thr Phe Pro Met Gln Cys Ser
         10                  15                  20 gca tta cgt aag aat ggt ttt gtg gtg ctc aag ggc cgg cca tgt aag     149
Ala Leu Arg Lys Asn Gly Phe Val Val Leu Lys Gly Arg Pro Cys Lys
     25                  30                  35 atc gtc gag atg tct act tcg aag act ggc aag cat ggc cat gcc aag     197
Ile Val Glu Met Ser Thr Ser Lys Thr Gly Lys His Gly His Ala Lys
 40                  45                  50                  55
```

```
                40                  45                  50                  55
gtc cat ctg gtt ggt att gat att ttt act ggg aag aaa tat gaa gat         245
Val His Leu Val Gly Ile Asp Ile Phe Thr Gly Lys Lys Tyr Glu Asp
                        60                  65                  70 atc tgc ccg tcg act cat aac atg gat gtc ccc aac atc aaa agg aat         293
Ile Cys Pro Ser Thr His Asn Met Asp Val Pro Asn Ile Lys Arg Asn
                75                  80                  85 gat ttc cag ctg att ggc atc cag gat ggg tac cta tcc ctc ctc cag         341
Asp Phe Gln Leu Ile Gly Ile Gln Asp Gly Tyr Leu Ser Leu Leu Gln
            90                  95                 100 gac agt ggg gag gta cga gag gac ctt cgt ctg cct gag gga gac ctt         389
Asp Ser Gly Glu Val Arg Glu Asp Leu Arg Leu Pro Glu Gly Asp Leu
        105                 110                 115 ggc aag gag att gag cag aag tat gac tgt gga gaa gag atc ctg atc         437
Gly Lys Glu Ile Glu Gln Lys Tyr Asp Cys Gly Glu Glu Ile Leu Ile
    120                 125                 130                 135 aca gtg ctg tcc gcc atg aca gag gag gca gct gtt gca atc aag gct         485
Thr Val Leu Ser Ala Met Thr Glu Glu Ala Ala Val Ala Ile Lys Ala
                140                 145                 150 cgag                                                                    489

<210> SEQ ID NO 16
<211> LENGTH: 151
<212> TYPE: PRT
<213> ORGANISM: Rattus sp.

<400> SEQUENCE: 16

Met Ala Asp Asp Leu Asp Phe Glu Thr Gly Asp Ala Gly Ala Ser Ala
 1               5                  10                  15

Thr Phe Pro Met Gln Cys Ser Ala Leu Arg Lys Asn Gly Phe Val Val
                20                  25                  30

Leu Lys Gly Arg Pro Cys Lys Ile Val Glu Met Ser Thr Ser Lys Thr
            35                  40                  45

Gly Lys His Gly His Ala Lys Val His Leu Val Gly Ile Asp Ile Phe
        50                  55                  60

Thr Gly Lys Lys Tyr Glu Asp Ile Cys Pro Ser Thr His Asn Met Asp
    65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala
145                 150

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
gtctgtgtat tattgggccc                                                    20
```

```
<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
gcgaagcttc catggctcga gtttttttttt tttttttttt tt                        42

<210> SEQ ID NO 19
<211> LENGTH: 1299
<212> TYPE: DNA
<213> ORGANISM: Homo sapiens

<400> SEQUENCE: 19
ggcacgaggg cggcggcggc ggtagaggcg gcggcggcgg cggcagcggg ctcggaggca      60
gcggttgggc tcgcggcgag cggacggggt cgagtcagtg cgttcgcgcg agttggaatc     120
gaagcctctt aaaatggcag atgacttgga cttcgagaca ggagatgcag gggcctcagc     180
caccttccca atgcagtgct cagcattacg taagaatggc tttgtggtgc tcaaaggccg     240
gccatgtaag atcgtcgaga tgtctacttc gaagactggc aagcacggcc acgccaaggt     300
ccatctggtt ggtattgaca tctttactgg aagaaatat gaagatatct gcccgtcaac      360
tcataatatg gatgtcccca acatcaaaag gaatgacttc agctgattg gcatccagga      420 tgggtaccta tcactgctcc aggacagcgg ggaggtacga gaggaccttc gtctccctga     480
gggagacctt ggcaaggaga ttgagcagaa gtacgactgt ggagaagaga tcctgatcac     540
ggtgctgtct gccatgacag aggaggcagc tgttgcaatc aaggccatgg caaaataact     600
ggctcccagg atggcggtgg tggcagcagt gatcctctga acctgcagag gccccctccc     660
cgagcctggc ctggctctgg cccggtccta agctggactc ctcctacaca atttatttga     720 cgttttatt tggttttccc cacccccctca atctgtcggg gagcccctgc ccttcaccta     780
gctcccttgg ccaggagcga gcgaagctgt ggccttggtg aagctgccct cctcttctcc     840
cctcacacta cagccctggt gggggagaag ggggtgggtc ctgcttgtgg tttagtcttt     900
tttttttttt tttttttttt tttaaattca atctggaatc agaaagcggt ggattctggc     960
aaatggtcct tgtgccctcc ccactcatcc ctggtctggt ccctgttgc ccatagccct     1020 ttaccctgag caccacccca acagactggg gaccagcccc ctcgcctgcc tgtgtctctc    1080
cccaaacccc tttagatggg gagggaagag gaggagaggg gaggggacct gccccctcct    1140
caggcatctg ggagggccct gccccatgg gctttaccct tccctgcggg ctctctcccc     1200
gacacatttg ttaaaatcaa acctgaataa aactacaagt ttaatatgaa aaaaaaaaa     1260 aaaaaaaaa aaaaaaaaa aaaaaaaaa aaaaaaaaa                              1299

<210> SEQ ID NO 20
<211> LENGTH: 462
<212> TYPE: DNA
<213> ORGANISM: Rattus sp.

<400> SEQUENCE: 20
atggcagatg atttggactt cgagacagga gatgcagggg cctcagccac cttcccaatg      60
cagtgctcag cattacgtaa gaatggtttt gtggtgctca agggccggcc atgtaagatc     120
gtcgagatgt ctacttcgaa gactggcaag catggccatg ccaaggtcca tctggttggt     180
attgatattt ttactgggaa gaaatatgaa gatatctgcc cgtcgactca taacatggat     240
```

```
gtccccaaca tcaaaaggaa tgatttccag ctgattggca tccaggatgg gtacctatcc    300
ctgctccagg acagtgggga ggtacgagag gaccttcgtc tgcctgaggg agaccttggc    360
aaggagattg agcagaagta tgactgtgga gaagagatcc tgatcacagt gctgtccgcc    420
atgacagagg aggcagctgt tgcaatcaag gccatggcaa aa                       462
```

<210> SEQ ID NO 21
<211> LENGTH: 154
<212> TYPE: PRT
<213> ORGANISM: Homo sapiens

<400> SEQUENCE: 21

```
Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150
```

<210> SEQ ID NO 22
<211> LENGTH: 153
<212> TYPE: PRT
<213> ORGANISM: Homo sapiens

<400> SEQUENCE: 22

```
Met Ala Asp Glu Ile Asp Phe Thr Thr Gly Asp Ala Gly Ala Ser Ser
1               5                   10                  15

Thr Tyr Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Tyr Gln Leu Ile Cys Ile Gln Asp
                85                  90                  95

Gly Tyr Leu Ser Leu Leu Thr Glu Thr Gly Glu Val Arg Glu Asp Leu
            100                 105                 110

Lys Leu Pro Glu Gly Glu Leu Gly Lys Glu Ile Glu Gly Lys Tyr Asn
        115                 120                 125

Ala Gly Glu Asp Val Gln Val Ser Val Met Cys Ala Met Ser Glu Glu
    130                 135                 140
```

```
Tyr Ala Val Ala Ile Lys Pro Cys Lys
145                 150

<210> SEQ ID NO 23
<211> LENGTH: 154
<212> TYPE: PRT
<213> ORGANISM: Mus musculus

<400> SEQUENCE: 23

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
130                 135                 140

Ala Ala Val Ala Ile Lys Ala Met Ala Lys
145                 150

<210> SEQ ID NO 24
<211> LENGTH: 153
<212> TYPE: PRT
<213> ORGANISM: Homo sapiens

<400> SEQUENCE: 24

Met Ala Asp Glu Ile Asp Phe Thr Thr Gly Asp Ala Gly Ala Ser Ser
1               5                   10                  15

Thr Tyr Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Tyr Gln Leu Ile Cys Ile Gln Asp
                85                  90                  95

Gly Cys Leu Ser Leu Leu Thr Glu Thr Gly Glu Val Arg Glu Asp Leu
            100                 105                 110

Lys Leu Pro Glu Gly Glu Leu Gly Lys Glu Ile Glu Gly Lys Tyr Asn
        115                 120                 125

Ala Gly Glu Asp Val Gln Val Ser Val Met Cys Ala Met Ser Glu Glu
130                 135                 140

Tyr Ala Val Ala Ile Lys Pro Cys Lys
145                 150
```

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
gacttggact tcgagacagg                                               20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
gcacggccac gccaaggtc                                                19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
ggacagcggg gaggtacgag                                               20

<210> SEQ ID NO 28
<211> LENGTH: 153
<212> TYPE: PRT
<213> ORGANISM: Artificial Sequence
<220> FEATURE:
<223> OTHER INFORMATION: Description of Artificial Sequence: Illustrative consensus sequence

<400> SEQUENCE: 28

Met Ala Asp Glu Ile Asp Phe Thr Thr Gly Asp Ala Gly Ala Ser Ser
 1               5                  10                  15

Thr Tyr Pro Met Gln Cys Ser Ala Leu Arg Lys Asn Gly Phe Val Val
             20                  25                  30

Leu Lys Gly Arg Pro Cys Lys Ile Val Glu Met Ser Thr Ser Lys Thr
         35                  40                  45

Gly Lys His Gly His Ala Lys Val His Leu Val Gly Ile Asp Ile Phe
     50                  55                  60

Thr Gly Lys Lys Tyr Glu Asp Ile Cys Pro Ser Thr His Asn Met Asp
 65                  70                  75                  80

Val Pro Asn Ile Lys Arg Asn Asp Tyr Gln Leu Ile Cys Ile Gln Asp
                 85                  90                  95

Gly Cys Leu Ser Leu Leu Thr Glu Thr Gly Glu Val Arg Glu Asp Leu
            100                 105                 110

Lys Leu Pro Glu Gly Glu Leu Gly Lys Glu Ile Glu Gly Lys Tyr Asn
        115                 120                 125

Ala Gly Glu Asp Val Gln Val Ser Val Met Cys Ala Met Ser Glu Glu
    130                 135                 140

Tyr Ala Val Ala Ile Lys Pro Cys Lys
145                 150

<210> SEQ ID NO 29
<211> LENGTH: 1309
<212> TYPE: DNA
<213> ORGANISM: Homo sapiens

<400> SEQUENCE: 29

```
ggcacgaggg tagaggcggc ggcggcggcg gcagcgggct cggaggcagc ggttgggctc      60
gcggcgagcg gacggggtcg agtcagtgcg ttcgcgcgag ttggaatcga agcctcttaa     120
aatggcagat gacttggact tcgagacagg agatgcaggg gcctcagcca ccttcccaat     180
gcagtgctca gcattacgta agaatggctt tgtggtgctc aaaggccggc catgtaagat     240
cgtcgagatg tctacttcga agactggcaa gcacggccac gccaaggtcc atctggttgg     300
tattgacatc tttactggga agaaatatga agatatctgc ccgtcaactc ataatatgga     360
tgtccccaac atcaaaagga atgacttcca gctgattggc atccaggatg ggtacctatc     420
actgctccag gacagcgggg aggtacgaga ggaccttcgt ctccctgagg agacccttgg     480
caaggagatt gagcagaagt acgactgtgg agaagagatc ctgatcacgg tgctgtctgc     540
catgacagag gaggcagctg ttgcaatcaa ggccatggca aaataactgg ctcccaggat     600
ggcggtggtg gcagcagtga tcctctgaac ctgcagaggc cccctccccg agcctggcct     660
ggctctggcc cggtcctaag ctggactcct cctacacaat ttatttgacg ttttattttg     720
gttttccccca cccctcaat ctgtcgggga gcccctgccc ttcacctagc tcccttggcc     780
aggagcgagc gaagctgtgg ccttggtgaa gctgccctcc tcttctcccc tcacactaca     840
gccctggtgg gggagaaggg ggtgggtgct gcttgtggtt tagtcttttt tttttttttt     900
tttttttttt aaattcaatc tggaatcaga aagcggtgga ttctggcaaa tggtccttgt     960
gccctcccca ctcatccctg gtctggtccc ctgttgccca tagcccttta ccctgagcac    1020
caccccaaca gactgggac cagccccctc gcctgcctgt gtctctcccc aaacccctt     1080
agatggggag ggaagaggag gagaggggag gggacctgcc ccctcctcag gcatctggga    1140
gggccctgcc cccatgggct ttaccettec ctgcgggctc tctccccgac acatttgtta    1200
aaatcaaacc tgaataaaac tacaagttta atatgaaaaa aaaaaaaaaa aaaaaaaaa    1260
aaaaaaaaaa aaaaaaaaaa aaaaaaaaa aaaaaaaaa aaaaaaaa                   1309
```

<210> SEQ ID NO 30
<211> LENGTH: 23
<212> TYPE: DNA
<213> ORGANISM: Homo sapiens

<400> SEQUENCE: 30

```
aaaggaatga cttccagctg att                                              23
```

<210> SEQ ID NO 31
<211> LENGTH: 23
<212> TYPE: DNA
<213> ORGANISM: Homo sapiens

<400> SEQUENCE: 31

```
aagatcgtcg agatgtctac ttc                                              23
```

<210> SEQ ID NO 32
<211> LENGTH: 23
<212> TYPE: DNA
<213> ORGANISM: Homo sapiens

<400> SEQUENCE: 32
aaggtccatc tggttggtat tga                                                23

<210> SEQ ID NO 33
<211> LENGTH: 23
<212> TYPE: DNA
<213> ORGANISM: Homo sapiens

<400> SEQUENCE: 33
aagctggact cctcctacac aat                                                23

<210> SEQ ID NO 34
<211> LENGTH: 23
<212> TYPE: DNA
<213> ORGANISM: Homo sapiens

<400> SEQUENCE: 34
aaagtcgacc ttcagtaagg att                                                23

<210> SEQ ID NO 35
<211> LENGTH: 20
<212> TYPE: DNA
<213> ORGANISM: Homo sapiens

<400> SEQUENCE: 35
cctgtctcga agtccaagtc                                                    20

<210> SEQ ID NO 36
<211> LENGTH: 20
<212> TYPE: DNA
<213> ORGANISM: Homo sapiens

<400> SEQUENCE: 36
gacttggact tcgagacagg                                                    20

<210> SEQ ID NO 37
<211> LENGTH: 20
<212> TYPE: DNA
<213> ORGANISM: Homo sapiens

<400> SEQUENCE: 37
ggaccttggc gtggccgtgc                                                    20

<210> SEQ ID NO 38
<211> LENGTH: 20
<212> TYPE: DNA
<213> ORGANISM: Homo sapiens

<400> SEQUENCE: 38
gcacggccac gccaaggtcc                                                    20

<210> SEQ ID NO 39
<211> LENGTH: 20
<212> TYPE: DNA
<213> ORGANISM: Homo sapiens

<400> SEQUENCE: 39
ctcgtacctc cccgctctcc                                                    20

<210> SEQ ID NO 40
<211> LENGTH: 19
<212> TYPE: DNA
<213> ORGANISM: Homo sapiens

<400> SEQUENCE: 40

```
ggacagcggg gaggtacga                                                 19

<210> SEQ ID NO 41
<211> LENGTH: 465
<212> TYPE: DNA
<213> ORGANISM: Homo sapiens

<400> SEQUENCE: 41
atggcagatg acttggactt cgagacagga gatgcagggg cctcagccac cttcccaatg     60
cagtgctcag cattacgtaa gaatggcttt gtggtgctca aaggccggcc atgtaagatc    120
gtcgagatgt ctacttcgaa gactggcaag cacggccacg ccaaggtcca tctggttggt    180
attgacatct ttactgggaa gaaatatgaa gatatctgcc cgtcaactca taatatggat    240
gtccccaaca tcaaaaggaa tgacttccag ctgattggca tccaggatgg gtacctatca    300
ctgctccagg acagcgggga ggtacgagag gaccttcgtc tccctgaggg agaccttggc    360
aaggagattg agcagaagta cgactgtgga gaagagatcc tgatcacggt gctgtctgcc    420
atgacagagg aggcagctgt tgcaatcaag gccatggcaa ataa                     465

<210> SEQ ID NO 42
<211> LENGTH: 462
<212> TYPE: DNA
<213> ORGANISM: Homo sapiens

<400> SEQUENCE: 42
atggcagacg aaattgattt cactactgga gatgccgggg cttccagcac ttaccctatg     60
cagtgctcgg ccttgcgcaa aaacggcttc gtggtgctca aaggacgacc atgcaaaata    120
gtggagatgt caacttccaa aactggaaag catggtcatg ccaaggttca ccttgttgga    180
attgatattt tcacgggcaa aaaatatgaa gatatttgtc cttctactca aacatggat    240 gttccaaata ttaagagaaa tgattatcaa ctgatatgca ttcaagatgg ttacctttcc    300
ctgctgacag aaactggtga agttcgtgag gatcttaaac tgccagaagg tgaactaggc    360
aaagaaatag agggaaaata caatgcaggt gaagatgtac aggtgtctgt catgtgtgca    420
atgagtgaag aatatgctgt agccataaaa ccctgcaaat aa                      462

<210> SEQ ID NO 43
<211> LENGTH: 154
<212> TYPE: PRT
<213> ORGANISM: Homo sapiens

<400> SEQUENCE: 43

Met Ala Asp Asp Leu Asp Phe Glu Thr Gly Asp Ala Gly Ala Ser Ala
  1               5                  10                  15

Thr Phe Pro Met Gln Cys Ser Ala Leu Arg Lys Asn Gly Phe Val Val
                 20                  25                  30

Leu Lys Gly Trp Pro Cys Lys Ile Val Glu Met Ser Ala Ser Lys Thr
             35                  40                  45

Gly Lys His Gly His Ala Lys Val His Leu Val Gly Ile Asp Ile Phe
         50                  55                  60

Thr Gly Lys Lys Tyr Glu Asp Ile Cys Pro Ser Thr His Asn Met Asp
 65                  70                  75                  80

Val Pro Asn Ile Lys Arg Asn Asp Phe Gln Leu Ile Gly Ile Gln Asp
                 85                  90                  95

Gly Tyr Leu Ser Leu Leu Gln Asp Ser Gly Glu Val Pro Glu Asp Leu
            100                 105                 110

Arg Leu Pro Glu Gly Asp Leu Gly Lys Glu Ile Glu Gln Lys Tyr Asp
```

```
                115                 120                 125
Cys Gly Glu Glu Ile Leu Ile Thr Leu Leu Ser Ala Met Thr Glu Glu
        130                 135                 140

Ala Ala Val Ala Ile Lys Ala Met Ala Lys
145                 150
```

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aaaggaatga cttccagctg a                                              21

<210> SEQ ID NO 45
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 45
aaaggaauga cuuccagcug att                                            23

<210> SEQ ID NO 46
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 46
ucagcuggaa gucauuccuu utt                                            23

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aagatcgtcg agatgtctac t                                              21

<210> SEQ ID NO 48
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48
aagaucgucg agaugucuac utt                                    23

<210> SEQ ID NO 49
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
aguagacauc ucgacgaucu utt                                    23

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aaggtccatc tggttggtat t                                      21

<210> SEQ ID NO 51
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
aagguccauc ugguugguau utt                                    23

<210> SEQ ID NO 52
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
aauaccaacc agauggaccu utt                                    23

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aagctggact cctcctacac a                                      21

<210> SEQ ID NO 54
<211> LENGTH: 23
<212> TYPE: DNA

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 54
aagcuggacu ccuccuacac att                                             23

<210> SEQ ID NO 55
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 55
uguguaggag gaguccagcu utt                                             23

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
aaagtcgacc ttcagtaagg a                                               21

<210> SEQ ID NO 57
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 57
aaagucgacc uucaguaagg att                                             23

<210> SEQ ID NO 58
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 58
uccuuacuga aggucgacuu utt                                             23

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
```

```
                            primer

<400> SEQUENCE: 59
gccaagctta atggcagatg atttgg                                        26

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctgaattcca gttatttgc catgg                                          25

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aatgaattcc gccatgacag aggaggc                                       27

<210> SEQ ID NO 62
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcgaagcttc catggctcga gttttttttt tttttttttt tt                      42

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cctgtctcga agtccaagtc                                               20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ggaccttggc gtggccgtgc                                               20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 65
ctcgtacctc cccgctctcc                                               20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cgtaccggta cggttccagg                                               20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggaccttggc gtggccgtgc                                               20

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Cys Arg Leu Pro Glu Gly Asp Leu Gly Lys Glu Ile Glu Gln Lys Tyr
  1               5                  10                  15

Asp

<210> SEQ ID NO 69
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aaaggaatga cttccagctg acctgtctc                                     29

<210> SEQ ID NO 70
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aatcagctgg aagtcattcc tcctgtctc                                     29

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 71
aagatcgtcg agatgtctac tcctgtctc                                    29

<210> SEQ ID NO 72
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aaagtagaca tctcgacgat ccctgtctc                                    29

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aaggtccatc tggttggtat tcctgtctc                                    29

<210> SEQ ID NO 74
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aaaataccaa ccagatggac ccctgtctc                                    29

<210> SEQ ID NO 75
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
aagctggact cctcctacac acctgtctc                                    29

<210> SEQ ID NO 76
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aatgtgtagg aggagtccag ccctgtctc                                    29

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
```
aaagtcgacc ttcagtaagg acctgtctc                                          29

<210> SEQ ID NO 78
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aatccttact gaaggtcgac tcctgtctc                                          29

<210> SEQ ID NO 79
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
aagcuggacu ccuccuacac                                                    20

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
aaacacaucc uccucagguc g                                                  21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aaaggaatga cttccagctg a                                                  21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
aagatcgtcg agatgtctac t                                                  21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aaggtccatc tggttggtat t                                                  21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
aagctggact cctcctacac a                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aaagtcgacc ttcagtaagg a                                              21

<210> SEQ ID NO 86
<211> LENGTH: 21
<212> TYPE: RNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      siRNA sequence
<220> FEATURE:
<221> NAME/KEY: misc_feature
<222> LOCATION: (1)..(2)
<223> OTHER INFORMATION: a, t, c, g or u

<400> SEQUENCE: 86
nngcuggacu ccuccuacac a                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      siRNA sequence

<400> SEQUENCE: 87
gcuggacucc uccuacacat t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence

<400> SEQUENCE: 88
uguguaggag gaguccagct t                                              21

<210> SEQ ID NO 89
<211> LENGTH: 21
<212> TYPE: RNA

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      siRNA sequence
<220> FEATURE:
<221> NAME/KEY: misc_feature
<222> LOCATION: (1)..(2)
<223> OTHER INFORMATION: a, t, c, g or u

<400> SEQUENCE: 89
nnacacaucc uccucagguc g                                           21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      siRNA sequence

<400> SEQUENCE: 90
acacauccuc cucaggucgt t                                           21

<210> SEQ ID NO 91
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      siRNA sequence

<400> SEQUENCE: 91
cgaccugagg aggaugugut t                                           21

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      siRNA sequence

<400> SEQUENCE: 92
cggatggcaa catttagaat tagt                                        24

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 93
tgattgagac tgtaatcaag aacc                                        24

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Primer
```

```
<400> SEQUENCE: 94
ctgatgcccc catgttcgtc at                                            22

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 95
ccaccaccct gttgctgtag                                               20
```